US011497807B2

(12) United States Patent
Ciaramella et al.

(10) Patent No.: US 11,497,807 B2
(45) Date of Patent: Nov. 15, 2022

(54) ZOONOTIC DISEASE RNA VACCINES

(71) Applicant: ModernaTX, Inc., Cambridge, MA (US)

(72) Inventors: Giuseppe Ciaramella, Sudbury, MA (US); Sunny Himansu, Winchester, MA (US); Vladimir Presnyak, Manchester, NH (US); Kerry Benenato, Sudbury, MA (US); Ellalahewage Sathyajith Kumarasinghe, Harvard, MA (US)

(73) Assignee: ModernaTX, Inc., Cambridge, MA (US)

( * ) Notice: Subject to any disclaimer, the term of this patent is extended or adjusted under 35 U.S.C. 154(b) by 0 days.

(21) Appl. No.: 17/155,592

(22) Filed: Jan. 22, 2021

(65) Prior Publication Data

US 2021/0252129 A1   Aug. 19, 2021
US 2022/0118073 A9   Apr. 21, 2022

Related U.S. Application Data

(63) Continuation of application No. 16/494,988, filed as application No. PCT/US2018/022777 on Mar. 16, 2018, now abandoned.

(60) Provisional application No. 62/473,202, filed on Mar. 17, 2017, provisional application No. 62/473,219, filed on Mar. 17, 2017, provisional application No. 62/473,174, filed on Mar. 17, 2017.

(51) Int. Cl.
| | | |
|---|---|---|
| *A61K 39/12* | (2006.01) | |
| *A61P 31/14* | (2006.01) | |
| *A61K 31/7115* | (2006.01) | |
| *C12N 15/86* | (2006.01) | |
| *A61K 39/00* | (2006.01) | |

(52) U.S. Cl.
CPC .......... *A61K 39/12* (2013.01); *A61K 31/7115* (2013.01); *A61P 31/14* (2018.01); *C12N 15/86* (2013.01); *A61K 2039/53* (2013.01); *A61K 2039/545* (2013.01); *C12N 2760/14134* (2013.01); *C12N 2760/18634* (2013.01); *C12N 2770/20034* (2013.01)

(58) Field of Classification Search
CPC .......... A61K 39/12; A61K 31/7115; A61K 2039/53; A61K 2039/545; A61K 31/7105; A61P 31/14; A61P 31/16; A61P 37/04; C12N 15/86; C12N 2760/14134; C12N 2760/18634; C12N 2770/20034; C12N 2760/18211; C12N 2760/18234
See application file for complete search history.

(56) References Cited

U.S. PATENT DOCUMENTS

| | | |
|---|---|---|
| 3,906,092 A | 9/1975 | Hilleman et al. |
| 4,790,987 A | 12/1988 | Compans et al. |
| 5,427,782 A | 6/1995 | Compans et al. |
| 6,500,419 B1 | 12/2002 | Hone et al. |
| 6,514,948 B1 | 2/2003 | Raz et al. |
| 7,001,890 B1 | 2/2006 | Wagner et al. |
| 7,671,186 B2 | 3/2010 | Klein et al. |
| 8,691,966 B2 | 4/2014 | Kariko et al. |
| 8,692,292 B2 | 4/2014 | Umeda et al. |
| 8,710,200 B2 | 4/2014 | Schrum et al. |
| 8,734,853 B2 | 5/2014 | Sood et al. |
| 8,754,062 B2 | 6/2014 | De Fougerolles et al. |
| 8,822,663 B2 | 9/2014 | Schrum et al. |
| 8,927,206 B2 | 1/2015 | De Jong et al. |
| 8,999,380 B2 | 4/2015 | Bancel et al. |
| 9,192,661 B2 | 11/2015 | Jain et al. |
| 9,221,891 B2 | 12/2015 | Bancel et al. |
| 9,283,287 B2 | 3/2016 | Bancel et al. |
| 9,303,079 B2 | 4/2016 | Bancel et al. |
| 9,464,124 B2 | 10/2016 | Bancel et al. |
| 9,512,456 B2 | 12/2016 | Wang et al. |
| 9,533,047 B2 | 1/2017 | de Fougerolles et al. |
| 9,597,380 B2 | 3/2017 | Chakraborty et al. |
| 9,803,199 B2 | 10/2017 | Koizumi et al. |
| 9,868,691 B2 | 1/2018 | Benenato et al. |
| 9,868,692 B2 | 1/2018 | Benenato et al. |
| 9,872,900 B2 | 1/2018 | Ciaramella et al. |
| 10,064,934 B2 | 9/2018 | Ciaramella et al. |
| 10,064,935 B2 | 9/2018 | Ciaramella et al. |
| 10,124,055 B2 | 11/2018 | Ciaramella et al. |
| 10,207,010 B2 | 2/2019 | Besin et al. |
| 10,232,055 B2 | 3/2019 | Kariko et al. |
| 10,266,485 B2 | 4/2019 | Benenato |

(Continued)

FOREIGN PATENT DOCUMENTS

| | | |
|---|---|---|
| AU | 2015210364 A1 | 3/2017 |
| EP | 1083232 B1 | 2/2005 |

(Continued)

OTHER PUBLICATIONS

Chan YP, Lu M, Dutta S, Yan L, Barr J, Flora M, Feng YR, Xu K, Nikolov DB, Wang LF, Skiniotis G, Broder CC. Biochemical, conformational, and immunogenic analysis of soluble trimeric forms of henipavirus fusion glycoproteins. J Virol. Nov. 2012;86(21): 11457-71. Epub Aug. 22, 2012. (Year: 2012).*

(Continued)

*Primary Examiner* — Rachel B Gill
(74) *Attorney, Agent, or Firm* — Wolf, Greenfield & Sacks, P.C.

(57) ABSTRACT

Provide herein are Lassa virus, Nipah virus, and betacoronavirus ribonucleic acid vaccines as well as methods of using the vaccines and compositions comprising the vaccines.

20 Claims, 10 Drawing Sheets

Specification includes a Sequence Listing.

(56) References Cited

U.S. PATENT DOCUMENTS

| | | | |
|---|---|---|---|
| 10,273,269 B2 | 4/2019 | Ciaramella |
| 10,286,086 B2 | 5/2019 | Roy et al. |
| 10,323,076 B2 | 6/2019 | Ellsworth et al. |
| 10,385,088 B2 | 8/2019 | Fraley et al. |
| 10,442,756 B2 | 10/2019 | Benenato et al. |
| 10,449,244 B2 | 10/2019 | Ciaramella et al. |
| 10,465,190 B1 | 11/2019 | Chen et al. |
| 10,493,143 B2 | 12/2019 | Ciaramella et al. |
| 10,526,629 B2 | 1/2020 | Rabideau et al. |
| 10,653,712 B2 | 5/2020 | Hoge |
| 10,653,767 B2 | 5/2020 | Ciaramella et al. |
| 10,695,419 B2 | 6/2020 | Ciaramella et al. |
| 10,857,105 B2 | 12/2020 | Benenato et al. |
| 10,925,958 B2 | 2/2021 | Ciaramella |
| 11,045,540 B2 | 6/2021 | Ciaramella |
| 11,103,578 B2 | 8/2021 | Ciaramella et al. |
| 11,351,242 B1 | 6/2022 | Lori et al. |
| 11,384,352 B2 | 7/2022 | Miracco |
| 2003/0092653 A1 | 5/2003 | Kisich et al. |
| 2005/0032730 A1 | 2/2005 | Von Der Mulbe et al. |
| 2005/0250723 A1 | 11/2005 | Hoerr et al. |
| 2006/0172003 A1 | 8/2006 | Meers et al. |
| 2007/0280929 A1 | 12/2007 | Hoerr et al. |
| 2008/0025944 A1 | 1/2008 | Hoerr et al. |
| 2010/0068226 A1 | 3/2010 | Taylor et al. |
| 2010/0130588 A1 | 5/2010 | Yaworski et al. |
| 2010/0203076 A1 | 8/2010 | Fotin-Mleczek et al. |
| 2010/0272747 A1 | 10/2010 | Chow et al. |
| 2011/0250225 A1 | 10/2011 | Fotin-Mleczek et al. |
| 2011/0269950 A1 | 11/2011 | Von Der Mulbe et al. |
| 2012/0009221 A1 | 1/2012 | Hoerr et al. |
| 2012/0219573 A1 | 8/2012 | Baumhof et al. |
| 2013/0078281 A1 | 3/2013 | He et al. |
| 2013/0102034 A1 | 4/2013 | Schrum et al. |
| 2013/0121988 A1 | 5/2013 | Hoerr et al. |
| 2013/0142818 A1 | 6/2013 | Baumhof et al. |
| 2013/0156849 A1 | 6/2013 | De Fougerolles et al. |
| 2013/0183355 A1 | 7/2013 | Jain et al. |
| 2013/0195867 A1 | 8/2013 | Hoerr et al. |
| 2013/0195967 A1 | 8/2013 | Guild et al. |
| 2013/0195969 A1 | 8/2013 | Geall et al. |
| 2013/0202684 A1 | 8/2013 | Geall et al. |
| 2013/0236974 A1 | 9/2013 | De Fougerolles |
| 2013/0243848 A1 | 9/2013 | Lobovkina et al. |
| 2013/0245103 A1 | 9/2013 | de Fougerolles et al. |
| 2013/0259923 A1 | 10/2013 | Bancel et al. |
| 2013/0266640 A1 | 10/2013 | De Fougerolles et al. |
| 2013/0295043 A1 | 11/2013 | Kallen et al. |
| 2013/0336998 A1 | 12/2013 | Kallen et al. |
| 2014/0024076 A1 | 1/2014 | Tang et al. |
| 2014/0037660 A1 | 2/2014 | Folin-Mleczek et al. |
| 2014/0147432 A1 | 5/2014 | Bancel et al. |
| 2014/0148502 A1 | 5/2014 | Bancel et al. |
| 2014/0193482 A1 | 7/2014 | Bancel et al. |
| 2014/0206752 A1 | 7/2014 | Afeyan et al. |
| 2014/0220083 A1 | 8/2014 | Brito et al. |
| 2014/0227346 A1 | 8/2014 | Geall et al. |
| 2014/0248314 A1* | 9/2014 | Swanson ............... A61P 31/14 424/211.1 |
| 2014/0271699 A1 | 9/2014 | Kwong et al. |
| 2014/0378538 A1 | 12/2014 | Bancel |
| 2015/0030622 A1 | 1/2015 | Marshall et al. |
| 2015/0051268 A1 | 2/2015 | Bancel et al. |
| 2015/0056253 A1 | 2/2015 | Bancel et al. |
| 2015/0079121 A1 | 3/2015 | Weiner et al. |
| 2015/0093413 A1 | 4/2015 | Thess et al. |
| 2015/0141499 A1 | 5/2015 | Bancel et al. |
| 2015/0307542 A1 | 10/2015 | Roy et al. |
| 2015/0315541 A1 | 11/2015 | Bancel et al. |
| 2015/0335728 A1 | 11/2015 | Wong et al. |
| 2016/0024140 A1 | 1/2016 | Issa et al. |
| 2016/0024141 A1 | 1/2016 | Issa et al. |
| 2016/0032273 A1 | 2/2016 | Shahrokh et al. |
| 2016/0038612 A1 | 2/2016 | Hoge et al. |
| 2016/0090603 A1 | 3/2016 | Carnes et al. |
| 2016/0243221 A1 | 8/2016 | Hoge et al. |
| 2016/0317647 A1 | 11/2016 | Ciaramella et al. |
| 2017/0043037 A1 | 2/2017 | Kariko et al. |
| 2017/0202979 A1 | 7/2017 | Chakraborty et al. |
| 2017/0204152 A1 | 7/2017 | Nelson et al. |
| 2017/0210697 A1 | 7/2017 | Benenato et al. |
| 2017/0130255 A1 | 10/2017 | Wang et al. |
| 2018/0000953 A1 | 1/2018 | Almarsson et al. |
| 2018/0002393 A1 | 1/2018 | Bancel et al. |
| 2018/0237849 A1 | 8/2018 | Thompson |
| 2018/0243225 A1 | 8/2018 | Ciaramella |
| 2018/0243230 A1 | 8/2018 | Smith |
| 2018/0256628 A1 | 9/2018 | Hoge et al. |
| 2018/0271795 A1 | 9/2018 | Martini et al. |
| 2018/0271970 A1 | 9/2018 | Ciaramella et al. |
| 2018/0273977 A1 | 9/2018 | Mousavi et al. |
| 2018/0274009 A1 | 9/2018 | Marquardt et al. |
| 2018/0303929 A1 | 10/2018 | Ciaramella et al. |
| 2018/0311336 A1 | 11/2018 | Ciaramella et al. |
| 2018/0311343 A1 | 11/2018 | Huang et al. |
| 2018/0318409 A1 | 11/2018 | Valiante et al. |
| 2018/0363019 A1 | 12/2018 | Hoge |
| 2018/0369374 A1 | 12/2018 | Frederick et al. |
| 2018/0371047 A1 | 12/2018 | Ticho et al. |
| 2019/0002890 A1 | 1/2019 | Martini et al. |
| 2019/0008938 A1 | 1/2019 | Ciaramella et al. |
| 2019/0085368 A1 | 3/2019 | Bancel et al. |
| 2019/0099481 A1 | 4/2019 | Ciaramella et al. |
| 2019/0175517 A1 | 6/2019 | Martini et al. |
| 2019/0175727 A1 | 6/2019 | Huang et al. |
| 2019/0192646 A1 | 6/2019 | Cohen et al. |
| 2019/0192653 A1 | 6/2019 | Hoge et al. |
| 2019/0274968 A1 | 9/2019 | Weissman et al. |
| 2019/0275170 A1 | 9/2019 | Benenato et al. |
| 2019/0298657 A1 | 10/2019 | Martini et al. |
| 2019/0298658 A1 | 10/2019 | Benenato |
| 2019/0300906 A1 | 10/2019 | Martini et al. |
| 2019/0314292 A1 | 10/2019 | Benenato et al. |
| 2019/0314493 A1 | 10/2019 | Ciaramella et al. |
| 2019/0336452 A1 | 11/2019 | Brader |
| 2019/0336595 A1 | 11/2019 | Ciaramella |
| 2019/0351040 A1 | 11/2019 | Valiante et al. |
| 2019/0351044 A1 | 11/2019 | Jasny et al. |
| 2019/0351047 A1 | 11/2019 | Jasny et al. |
| 2019/0382774 A1 | 12/2019 | Hoge et al. |
| 2019/0390181 A1 | 12/2019 | Benenato et al. |
| 2020/0030432 A1 | 1/2020 | Ciaramella et al. |
| 2020/0032274 A1 | 1/2020 | Mauger et al. |
| 2020/0038499 A1 | 2/2020 | Narayanan et al. |
| 2020/0054737 A1 | 2/2020 | Ciaramella et al. |
| 2020/0069599 A1 | 3/2020 | Smith et al. |
| 2020/0069793 A1 | 3/2020 | Ciaramella |
| 2020/0069794 A1 | 3/2020 | Ciaramella et al. |
| 2020/0071689 A1 | 3/2020 | Miracco |
| 2020/0085916 A1 | 3/2020 | Martini et al. |
| 2020/0109420 A1 | 4/2020 | Brito et al. |
| 2020/0129608 A1 | 4/2020 | Ciaramella et al. |
| 2020/0129615 A1 | 4/2020 | Ciaramella et al. |
| 2020/0163878 A1 | 5/2020 | Baumhof et al. |
| 2020/0239869 A1 | 7/2020 | Issa et al. |
| 2020/0254086 A1 | 8/2020 | Hoge et al. |
| 2020/0282047 A1 | 9/2020 | Ciaramella et al. |
| 2021/0046173 A1 | 2/2021 | Ciaramella et al. |
| 2021/0163919 A1 | 6/2021 | Issa et al. |
| 2021/0187097 A1 | 6/2021 | Ciaramella et al. |
| 2021/0217484 A1 | 7/2021 | Giessel et al. |
| 2021/0228707 A1 | 7/2021 | Mektar et al. |
| 2021/0268086 A1 | 9/2021 | Zhong et al. |
| 2021/0299242 A1* | 9/2021 | Graham ............... A61K 39/155 |
| 2021/0309976 A1 | 10/2021 | Dousis et al. |
| 2022/0031631 A1 | 2/2022 | Almarsson et al. |
| 2022/0047518 A1 | 2/2022 | Hennessy et al. |
| 2022/0054653 A1 | 2/2022 | Martini et al. |
| 2022/0062408 A1 | 3/2022 | Kramarczyk et al. |

(56) References Cited

U.S. PATENT DOCUMENTS

| | | |
|---|---|---|
| 2022/0125899 A1 | 4/2022 | Ashburn et al. |
| 2022/0145381 A1 | 5/2022 | Elich et al. |

FOREIGN PATENT DOCUMENTS

| | | |
|---|---|---|
| EP | 1026253 B2 | 12/2012 |
| EP | 2548960 A1 | 1/2013 |
| WO | WO 1990/11092 A1 | 10/1990 |
| WO | WO 1993/14778 | 8/1993 |
| WO | WO 1995/26204 | 10/1995 |
| WO | WO 1995/33835 | 12/1995 |
| WO | WO 2005/009346 | 2/2005 |
| WO | WO 2006/071903 | 7/2006 |
| WO | WO 2007/019247 A2 | 2/2007 |
| WO | WO 2007/095976 A2 | 8/2007 |
| WO | WO 2008/052770 A2 | 5/2008 |
| WO | WO 2008/103276 A2 | 8/2008 |
| WO | WO 2009/030254 A1 | 3/2009 |
| WO | WO 2009/030481 A1 | 3/2009 |
| WO | WO 2009/095226 | 8/2009 |
| WO | WO 2009/127230 A1 | 10/2009 |
| WO | WO 2010/037408 A1 | 4/2010 |
| WO | WO 2010/037539 A1 | 4/2010 |
| WO | WO 2010/042877 A1 | 4/2010 |
| WO | WO 2010/054406 A1 | 5/2010 |
| WO | WO 2010/088927 A1 | 8/2010 |
| WO | WO 2010/149743 A2 | 12/2010 |
| WO | WO 2011/005799 A2 | 1/2011 |
| WO | WO 2011/026641 A9 | 3/2011 |
| WO | WO 2011/068810 A1 | 6/2011 |
| WO | WO 2011/069529 A1 | 6/2011 |
| WO | WO 2011/069586 A1 | 6/2011 |
| WO | WO 2011/140627 A1 | 11/2011 |
| WO | WO 2011/144358 A1 | 11/2011 |
| WO | WO 2012/019630 A1 | 2/2012 |
| WO | WO 2012/019780 A1 | 2/2012 |
| WO | WO 2012/116714 A1 | 9/2012 |
| WO | WO 2012/116715 A1 | 9/2012 |
| WO | WO 2012/116810 A1 | 9/2012 |
| WO | WO 2012/116811 A1 | 9/2012 |
| WO | WO 2012/149536 A1 | 11/2012 |
| WO | WO 2013/055418 A2 | 4/2013 |
| WO | WO 2013/055905 A1 | 4/2013 |
| WO | WO 2013/102203 A1 | 7/2013 |
| WO | WO 2013/120628 A1 | 8/2013 |
| WO | WO 2013/120629 A1 | 8/2013 |
| WO | WO 2013/185069 A1 | 12/2013 |
| WO | WO 2014/089239 A1 | 6/2014 |
| WO | WO 2014/089486 A1 | 6/2014 |
| WO | WO 2014/152774 A1 | 9/2014 |
| WO | WO 2014/152940 A1 | 9/2014 |
| WO | WO 2014/160243 A1 | 10/2014 |
| WO | WO 2014/174018 A1 | 10/2014 |
| WO | WO 2014/202570 A1 | 12/2014 |
| WO | WO 2015/024667 A1 | 2/2015 |
| WO | WO 2015/024669 A1 | 2/2015 |
| WO | WO 2015/081155 A1 | 6/2015 |
| WO | WO 2015/095346 A1 | 6/2015 |
| WO | WO 2015/101414 A2 | 7/2015 |
| WO | WO 2015/101415 A1 | 7/2015 |
| WO | WO 2015/130584 A2 | 9/2015 |
| WO | WO 2015/164674 A1 | 10/2015 |
| WO | WO 2016/164762 A1 | 10/2016 |
| WO | WO 2016/176330 A1 | 11/2016 |
| WO | WO 2016/201377 A1 | 12/2016 |
| WO | WO 2017/011773 A2 | 1/2017 |
| WO | WO 2017/015457 A1 | 1/2017 |
| WO | WO 2017/066789 A1 | 4/2017 |
| WO | WO 2017/070601 A1 | 4/2017 |
| WO | WO 2017/070624 A1 | 4/2017 |
| WO | WO 2017/070626 A2 | 4/2017 |
| WO | WO 2017/075038 A1 | 5/2017 |
| WO | WO 2017/075531 A1 | 5/2017 |
| WO | WO 2017/081082 A1 | 5/2017 |
| WO | WO 2017/127750 A1 | 7/2017 |
| WO | WO 2017/201333 A1 | 11/2017 |
| WO | WO 2018/115525 A1 | 12/2017 |
| WO | WO 2016/091391 A1 | 2/2018 |
| WO | WO 2018/115507 A2 | 6/2018 |
| WO | WO 2018/115527 A2 | 6/2018 |
| WO | WO 2018/157009 A1 | 8/2018 |
| WO | WO 2018/170245 A1 | 9/2018 |
| WO | WO 2018/170256 A1 | 9/2018 |
| WO | WO 2018/170260 A1 | 9/2018 |
| WO | WO 2018/187590 A2 | 10/2018 |
| WO | WO 2018/232355 A1 | 12/2018 |
| WO | WO 2018/232357 A1 | 12/2018 |
| WO | WO 2019/036670 A1 | 2/2019 |
| WO | WO 2019/036683 A1 | 2/2019 |
| WO | WO 2019/036685 A1 | 2/2019 |
| WO | WO 2019/103993 A1 | 5/2019 |
| WO | WO 2019/148101 A1 | 8/2019 |
| WO | WO 2019/169120 A1 | 9/2019 |
| WO | WO 2020/006242 A1 | 1/2020 |
| WO | WO 2020/056370 A1 | 3/2020 |
| WO | WO 2020/061284 A1 | 3/2020 |
| WO | WO 2020/061295 A1 | 3/2020 |
| WO | WO 2020/061367 A1 | 3/2020 |
| WO | WO 2020/097291 A1 | 5/2020 |
| WO | WO 2020/146814 A1 | 7/2020 |
| WO | WO 2020/172239 A1 | 8/2020 |
| WO | WO 2020/185811 A1 | 9/2020 |
| WO | WO 2020/190750 A1 | 9/2020 |
| WO | WO 2020/243561 A1 | 12/2020 |
| WO | WO 2021/030533 A1 | 2/2021 |
| WO | WO 2021/050864 A1 | 3/2021 |
| WO | WO 2021/055811 A1 | 3/2021 |
| WO | WO 2021/155243 A1 | 8/2021 |
| WO | WO 2021/159040 A2 | 8/2021 |
| WO | WO 2021/159130 A2 | 8/2021 |
| WO | WO 2021/204175 A1 | 10/2021 |
| WO | WO 2021/211343 A1 | 10/2021 |
| WO | WO 2021/222304 A1 | 11/2021 |
| WO | WO 2021/231929 A1 | 11/2021 |
| WO | WO 2021/231963 A1 | 11/2021 |
| WO | WO 2021/237084 A1 | 11/2021 |
| WO | WO 2021/247817 A1 | 12/2021 |
| WO | WO 2022/067010 A1 | 3/2022 |
| WO | WO 2022/150717 A1 | 7/2022 |

OTHER PUBLICATIONS

Xu K, Chan YP, Bradel-Tretheway B, Akyol-Ataman Z, Zhu Y, Dutta S, Yan L, Feng Y, Wang LF, Skiniotis G, Lee B, Zhou ZH, Broder CC, et. al. Crystal Structure of the Pre-fusion Nipah Virus Fusion Glycoprotein Reveals a Novel Hexamer-of-Trimers Assembly. PLoS Pathog. Dec. 8, 2015;11(12):e1005322. (Year: 2015).*
Gindy ME, Feuston B, Glass A, Arrington L, Haas RM, Schariter J, Stirdivant SM. Stabilization of Ostwald ripening in low molecular weight amino lipid nanoparticles for systemic delivery of siRNA therapeutics. Mol Pharm. Nov. 3, 2014;11(11):4143-53. doi: 10.1021/mp500367k. Epub Oct. 15, 2014. (Year: 2014).*
Loomis RJ, Stewart-Jones GBE, Tsybovsky Y, Caringal RT, Morabito KM, McLellan JS, Chamberlain AL, Nugent ST, Hutchinson GB, Kueltzo LA, et. al. Structure-Based Design of Nipah Virus Vaccines: A Generalizable Approach to Paramyxovirus Immunogen Development. Front Immunol. Jun. 11, 2020;11:842. (Year: 2020).*
U.S. Appl. No. 15/748,782, filed Jan. 30, 2018, Mousavi et al.
U.S. Appl. No. 15/746,286, filed Jan. 19, 2018, Ciaramella et al.
U.S. Appl. No. 16/880,829, filed May 21, 2020, Ciaramella et al.
U.S. Appl. No. 16/348,943, filed May 10, 2019, Ciaramella.
U.S. Appl. No. 16/467,142, filed Jun. 6, 2019, Ciaramella et al.
U.S. Appl. No. 16/657,122, filed Oct. 18, 2019, Rabideau et al.
U.S. Appl. No. 16/494,162, filed Sep. 13, 2019, Ciaramella.
U.S. Appl. No. 16/608,451, filed Oct. 25, 2019, Ciaramella et al.
PCT/US2018/022777, Jun. 29, 2018, International Search Report and Written Opinion.
International Search Report and Written Opinion for Application No. PCT/US2018/022777, dated Jun. 29, 2018.
[No Author Listed], "Messenger RNA", Internet: Wikipedia. Jun. 19, 2013, XP002699196, Retrieved from the Internet: URL: http:--en.wikipedia.org-wiki-Messenger RNA.

(56) References Cited

OTHER PUBLICATIONS

[No Author Listed], CDC: Centers for Disease Control and Prevention: "Coronavirus"; "Prevention and Treatment", National Center for Immunization and Respiratory Diseases (NCIRD), Division of Viral Diseases [Internet] Internet URL: https://www.cdc.gov/coronavirus/about/prevention.html (page viewed Jun. 27, 2018).

[No Author Listed], CDC: Centers for Disease Control and Prevention: "Lassa Fever"; "Prevention", Centers for Disease Control and Prevention National Center for Emerging and Zoonotic Infectious Diseases (NCEZID) Division of High-Consequence Pathogens and Pathology (DHCPP) Viral Special Pathogens Branch (VSPB) [Internet] Internet URL: https://www.cdc.gov/vhf/lassa/prevention/index.html (page viewed Jun. 27, 2018).

[No Author Listed], CDC: Centers for Disease Control and Prevention: "Nipah Virus (NiV)"; "Prevention", Centers for Disease Control and Prevention National Center for Emerging and Zoonotic Infectious Diseases (NCEZID) Division of High-Consequence Pathogens and Pathology (DHCPP) Viral Special Pathogens Branch (VSPB) [Internet] Internet URL: https://www.cdc.gov/vhf/nipah/prevention/index.html (page viewed Jun. 27, 2018).

Agrawal et al., Immunization with inactivated Middle East Respiratory Syndrome coronavirus vaccine leads to lung immunopathology on challenge with live virus. Hum Vaccin Immunother. Sep. 2016;12(9):2351-6. doi:10.1080/21645515.2016.1177688. Epub Jun. 7, 2016.

Archer, S.J., Induction of a T-cell specific antigen on bone marrow lymphocytes with thymus RNA. Immunology. Jan. 1978;34(1):123-9.

Bettinger, T. et al., Peptide-mediated RNA delivery: a novel approach for enhanced transfection of primary and post-mitotic cells. Nucleic Acids Res. Sep. 15, 2001;29(18):3882-91.

Bowen et al., Genetic diversity among Lassa virus strains. J Virol. Aug. 2000;74(15):6992-7004.

Chahal et al., Dendrimer-RNA nanoparticles generate protective immunity against lethal Ebola, H1N1 influenza, and Toxoplasma gondii challenges with a single dose. Proc Natl Acad Sci U S A. Jul. 19, 2016;113(29):E4133-42. doi: 10.1073/pnas.1600299113. Epub Jul. 5, 2016. Correction: Proc Natl Acad Sci U S A. Aug. 30, 2016;113(35):E5250.

Chen et al., Influence of Particle Size on the in Vivo Potency of Lipid Nanoparticle Formulations of siRNA. J Control Release. Aug. 10, 2016;235:236-244. doi: 10.1016/j.jconrel.2016.05.059. Epub May 26, 2016.

Conry, R.M. et al., Characterization of a messenger RNA polynucleotide vaccine vector. Cancer Res. Apr. 1, 1995 ;55 (7):1397-1400.

Dahlman, James E. et al., In vivo endothelial siRNA delivery using polymeric nanoparticles with low molecular weight, Nature Nanotechnology, 2014, No. vol.#, pp. 1-8.

Durbin et al., RNAs Containing Modified Nucleotides Fail to Trigger RIG-I Conformational Changes for Innate Immune Signaling. mBio. Sep. 20, 2016;7(5):e00833-16. doi: 10.1128/mBio.00833-16.

Ernsting et al., Factors controlling the pharmacokinetics, biodistribution and intratumoral penetration of nanoparticles. J Control Release. Dec. 28, 2013;172(3):782-94. doi: 10.1016/j.jconrel.2013.09.013. Epub Sep. 25, 2013.

Geall et al., Nonviral delivery of self-amplifying RNA vaccines. Proc Natl Acad Sci U S A. Sep. 4, 2012;109(36):14604-9. doi:10.1073-pnas.1209367109. Epub Aug. 20, 2012.

Greer et al., Long-term protection in hamsters against human parainfluenza virus type 3 following mucosal or combinations of mucosal and systemic immunizations with chimeric alphavirus-based replicon particles. Scand J Immunol. Dec. 2007;66(6):645-53. Epub Oct. 17, 2007.

Hassett et al., Optimization of Lipid Nanoparticles for Intramuscular Administration of mRNA Vaccines. Mol Ther Nucleic Acids. Apr. 15, 2019;15:1-11. Epub Feb. 7, 2019.

Heyes et al., Cationic lipid saturation influences intracellular delivery of encapsulated nucleic acids. J Control Release. Oct. 3, 2005;107(2):276-87.

Hoerr, I. et al., In vivo application of RNA leads to induction of specific cytotoxic T lymphocytes and antibodies. EurJ Immunol. Jan. 2000;30(1):1-7.

Hoerr, I. et al., Stabilized Messenger RNA (RNActiveTM) as a Tool for Innovative Gene Delivery. Tissue Engineering. Apr. 2007; 13(4): 865-925.

Hoerr, More than a messenger: A new class of drugs-mRNA-based therapeutics. Genetic Engineering & Biotechnology News. Jun. 18, 2013. http:--www.genengnews.com-gen-articles-more-than-a-messenger-a-new-class-of-drugs-mrna-based-therapeutics-4916- [last accessed Mar. 25, 2016].

Holtkamp, S. et al., Modification of antigen-encoding RNA increases stability, translational efficacy, and T-cell stimulatory capacity of dendritic cells. Blood. Dec. 15, 2006;108(13):4009-17.

Kallen et al., A development that may evolve into a revolution in medicine: mRNA as the basis for novel, nucleotide-based vaccines and drugs. Ther Adv Vaccines. Jan. 2014;2(1):10-31. doi: 10.1177-2051013613508729.

Kallen et al., A novel, disruptive vaccination technology: self-adjuvanted RNActive(®) vaccines. Hum Vaccin Immunother. Oct. 2013;9(10):2263-76. doi: 10.4161-hv.25181. Epub Jun. 4, 2013. Review.

Kalra et al., Virosomes: As a Drug Delivery Carrier. American Journal of Advanced Drug Delivery. 2013;1:29-35.

Kariko, K., et al., Generating the optimal mRNA for therapy: HPLC purification eliminates immune activation and improves translation of nucleoside-modified, protein-encoding mRNA, Nucleic Acids Research, Oxford University Press, GB, vol. 39, No. 21, Sep. 2, 2011 (Sep. 2, 2011), e142. doi: 10.1093-nar-gkr695. Epub Sep. 2, 2011.

Kauffman et al., Materials for non-viral intracellular delivery of messenger RNA therapeutics. J Control Release. Oct. 28, 2016;240:227-234. doi: 10.1016/j.jconrel.2015.12.032. Epub Dec. 21, 2015.

Kauffman et al., Optimization of Lipid Nanoparticle Formulations for mRNA Delivery in Vivo with Fractional Factorial and Definitive Screening Designs. Nano Lett. Nov. 11, 2015;15(11):7300-6. doi: 10.1021-acs.nanolett.5b02497. Epub Oct. 20, 2015.

Keshwara et al., Rabies-based vaccine induces potent immune responses against Nipah virus. NPJ Vaccines. Apr. 15, 2019;4:15. Erratum in: NPJ Vaccines. May 13, 2019;4:18.

Kuhn, A.N., et al., mRNA as a versatile tool for exogenous protein expression. Current Gene Therapy. Oct. 2012; 12 (5): 347-361.

Kurimoto et al., PEG-OligoRNA Hybridization of mRNA for Developing Sterically Stable Lipid Nanoparticles toward In Vivo Administration. Molecules. Apr. 3, 2019;24(7):1303. doi: 10.3390/molecules24071303.

Leitner, W.W. et al., DNA and RNA-based vaccines: principles, progress and prospects. Vaccine. Dec. 10, 1999;18 (9-10):765-77.

Leroueil et al., Wide varieties of cationic nanoparticles induce defects in supported lipid bilayers. Nano Lett. Feb. 2008;8(2):420-4. doi: 10.1021/nl0722929. Epub Jan. 25, 2008.

Li, L. et al., Overcoming obstacles to develop effective and safe siRNA therapeutics. Expert Opin Biol Ther. May 2009; 9(5): 609-19.

Lindgren et al., Induction of Robust B Cell Responses after Influenza mRNA Vaccination Is Accompanied by Circulating Hemagglutinin-Specific ICOS+ PD-1+ CXCR3+ T Follicular Helper Cells. Front Immunol. Nov. 13, 2017;8:1539. doi: 10.3389/fimmu.2017.01539. eCollection 2017.

Lorenzi, J.C., et al., Intranasal vaccination with messenger RNA as a new approach in gene therapy: Use against tuberculosis. BMC Biotechnol. Oct. 2010; 10(77): 1-11.

Martinon, F. et al., Induction of virus-specific cytotoxic T lymphocytes in vivo by liposome-entrapped mRNA. EurJ Immunol. Jul. 1993;23(7):1719-22.

Mateo et al., Vaccines inducing immunity to Lassa virus glycoprotein and nucleoprotein protect macaques after a single shot. Sci Transl Med. Oct. 2, 2019;11(512):eaaw3163. doi: 10.1126/scitranslmed.aaw3163.

Middleton et al., Hendra virus vaccine, a one health approach to protecting horse, human, and environmental health. Emerg Infect Dis. Mar. 2014;20(3):372-9. doi: 10.3201/eid2003.131159.

(56) References Cited

OTHER PUBLICATIONS

Midoux et al., Lipid-based mRNA vaccine delivery systems. Expert Rev Vaccines. Feb. 2015;14(2):221-34. doi: 10.1586-14760584.2015.986104. Epub Dec. 26, 2014. Review.
Narayanan et al., Interplay between viruses and host mRNA degradation. Biochim Biophys Acta. Jun.-Jul. 2013;1829(6-7):732-41. doi: 10.1016-j.bbagrm.2012.12.003. Epub Dec. 26, 2012.
Poveda et al., Establishing Preferred Product Characterization for the Evaluation of RNA Vaccine Antigens. Vaccines (Basel). Sep. 27, 2019;7(4):131. doi: 10.3390/vaccines7040131.
Rabinovich, P.M., et al., Synthetic messenger RNA as a tool for gene therapy. Hum. Gene Ther. Oct. 2006; 17: 1027-1035.
Rittig et al., Intradermal vaccinations with RNA coding for TAA generate CD8+ and CD4+ immune responses and induce clinical benefit in vaccinated patients. Mol Ther. May 2011;19(5):990-9. doi: 10.1038-mt.2010.289. Epub Dec. 28, 2010.
Sahin et al., mRNA-based therapeutics—developing a new class of drugs. Nat Rev Drug Discov. Oct. 2014;13(10):759-80. doi: 10.1038-nrd4278. Epub Sep. 19, 2014.
Schott, J.W., et al., Viral and non-viral approaches for transient delivery of mRNA and proteins. Current Gene Ther. 2011; 11 (5): 382-398.
Segura, J., et al., Monitoring gene therapy by external imaging of mRNA: Pilot study on murine erythropoietin. Ther Drug Monit. Oct. 2007; 29(5): 612-8.
Sohn, R.L., et al., In-vivo particle mediated delivery of mRNA to mammalian tissues: ballistic and biological effects. Wound Rep and Regen. Jul.-Aug. 2001; 287-296.
Sullenger, BA et al., Emerging clinical applications of RNA. Nature. Jul. 11, 2002;418(6894):252-8.
Szebeni et al., Activation of complement by therapeutic liposomes and other lipid excipient-based therapeutic products: prediction and prevention. Adv Drug Deliv Rev. Sep. 16, 2011;63(12):1020-30. doi: 10.1016/j.addr.2011.06.017. Epub Jul. 14, 2011.
Szebeni, Complement activation-related pseudoallergy: a stress reaction in blood triggered by nanomedicines and biologicals. Mol Immunol. Oct. 2014;61(2):163-73. doi: 10.1016/j.molimm.2014.06.038. Epub Aug. 12, 2014.
Tavernier, G., et al., mRNA as gene therapeutic: How to control protein expression. J. of Controlled Release. Mar. 2011; 150(3): 238-247.
Teufel, R. et al., Human peripheral blood mononuclear cells transfected with messenger RNA stimulate antigen-specific cytotoxic T-lymphocytes in vitro. Cell Mol Life Sci. Aug. 2005;62(15):1755-62.
Thess et al., Sequence-engineered mRNA Without Chemical Nucleoside Modifications Enables an Effective Protein Therapy in Large Animals. Mol Ther. Sep. 2015;23(9):1456-64.doi: 10.1038-mt.2015.103. Epub Jun. 8, 2015.
Torrecilla et al., Lipid Nanoparticles as Carriers for RNAi Against Viral Infections: Current Status and Future Perspectives. Biomed Res Int. 2014;2014:161794. doi: 10.1155/2014/161794. Epub Aug. 12, 2014.
Xue et al., Lipid-Based Nanocarriers for RNA Delivery. Curr Pharm Des. 2015;21(22):3140-7.
Yamamoto et al., Current prospects for mRNA gene delivery, European Journal of Pharmaceutics and Biopharmaceutics 71 (2009) 484-489.
Zumla et al., Taking forward a 'One Health' approach for turning the tide against the Middle East respiratory syndrome coronavirus and other zoonotic pathogens with epidemic potential. Int J Infect Dis. Jun. 2016;47:5-9. doi: 10.1016/j.ijid.2016.06.012. Epub Jun. 15, 2016.
U.S. Appl. No. 17/204,801, filed Mar. 17, 2021, Ciaramella et al.
U.S. Appl. No. 16/853,973, filed Apr. 21, 2020, Ciaramella et al.
U.S. Appl. No. 16/850,519, filed Apr. 16, 2020, Ciaramella et al.
U.S. Appl. No. 16/898,268, filed Jun. 10, 2020, Ciaramella et al.
U.S. Appl. No. 16/599,661, filed Oct. 11, 2019, Besin et al.
U.S. Appl. No. 16/333,330, filed Mar. 14, 2019, Hoge et al.
U.S. Appl. No. 16/864,566, filed May 1, 2020, Ciaramella et al.
U.S. Appl. No. 16/468,838, filed Jun. 12, 2019, Miracco.
U.S. Appl. No. 16/848,318, filed Apr. 14, 2020, Ciaramella et al.
U.S. Appl. No. 16/788,182, filed Feb. 11, 2020, Panther et al.
U.S. Appl. No. 17/000,215, filed Aug. 21, 2020, Stewart-Jones et al.
[No Author Listed], Welcome Trust Public Release. Jan. 18, 2017. "Global partnership launched to prevent epidemics with new vaccines." https://www.eurekalert.org/pub_releases/2017-01/wt-gpl011717.php (Year: 2017).
Bossart et al., A Hendra virus G glycoprotein subunit vaccine protects African green monkeys from Nipah virus challenge. Sci Transl Med. Aug. 8, 2012;4(146):146ra107. doi: 10.1126/scitranslmed.3004241.
Cullis et al., Lipid Nanoparticle Systems for Enabling Gene Therapies. Mol Ther. Jul. 5, 2017;25(7):1467-1475. doi: 10.1016/j.ymthe.2017.03.013. Epub Apr. 13, 2017.
Hadinoto et al., Lipid-polymer Hybrid Nanoparticles as a New Generation Therapeutic Delivery Platform: A Review. Eur J Pharm Biopharm. Nov. 2013;85(3 Pt A):427-43. doi: 10.1016/j.ejpb.2013.07.002. Epub Jul. 17, 2013.
Kowalski et al., Delivering the Messenger: Advances in Technologies for Therapeutic mRNA Delivery. Molecular Therapy vol. 27 No. 4 Apr. 2019.
Lo et al., Evaluation of a Single-Dose Nucleoside-Modified Messenger RNA Vaccine Encoding Hendra Virus-Soluble Glycoprotein Against Lethal Nipah virus Challenge in Syrian Hamsters. J Infect Dis. May 11, 2020;221(Suppl 4):S493-S498. doi: 10.1093/infdis/jiz553.
Maier et al., Biodegradable Lipids Enabling Rapidly Eliminated Lipid Nanoparticles for Systemic Delivery of RNAi Therapeutics. Mol Ther. Aug. 2013; 21(8): 1570-1578.
Pallister et al., Vaccination of ferrets with a recombinant G glycoprotein subunit vaccine provides protection against Nipah virus disease for over 12 months. Virol J. Jul. 16, 2013;10:237. doi: 10.1186/1743-422X-10-237.
Pardi et al., Expression Kinetics of Nucleoside-Modified mRNA Delivered in Lipid Nanoparticles to Mice by Various Routes. J Control Release. Nov. 10, 2015;217:345-51. doi: 10.1016/j.jconrel.2015.08.007. Epub Aug. 8, 2015.
Pardi et al., mRNA vaccines—a new era in vaccinology. Nat Rev Drug Discov. Apr. 2018;17(4):261-279. doi: 10.1038/nrd.2017.243. Epub Jan. 12, 2018.
Reichmuth et al., mRNA Vaccine Delivery Using Lipid Nanoparticles. Ther Deliv. 2016;7(5):319-34. doi: 10.4155/tde-2016-0006.
Schlake et al., Developing mRNA-vaccine technologies. RNA Biol. Nov. 2012;9(11):1319-30. doi: 10.4161/rna.22269. Epub Oct. 12, 2012.
Zhao et al., Nanoparticle vaccines. Vaccine. Jan. 9, 2014;32(3):327-37. doi: 10.1016/j.vaccine.2013.11.069. Epub Dec. 2, 2013.
Maruggi et al., mRNA as a Transformative Technology for Vaccine Development to Control Infectious Diseases. Mol Ther. Apr. 10, 2019;27(4):757-772. doi: 10.1016/j.ymthe.2019.01.020. Epub Feb. 7, 2019.
Terada et al., Characterization of Lipid Nanoparticles Containing Ionizable Cationic Lipids Using Design-of-Experiments Approach. Langmuir. Jan. 26, 2021;37(3):1120-1128. doi: 10.1021/acs.langmuir.0c03039. Epub Jan. 13, 2021.
U.S. Appl. No. 16/036,318, filed Jul. 16, 2018, Ciaramella et al.
U.S. Appl. No. 16/144,394, filed Sep. 27, 2018, Ciaramella et al.
U.S. Appl. No. 17/683,171, filed Feb. 28, 2022, Ciaramella et al.
U.S. Appl. No. 15/748,773, filed Jan. 30, 2018, Ciaramella et al.
U.S. Appl. No. 17/554,182, filed Dec. 17, 2021, Ciaramella et al.
U.S. Appl. No. 15/753,293, filed Feb. 17, 2018, Smith.
U.S. Appl. No. 15/767,587, filed Apr. 11, 2018, Ciaramella.
U.S. Appl. No. 16/833,409, filed Mar. 27, 2020, Ciaramella.
U.S. Appl. No. 15/767,600, filed Apr. 11, 2018, Ciaramella et al.
U.S. Appl. No. 15/769,710, filed Apr. 19, 2018, Ciaramella et al.
U.S. Appl. No. 15/767,609, filed Apr. 11, 2018, Ciaramella et al.
U.S. Appl. No. 15/767,613, filed Apr. 11, 2018, Ciaramella et al.
U.S. Appl. No. 15/767,618, filed Apr. 11, 2018, Ciaramella et al.
U.S. Appl. No. 17/590,479, filed Feb. 1, 2022, Ciaramella et al.
U.S. Appl. No. 16/897,859, filed Jun. 10, 2020, Ciaramella et al.
U.S. Appl. No. 17/737,532, filed May 5, 2022, Ciaramella et al.
U.S. Appl. No. 17/583,674, filed Jan. 25, 2022, Besin et al.
U.S. Appl. No. 17/523,034, filed Nov. 10, 2021, Hoge et al.

(56) References Cited

OTHER PUBLICATIONS

U.S. Appl. No. 17/523,060, filed Nov. 10, 2021, Hoge et al.
U.S. Appl. No. 17/548,172, filed Dec. 10, 2021, Ciaramella et al.
U.S. Appl. No. 17/839,401, filed Jun. 13, 2022, Ciaramella et al.
U.S. Appl. No. 16/897,734, filed Jun. 10, 2020, Ciaramella et al.
U.S. Appl. No. 17/830,742, filed Jun. 2, 2022, Miracco.
U.S. Appl. No. 16/001,765, filed Jun. 6, 2018, Marquardt et al.
U.S. Appl. No. 17/852,974, filed Jun. 29, 2022, Marquardt et al.
U.S. Appl. No. 17/127,949, filed Dec. 18, 2020, Ciaramella.
U.S. Appl. No. 17/385,655, filed Jul. 26, 2021, Ciaramella et al.
U.S. Appl. No. 16/603,111, filed Oct. 4, 2019, Brito et al.
U.S. Appl. No. 16/482,844, filed Aug. 1, 2019, Valiante et al.
U.S. Appl. No. 16/496,135, filed Sep. 20, 2019, Narayanan et al.
U.S. Appl. No. 16/483,012, filed Aug. 1, 2019, Mauger et al.
U.S. Appl. No. 17/350,662, filed Jun. 17, 2021, Rabideau et al.
U.S. Appl. No. 16/362,366, filed Mar. 22, 2019, Ciaramella.
U.S. Appl. No. 16/493,986, filed Sep. 13, 2019, Ciaramella et al.
U.S. Appl. No. 16/494,130, filed Sep. 13, 2019, Ciaramella et al.
U.S. Appl. No. 16/494,103, filed Sep. 13, 2019, Ciaramella et al.
U.S. Appl. No. 17/245,973, filed Apr. 30, 2021, Ciaramella.
U.S. Appl. No. 16/494,988, filed Sep. 17, 2019, Ciaramella et al.
U.S. Appl. No. 16/639,265, filed Feb. 14, 2020, Issa et al.
U.S. Appl. No. 16/639,305, filed Feb. 14, 2020, Issa et al.
U.S. Appl. No. 16/765,285, filed May 19, 2020, Ciaramella et al.
U.S. Appl. No. 16/302,607, filed Nov. 16, 2018, Benenato et al.
U.S. Appl. No. 16/623,069, filed Dec. 16, 2019, Hoge et al.
U.S. Appl. No. 16/639,403, filed Feb. 14, 2020, Hoge et al.
U.S. Appl. No. 17/531,211, filed Nov. 19, 2021, Ciaramella et al.
U.S. Appl. No. 16/965,589, filed Jul. 28, 2020, Ciaramella et al.
U.S. Appl. No. 17/255,949, filed Dec. 23, 2020, Zhong et al.
U.S. Appl. No. 17/277,423, filed Mar. 18, 2021, Almarsson et al.
U.S. Appl. No. 17/277,452, filed Mar. 18, 2021, Hennessy et al.
U.S. Appl. No. 17/276,112, filed Mar. 12, 2021, Martini et al.
U.S. Appl. No. 17/438,049, filed Sep. 10, 2021, Elich et al.
U.S. Appl. No. 17/634,939, filed Feb. 11, 2022, Shamashkin et al.
U.S. Appl. No. 17/291,947, filed May 6, 2021, Ashburn et al.
U.S. Appl. No. 17/439,198, filed Sep. 14, 2021, Lusso et al.
U.S. Appl. No. 17/325,883, filed May 20, 2021, Dousis et al.
U.S. Appl. No. 17/737,581, filed May 5, 2022, Panther et al.
U.S. Appl. No. 16/794,318, filed Feb. 19, 2020, Mauger et al.
U.S. Appl. No. 17/761,420, filed Mar. 17, 2022, Amato et al.
U.S. Appl. No. 17/145,164, filed Jan. 8, 2021, Giessel et al.
U.S. Appl. No. 17/615,202, filed Nov. 30, 2021, Hopson.
U.S. Appl. No. 17/641,967, filed Mar. 10, 2022, John et al.
U.S. Appl. No. 17/411,896, filed Aug. 25, 2021, Kramarczyk et al.
U.S. Appl. No. 17/840,478, filed Jun. 14, 2022, Kramarczyk et al.
U.S. Appl. No. 17/000,201, filed Aug. 21, 2020, Stewart-Jones et al.
U.S. Appl. No. 17/518,542, filed Nov. 3, 2021, Metkar et al.
U.S. Appl. No. 17/572,465, filed Jan. 10, 2022, Nachbagauer et al.
U.S. Appl. No. 17/726,971, filed Apr. 22, 2022, Hennessy.
Zeng et al., Formulation and Delivery Technologies for mRNA Vaccines. Curr Top Microbiol Immunol. Jun. 2, 2020;10.1007/82_2020_217. doi: 10.1007/82_2020_217.

* cited by examiner

| Group | N animals | Vaccine | Dose | Route |
|---|---|---|---|---|
| A | 5 | Ag 1 | 20 ug/100 ul | IM |
| B | 5 | Ag 2 | 20 ug/100 ul | IM |
| C | 5 | PBS | 100 ul | IM |

Timeline (Days)

0 — Collect Serum, Immunization, 20 μg
21 — Collect Serum, Boost, 20 μg
42 — Collect Serum, Intraperitoneal Challenge with 1000 pfu GP-adapted Ebola
45, 48, 51, 54 — Collect Serum
Serial bleeds to determine Viremia
63 — Weight
70 — Weight, Euthanize

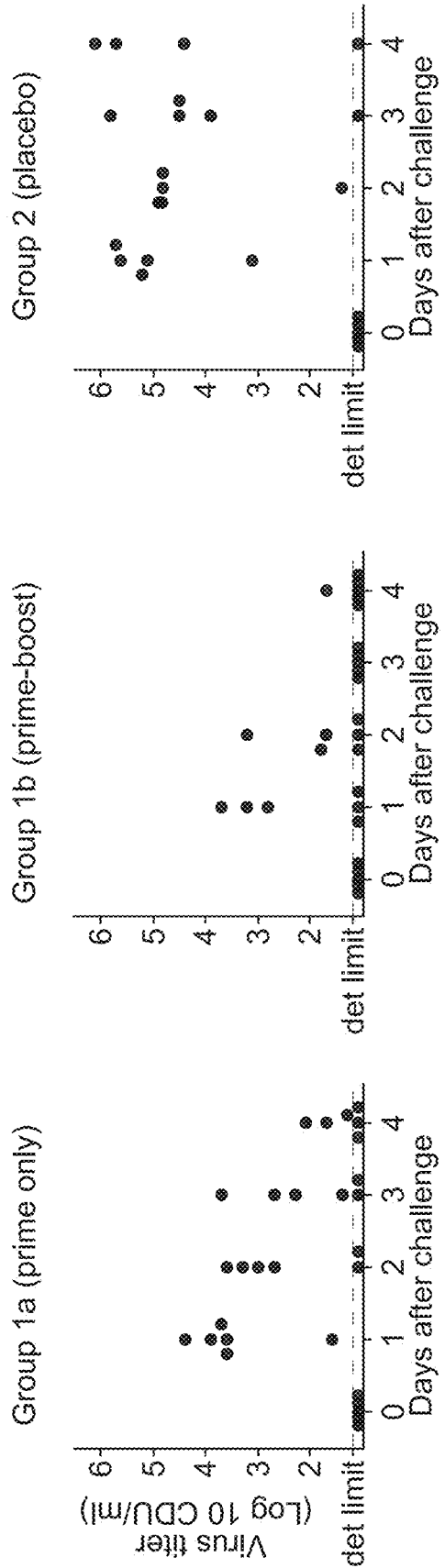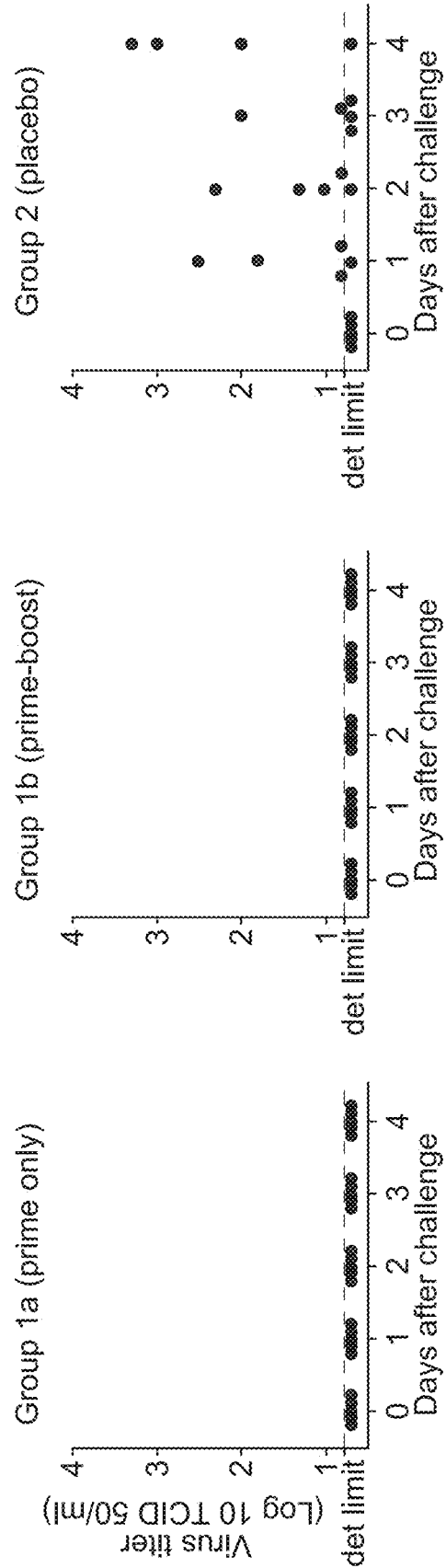

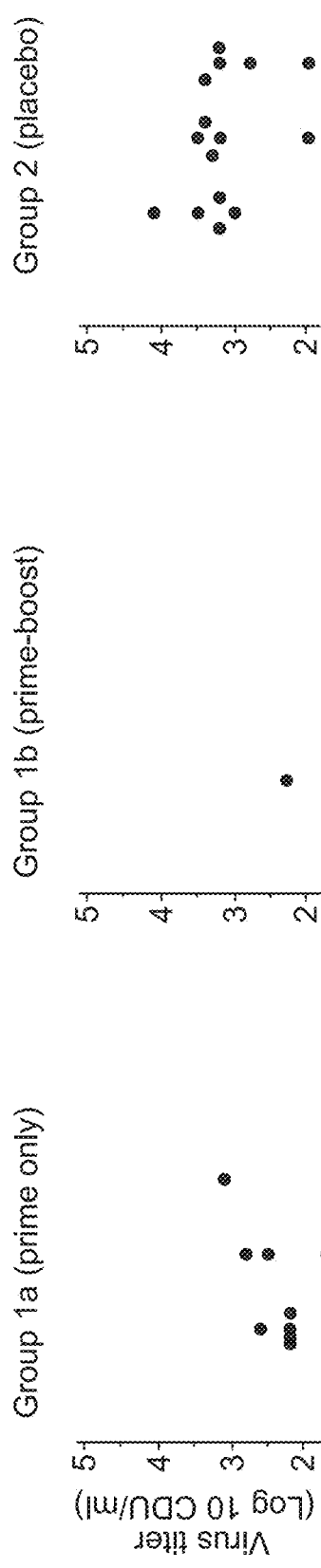

ZOONOTIC DISEASE RNA VACCINES

RELATED APPLICATIONS

This application is a continuation of U.S. application Ser. No. 16/494,988, filed Sep. 17, 2019, which is a national stage filing under 35 U.S.C. § 371 of international application number PCT/US2018/022777, filed Mar. 16, 2018, which was published under PCT Article 21(2) in English and claims the benefit under 35 U.S.C. § 119(e) of U.S. provisional application No. 62/473,174, filed Mar. 17, 2017, U.S. provisional application No. 62/473,202, filed Mar. 17, 2017, and U.S. provisional application No. 62/473,219, filed Mar. 17, 2017, each of which is incorporated by reference herein in its entirety.

BACKGROUND

Zoonotic diseases are infectious diseases that are naturally transmitted from vertebrate animals to humans and vice versa. They are caused by all types of pathogenic agents, including bacteria, parasites, fungi, viruses and prions. In regions densely populated with both people and livestock, zoonotic diseases can spread very quickly. With changes in the environment, human behavior and habitat, increasingly these infections are emerging from wildlife species. Specific examples of zoonotic viruses include Lassa virus, Nipah virus, and betacoronaviruses.

Lassa Virus. Lassa virus (LASV), a segmented negative-sense RNA virus that belongs to the family Arenaviridae, is endemic to West Africa. Transmission typically occurs through contact with infected rodents or virus-contaminated rodent excreta, and person-to-person transmission. The LASV expresses just one protein on its surface, termed GPC, which mediates both attachment to and entry of host cells. GPC is a class I viral fusion protein that forms trimers on the viral surface. Each monomer in the trimer is assembled by distinct GP1 and GP2 subunits that mediate receptor binding and membrane fusion, respectively. Notably, on the viral surface, GP2 is coiled about the base of GP1 in a structure that is only metastable. The complex is prone to rapid disassembly of GP1 from GP2 and rearrangement of the GP2 into a much more stable six-helix bundle. The release of energy achieved by collapsing of the metastable viral-surface conformation to the much more stable six-helix bundle conformation drives fusion of viral and host membranes during infection. Because of its metastability, it is difficult to maintain GPC on its trimeric pre-fusion configuration when expressed recombinantly or even when expressed on some particle surfaces. Antibodies against the resulting separated subunits are not potently neutralizing. As a result, prior vaccine approaches that included natural GPC failed to elicit an effective antibody response, leading vaccine manufacturers to instead focus on induction of cell-mediated immunity as the most likely correlate of protection. Further, in the absence of knowledge about how to create or purify stabilized Lassa virus GPC trimeric, vaccine makers did not have the necessary reagents to evaluate the most ideal antibody responses.

The structure of the viral surface GP trimer remained unknown for Lassa and all other arenaviruses until this year. After a ten-year effort in engineering LASV GPC, using the GOC to evaluate human antibody responses from survivors, several high-resolution three-dimensional structures of the Lassa virus GPC in complex with these antibodies have been identified.

Nipah Virus. Nipah virus (NiV), of the genus henipahvirus (which includes Hendra virus) is part of the paramyxovirus family (see FIG. 7). Nipah first emerged in Malaysia in 1998, initially in domestic pigs and subsequently causing severe disease in humans, eventually killing over 1000 people. New outbreaks have occurred every year since, with fatality rates ranging from 40-70%. Nipah virus is classified as a BSL-4 agent and as a Category C priority pathogen by the CDC and NIAID. The primary reservoir is Pteropus bats; however, the virus is able to infect and replicate in many mammals (Luby et al 2013; Angeletti et al 2016).

There are no vaccines currently available against Nipah virus. Considering that the population of people that live in the same regions as pteropus bats is approximately 2 billion, the unmet need for a protective vaccine is high.

Coronavirus. Human Coronaviruses are highly contagious enveloped, positive single stranded RNA viruses of the Coronaviridae family. They are the common etiological agents of mild to moderate upper respiratory tract infections. However, novel coronaviruses such as Middle Eastern Respiratory Syndrome Coronavirus (MERS-CoV) can result in severe lower respiratory tract infections and high mortality. MERS-CoV was first identified in 2012 within the Arabian Peninsula and since its initial outbreak, Sporadic MERS-CoV infections continue to appear within the Arabian Peninsula. The epidemiology of MERS-CoV infection in humans remains unclear and convoluted with Bats and Dromedary Camels being the major reservoirs for the virus. As of June 2016, the World Health Organization has reported a total of 1,769 MERS-CoV infections with a mortality rate of 36% and an ongoing risk of human to human transmission. The absence of a vaccine for MERS-CoV poses a severe global health threat due to its pandemic potential.

SUMMARY

Some aspects of the present disclosure provide zoonotic disease vaccines, comprising a ribonucleic acid (RNA) comprising an open reading frame (ORF) encoding an antigen selected from Lassa virus antigens, Nipah virus antigens, and betacoronavirus antigens, wherein intramuscular (IM) administration of a therapeutically effective amount of the vaccine to a subject induces an immune response in the subject.

In some embodiments, the ORF encodes a Lassa virus antigen.

In some embodiments, the Lassa virus antigen comprises a glycoprotein.

In some embodiments, the Lassa virus antigen comprises a Lassa virus glycoprotein precursor (GPC), a structurally stabilized Lassa virus GPC, an ectodomain of Lassa virus glycoprotein 1 (GP1), or a Lassa virus glycoprotein 2 (GP2).

In some embodiments, the Lassa virus antigen comprises amino acid residues 59-259 of a Lassa virus GPC.

In some embodiments, the Lassa virus antigen comprises a nucleocapsid protein (NP).

In some embodiments, the Lassa virus antigen has an amino acid sequence that has at least 90%, at least 95%, or at least 99% identity to an amino acid sequence identified by any one of SEQ ID NO: 1-3, but does not include wild-type protein sequence.

In some embodiments, the Lassa virus antigen has an amino acid sequence of any one of SEQ ID NO: 1-3.

In some embodiments, the RNA comprising an ORF sequence has at least 90%, at least 95%, or at least 99% identity to a nucleic acid sequence identified by any one of SEQ ID NO: 6, or 9, but does not include wild-type protein sequence.

In some embodiments, the RNA comprising an ORF sequence comprises a nucleic acid sequence of any one of SEQ ID NO: 6, 7 or 9.

In some embodiments, the ORF encodes a Nipah virus antigen and/or a Hendra virus antigen.

In some embodiments, the Nipah virus antigen and/or a Hendra virus antigen comprises a hemagglutinin-neuraminidase protein (HN), a hemagglutinin protein (H), or a glycoprotein (G).

In some embodiments, the Nipah virus antigen and/or a Hendra virus antigen comprises an attachment glycoprotein, optionally a type II membrane protein.

In some embodiments, the Nipah virus antigen and/or a Hendra virus antigen comprises a fusion (F) glycoprotein.

In some embodiments, the F glycoprotein comprises a trimeric class I fusogenic envelope glycoprotein containing two heptad repeat (HR) regions and a hydrophobic fusion peptide.

In some embodiments, the Nipah virus antigen and/or a Hendra virus antigen is a Nipah virus antigen.

In some embodiments, the Nipah virus antigen and/or a Hendra virus antigen is a Hendra virus antigen.

In some embodiments, the Nipah virus antigen and/or a Hendra virus antigen has an amino acid sequence that has at least 90%, at least 95%, or at least 99% identity to an amino acid sequence identified by any one of SEQ ID NO: 10-13 but does not include wild-type protein sequence.

In some embodiments, the Nipah virus antigen and/or a Hendra virus antigen has an amino acid sequence of any one of SEQ ID NO: 10-13.

In some embodiments, the RNA comprising an ORF sequence has at least 90%, at least 95%, or at least 99% identity to a nucleic acid sequence identified by SEQ ID NO: 16 or 17, but does not include wild-type protein sequence.

In some embodiments, the RNA comprising an ORF sequence comprises a nucleic acid sequence of SEQ ID NO: 16 or 17.

In some embodiments, the ORF encodes a middle east respiratory syndrome coronavirus (MERS-CoV) antigen and/or a severe acute respiratory syndrome-like coronavirus WIV1 (SL-CoV-WIV1) antigen.

In some embodiments, the MERS-CoV antigen and/or a SL-CoV-WIV1 antigen comprises a betacoronavirus structural protein.

In some embodiments, the betacoronavirus structural protein is spike protein, envelope protein, nucleocapsid protein, or membrane protein.

In some embodiments, rein the betacoronavirus structural protein is spike protein.

In some embodiments, the betacoronavirus structural protein a S1 subunit of the spike protein or a S2 subunit of the spike protein.

In some embodiments, the MERS-CoV antigen and/or a SL-CoV-WIV1 antigen is a MERS-CoV antigen.

In some embodiments, the MERS-CoV antigen and/or a SL-CoV-WIV1 antigen is a SL-CoV-WIV1 antigen.

In some embodiments, wherein the MERS-CoV antigen and/or a SL-CoV-WIV1 antigen has an amino acid sequence that has at least 90%, at least 95%, or at least 99% identity to an amino acid sequence identified SEQ ID NO: 18 but does not include wild-type protein sequence.

In some embodiments, the MERS-CoV antigen and/or a SL-CoV-WIV1 antigen has an amino acid sequence of SEQ ID NO: 18.

In some embodiments, the RNA comprising an ORF sequence has at least 90%, at least 95%, or at least 99% identity to a nucleic acid sequence identified by SEQ ID NO: 18, but does not include wild-type protein sequence.

In some embodiments, the RNA comprising an ORF sequence comprises a nucleic acid sequence of SEQ ID NO: 18.

In some embodiments, IM administration of a therapeutically effective amount of the vaccine to a subject induces a neutralizing antibody titer in the subject.

In some embodiments, the neutralizing antibody titer is at least 100 neutralizing units per milliliter (NU/mL), at least 500 NU/mL, or at least 1000 NU/mL.

In some embodiments, the neutralizing antibody titer is sufficient to reduce viral infection of B cells by at least 50% relative to a neutralizing antibody titer of an unvaccinated control subject or relative to a neutralizing antibody titer of a subject vaccinated with a live attenuated viral vaccine, an inactivated viral vaccine, or a protein subunit viral vaccine.

In some embodiments, the neutralizing antibody titer is induced in the subject following fewer than three doses of the vaccine.

In some embodiments, a single dose is of 10 μg-100 μg.

In some embodiments, the neutralizing antibody titer and/or a T cell immune response is sufficient to reduce the rate of asymptomatic viral infection relative to the neutralizing antibody titer of unvaccinated control subjects.

In some embodiments, the neutralizing antibody titer and/or a T cell immune response is sufficient to prevent viral latency the subject.

In some embodiments, the neutralizing antibody titer is sufficient to block fusion of virus with epithelial cells and/or B cells of the subject.

In some embodiments, the neutralizing antibody titer is induced within 20 days following a single 10-100 μg of the vaccine, or within 40 days following a second 10-100 μg dose of the vaccine.

In some embodiments, IM administration of a therapeutically effective amount of the vaccine to a subject induces a T cell immune response in the subject.

In some embodiments, the T cell immune response comprises a CD4$^+$ T cell immune response and/or a CD8$^+$ T cell immune response.

In some embodiments, the antigen is expressed on the surface of cells of the subject.

In some embodiments, the vaccine comprises (a) a ribonucleic acid (RNA) having an open reading frame (ORF) encoding two antigens, or (b) two RNAs, each having an ORF encoding an antigen.

In some embodiments, the vaccine comprises a RNA having an ORF encoding two antigens formulated in a lipid nanoparticle.

In some embodiments, the vaccine comprises two RNAs, each having an ORF encoding an antigen, wherein the two RNAs are formulated in a single lipid nanoparticle or wherein the each RNAs is formulated in a single lipid nanoparticle.

In some embodiments, the vaccine further comprises at least one additional RNA having an ORF encoding at least one additional antigen.

In some embodiments, the lipid nanoparticle comprises a molar ratio of 20-60% ionizable cationic lipid, 5-25% non-cationic lipid, 25-55% sterol, and 0.5-15% PEG-modified lipid In some embodiments, the antigen is fused to a signal peptide.

In some embodiments, the antigen is fused to a scaffold moiety.

In some embodiments, the scaffold moiety is selected from the group consisting of: ferritin, encapsulin, lumazine synthase, hepatitis B surface antigen, and hepatitis B core antigen.

In some embodiments, the RNA comprises messenger RNA (mRNA).

In some embodiments, the RNA further comprises a 5'UTR and/or a 3'UTR.

In some embodiments, the RNA is unmodified.

In some embodiments, the RNA comprise a modified nucleotide.

In some embodiments, at least 80% of the uracil in the ORF comprise 1-methyl-pseudouridine modification.

Some aspects of the present disclosure provide methods comprising administering to a subject the zoonotic disease vaccine in a therapeutically effective amount to induce an immune response in the subject.

In some embodiments, the therapeutically effective amount induces a neutralizing antibody titer and/or a T cell immune response in the subject.

In some embodiments, the vaccine is at least 80% relative to unvaccinated control subjects.

In some embodiments, detectable levels of the antigen are produced in the serum of the subject at 1-72 hours post administration of the vaccine.

In some embodiments, a neutralizing antibody titer of at least 100 NU/ml, at least 500 NU/ml, or at least 1000 NU/ml is produced in the serum of the subject at 1-72 hours post administration of the vaccine.

In some embodiments, the therapeutically effective amount is a total dose of 20 µg-200 µg or a total dose of 50 µg-100 µg.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

Figures 1, 2:
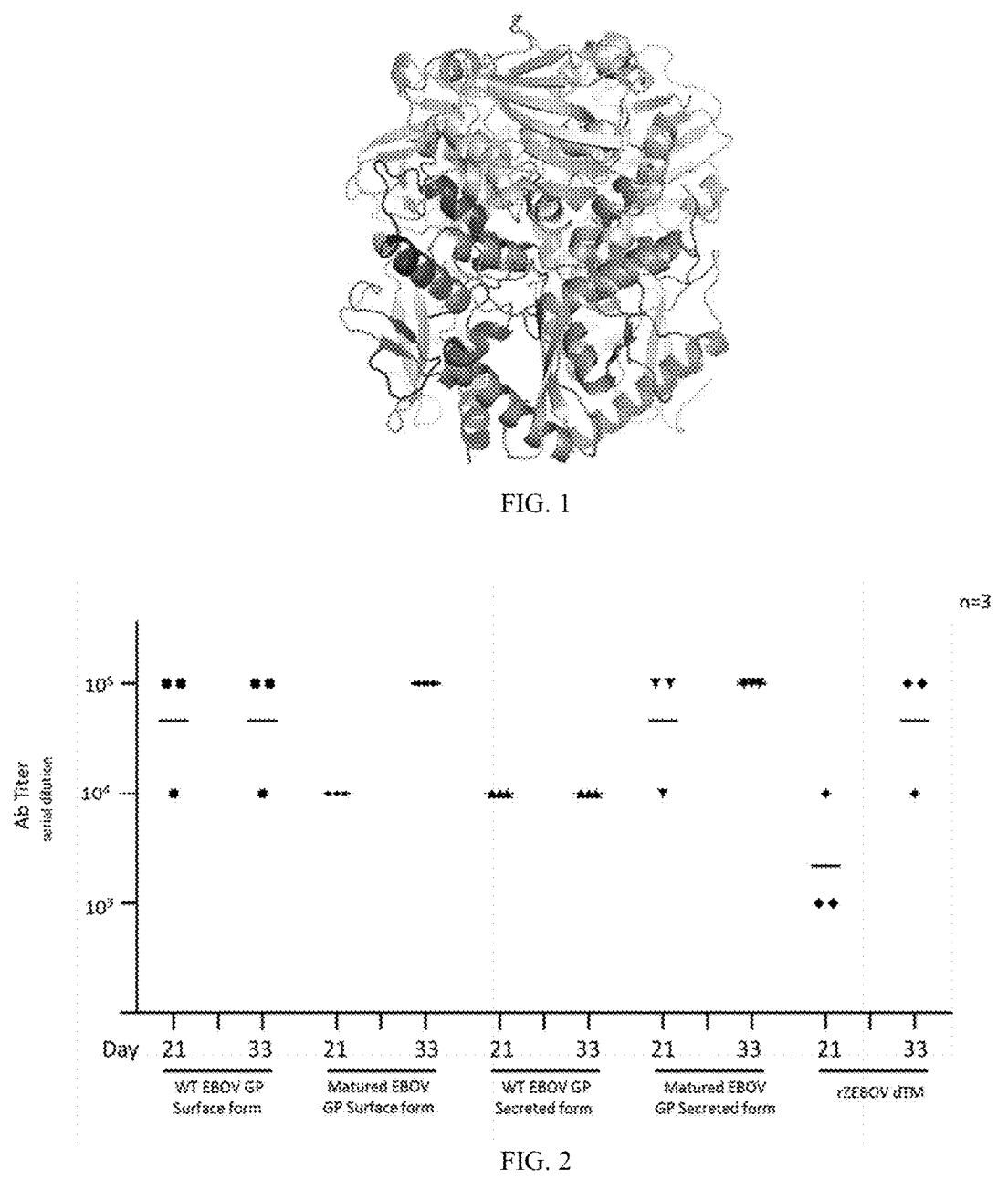

FIG. 1 shows the crystal structure of Fassa virus GPC in its trimeric, pre-fusion viral surface conformation. The three monomers are shown (left, center, right), with the GP1 subunits in a light shade and GP2 subunits in a darker shade of each color. These structures illustrate the assembly surfaces of the trimer and quaternary epitopes at the base and apex that are formed only when the subunits assemble together in the trimer.

FIG. 2 shows anti-Ebola virus glycoprotein mouse IgG titers on 7 and 19 days post dose 2.

FIG. 3 shows the Ebola lethal challenge model study design. AG1 represents the designated Ebola GP mRNA vaccine, and AG2 represents the mRNA vaccine expressing wild type GP.

FIG. 4 shows mortality analysis of Guinea pigs in the Ebola challenge model.

FIGS. 13A-13F show MERS-CoV PCR and titration levels in nose swabs after challenge in prime only (FIGS. 13A and 13D), prime-boost (FIGS. 13B and 13E) or placebo (FIGS. 13C and 13F) treated animals. FIGS. 13A-13C: Individual PCR values are shown as well as the lower limit of detection (1.2 log 10 CDU/mL). Samples below the lower limit of detection are plotted as 1.1 log 10 CDU/mL. FIGS. 13D-13F: Individual viral titration values are shown as well as the lower limit of detection (0.8 log 10 TCID50/mL). Samples below the lower limit of detection are plotted as 0.7 log 10 TCID50/mL.

FIGS. 14A-14F show MERS-CoV PCR and titration levels in throat swabs after challenge in prime only (FIGS. 14A and 14D), prime-boost (FIGS. 14B and 14E) or placebo (FIGS. 14C and 14F) treated animals. FIGS. 14A-14C: Individual PCR values are shown as well as the lower limit of detection (1.2 log 10 CDU/mL). Samples below the lower limit of detection are plotted as 1.1 log 10 CDU/mL. FIGS. 14D-14F: Individual titration values are shown as well as the lower limit of detection (0.8 log 10 TCID50/mL). Samples below the lower limit of detection are plotted as 0.7 log 10 TCID50/mL.

DETAILED DESCRIPTION

Lassa Virus Vaccines

Figure 5:
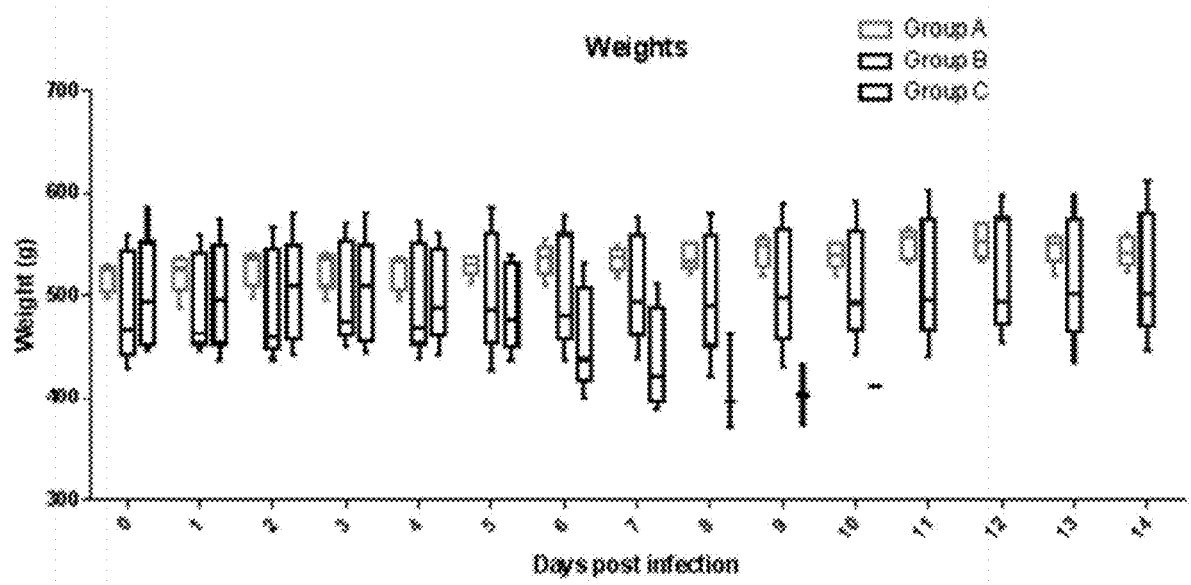
FIG. 5 shows the average group weight loss post Ebola challenge.
Figure 6:
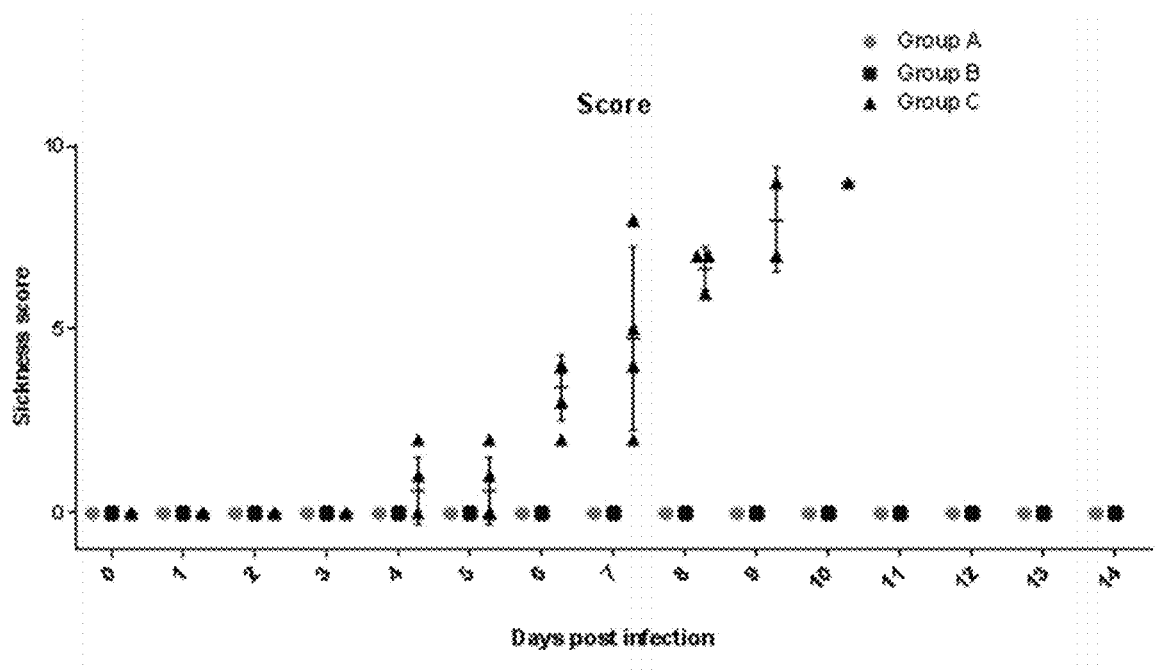
FIG. 6 shows morbidity scores for individual animals.
Figure 7:
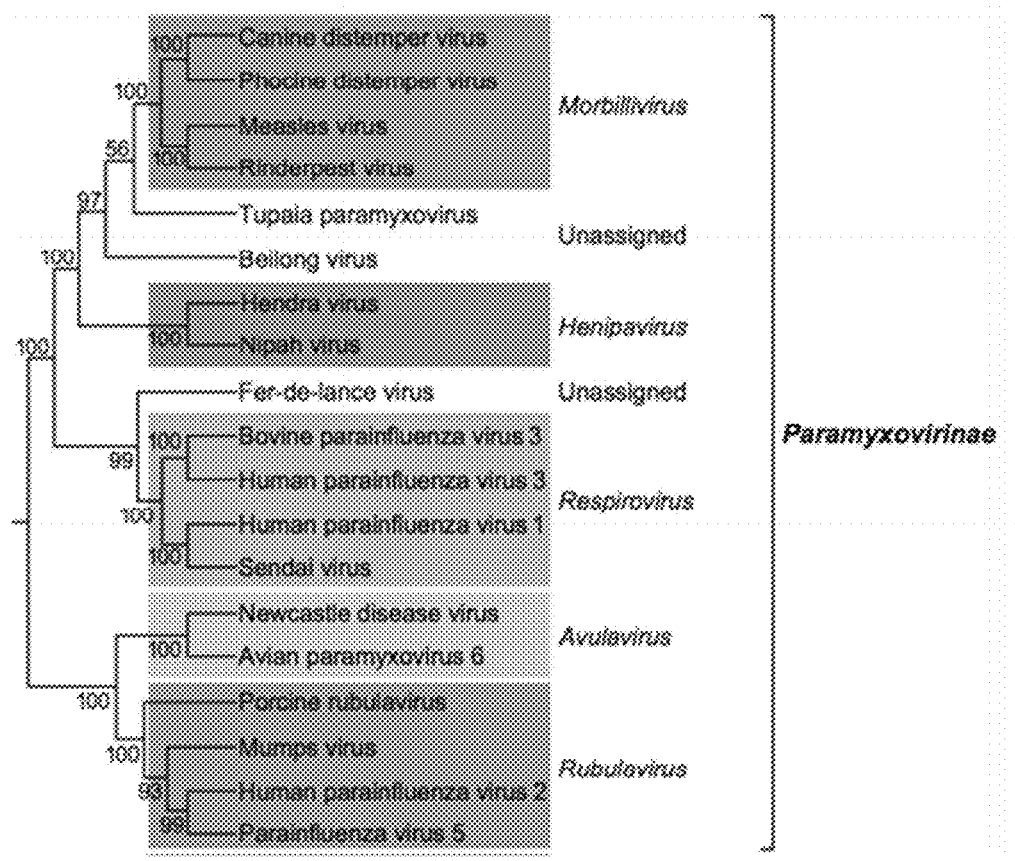
FIG. 7 shows the paramyxovirus family.
Figure 8:
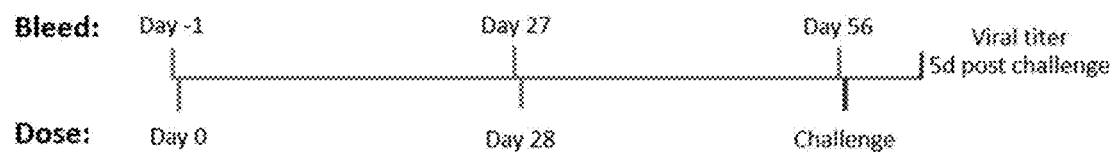
FIG. 8 shows experimental design for the cotton rat challenge study.

LASV (LASV) is an arenavirus (negative ssRNA) that represents a significant unmet global health care need. LASV expresses just one protein on its surface, termed GPC, which mediates both attachment to and entry of host cells. GPC is a class I viral fusion protein that forms trimers on the viral surface. Each monomer in the trimer is assembled by distinct GP1 and GP2 subunits that mediate receptor binding and membrane fusion, respectively. Notably, on the viral surface, GP2 is coiled about the base of GP1 in structure that is only metastable. The complex is prone to rapid disassembly of GP1 from GP2 and rearrangement of the GP2 into a much more stable six-helix bundle. The release of energy achieved by collapsing of the metastable viral-surface conformation to the much more stable six-helix bundle conformation drives fusion of viral and host membranes during infection. However, because of its metastability, it is difficult to maintain GPC on its trimeric pre-fusion configuration when expressed recombinantly or even when expressed on some particle surfaces. Antibodies against the resulting separated subunits are not potently neutralizing. As a result, prior vaccine approaches that included natural GPC failed to elicit an effective antibody response, leading vaccine manufacturers to instead focus on induction of cell-mediated immunity as the most likely correlate of protection. Further, in the absence of knowledge about how to create or purify stabilized LASV GPC trimeric, vaccine makers did not have the necessary reagents to evaluate the most ideal antibody responses.

The mRNA vaccines of the disclosure have been designed to express viral membrane bound proteins (B cell antigens) as well as intracellular proteins (T cell antigens). Arenaviruses including LASV are pleomorphic enveloped viruses with membrane GP glycoprotein as the major surface antigen. In some respects the Lassa glycoprotein is a potent vaccine antigen with structural similarities to Ebola glycoproteins. The disclosure in some aspects includes, a mRNA vaccine expressing full length-membrane bound Lassa glycoprotein precursor GPC. The GPC precursor mRNA once translated will be matured through a natural process by the cellular proteases into the fully matured GP glycoprotein. The membrane anchored version of this protein will form trimers on cell surfaces and recognized by the immune system to generate humoral and cellular responses.

The most effective anti LASV antibodies are directed against a quaternary epitopes on GPC (those only formed when both GP1 and GP2 are intertwined, and three GP1-GP2 monomers form the proper trimer). Engineering and stabilization of GPC to firmly remain in this assembly allows recognition by the most potent human antibodies, and that the potent antibodies themselves are sufficient to provide post-exposure protection, even late in the disease course. The properly stabilized GPC trimer displays key quaternary epitopes that lead to broadly reactive, potent, and protective antibodies. The mRNA vaccines of the disclosure in some embodiments are designed to produce these unique stabilized GPCs in order to provoke production of the type and quality of neutralizing antibody necessary for eliminating the virus in the host.

Nipah Virus Vaccines

Nipah virus (NiV) and Hendra virus (HeV) are part of the paramyxovirus family. Virus-cell fusion by the paramyxoviruses is mediated by both an attachment protein (which can vary by genus) and a fusion (F) protein, which is well conserved throughout the family. There are currently no commercially available vaccines available against Nipah virus.

Parainfluenza virus 3 (PIV3, genus respirovirus), is closely related to Nipah virus. A mRNA vaccine against PIV3 encoding the PIV3 F protein, which exists functionally as a membrane bound trimer of two disulfide-linked subunits has been developed. Applicants have demonstrated that this PIV3 mRNA vaccine drives the efficient expression of this protein in its biologically relevant conformation, thus generating a robust neutralizing response.

Paramyxoviruses such as HeV and NiV possess two major membrane-anchored glycoproteins in the envelope of the viral particle. One glycoprotein is required for virion attachment to receptors on host cells and is designated as either hemagglutinin-neuraminidase protein (HN) or hemagglutinin protein (H), and the other is glycoprotein (G), which has neither hemagglutination nor neuraminidase activities. The attachment glycoproteins are type II membrane proteins, where the molecule's amino (N) terminus is oriented toward the cytoplasm and the protein's carboxy (C) terminus is extracellular. The other major glycoprotein is the fusion (F) glycoprotein, which is a trimeric class I fusogenic envelope glycoprotein containing two heptad repeat (HR) regions and a hydrophobic fusion peptide. HeV and NiV infect cells though a pH-independent membrane fusion process into receptive host cells through the concerted action of their attachment G glycoprotein and F glycoprotein following receptor binding. The primary function of the HeV and NiV attachment G glycoprotein is to engage appropriate receptors on the surfaces of host cells, which for the majority of well-characterized paramyxoviruses are sialic acid moieties. The HeV and NiV G glycoproteins utilize the host cell protein receptors ephrin B2 and/or ephrin B3 and antibodies have been developed which block viral attachment by the G glycoprotein.

According to the disclosure, mRNA vaccines based on Nipah and Hendra F proteins have been developed. Additionally, soluble Nipah glycoprotein (G) vaccines and Hendra glycoprotein (G) vaccines are encompassed by the disclosure. In some aspects the vaccines may include F and G alone and/or in combination at different ratios.

The fusion glycoprotein (F) of Nipah virus mediates membrane fusion and is required for viral entry. Nipah F, like RSV F, is a class I fusion protein and they have similar structures and functions. The vaccines of the disclosure include stabilizing mutations to maintain the prefusion structure of Nipah F. Ideally stabilized mutants will maintain biophysical properties including structure and antigenicity.

Betacoronavirus Vaccines

Embodiments of the present disclosure provide RNA (e.g., mRNA) vaccines that include polynucleotide encoding a Middle East respiratory syndrome coronavirus (MERS-CoV) antigen and/or Bat SARS-like coronavirus WIV1, (SL-CoV-WIV1).

MERS-CoV is a positive-sense, single-stranded RNA virus of the genus Betacoronavirus. The genomes are phylogenetically classified into two clades, clade A and clade B. It has a strong tropism for non-ciliated bronchial epithelial cells, evades the innate immune response and antagonizes interferon (IFN) production in infected cells. Dipeptyl peptidase 4 (DDP4, also known as CD26) has been identified as a functional cellular receptor for MERS-CoV. Its enzymatic activity is not required for infection, although its amino acid sequence is highly conserved across species and is expressed in the human bronchial epithelium and kidneys. Most infected individuals develop severe acute respiratory illnesses, including fever, cough, and shortness of breath, and the virus can be fatal. The disease may be transmitted among humans, generally among those in close contact.

Bat SARS-like coronavirus WIV1, (SL-CoV-WIV1) or SARS-like coronavirus WIV1 (WIV1), was isolated recently from Chinese rufous horseshoe bats. It is a single-stranded, enveloped, positive-sense RNA betacoronavirus. It has been demonstrated by phylogenetic analysis direct transmission of SARS from bats to humans may occur without intermediary Chinese civets.

The genome of MERS-CoV encodes at least four unique accessory proteins, such as 3, 4a, 4b and 5, two replicase proteins (open reading frame 1a and 1b), and four major structural proteins, including spike (S), envelope (E), nucleocapsid (N), and membrane (M) proteins (Almazan F et al. MBio 2013; 4(5):e00650-13). The accessory proteins play nonessential roles in MERS-CoV replication, but they are likely structural proteins or interferon antagonists, modulating in vivo replication efficiency and/or pathogenesis, as in the case of SARS-CoV (Almazan F et al. MBio 2013; 4(5):e00650-13; Totura A L et al. Curr Opin Virol 2012; 2(3):264-75; Scobey T et al. Proc Natl Acad Sci USA 2013; 110(40): 16157-62). The other proteins of MERS-CoV maintain different functions in virus replication. The E protein, for example, involves in virulence, and deleting the E-coding gene results in replication-competent and propagation-defective viruses or attenuated viruses (Almazan F et al. MBio 2013; 4(5):e00650-13). The S protein is particularly essential in mediating virus binding to cells expressing receptor dipeptidyl peptidase-4 (DPP4) through receptor-binding domain (RBD) in the S1 subunit, whereas the S2 subunit subsequently mediates virus entry via fusion of the virus and target cell membranes (Li F. J Virol 2015; 89(4): 1954-64; Raj V S et al. Nature 2013; 495(7440):251-4).

In some aspects of the disclosure, the vaccine encodes the major antigenic component for MERS-CoV or SL-CoV-WIV1, the spike (S) glycoprotein. Spike protein is a typical type I viral fusion protein that exists as trimer on the viral surface with each monomer consisting of a Head (S1) and stem (S2) domain similar to influenza Hemagglutinin (HA). The S1 domain of the spike glycoprotein includes the receptor binding domain (RBD) that engages with the dipeptidyl peptidase-4 (DPP4) receptor and mediates viral fusion into the host cell, an N-terminal domain that may make initial contact with target cells, and 2 subdomains, all of which are susceptible to neutralizing antibodies. S2 domain consists of a six helix bundle fusion core involved in membrane fusion with the host endosomal membrane and is also a target for neutralization. Spike protein for betacoronaviruses has been shown to be an effective target for vaccines as antibodies against this protein are generated during natural infection and are protective in a passive transfer animal model (REF). It has been demonstrated that mRNA vaccine for MERS-CoV elicits high levels of neutralizing antibodies and significantly reduces viral load in infected animals (see Examples).

The data demonstrate that expressing a stable trimeric Spike protein in its prefusion conformation (pre-S) (pre-S trimer) increases the magnitude and breadth of neutralizing activity against diverse strains of MERS CoV.

The zoonotic disease RNA vaccines described herein are superior to current vaccines in several ways. For example, the lipid nanoparticle (LNP) delivery system used herein increases the efficacy of RNA vaccines in comparison to other formulations, including a protamine-based approach described in the literature. The use of this LNP delivery system enables the effective delivery of chemically-modified RNA vaccines or unmodified RNA vaccines, without requiring additional adjuvant to produce a therapeutic result (e.g., production neutralizing antibody titer and/or a T cell response). In some embodiments, the zoonotic disease RNA vaccines disclosed herein are superior to conventional vaccines by a factor of at least 10 fold, 20, fold, 40, fold, 50 fold, 100 fold, 500 fold, or 1,000 fold when administered intramuscularly (IM) or intradermally (ID). These results can be achieved even when significantly lower doses of the RNA (e.g., mRNA) are administered in comparison with RNA doses used in other classes of lipid based formulations.

The LNP used in the studies described herein has been used previously to deliver siRNA in various animal models as well as in humans. In view of the observations made in association with the siRNA delivery of LNP formulations, the fact that LNP is useful in vaccines is quite surprising, particularly when immunity to an antigen has been hard to generate. It has been observed that therapeutic delivery of siRNA formulated in LNP causes an undesirable inflammatory response associated with a transient IgM response, typically leading to a reduction in antigen production and a compromised immune response. In contrast to the findings observed with siRNA, the LNP-mRNA formulations of the present disclosure are demonstrated herein to generate enhanced IgG levels, sufficient for prophylactic and therapeutic methods rather than transient IgM responses.

Exemplary Zoonotic Disease Antigens

Antigens are proteins capable of inducing an immune response (e.g., causing an immune system to produce antibodies against the antigens). Herein, use of the term antigen encompasses immunogenic proteins and immunogenic fragments (an immunogenic fragment that induces (or is capable of inducing) an immune response to a zoonotic disease antigen), unless otherwise stated. It should be understood that the term "protein" encompasses peptides and the term "antigen" encompasses antigenic fragments.

A number of different antigens are associated with zoonotic diseases such as Lassa virus, Nipah virus, and betacoronavirus. Zoonotic disease vaccines, as provided herein, comprise at least one (one or more) ribonucleic acid (RNA, e.g., mRNA) having an open reading frame encoding at least one Lassa virus, Nipah virus, or betacoronavirus antigen. Non-limiting examples of zoonotic disease antigens are provided below.

Exemplary zoonotic disease antigens are provided in the Sequence Listing elsewhere herein. For example, the antigens may be encoded by (thus the RNA may comprise or consist of) any one of sequences set forth in SEQ ID NO: 6, 7, 9, 16, 17, or 20. In some embodiments, the antigens comprise a sequence set forth in SEQ ID NO: 1, 2, 3, 10, 11, 12, 13, or 18. In some embodiments, the aforementioned sequences may further comprise a 5' cap (e.g., 7mG(5')ppp (5')NlmpNp), a polyA tail, or a 5' cap and a polyA tail.

It should be understood that the zoonotic disease vaccines of the present disclosure may comprise any of the RNA open reading frames (ORFs), or encode any of the protein ORFs, described herein, with or without a signal sequence. It should also be understood that the zoonotic disease vaccines of the present disclosure may include any 5' untranslated region (UTR) and/or any 3' UTR. Any UTR sequence (e.g., of the prior art) may be used or exchanged for any of the UTR sequences described herein. UTRs may also be omitted from the vaccine constructs provided herein.

Nucleic Acids

The zoonotic disease vaccines of the present disclosure comprise at least one (one or more) ribonucleic acid (RNA) having an open reading frame encoding at least one zoonotic disease antigen. In some embodiments, the zoonotic disease antigen is a Lassa virus antigen. In some embodiments, the zoonotic disease antigen is a Nipah virus antigen. In some embodiments, the zoonotic disease antigen is a betcoronavirus antigen. In some embodiments, the RNA is a messenger RNA (mRNA) having an open reading frame encoding at least one zoonotic disease antigen. In some embodiments, the RNA (e.g., mRNA) further comprises a (at least one) 5' UTR, 3' UTR, a poly A tail and/or a 5' cap.

Nucleic acids comprise a polymer of nucleotides (nucleotide monomers), also referred to as polynucleotides. Nucleic acids may be or may include, for example, deoxyribonucleic acids (DNAs), ribonucleic acids (RNAs), threose nucleic acids (TNAs), glycol nucleic acids (GNAs), peptide nucleic acids (PNAs), locked nucleic acids (LNAs, including LNA having a β-D-ribo configuration, α-LNA having an α-L-ribo configuration (a diastereomer of LNA), 2'-amino-LNA having a 2'-amino functionalization, and 2'-amino-α-LNA having a 2'-amino functionalization), ethylene nucleic acids (ENA), cyclohexenyl nucleic acids (CeNA) and/or chimeras and/or combinations thereof.

Messenger RNA (mRNA) is any ribonucleic acid that encodes a (at least one) protein (a naturally-occurring, non-naturally-occurring, or modified polymer of amino acids) and can be translated to produce the encoded protein in vitro, in vivo, in situ or ex vivo. The skilled artisan will appreciate that, except where otherwise noted, nucleic acid sequences set forth in the instant application may recite "T"s in a representative DNA sequence but where the sequence represents RNA (e.g., mRNA), the "T"s would be substituted for "U"s. Thus, any of the DNAs disclosed and identified by a particular sequence identification number herein also disclose the corresponding RNA (e.g., mRNA) sequence complementary to the DNA, where each "T" of the DNA sequence is substituted with "U."

It should be understood that the mRNA polynucleotides of the vaccines as provided herein are synthetic molecules, i.e., they are not naturally-occurring molecules. That is, the mRNA polynucleotides of the present disclosure are isolated mRNA polynucleotides. As is known in the art, "isolated polynucleotides" refer to polynucleotides that are substantially physically separated from other cellular material (e.g., separated from cells and/or systems that produce the polynucleotides) or from other material that hinders their use in the vaccines of the present disclosure. Isolated polynucleotides are substantially pure in that they have been substantially separated from the substances with which they may be associated in living or viral systems. Thus, mRNA polynucleotide vaccines are not associated with living or viral systems, such as cells or viruses. The mRNA polynucleotide vaccines do not include viral components (e.g., viral capsids, viral enzymes, or other viral proteins, for example, those needed for viral-based replication), and the mRNA polynucleotide vaccines are not packaged within, encapsulated within, linked to, or otherwise associated with a virus or viral particle. In some embodiments, the mRNA vaccines comprise a lipid nanoparticle that consists of, or consists essentially of, one or more mRNA polynucleotides (e.g., mRNA polynucleotides encoding one or more zoonotic viral antigen(s)).

An open reading frame (ORF) is a continuous stretch of DNA or RNA beginning with a start codon (e.g., methionine (ATG or AUG)) and ending with a stop codon (e.g., TAA, TAG or TGA, or UAA, UAG or UGA). An ORF typically encodes a protein. It will be understood that the sequences disclosed herein may further comprise additional elements, e.g., 5' and 3' UTRs, but that those elements, unlike the ORF, need not necessarily be present in a vaccine of the present disclosure.

Variants

In some embodiments, an RNA of the present disclosure encodes a zoonotic disease antigen variant. Antigen or other polypeptide variants refers to molecules that differ in their amino acid sequence from a wild-type, native or reference sequence. The antigen/polypeptide variants may possess substitutions, deletions, and/or insertions at certain positions within the amino acid sequence, as compared to a native or reference sequence. Ordinarily, variants possess at least 50% identity to a wild-type, native or reference sequence. In some embodiments, variants share at least 80%, or at least 90% identity with a wild-type, native or reference sequence.

Variant antigens/polypeptides encoded by nucleic acids of the disclosure may contain amino acid changes that confer any of a number of desirable properties, e.g., that enhance their immunogenicity, enhance their expression, and/or improve their stability or PK/PD properties in a subject. Variant antigens/polypeptides can be made using routine mutagenesis techniques and assayed as appropriate to determine whether they possess the desired property. Assays to determine expression levels and immunogenicity are well known in the art and exemplary such assays are set forth in the Examples section. Similarly, PK/PD properties of a protein variant can be measured using art recognized techniques, e.g., by determining expression of antigens in a vaccinated subject over time and/or by looking at the durability of the induced immune response. The stability of protein(s) encoded by a variant nucleic acid may be measured by assaying thermal stability or stability upon urea denaturation or may be measured using in silico prediction. Methods for such experiments and in silico determinations are known in the art.

In some embodiments, a zoonotic disease vaccine comprises an mRNA ORF having a nucleotide sequence identified by any one of the sequences provided herein (see e.g., Sequence Listing), or having a nucleotide sequence at least 80%, at least 85%, at least 90%, at least 95%, at least 96%, at least 97%, at least 98%, or at least 99% identical to a nucleotide sequence identified by any one of the sequence provided herein.

The term "identity" refers to a relationship between the sequences of two or more polypeptides (e.g. antigens) or polynucleotides (nucleic acids), as determined by comparing the sequences. Identity also refers to the degree of sequence relatedness between or among sequences as determined by the number of matches between strings of two or more amino acid residues or nucleic acid residues. Identity measures the percent of identical matches between the smaller of two or more sequences with gap alignments (if any) addressed by a particular mathematical model or computer program (e.g., "algorithms"). Identity of related antigens or nucleic acids can be readily calculated by known methods. "Percent (%) identity" as it applies to polypeptide or polynucleotide sequences is defined as the percentage of residues (amino acid residues or nucleic acid residues) in the candidate amino acid or nucleic acid sequence that are identical with the residues in the amino acid sequence or nucleic acid sequence of a second sequence after aligning the sequences and introducing gaps, if necessary, to achieve the maximum percent identity. Methods and computer programs for the alignment are well known in the art. It is understood that identity depends on a calculation of percent identity but may differ in value due to gaps and penalties introduced in the calculation. Generally, variants of a particular polynucleotide or polypeptide (e.g., antigen) have at least 40%, 45%, 50%, 55%, 60%, 65%, 70%, 75%, 80%, 85%, 90%, 91%, 92%, 93%, 94%, 95%, 96%, 97%, 98%, 99% but less than 100% sequence identity to that particular reference polynucleotide or polypeptide as determined by sequence alignment programs and parameters described herein and known to those skilled in the art. Such tools for alignment include those of the BLAST suite (Stephen F. Altschul, et at (1997), "Gapped BLAST and PSI-BLAST: a new generation of protein database search programs", *Nucleic Acids Res.* 25:3389-3402). Another popular local alignment technique is based on the Smith-Waterman algorithm (Smith, T. F. & Waterman, M. S. (1981) "Identification of common molecular subsequences." *J. Mol. Biol.* 147:195-197). A general global alignment technique based on dynamic programming is the Needleman-Wunsch algorithm (Needleman, S. B. & Wunsch, C. D. (1970) "A general method applicable to the search for similarities in the amino acid sequences of two proteins." *J. Mol. Biol.* 48:443-453). More recently a Fast Optimal Global Sequence Alignment Algorithm (FOGSAA) has been developed that purportedly produces global alignment of nucleotide and protein sequences faster than other optimal global alignment methods, including the Needleman-Wunsch algorithm.

As such, polynucleotides encoding peptides or polypeptides containing substitutions, insertions and/or additions, deletions and covalent modifications with respect to reference sequences, in particular the polypeptide (e.g., antigen) sequences disclosed herein, are included within the scope of this disclosure. For example, sequence tags or amino acids, such as one or more lysines, can be added to peptide sequences (e.g., at the N-terminal or C-terminal ends). Sequence tags can be used for peptide detection, purification or localization. Lysines can be used to increase peptide solubility or to allow for biotinylation. Alternatively, amino acid residues located at the carboxy and amino terminal regions of the amino acid sequence of a peptide or protein may optionally be deleted providing for truncated sequences. Certain amino acids (e.g., C-terminal or N-terminal residues) may alternatively be deleted depending on the use of the sequence, as for example, expression of the sequence as part of a larger sequence which is soluble, or linked to a solid support. In some embodiments, sequences for (or encoding) signal sequences, termination sequences, transmembrane domains, linkers, multimerization domains (such as, e.g., foldon regions) and the like may be substituted with alternative sequences that achieve the same or a similar function. In some embodiments, cavities in the core of proteins can be filled to improve stability, e.g., by introducing larger amino acids. In other embodiments, buried hydrogen bond networks may be replaced with hydrophobic resides to improve stability. In yet other embodiments, glycosylation sites may be removed and replaced with appropriate residues. Such sequences are readily identifiable to one of skill in the art. It should also be understood that some of the sequences provided herein contain sequence tags or terminal peptide sequences (e.g., at the N-terminal or C-terminal ends) that may be deleted, for example, prior to use in the preparation of an RNA (e.g., mRNA) vaccine.

As recognized by those skilled in the art, protein fragments, functional protein domains, and homologous proteins are also considered to be within the scope of zoonotic disease antigens of interest. For example, provided herein is any protein fragment (meaning a polypeptide sequence at least one amino acid residue shorter than a reference antigen sequence but otherwise identical) of a reference protein, provided that the fragment is immunogenic and confers a protective immune response to the zoonotic disease pathogen. In addition to variants that are identical to the reference protein but are truncated, in some embodiments, an antigen includes 2, 3, 4, 5, 6, 7, 8, 9, 10, or more mutations, as shown in any of the sequences provided or referenced herein. Antigens/antigenic polypeptides can range in length from about 4, 6, or 8 amino acids to full length proteins.

Stabilizing Elements

Naturally-occurring eukaryotic mRNA molecules can contain stabilizing elements, including, but not limited to untranslated regions (UTR) at their 5'-end (5' UTR) and/or at their 3'-end (3' UTR), in addition to other structural features, such as a 5'-cap structure or a 3'-poly(A) tail. Both the 5' UTR and the 3' UTR are typically transcribed from the genomic DNA and are elements of the premature mRNA. Characteristic structural features of mature mRNA, such as the 5'-cap and the 3'-poly(A) tail are usually added to the transcribed (premature) mRNA during mRNA processing.

In some embodiments, a vaccine includes at least one RNA polynucleotide having an open reading frame encoding at least one antigenic polypeptide having at least one modification, at least one 5' terminal cap, and is formulated within a lipid nanoparticle. 5'-capping of polynucleotides may be completed concomitantly during the in vitro-transcription reaction using the following chemical RNA cap analogs to generate the 5'-guanosine cap structure according to manufacturer protocols: 3'-O-Me-m7G(5')ppp(5') G [the ARCA cap]; G(5')ppp(5')A; G(5')ppp(5')G; m7G(5')ppp(5')A; m7G (5')ppp(5')G (New England BioLabs, Ipswich, Mass.). 5'-capping of modified RNA may be completed post-transcriptionally using a Vaccinia Virus Capping Enzyme to generate the "Cap 0" structure: m7G(5')ppp(5')G (New England BioLabs, Ipswich, Mass.). Cap 1 structure may be generated using both Vaccinia Virus Capping Enzyme and a 2'-0 methyl-transferase to generate: m7G(5')ppp(5')G-2'-O-methyl. Cap 2 structure may be generated from the Cap 1 structure followed by the 2'-O-methylation of the 5'-antepenultimate nucleotide using a 2'-0 methyl-transferase. Cap 3 structure may be generated from the Cap 2 structure followed by the 2'-O-methylation of the 5'-preantepenultimate nucleotide using a 2'-0 methyl-transferase. Enzymes may be derived from a recombinant source.

The 3'-poly(A) tail is typically a stretch of adenine nucleotides added to the 3'-end of the transcribed mRNA. It can, in some instances, comprise up to about 400 adenine nucleotides. In some embodiments, the length of the 3'-poly (A) tail may be an essential element with respect to the stability of the individual mRNA.

In some embodiments, zoonotic disease RNA vaccines may include one or more stabilizing elements. Stabilizing elements may include for instance a histone stem-loop. A stem-loop binding protein (SLBP), a 32 kDa protein has been identified. It is associated with the histone stem-loop at the 3'-end of the histone messages in both the nucleus and the cytoplasm. Its expression level is regulated by the cell cycle; it peaks during the S-phase, when histone mRNA levels are also elevated. The protein has been shown to be essential for efficient 3'-end processing of histone pre-mRNA by the U7 snRNP. SLBP continues to be associated with the stem-loop after processing, and then stimulates the translation of mature histone mRNAs into histone proteins in the cytoplasm. The RNA binding domain of SLBP is conserved through metazoa and protozoa; its binding to the histone stem-loop depends on the structure of the loop. The minimum binding site includes at least three nucleotides 5' and two nucleotides 3' relative to the stem-loop.

In some embodiments, zoonotic disease RNA vaccines include a coding region, at least one histone stem-loop, and optionally, a poly(A) sequence or polyadenylation signal. The poly(A) sequence or polyadenylation signal generally should enhance the expression level of the encoded protein. The encoded protein, in some embodiments, is not a histone protein, a reporter protein (e.g. Luciferase, GFP, EGFP, β-Galactosidase, EGFP), or a marker or selection protein (e.g. alpha-Globin, Galactokinase and Xanthine:guanine phosphoribosyl transferase (GPT)).

In some embodiments, the combination of a poly(A) sequence or polyadenylation signal and at least one histone stem-loop, even though both represent alternative mechanisms in nature, acts synergistically to increase the protein expression beyond the level observed with either of the individual elements. The synergistic effect of the combination of poly (A) and at least one histone stem-loop does not depend on the order of the elements or the length of the poly(A) sequence.

In some embodiments, zoonotic disease RNA vaccines do not comprise a histone downstream element (HDE). "Histone downstream element" (HDE) includes a purine-rich polynucleotide stretch of approximately 15 to 20 nucleotides 3' of naturally occurring stem-loops, representing the binding site for the U7 snRNA, which is involved in processing of histone pre-mRNA into mature histone mRNA. In some embodiments, the nucleic acid does not include an intron.

In some embodiments, zoonotic disease RNA vaccines may or may not contain an enhancer and/or promoter sequence, which may be modified or unmodified or which may be activated or inactivated. In some embodiments, the histone stem-loop is generally derived from histone genes, and includes an intramolecular base pairing of two neighbored partially or entirely reverse complementary sequences separated by a spacer, consisting of a short sequence, which forms the loop of the structure. The unpaired loop region is typically unable to base pair with either of the stem loop elements. It occurs more often in RNA, as is a key component of many RNA secondary structures, but may be present in single-stranded DNA as well. Stability of the stem-loop structure generally depends on the length, number of mismatches or bulges, and base composition of the paired region. In some embodiments, wobble base pairing (non-Watson-Crick base pairing) may result. In some embodiments, the at least one histone stem-loop sequence comprises a length of 15 to 45 nucleotides.

In some embodiments, zoonotic disease RNA vaccines may have one or more AU-rich sequences removed. These sequences, sometimes referred to as AURES are destabilizing sequences found in the 3'UTR. The AURES may be removed from the RNA vaccines. Alternatively the AURES may remain in the RNA vaccine.

Signal Peptides

In some embodiments, a zoonotic disease vaccine comprises a RNA having an ORF that encodes a signal peptide fused to the zoonotic disease antigen. Signal peptides, comprising the N-terminal 15-60 amino acids of proteins, are typically needed for the translocation across the membrane on the secretory pathway and, thus, universally control the entry of most proteins both in eukaryotes and prokaryotes to the secretory pathway. In eukaryotes, the signal peptide of a nascent precursor protein (pre-protein) directs the ribosome to the rough endoplasmic reticulum (ER) membrane and initiates the transport of the growing peptide chain across it for processing. ER processing produces mature proteins, wherein the signal peptide is cleaved from precursor proteins, typically by a ER-resident signal peptidase of the host cell, or they remain uncleaved and function as a membrane anchor. A signal peptide may also facilitate the targeting of the protein to the cell membrane.

A signal peptide may have a length of 15-60 amino acids. For example, a signal peptide may have a length of 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or amino acids. In some embodiments, a signal peptide has a length of 20-60, 25-60, 30-60, 35-60, 40-60, 45-60, 50-60, 55-60, 15-55, 20-55, 25-55, 30-55, 35-55, 40-55, 45-55, 50-55, 15-50, 20-50, 25-50, 30-50, 35-50, 40-50, 45-50, 15-45, 20-45, 25-45, 30-45, 35-45, 40-45, 15-40, 20-40, 25-40, 30-40, 35-40, 15-35, 20-35, 25-35, 30-35, 15-30, 20-30, 25-30, 15-25, 20-25, or 15-20 amino acids.

Signal peptides from heterologous genes (which regulate expression of genes other than zoonotic disease antigens in nature) are known in the art and can be tested for desired properties and then incorporated into a nucleic acid of the disclosure. In some embodiments, the signal peptide may comprise one of the following sequences:

| | |
|---|---|
| MDSKGSSQKGSRLLLLLVVSNLLLPQGVVG, | (SEQ ID NO: 21) |
| MDWTWILFLVAAATRVHS; | (SEQ ID NO: 22) |
| METPAQLLFLLLLWLPDTTG; | (SEQ ID NO: 23) |
| MLGSNSGQRVVFTILLLLVAPAYS; | (SEQ ID NO: 24) |
| MKCLLYLAFLFIGVNCA; | (SEQ ID NO: 25) |
| MWLVSLAIVTACAGA. | (SEQ ID NO: 26) |

Fusion Proteins

In some embodiments, a zoonotic disease RNA vaccine of the present disclosure includes an RNA encoding an antigenic fusion protein. Thus, the encoded antigen or antigens may include two or more proteins (e.g., protein and/or protein fragment) joined together. Alternatively, the protein to which a protein antigen is fused does not promote a strong immune response to itself, but rather to the zoonotic disease antigen. Antigenic fusion proteins, in some embodiments, retain the functional property from each original protein.

Scaffold Moieties

The RNA (e.g., mRNA) vaccines as provided herein, in some embodiments, encode fusion proteins which comprise zoonotic disease antigens linked to scaffold moieties. In some embodiments, such scaffold moieties impart desired properties to an antigen encoded by a nucleic acid of the disclosure. For example scaffold proteins may improve the immunogenicity of an antigen, e.g., by altering the structure of the antigen, altering the uptake and processing of the antigen, and/or causing the antigen to bind to a binding partner.

In some embodiments, the scaffold moiety is protein that can self-assemble into protein nanoparticles that are highly symmetric, stable, and structurally organized, with diameters of 10-nm, a highly suitable size range for optimal interactions with various cells of the immune system. In some embodiments, viral proteins or virus-like particles can be used to form stable nanoparticle structures. Examples of such viral proteins are known in the art. For example, in some embodiments, the scaffold moiety is a hepatitis B surface antigen (HBsAg). HBsAg forms spherical particles with an average diameter of ~22 nm and which lacked nucleic acid and hence are non-infectious (Lopez-Sagaseta, J. et al. *Computational and Structural Biotechnology Journal* 14 (2016) 58-68). In some embodiments, the scaffold moiety is a hepatitis B core antigen (HBcAg) self-assembles into particles of 24-31 nm diameter, which resembled the viral cores obtained from HBV-infected human liver. HBcAg produced in self-assembles into two classes of differently sized nanoparticles of 300 Å and 360 Å diameter, corresponding to 180 or protomers. In some embodiments a zoonotic disease antigen is fused to HBsAG or HBcAG to facilitate self-assembly of nanoparticles displaying the zoonotic disease antigen.

In another embodiment, bacterial protein platforms may be used. Non-limiting examples of these self-assembling proteins include ferritin, lumazine and encapsulin.

Ferritin is a protein whose main function is intracellular iron storage. Ferritin is made of subunits, each composed of a four-alpha-helix bundle, that self-assemble in a quaternary structure with octahedral symmetry (Cho K. J. et al. *J Mol Biol.* 2009; 390:83-98). Several high-resolution structures of ferritin have been determined, confirming that *Helicobacter*

*pylori* ferritin is made of 24 identical protomers, whereas in animals, there are ferritin light and heavy chains that can assemble alone or combine with different ratios into particles of 24 subunits (Granier T. et al. *J Biol Inorg Chem.* 2003; 8:105-111; Lawson D. M. et al. *Nature.* 1991; 349: 541-544). Ferritin self-assembles into nanoparticles with robust thermal and chemical stability. Thus, the ferritin nanoparticle is well-suited to carry and expose antigens.

Lumazine synthase (LS) is also well-suited as a nanoparticle platform for antigen display. LS, which is responsible for the penultimate catalytic step in the biosynthesis of riboflavin, is an enzyme present in a broad variety of organisms, including archaea, bacteria, fungi, plants, and eubacteria (Weber S. E. *Flavins and Flavoproteins*. Methods and Protocols, Series: Methods in Molecular Biology. 2014). The LS monomer is 150 amino acids long, and consists of beta-sheets along with tandem alpha-helices flanking its sides. A number of different quaternary structures have been reported for LS, illustrating its morphological versatility: from homopentamers up to symmetrical assemblies of 12 pentamers forming capsids of 150 Å diameter. Even LS cages of more than 100 subunits have been described (Zhang X. et al. *J Mol Biol.* 2006; 362:753-770).

Encapsulin, a novel protein cage nanoparticle isolated from thermophile *Thermotoga maritima*, may also be used as a platform to present antigens on the surface of self-assembling nanoparticles. Encapsulin is assembled from 60 copies of identical 31 kDa monomers having a thin and icosahedral T=1 symmetric cage structure with interior and exterior diameters of 20 and 24 nm, respectively (Sutter M. et al. *Nat Struct Mol Biol.* 2008, 15: 939-947). Although the exact function of encapsulin in *T. maritima* is not clearly understood yet, its crystal structure has been recently solved and its function was postulated as a cellular compartment that encapsulates proteins such as DyP (Dye decolorizing peroxidase) and Flp (Ferritin like protein), which are involved in oxidative stress responses (Rahmanpour R. et al. *FEBS J.* 2013, 280: 2097-2104).

Linkers and Cleavable Peptides

In some embodiments, the mRNAs of the disclosure encode more than one polypeptide, referred to herein as fusion proteins. In some embodiments, the mRNA further encodes a linker located between at least one or each domain of the fusion protein. The linker can be, for example, a cleavable linker or protease-sensitive linker. In some embodiments, the linker is selected from the group consisting of F2A linker, P2A linker, T2A linker, E2A linker, and combinations thereof. This family of self-cleaving peptide linkers, referred to as 2A peptides, has been described in the art (see for example, Kim, J. H. et al. (2011) *PLoS ONE* 6:e18556). In some embodiments, the linker is an F2A linker. In some embodiments, the linker is a GGGS linker. In some embodiments, the fusion protein contains three domains with intervening linkers, having the structure: domain-linker-domain-linker-domain.

Cleavable linkers known in the art may be used in connection with the disclosure. Exemplary such linkers include: F2A linkers, T2A linkers, P2A linkers, E2A linkers (See, e.g., WO2017/127750). The skilled artisan will appreciate that other art-recognized linkers may be suitable for use in the constructs of the disclosure (e.g., encoded by the nucleic acids of the disclosure). The skilled artisan will likewise appreciate that other polycistronic constructs (mRNA encoding more than one antigen/polypeptide separately within the same molecule) may be suitable for use as provided herein.

Sequence Optimization

In some embodiments, an ORF encoding an antigen of the disclosure is codon optimized. Codon optimization methods are known in the art. For example, an ORF of any one or more of the sequences provided herein may be codon optimized. Codon optimization, in some embodiments, may be used to match codon frequencies in target and host organisms to ensure proper folding; bias GC content to increase mRNA stability or reduce secondary structures; minimize tandem repeat codons or base runs that may impair gene construction or expression; customize transcriptional and translational control regions; insert or remove protein trafficking sequences; remove/add post translation modification sites in encoded protein (e.g., glycosylation sites); add, remove or shuffle protein domains; insert or delete restriction sites; modify ribosome binding sites and mRNA degradation sites; adjust translational rates to allow the various domains of the protein to fold properly; or reduce or eliminate problem secondary structures within the polynucleotide. Codon optimization tools, algorithms and services are known in the art—non-limiting examples include services from GeneArt (Fife Technologies), DNA2.0 (Menlo Park Calif.) and/or proprietary methods. In some embodiments, the open reading frame (ORF) sequence is optimized using optimization algorithms.

In some embodiments, a codon optimized sequence shares less than 95% sequence identity to a naturally-occurring or wild-type sequence ORF (e.g., a naturally-occurring or wild-type mRNA sequence encoding a zoonotic disease antigen). In some embodiments, a codon optimized sequence shares less than 90% sequence identity to a naturally-occurring or wild-type sequence (e.g., a naturally-occurring or wild-type mRNA sequence encoding a zoonotic disease antigen). In some embodiments, a codon optimized sequence shares less than 85% sequence identity to a naturally-occurring or wild-type sequence (e.g., a naturally-occurring or wild-type mRNA sequence encoding a zoonotic disease antigen). In some embodiments, a codon optimized sequence shares less than 80% sequence identity to a naturally-occurring or wild-type sequence (e.g., a naturally-occurring or wild-type mRNA sequence encoding a zoonotic disease antigen). In some embodiments, a codon optimized sequence shares less than 75% sequence identity to a naturally-occurring or wild-type sequence (e.g., a naturally-occurring or wild-type mRNA sequence encoding a zoonotic disease antigen).

In some embodiments, a codon optimized sequence shares between 65% and 85% (e.g., between about 67% and about 85% or between about 67% and about 80%) sequence identity to a naturally-occurring or wild-type sequence (e.g., a naturally-occurring or wild-type mRNA sequence encoding a zoonotic disease antigen). In some embodiments, a codon optimized sequence shares between 65% and 75% or about 80% sequence identity to a naturally-occurring or wild-type sequence (e.g., a naturally-occurring or wild-type mRNA sequence encoding a zoonotic disease antigen).

In some embodiments, a codon-optimized sequence encodes an antigen that is as immunogenic as, or more immunogenic than (e.g., at least 10%, at least 20%, at least 30%, at least 40%, at least 50%, at least 100%, or at least 200% more), than a zoonotic disease antigen encoded by a non-codon-optimized sequence. In some embodiments, a codon-optimized sequence shares between 65% and 85% (e.g., between about 67% and about 85%, or between about 67% and about 80%) sequence identity to a naturally-occurring sequence or a wild-type sequence (e.g., a naturally-occurring or wild-type mRNA sequence encoding a polypeptide or protein of interest (e.g., an antigenic protein or polypeptide)). In some embodiments, a codon-optimized sequence shares between 65% and 75%, or about 80% sequence identity to a naturally-occurring sequence or wild-type sequence (e.g., a naturally-occurring or wild-type mRNA sequence encoding a polypeptide or protein of interest (e.g., an antigenic protein or polypeptide)).

When transfected into mammalian host cells, the modified mRNAs have a stability of between 12-18 hours, or greater than 18 hours, e.g., 24, 36, 48, 60, 72, or greater than 72 hours and are capable of being expressed by the mammalian host cells.

In some embodiments, a codon optimized RNA may be one in which the levels of G/C are enhanced. The G/C-content of nucleic acid molecules (e.g., mRNA) may influence the stability of the RNA. RNA having an increased amount of guanine (G) and/or cytosine (C) residues may be functionally more stable than RNA containing a large amount of adenine (A) and thymine (T) or uracil (U) nucleotides. As an example, WO02/098443 discloses a pharmaceutical composition containing an mRNA stabilized by sequence modifications in the translated region. Due to the degeneracy of the genetic code, the modifications work by substituting existing codons for those that promote greater RNA stability without changing the resulting amino acid. The approach is limited to coding regions of the RNA.

Chemically Unmodified Nucleotides

In some embodiments, at least one RNA (e.g., mRNA) of a zoonotic disease vaccines of the present disclosure is not chemically modified and comprises the standard ribonucleotides consisting of adenosine, guanosine, cytosine and uridine. In some embodiments, nucleotides and nucleosides of the present disclosure comprise standard nucleoside residues such as those present in transcribed RNA (e.g. A, G, C, or U). In some embodiments, nucleotides and nucleosides of the present disclosure comprise standard deoxyribonucleosides such as those present in DNA (e.g. dA, dG, dC, or dT).

Chemical Modifications

Zoonotic disease RNA vaccines of the present disclosure comprise, in some embodiments, at least one nucleic acid (e.g., RNA) having an open reading frame encoding at least one zoonotic disease antigen, wherein the nucleic acid comprises nucleotides and/or nucleosides that can be standard (unmodified) or modified as is known in the art. In some embodiments, nucleotides and nucleosides of the present disclosure comprise modified nucleotides or nucleosides. Such modified nucleotides and nucleosides can be naturally-occurring modified nucleotides and nucleosides or non-naturally occurring modified nucleotides and nucleosides. Such modifications can include those at the sugar, backbone, or nucleobase portion of the nucleotide and/or nucleoside as are recognized in the art.

In some embodiments, a naturally-occurring modified nucleotide or nucleotide of the disclosure is one as is generally known or recognized in the art. Non-limiting examples of such naturally occurring modified nucleotides and nucleotides can be found, inter alia, in the widely recognized MODOMICS database.

In some embodiments, a non-naturally occurring modified nucleotide or nucleoside of the disclosure is one as is generally known or recognized in the art. Non-limiting examples of such non-naturally occurring modified nucleotides and nucleosides can be found, inter alia, in published US application Nos. PCT/US2012/058519; PCT/US2013/075177; PCT/US2014/058897; PCT/US2014/058891; PCT/US2014/070413; PCT/US2015/36773; PCT/US2015/36759; PCT/US2015/36771; or PCT/IB2017/051367 all of which are incorporated by reference herein.

Hence, nucleic acids of the disclosure (e.g., DNA nucleic acids and RNA nucleic acids, such as mRNA nucleic acids) can comprise standard nucleotides and nucleosides, naturally-occurring nucleotides and nucleosides, non-naturally-occurring nucleotides and nucleosides, or any combination thereof.

Nucleic acids of the disclosure (e.g., DNA nucleic acids and RNA nucleic acids, such as mRNA nucleic acids), in some embodiments, comprise various (more than one) different types of standard and/or modified nucleotides and nucleosides. In some embodiments, a particular region of a nucleic acid contains one, two or more (optionally different) types of standard and/or modified nucleotides and nucleosides.

In some embodiments, a modified RNA nucleic acid (e.g., a modified mRNA nucleic acid), introduced to a cell or organism, exhibits reduced degradation in the cell or organism, respectively, relative to an unmodified nucleic acid comprising standard nucleotides and nucleosides.

In some embodiments, a modified RNA nucleic acid (e.g., a modified mRNA nucleic acid), introduced into a cell or organism, may exhibit reduced immunogenicity in the cell or organism, respectively (e.g., a reduced innate response) relative to an unmodified nucleic acid comprising standard nucleotides and nucleosides.

Nucleic acids (e.g., RNA nucleic acids, such as mRNA nucleic acids), in some embodiments, comprise non-natural modified nucleotides that are introduced during synthesis or post-synthesis of the nucleic acids to achieve desired functions or properties. The modifications may be present on internucleotide linkages, purine or pyrimidine bases, or sugars. The modification may be introduced with chemical synthesis or with a polymerase enzyme at the terminal of a chain or anywhere else in the chain. Any of the regions of a nucleic acid may be chemically modified.

The present disclosure provides for modified nucleosides and nucleotides of a nucleic acid (e.g., RNA nucleic acids, such as mRNA nucleic acids). A "nucleoside" refers to a compound containing a sugar molecule (e.g., a pentose or ribose) or a derivative thereof in combination with an organic base (e.g., a purine or pyrimidine) or a derivative thereof (also referred to herein as "nucleobase"). A "nucleotide" refers to a nucleoside, including a phosphate group. Modified nucleotides may by synthesized by any useful method, such as, for example, chemically, enzymatically, or recombinantly, to include one or more modified or non-natural nucleosides. Nucleic acids can comprise a region or regions of linked nucleosides. Such regions may have variable backbone linkages. The linkages can be standard phosphodiester linkages, in which case the nucleic acids would comprise regions of nucleotides.

Modified nucleotide base pairing encompasses not only the standard adenosine-thymine, adenosine-uracil, or guanosine-cytosine base pairs, but also base pairs formed between nucleotides and/or modified nucleotides comprising non-standard or modified bases, wherein the arrangement of hydrogen bond donors and hydrogen bond acceptors permits hydrogen bonding between a non-standard base and a standard base or between two complementary non-standard base structures, such as, for example, in those nucleic acids having at least one chemical modification. One example of such non-standard base pairing is the base pairing between the modified nucleotide inosine and adenine, cytosine or uracil. Any combination of base/sugar or linker may be incorporated into nucleic acids of the present disclosure.

In some embodiments, modified nucleobases in nucleic acids (e.g., RNA nucleic acids, such as mRNA nucleic acids) comprise 1-methyl-pseudouridine (m1ψ), 1-ethyl-pseudouridine (e1ψ), 5-methoxy-uridine (mo5U), 5-methyl-cytidine (m5C), and/or pseudouridine (ψ). In some embodiments, modified nucleobases in nucleic acids (e.g., RNA nucleic acids, such as mRNA nucleic acids) comprise 5-methoxymethyl uridine, 5-methylthio uridine, 1-methoxymethyl pseudouridine, 5-methyl cytidine, and/or 5-methoxy cytidine. In some embodiments, the polyribonucleotide includes a combination of at least two (e.g., 2, 3, 4 or more) of any of the aforementioned modified nucleobases, including but not limited to chemical modifications.

In some embodiments, a RNA nucleic acid of the disclosure comprises 1-methyl-pseudouridine (m1ψ) substitutions at one or more or all uridine positions of the nucleic acid.

In some embodiments, a RNA nucleic acid of the disclosure comprises 1-methyl-pseudouridine (m1ψ) substitutions at one or more or all uridine positions of the nucleic acid and 5-methyl cytidine substitutions at one or more or all cytidine positions of the nucleic acid.

In some embodiments, a RNA nucleic acid of the disclosure comprises pseudouridine (ψ) substitutions at one or more or all uridine positions of the nucleic acid.

In some embodiments, a RNA nucleic acid of the disclosure comprises pseudouridine (ψ) substitutions at one or more or all uridine positions of the nucleic acid and 5-methyl cytidine substitutions at one or more or all cytidine positions of the nucleic acid.

In some embodiments, a RNA nucleic acid of the disclosure comprises uridine at one or more or all uridine positions of the nucleic acid.

In some embodiments, nucleic acids (e.g., RNA nucleic acids, such as mRNA nucleic acids) are uniformly modified (e.g., fully modified, modified throughout the entire sequence) for a particular modification. For example, a nucleic acid can be uniformly modified with 1-methyl-pseudouridine, meaning that all uridine residues in the mRNA sequence are replaced with 1-methyl-pseudouridine. Similarly, a nucleic acid can be uniformly modified for any type of nucleoside residue present in the sequence by replacement with a modified residue such as those set forth above.

The nucleic acids of the present disclosure may be partially or fully modified along the entire length of the molecule. For example, one or more or all or a given type of nucleotide (e.g., purine or pyrimidine, or any one or more or all of A, G, U, C) may be uniformly modified in a nucleic acid of the disclosure, or in a predetermined sequence region thereof (e.g., in the mRNA including or excluding the polyA tail). In some embodiments, all nucleotides X in a nucleic acid of the present disclosure (or in a sequence region thereof) are modified nucleotides, wherein X may be any one of nucleotides A, G, U, C, or any one of the combinations A+G, A+U, A+C, G+U, G+C, U+C, A+G+U, A+G+C, G+U+C or A+G+C.

The nucleic acid may contain from about 1% to about 100% modified nucleotides (either in relation to overall nucleotide content, or in relation to one or more types of nucleotide, i.e., any one or more of A, G, U or C) or any intervening percentage (e.g., from 1% to 20%, from 1% to 25%, from 1% to 50%, from 1% to 60%, from 1% to 70%, from 1% to 80%, from 1% to 90%, from 1% to 95%, from 10% to 20%, from 10% to 25%, from 10% to 50%, from 10% to 60%, from 10% to 70%, from 10% to 80%, from 10% to 90%, from 10% to 95%, from 10% to 100%, from 20% to 25%, from 20% to 50%, from 20% to 60%, from 20% to 70%, from 20% to 80%, from 20% to 90%, from 20% to 95%, from 20% to 100%, from 50% to 60%, from 50% to 70%, from 50% to 80%, from 50% to 90%, from 50% to 95%, from 50% to 100%, from 70% to 80%, from 70% to 90%, from 70% to 95%, from 70% to 100%, from 80% to 90%, from 80% to 95%, from 80% to 100%, from 90% to 95%, from 90% to 100%, and from 95% to 100%). It will be understood that any remaining percentage is accounted for by the presence of unmodified A, G, U, or C.

The nucleic acids may contain at a minimum 1% and at maximum 100% modified nucleotides, or any intervening percentage, such as at least 5% modified nucleotides, at least 10% modified nucleotides, at least 25% modified nucleotides, at least 50% modified nucleotides, at least 80% modified nucleotides, or at least 90% modified nucleotides. For example, the nucleic acids may contain a modified pyrimidine such as a modified uracil or cytosine. In some embodiments, at least 5%, at least 10%, at least 25%, at least 50%, at least 80%, at least 90% or 100% of the uracil in the nucleic acid is replaced with a modified uracil (e.g., a 5-substituted uracil). The modified uracil can be replaced by a compound having a single unique structure, or can be replaced by a plurality of compounds having different structures (e.g., 2, 3, 4 or more unique structures). In some embodiments, at least 5%, at least 10%, at least 25%, at least 50%, at least 80%, at least 90% or 100% of the cytosine in the nucleic acid is replaced with a modified cytosine (e.g., a 5-substituted cytosine). The modified cytosine can be replaced by a compound having a single unique structure, or can be replaced by a plurality of compounds having different structures (e.g., 2, 3, 4 or more unique structures).

Untranslated Regions (UTRs)

The nucleic acids of the present disclosure may comprise one or more regions or parts which act or function as an untranslated region. Where nucleic acids are designed to encode at least one antigen of interest, the nucleic may comprise one or more of these untranslated regions (UTRs). Wild-type untranslated regions of a nucleic acid are transcribed but not translated. In mRNA, the 5' UTR starts at the transcription start site and continues to the start codon but does not include the start codon; whereas, the 3' UTR starts immediately following the stop codon and continues until the transcriptional termination signal. There is growing body of evidence about the regulatory roles played by the UTRs in terms of stability of the nucleic acid molecule and translation. The regulatory features of a UTR can be incorporated into the polynucleotides of the present disclosure to, among other things, enhance the stability of the molecule. The specific features can also be incorporated to ensure controlled down-regulation of the transcript in case they are misdirected to undesired organs sites. A variety of 5'UTR and 3'UTR sequences are known and available in the art.

A 5' UTR is region of an mRNA that is directly upstream (5') from the start codon (the first codon of an mRNA transcript translated by a ribosome). A 5' UTR does not encode a protein (is non-coding). Natural 5'UTRs have features that play roles in translation initiation. They harbor signatures like Kozak sequences which are commonly known to be involved in the process by which the ribosome initiates translation of many genes. Kozak sequences have the consensus CCR(A/G)CCAUGG (SEQ ID NO: 27), where R is a purine (adenine or guanine) three bases upstream of the start codon (AUG), which is followed by another 'G'0.5'UTR also have been known to form secondary structures which are involved in elongation factor binding.

In some embodiments of the disclosure, a 5' UTR is a heterologous UTR, i.e., is a UTR found in nature associated with a different ORF. In another embodiment, a 5' UTR is a synthetic UTR, i.e., does not occur in nature. Synthetic UTRs include UTRs that have been mutated to improve their properties, e.g., which increase gene expression as well as those which are completely synthetic. Exemplary 5' UTRs include Xenopus or human derived a-globin or b-globin (U.S. Pat. Nos. 8,278,063; 9,012,219), human cytochrome b-245 a polypeptide, and hydroxy steroid (17b) dehydrogenase, and Tobacco etch virus (U.S. Pat. Nos. 8,278,063, 9,012,219). CMV immediate-early 1 (IE1) gene (US2014/0206753, WO2013/185069), the sequence GGGAUCCUACC (SEQ ID NO: 28) (WO2014/144196) may also be used. In another embodiment, 5' UTR of a TOP gene is a 5' UTR of a TOP gene lacking the 5' TOP motif (the oligopyrimidine tract) (e.g., WO2015/101414, WO2015/101415, WO2015/062738, WO2015/024667, WO2015/024667; 5' UTR element derived from ribosomal protein Large 32 (L32) gene (WO2015/101414, WO2015/101415, WO2015/062738), 5' UTR element derived from the 5'UTR of an hydroxy steroid (17-β) dehydrogenase 4 gene (HSD17B4) (WO2015/024667), or a 5' UTR element derived from the 5' UTR of ATP5A1 (WO2015/024667) can be used. In some embodiments, an internal ribosome entry site (IRES) is used instead of a 5' UTR.

A 3' UTR is region of an mRNA that is directly downstream (3') from the stop codon (the codon of an mRNA transcript that signals a termination of translation). A 3' UTR does not encode a protein (is non-coding). Natural or wild type 3' UTRs are known to have stretches of adenosines and uridines embedded in them. These AU rich signatures are particularly prevalent in genes with high rates of turnover. Based on their sequence features and functional properties, the AU rich elements (AREs) can be separated into three classes (Chen et al, 1995): Class I AREs contain several dispersed copies of an AUUUA motif within U-rich regions. C-Myc and MyoD contain class I AREs. Class II AREs possess two or more overlapping UUAUUUA(U/A)(U/A) (SEQ ID NO: 29) nonamers. Molecules containing this type of AREs include GM-CSF and TNF-α. Class III ARES are less well defined. These U rich regions do not contain an AUUUA motif. c-Jun and Myogenin are two well-studied examples of this class. Most proteins binding to the AREs are known to destabilize the messenger, whereas members of the ELAV family, most notably HuR, have been documented to increase the stability of mRNA. HuR binds to AREs of all the three classes. Engineering the HuR specific binding sites into the 3' UTR of nucleic acid molecules will lead to HuR binding and thus, stabilization of the message in vivo.

Introduction, removal or modification of 3' UTR AU rich elements (AREs) can be used to modulate the stability of nucleic acids (e.g., RNA) of the disclosure. When engineering specific nucleic acids, one or more copies of an ARE can be introduced to make nucleic acids of the disclosure less stable and thereby curtail translation and decrease production of the resultant protein. Likewise, AREs can be identified and removed or mutated to increase the intracellular stability and thus increase translation and production of the resultant protein. Transfection experiments can be conducted in relevant cell lines, using nucleic acids of the disclosure and protein production can be assayed at various time points post-transfection. For example, cells can be transfected with different ARE-engineering molecules and by using an ELISA kit to the relevant protein and assaying protein produced at 6 hour, 12 hour, 24 hour, 48 hour, and 7 days post-transfection.

3' UTRs may be heterologous or synthetic. With respect to 3' UTRs, globin UTRs, including Xenopus β-globin UTRs and human β-globin UTRs are known in the art (U.S. Pat. Nos. 8,278,063, 9,012,219, US2011/0086907). A modified β-globin construct with enhanced stability in some cell types by cloning two sequential human β-globin 3'UTRs head to tail has been developed and is well known in the art (US2012/0195936, WO2014/071963). In addition a2-globin, a1-globin, UTRs and mutants thereof are also known in the art (WO2015/101415, WO2015/024667). Other 3' UTRs described in the mRNA constructs in the non-patent literature include CYBA (Ferizi et al., 2015) and albumin (Thess et al., 2015). Other exemplary 3' UTRs include that of bovine or human growth hormone (wild type or modified) (WO2013/185069, US2014/0206753, WO2014/152774), rabbit β globin and hepatitis B virus (HBV), α-globin 3' UTR and Viral VEEV 3' UTR sequences are also known in the art. In some embodiments, the sequence UUUGAAUU (WO2014/144196) is used. In some embodiments, 3' UTRs of human and mouse ribosomal protein are used. Other examples include rps9 3'UTR (WO2015/101414), FIG. 4 (WO2015/101415), and human albumin 7 (WO2015/101415).

Those of ordinary skill in the art will understand that 5'UTRs that are heterologous or synthetic may be used with any desired 3' UTR sequence. For example, a heterologous 5'UTR may be used with a synthetic 3'UTR with a heterologous 3" UTR.

Non-UTR sequences may also be used as regions or subregions within a nucleic acid. For example, introns or portions of introns sequences may be incorporated into regions of nucleic acid of the disclosure. Incorporation of intronic sequences may increase protein production as well as nucleic acid levels.

Combinations of features may be included in flanking regions and may be contained within other features. For example, the ORF may be flanked by a 5' UTR which may contain a strong Kozak translational initiation signal and/or a 3' UTR which may include an oligo(dT) sequence for templated addition of a poly-A tail. 5' UTR may comprise a first polynucleotide fragment and a second polynucleotide fragment from the same and/or different genes such as the 5' UTRs described in US Patent Application Publication No. 2010/0293625 and PCT/US2014/069155, herein incorporated by reference in its entirety.

It should be understood that any UTR from any gene may be incorporated into the regions of a nucleic acid. Furthermore, multiple wild-type UTRs of any known gene may be utilized. It is also within the scope of the present disclosure to provide artificial UTRs which are not variants of wild type regions. These UTRs or portions thereof may be placed in the same orientation as in the transcript from which they were selected or may be altered in orientation or location. Hence a 5' or 3' UTR may be inverted, shortened, lengthened, made with one or more other 5' UTRs or 3' UTRs. As used herein, the term "altered" as it relates to a UTR sequence, means that the UTR has been changed in some way in relation to a reference sequence. For example, a 3' UTR or 5' UTR may be altered relative to a wild-type or native UTR by the change in orientation or location as taught above or may be altered by the inclusion of additional nucleotides, deletion of nucleotides, swapping or transposition of nucleotides. Any of these changes producing an "altered" UTR (whether 3' or 5') comprise a variant UTR.

In some embodiments, a double, triple or quadruple UTR such as a 5' UTR or 3' UTR may be used. As used herein, a "double" UTR is one in which two copies of the same UTR are encoded either in series or substantially in series. For example, a double beta-globin 3' UTR may be used as described in US Patent publication 20100129877, the contents of which are incorporated herein by reference in its entirety.

It is also within the scope of the present disclosure to have patterned UTRs. As used herein "patterned UTRs" are those UTRs which reflect a repeating or alternating pattern, such as ABABAB or AABBAABBAABB or ABCABCABC or variants thereof repeated once, twice, or more than 3 times. In these patterns, each letter, A, B, or C represent a different UTR at the nucleotide level.

In some embodiments, flanking regions are selected from a family of transcripts whose proteins share a common function, structure, feature or property. For example, polypeptides of interest may belong to a family of proteins which are expressed in a particular cell, tissue or at some time during development. The UTRs from any of these genes may be swapped for any other UTR of the same or different family of proteins to create a new polynucleotide. As used herein, a "family of proteins" is used in the broadest sense to refer to a group of two or more polypeptides of interest which share at least one function, structure, feature, localization, origin, or expression pattern.

The untranslated region may also include translation enhancer elements (TEE). As a non-limiting example, the TEE may include those described in US Application No. 2009/0226470, herein incorporated by reference in its entirety, and those known in the art.

In Vitro Transcription of RNA cDNA encoding the polynucleotides described herein may be transcribed using an in vitro transcription (IVT) system. In vitro transcription of RNA is known in the art and is described in International Publication WO2014/152027, which is incorporated by reference herein in its entirety.

In some embodiments, the RNA transcript is generated using a non-amplified, linearized DNA template in an in vitro transcription reaction to generate the RNA transcript. In some embodiments, the template DNA is isolated DNA. In some embodiments, the template DNA is cDNA. In some embodiments, the cDNA is formed by reverse transcription of a RNA polynucleotide, for example, but not limited to Lassa virus, Nipah virus, or betacoronavirus RNA, e.g. mRNA. In some embodiments, cells, e.g., bacterial cells, e.g., *E. coli*, e.g., DH-1 cells are transfected with the plasmid DNA template. In some embodiments, the transfected cells are cultured to replicate the plasmid DNA which is then isolated and purified. In some embodiments, the DNA template includes a RNA polymerase promoter, e.g., a T7 promoter located 5' to and operably linked to the gene of interest.

In some embodiments, an in vitro transcription template encodes a 5' untranslated (UTR) region, contains an open reading frame, and encodes a 3' UTR and a polyA tail. The particular nucleic acid sequence composition and length of an in vitro transcription template will depend on the mRNA encoded by the template.

A "5' untranslated region" (UTR) refers to a region of an mRNA that is directly upstream (i.e., 5') from the start codon (i.e., the first codon of an mRNA transcript translated by a ribosome) that does not encode a polypeptide. When RNA transcripts are being generated, the 5' UTR may comprise a promoter sequence. Such promoter sequences are known in the art. It should be understood that such promoter sequences will not be present in a vaccine of the disclosure.

A "3' untranslated region" (UTR) refers to a region of an mRNA that is directly downstream (i.e., 3') from the stop codon (i.e., the codon of an mRNA transcript that signals a termination of translation) that does not encode a polypeptide.

An "open reading frame" is a continuous stretch of DNA beginning with a start codon (e.g., methionine (ATG)), and ending with a stop codon (e.g., TAA, TAG or TGA) and encodes a polypeptide.

A "polyA tail" is a region of mRNA that is downstream, e.g., directly downstream (i.e., 3'), from the 3' UTR that contains multiple, consecutive adenosine monophosphates. A polyA tail may contain 10 to 300 adenosine monophosphates. For example, a polyA tail may contain 10, 20, 30, 40, 50, 60, 70, 80, 90, 100, 110, 120, 130, 140, 150, 160, 170, 180, 190, 200, 210, 220, 230, 240, 250, 260, 270, 280, 290 or 300 adenosine monophosphates. In some embodiments, a polyA tail contains 50 to 250 adenosine monophosphates. In a relevant biological setting (e.g., in cells, in vivo) the poly(A) tail functions to protect mRNA from enzymatic degradation, e.g., in the cytoplasm, and aids in transcription termination, and/or export of the mRNA from the nucleus and translation.

In some embodiments, a nucleic acid includes 200 to 3,000 nucleotides. For example, a nucleic acid may include 200 to 500, 200 to 1000, 200 to 1500, 200 to 3000, 500 to 1000, 500 to 1500, 500 to 2000, 500 to 3000, 1000 to 1500, 1000 to 2000, 1000 to 3000, 1500 to 3000, or to 3000 nucleotides).

An in vitro transcription system typically comprises a transcription buffer, nucleotide triphosphates (NTPs), an RNase inhibitor and a polymerase.

The NTPs may be manufactured in house, may be selected from a supplier, or may be synthesized as described herein. The NTPs may be selected from, but are not limited to, those described herein including natural and unnatural (modified) NTPs.

Any number of RNA polymerases or variants may be used in the method of the present disclosure. The polymerase may be selected from, but is not limited to, a phage RNA polymerase, e.g., a T7 RNA polymerase, a T3 RNA polymerase, a SP6 RNA polymerase, and/or mutant polymerases such as, but not limited to, polymerases able to incorporate modified nucleic acids and/or modified nucleotides, including chemically modified nucleic acids and/or nucleotides. Some embodiments exclude the use of DNase.

In some embodiments, the RNA transcript is capped via enzymatic capping. In some embodiments, the RNA comprises 5' terminal cap, for example, 7mG(5')ppp(5')NlmpNp.

Chemical Synthesis

Solid-phase chemical synthesis. Nucleic acids the present disclosure may be manufactured in whole or in part using solid phase techniques. Solid-phase chemical synthesis of nucleic acids is an automated method wherein molecules are immobilized on a solid support and synthesized step by step in a reactant solution. Solid-phase synthesis is useful in site-specific introduction of chemical modifications in the nucleic acid sequences.

Liquid Phase Chemical Synthesis. The synthesis of nucleic acids of the present disclosure by the sequential addition of monomer building blocks may be carried out in a liquid phase.

Combination of Synthetic Methods. The synthetic methods discussed above each has its own advantages and limitations. Attempts have been conducted to combine these methods to overcome the limitations. Such combinations of methods are within the scope of the present disclosure. The use of solid-phase or liquid-phase chemical synthesis in combination with enzymatic ligation provides an efficient way to generate long chain nucleic acids that cannot be obtained by chemical synthesis alone.

Ligation of Nucleic Acid Regions or Subregions

Assembling nucleic acids by a ligase may also be used. DNA or RNA ligases promote intermolecular ligation of the 5' and 3' ends of polynucleotide chains through the formation of a phosphodiester bond. Nucleic acids such as chimeric polynucleotides and/or circular nucleic acids may be prepared by ligation of one or more regions or subregions. DNA fragments can be joined by a ligase catalyzed reaction to create recombinant DNA with different functions. Two oligodeoxynucleotides, one with a 5' phosphoryl group and another with a free 3' hydroxyl group, serve as substrates for a DNA ligase.

Purification

Purification of the nucleic acids described herein may include, but is not limited to, nucleic acid clean-up, quality assurance and quality control. Clean-up may be performed by methods known in the arts such as, but not limited to, AGENCOURT® beads (Beckman Coulter Genomics, Danvers, Mass.), poly-T beads, LNA™ oligo-T capture probes (EXIQON® Inc, Vedbaek, Denmark) or HPLC based purification methods such as, but not limited to, strong anion exchange HPLC, weak anion exchange HPLC, reverse phase HPLC (RP-HPLC), and hydrophobic interaction HPLC (HIC-HPLC). The term "purified" when used in relation to a nucleic acid such as a "purified nucleic acid" refers to one that is separated from at least one contaminant. A "contaminant" is any substance that makes another unfit, impure or inferior. Thus, a purified nucleic acid (e.g., DNA and RNA) is present in a form or setting different from that in which it is found in nature, or a form or setting different from that which existed prior to subjecting it to a treatment or purification method.

A quality assurance and/or quality control check may be conducted using methods such as, but not limited to, gel electrophoresis, UV absorbance, or analytical HPLC.

In some embodiments, the nucleic acids may be sequenced by methods including, but not limited to reverse-transcriptase-PCR.

Quantification

In some embodiments, the nucleic acids of the present disclosure may be quantified in exosomes or when derived from one or more bodily fluid. Bodily fluids include peripheral blood, serum, plasma, ascites, urine, cerebrospinal fluid (CSL), sputum, saliva, bone marrow, synovial fluid, aqueous humor, amniotic fluid, cerumen, breast milk, broncheoalveolar lavage fluid, semen, prostatic fluid, cowper's fluid or pre-ejaculatory fluid, sweat, fecal matter, hair, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates, blastocyl cavity fluid, and umbilical cord blood. Alternatively, exosomes may be retrieved from an organ selected from the group consisting of lung, heart, pancreas, stomach, intestine, bladder, kidney, ovary, testis, skin, colon, breast, prostate, brain, esophagus, liver, and placenta.

Assays may be performed using construct specific probes, cytometry, qRT-PCR, real-time PCR, PCR, flow cytometry, electrophoresis, mass spectrometry, or combinations thereof while the exosomes may be isolated using immunohistochemical methods such as enzyme linked immunosorbent assay (ELISA) methods. Exosomes may also be isolated by size exclusion chromatography, density gradient centrifugation, differential centrifugation, nanomembrane ultrafiltration, immunoabsorbent capture, affinity purification, microfluidic separation, or combinations thereof.

These methods afford the investigator the ability to monitor, in real time, the level of nucleic acids remaining or delivered. This is possible because the nucleic acids of the present disclosure, in some embodiments, differ from the endogenous forms due to the structural or chemical modifications.

In some embodiments, the nucleic acid may be quantified using methods such as, but not limited to, ultraviolet visible spectroscopy (UV/Vis). A non-limiting example of a UV/Vis spectrometer is a NANODROP® spectrometer (ThermoFisher, Waltham, Mass.). The quantified nucleic acid may be analyzed in order to determine if the nucleic acid may be of proper size, check that no degradation of the nucleic acid has occurred. Degradation of the nucleic acid may be checked by methods such as, but not limited to, agarose gel electrophoresis, HPLC based purification methods such as, but not limited to, strong anion exchange HPLC, weak anion exchange HPLC, reverse phase HPLC (RP-HPLC), and hydrophobic interaction HPLC (HIC-HPLC), liquid chromatography-mass spectrometry (LCMS), capillary electrophoresis (CE) and capillary gel electrophoresis (CGE).

Lipid Nanoparticles (LNPs)

In some embodiments, zoonotic disease RNA (e.g., mRNA) vaccines of the disclosure are formulated in a lipid nanoparticle (LNP). Lipid nanoparticles typically comprise ionizable cationic lipid, non-cationic lipid, sterol and PEG lipid components along with the nucleic acid cargo of interest. The lipid nanoparticles of the disclosure can be generated using components, compositions, and methods as are generally known in the art, see for example PCT/US2016/052352; PCT/US2016/068300; PCT/US2017/037551; PCT/US2015/027400; PCT/US2016/047406; PCT/US2016000129; PCT/US2016/014280; PCT/US2016/014280; PCT/US2017/038426; PCT/US2014/027077; PCT/US2014/055394; PCT/US2016/52117; PCT/US2012/069610; PCT/US2017/027492; PCT/US2016/059575 and PCT/US2016/069491, all of which are incorporated by reference herein in their entirety.

Vaccines of the present disclosure are typically formulated in lipid nanoparticle. In some embodiments, the lipid nanoparticle comprises at least one ionizable cationic lipid, at least one non-cationic lipid, at least one sterol, and/or at least one polyethylene glycol (PEG)-modified lipid.

In some embodiments, the lipid nanoparticle comprises a molar ratio of 20-60% ionizable cationic lipid. For example, the lipid nanoparticle may comprise a molar ratio of 20-50%, 20-40%, 20-30%, 30-60%, 30-50%, 30-40%, 40-60%, 40-50%, or 50-60% ionizable cationic lipid. In some embodiments, the lipid nanoparticle comprises a molar ratio of 20%, 30%, 40%, 50, or 60% ionizable cationic lipid.

In some embodiments, the lipid nanoparticle comprises a molar ratio of 5-25% non-cationic lipid. For example, the lipid nanoparticle may comprise a molar ratio of 5-20%, 5-15%, 5-10%, 10-25%, 10-20%, 10-25%, 15-25%, 15-20%, or 20-25% non-cationic lipid. In some embodiments, the lipid nanoparticle comprises a molar ratio of 5%, 10%, 15%, 20%, or 25% non-cationic lipid.

In some embodiments, the lipid nanoparticle comprises a molar ratio of 25-55% sterol. For example, the lipid nanoparticle may comprise a molar ratio of 25-50%, 25-45%, 25-40%, 25-35%, 25-30%, 30-55%, 30-50%, 30-45%, 30-40%, 30-35%, 35-55%, 35-50%, 35-45%, 35-40%, 40-55%, 40-50%, 40-45%, 45-55%, 45-50%, or 50-55% sterol. In some embodiments, the lipid nanoparticle comprises a molar ratio of 25%, 30%, 35%, 40%, 45%, 50%, or 55% sterol.

In some embodiments, the lipid nanoparticle comprises a molar ratio of 0.5-15% PEG-modified lipid. For example, the lipid nanoparticle may comprise a molar ratio of 0.5-10%, 0.5-5%, 1-15%, 1-10%, 1-5%, 2-15%, 2-10%, 2-5%, 5-15%, 5-10%, or 10-15%. In some embodiments, the lipid nanoparticle comprises a molar ratio of 0.5%, 1%, 2%, 3%, 4%, 5%, 6%, 7%, 8%, 9%, 10%, 11%, 12%, 13%, 14%, or 15% PEG-modified lipid.

In some embodiments, the lipid nanoparticle comprises a molar ratio of 20-60% ionizable cationic lipid, 5-25% non-cationic lipid, 25-55% sterol, and 0.5-15% PEG-modified lipid.

In some embodiments, an ionizable cationic lipid of the disclosure comprises a compound of Formula (I):

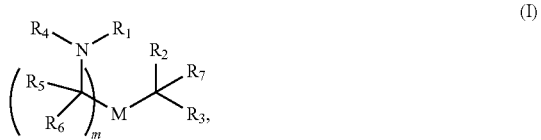

(I)

or a salt or isomer thereof, wherein:

$R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —(CH$_2$)$_n$Q, —(CH$_2$)$_n$CHQR, —CHQR, —CQ(R)$_2$, and unsubstituted $C_{1-6}$ alkyl, where Q is selected from a carbocycle, heterocycle, —OR, —O(CH$_2$)$_n$N(R)$_2$, —C(O)OR, —OC(O)R, —CX$_3$, —CX$_2$H, —CXH$_2$, —CN, —N(R)$_2$, —C(O)N(R)$_2$, —N(R)C(O)R, —N(R)S(O)$_2$R, —N(R)C(O)N(R)$_2$, —N(R)C(S)N(R)$_2$, —N(R)R$_8$, —O(CH$_2$)$_n$OR, —N(R)C(=NR$_9$)N(R)$_2$, —N(R)C(=CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=NR$_9$)N(R)$_2$, —N(OR)C(=CHR$_9$)N(R)$_2$, —C(=NR$_9$)N(R)$_2$, —C(=NR$_9$)R, —C(O)N(R)OR, and —C(R)N(R)$_2$C(O)OR, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, NO$_2$, $C_{1-6}$ alkyl, —OR, —S(O)$_2$R, —S(O)$_2$N(R)$_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of CMS alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13.

In some embodiments, a subset of compounds of Formula (I) includes those in which when $R_4$ is —(CH$_2$)$_n$Q, —(CH$_2$)$_n$CHQR, —CHQR, or —CQ(R)$_2$, then (i) Q is not —N(R)$_2$ when n is 1, 2, 3, 4 or 5, or (ii) Q is not 5, 6, or 7-membered heterocycloalkyl when n is 1 or 2.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —(CH$_2$)$_n$Q, —(CH$_2$)$_n$CHQR, —CHQR, —CQ(R)$_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —O(CH$_2$)$_n$N(R)$_2$, —C(O)OR, —OC(O)R, —CX$_3$, —CX$_2$H, —CXH$_2$, —CN, —C(O)N(R)$_2$, —N(R)C(O)R, —N(R)S(O)$_2$R, —N(R)C(O)N(R)$_2$, —N(R)C(S)N(R)$_2$, —CRN(R)$_2$C(O)OR, —N(R)R$_8$, —O(CH$_2$)$_n$OR, —N(R)C(=NR$_9$)N(R)$_2$, —N(R)C(=CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=NR$_9$)N(R)$_2$, —N(OR)C(=CHR$_9$)N(R)$_2$, —C(=NR$_9$)N(R)$_2$, —C(=NR$_9$)R, —C(O)N(R)OR, and a 5- to 14-membered heterocycloalkyl having one or more heteroatoms selected from N, O, and S which is substituted with one or more substituents selected from oxo (=O), OH, amino, mono- or di-alkylamino, and $C_{1-3}$ alkyl, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, NO$_2$, $C_{1-6}$ alkyl, —OR, —S(O)$_2$R, —S(O)$_2$N(R)$_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of CMS alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —(CH$_2$)$_n$Q, —(CH$_2$)$_n$CHQR, —CHQR, —CQ(R)$_2$, and unsubstituted $C_{1-6}$ alkyl, where Q is selected from a $C_{3-6}$ carbocycle, a 5- to 14-membered heterocycle having one or more heteroatoms selected from N, O, and S, —OR, —O(CH$_2$)$_n$N(R)$_2$, —C(O)OR, —OC(O)R, —CX$_3$, —CX$_2$H, —CXH$_2$, —CN, —C(O)N(R)$_2$, —N(R)C(O)R, —N(R)S(O)$_2$R, —N(R)C(O)N(R)$_2$, —N(R)C(S)N(R)$_2$, —CRN(R)$_2$C(O)OR, —N(R)R$_8$, —O(CH$_2$)$_n$OR, —N(R)C(=NR$_9$)N(R)$_2$, —N(R)C(=CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=NR$_9$)N(R)$_2$, —N(OR)C(=CHR$_9$)N(R)$_2$, —C(=NR$_9$)R, —C(O)N(R)OR, and —C(=NR$_9$)N(R)$_2$, and each n is independently selected from 1, 2, 3, 4, and 5; and when Q is a 5- to 14-membered heterocycle and (i) $R_4$ is —(CH$_2$)$_n$Q in which n is 1 or 2, or (ii) $R_4$ is —(CH$_2$)$_n$CHQR in which n is 1, or (iii) $R_4$ is —CHQR, and —CQ(R)$_2$, then Q is either a 5- to 14-membered heteroaryl or 8- to 14-membered heterocycloalkyl;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, NO$_2$, $C_{1-6}$ alkyl, —OR, —S(O)$_2$R, —S(O)$_2$N(R)$_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —(CH$_2$)$_n$Q, —(CH$_2$)$_n$CHQR, —CHQR, —CQ(R)$_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —O(CH$_2$)$_n$N(R)$_2$, —C(O)OR, —OC(O)R, —CX$_3$, —CX$_2$H, —CXH$_2$, —CN, —C(O)N(R)$_2$, —N(R)C(O)R, —N(R)S(O)$_2$R, —N(R)C(O)N(R)$_2$, —N(R)C(S)N(R)$_2$, —CRN(R)$_2$C(O)OR, —N(R)R$_8$, —O(CH$_2$)$_n$OR, —N(R)C(=NR$_9$)N(R)$_2$, —N(R)C(=CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=NR$_9$)N(R)$_2$, —N(OR)C(=CHR$_9$)N(R)$_2$, —C(=NR$_9$)R, —C(O)N(R)OR, and —C(=NR$_9$)N(R)$_2$, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, NO$_2$, $C_{1-6}$ alkyl, —OR, —S(O)$_2$R, —S(O)$_2$N(R)$_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{2-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is —(CH$_2$)$_n$Q or —(CH$_2$)$_n$CHQR, where Q is —N(R)$_2$, and n is selected from 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

R$_7$ is selected from the group consisting of C$_{1-3}$ alkyl, C$_{2-3}$ alkenyl, and H;

each R is independently selected from the group consisting of C$_{1-3}$ alkyl, C$_{2-3}$ alkenyl, and H;

each R' is independently selected from the group consisting of CMS alkyl, C$_{2-18}$ alkenyl, —R*YR", —YR", and H;

each R" is independently selected from the group consisting of C$_{3-14}$ alkyl and C$_{3-14}$ alkenyl;

each R* is independently selected from the group consisting of C$_{1-12}$ alkyl and C$_{1-12}$ alkenyl;

each Y is independently a C$_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which R$_1$ is selected from the group consisting of C$_{5-30}$ alkyl, C$_{5-20}$ alkenyl, —R*YR", —YR", and —R"M'R';

R$_2$ and R$_3$ are independently selected from the group consisting of C$_{1-14}$ alkyl, C$_{2-14}$ alkenyl, —R*YR", —YR", and —R*OR", or R$_2$ and R$_3$, together with the atom to which they are attached, form a heterocycle or carbocycle;

R$_4$ is selected from the group consisting of —(CH$_2$)$_n$Q, —(CH$_2$)$_n$CHQR, —CHQR, and —CQ(R)$_2$, where Q is —N(R)$_2$, and n is selected from 1, 2, 3, 4, and 5;

each R$_5$ is independently selected from the group consisting of C$_{1-3}$ alkyl, C$_{2-3}$ alkenyl, and H;

each R$_6$ is independently selected from the group consisting of C$_{1-3}$ alkyl, C$_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

R$_7$ is selected from the group consisting of C$_{1-3}$ alkyl, C$_{2-3}$ alkenyl, and H;

each R is independently selected from the group consisting of C$_{1-3}$ alkyl, C$_{2-3}$ alkenyl, and H;

each R' is independently selected from the group consisting of CMS alkyl, C$_{2-18}$ alkenyl, —R*YR", —YR", and H;

each R" is independently selected from the group consisting of C$_{3-14}$ alkyl and C$_{3-14}$ alkenyl;

each R* is independently selected from the group consisting of C$_{1-12}$ alkyl and C$_{1-12}$ alkenyl;

each Y is independently a C$_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, a subset of compounds of Formula (I) includes those of Formula (IA):

$$\text{(IA)}$$

or a salt or isomer thereof, wherein 1 is selected from 1, 2, 3, 4, and 5; m is selected from 5, 6, 7, 8, and 9; M$_1$ is a bond or M'; R$_4$ is unsubstituted C$_{1-3}$ alkyl, or —(CH$_2$)$_n$Q, in which Q is OH, —NHC(S)N(R)$_2$, —NHC(O)N(R)$_2$, —N(R)C(O)R, —N(R)S(O)$_2$R, —N(R)R$_8$, —NHC(=NR$_9$)N(R)$_2$, —NHC(=CHR$_9$)N(R)$_2$, —OC(O)N(R)$_2$, —N(R)C(O)OR, heteroaryl or heterocycloalkyl; M and M' are independently selected from —C(O)O—, —OC(O)—, —C(O)N(R')—, —P(O)(OR')O—, —S—S—, an aryl group, and a heteroaryl group; and R$_2$ and R$_3$ are independently selected from the group consisting of H, C$_{1-14}$ alkyl, and C$_{2-14}$ alkenyl.

In some embodiments, a subset of compounds of Formula (I) includes those of Formula (II):

$$\text{(II)}$$

or a salt or isomer thereof, wherein 1 is selected from 1, 2, 3, 4, and 5; M$_1$ is a bond or M'; R$_4$ is unsubstituted C$_{1-3}$ alkyl, or —(CH$_2$)$_n$Q, in which n is 2, 3, or 4, and Q is OH, —NHC(S)N(R)$_2$, —NHC(O)N(R)$_2$, —N(R)C(O)R, —N(R)S(O)$_2$R, —N(R)R$_8$, —NHC(=NR$_9$)N(R)$_2$, —NHC(=CHR$_9$)N(R)$_2$, —OC(O)N(R)$_2$, —N(R)C(O)OR, heteroaryl or heterocycloalkyl; M and M' are independently selected from —C(O)O—, —OC(O)—, —C(O)N(R')—, —P(O)(OR')O—, —S—S—, an aryl group, and a heteroaryl group; and R$_2$ and R$_3$ are independently selected from the group consisting of H, C$_{1-14}$ alkyl, and C$_{2-14}$ alkenyl.

In some embodiments, a subset of compounds of Formula (I) includes those of Formula (IIa), (IIb), (IIc), or (IIe):

$$\text{(IIa)}$$

$$\text{(IIb)}$$

$$\text{(IIc)}$$

, or

-continued

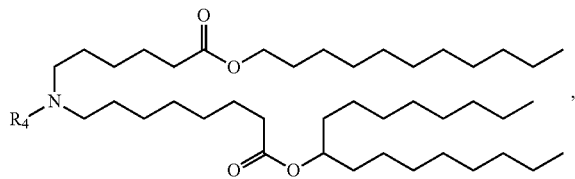
(IIe)

or a salt or isomer thereof, wherein $R_4$ is as described herein.

In some embodiments, a subset of compounds of Formula (I) includes those of Formula (IId):

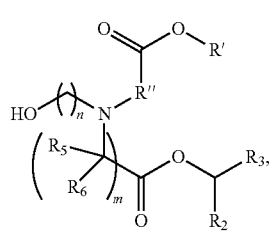
(IId)

or a salt or isomer thereof, wherein n is 2, 3, or 4; and m, R', R", and $R_2$ through $R_6$ are as described herein. For example, each of $R_2$ and $R_3$ may be independently selected from the group consisting of $C_{5-14}$ alkyl and $C_{5-14}$ alkenyl.

In some embodiments, an ionizable cationic lipid of the disclosure comprises a compound having structure:

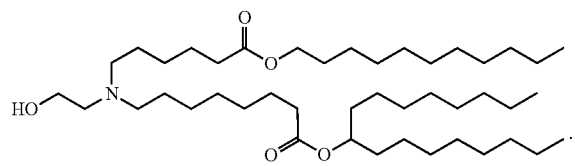
(Compound 1)

In some embodiments, an ionizable cationic lipid of the disclosure comprises a compound having structure:

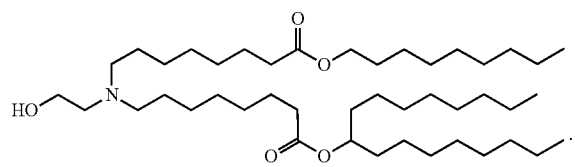
(Compound 2)

In some embodiments, a non-cationic lipid of the disclosure comprises 1,2-distearoyl-sn-glycero-3-phosphocholine (DSPC), 1,2-dioleoyl-sn-glycero-3-phosphoethanolamine (DOPE), 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2 cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), sphingomyelin, and mixtures thereof.

In some embodiments, a PEG modified lipid of the disclosure comprises a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and mixtures thereof. In some embodiments, the PEG-modified lipid is PEG-DMG, PEG-c-DOMG (also referred to as PEG-DOMG), PEG-DSG and/or PEG-DPG.

In some embodiments, a sterol of the disclosure comprises cholesterol, fecosterol, sitosterol, ergosterol, campesterol, stigmasterol, brassicasterol, tomatidine, ursolic acid, alpha-tocopherol, and mixtures thereof.

In some embodiments, a LNP of the disclosure comprises an ionizable cationic lipid of Compound 1, wherein the non-cationic lipid is DSPC, the structural lipid that is cholesterol, and the PEG lipid is PEG-DMG.

In some embodiments, a LNP of the disclosure comprises an N:P ratio of from about 2:1 to about 30:1.

In some embodiments, a LNP of the disclosure comprises an N:P ratio of about 6:1.

In some embodiments, a LNP of the disclosure comprises an N:P ratio of about 3:1.

In some embodiments, a LNP of the disclosure comprises a wt/wt ratio of the ionizable cationic lipid component to the RNA of from about 10:1 to about 100:1.

In some embodiments, a LNP of the disclosure comprises a wt/wt ratio of the ionizable cationic lipid component to the RNA of about 20:1.

In some embodiments, a LNP of the disclosure comprises a wt/wt ratio of the ionizable cationic lipid component to the RNA of about 10:1.

In some embodiments, a LNP of the disclosure has a mean diameter from about 50 nm to about 150 nm.

In some embodiments, a LNP of the disclosure has a mean diameter from about 70 nm to about 120 nm.

Multivalent Vaccines

The zoonotic disease vaccines, as provided herein, may include an RNA (e.g. mRNA) or multiple RNAs encoding two or more antigens of the same or different zoonotic disease species. In some embodiments, a zoonotic disease vaccine includes an RNA or multiple RNAs encoding two or more antigens. In some embodiments, the RNA (at least one RNA) of a zoonotic disease vaccine may encode 1, 2, 3, 4, 5, 6, 7, 8, 9, 10, 11, 12, or more antigens.

In some embodiments, two or more different RNA (e.g., mRNA) encoding antigens may be formulated in the same lipid nanoparticle. In other embodiments, two or more different RNA encoding antigens may be formulated in separate lipid nanoparticles (each RNA formulated in a single lipid nanoparticle). The lipid nanoparticles may then be combined and administered as a single vaccine composition (e.g., comprising multiple RNA encoding multiple antigens) or may be administered separately.

Broad Spectrum RNA (e.g., mRNA) Vaccines

There may be situations where persons are at risk for infection with more than one strain of LASV. RNA (e.g., mRNA) therapeutic vaccines are particularly amenable to combination vaccination approaches due to a number of factors including, but not limited to, speed of manufacture, ability to rapidly tailor vaccines to accommodate perceived geographical threat, and the like. Moreover, because the vaccines utilize the human body to produce the antigenic protein, the vaccines are amenable to the production of larger, more complex antigenic proteins, allowing for proper folding, surface expression, antigen presentation, etc. in the human subject. To protect against more than one strain of a viral infection, a combination vaccine can be administered that includes RNA (e.g., mRNA) encoding at least one antigenic polypeptide protein (or antigenic portion thereof) of a first virus and further includes RNA encoding at least one antigenic polypeptide protein (or antigenic portion thereof) of a second virus. RNA (e.g., mRNA) can be co-formulated, for example, in a single lipid nanoparticle (LNP) or can be formulated in separate LNPs for co-administration.

Combination Vaccines

The zoonotic disease vaccines, as provided herein, may include an RNA or multiple RNAs encoding two or more antigens of the same or different viral strains. Also provided herein are combination vaccines that include RNA encoding one or more zoonotic disease antigen(s) and one or more antigen(s) of a different organisms (e.g., bacterial and/or viral organism). Thus, the vaccines of the present disclosure may be combination vaccines that target one or more antigens of the same strain/species, or one or more antigens of different strains/species, e.g., antigens which induce immunity to organisms which are found in the same geographic areas where the risk of Lassa virus, Nipah virus, or beta-coronavirus infection is high or organisms to which an individual is likely to be exposed to when exposed to the virus.

Flagellin Adjuvants

Flagellin is an approximately 500 amino acid monomeric protein that polymerizes to form the flagella associated with bacterial motion. Flagellin is expressed by a variety of flagellated bacteria (*Salmonella typhimurium* for example) as well as non-flagellated bacteria (such as *Escherichia coli*). Sensing of flagellin by cells of the innate immune system (dendritic cells, macrophages, etc.) is mediated by the Toll-like receptor 5 (TLR5) as well as by Nod-like receptors (NLRs) Ipaf and Naip5. TLRs and NLRs have been identified as playing a role in the activation of innate immune response and adaptive immune response. As such, flagellin provides an adjuvant effect in a vaccine.

The nucleotide and amino acid sequences encoding known flagellin polypeptides are publicly available in the NCBI GenBank database. The flagellin sequences from *S. typhimurium, H. pylori, V. cholera, S. marcesens, S. flexneri, T. Pallidum, L. pneumophila, B. burgdorferei, C. difficile, R. meliloti, A. tumefaciens, R. lupini, B. clarridgeiae, P. Mirabilis, B. subtilus, L. monocytogenes, P. aeruginosa*, and *E. coli*, among others are known.

A flagellin polypeptide, as used herein, refers to a full length flagellin protein, immunogenic fragments thereof, and peptides having at least 50% sequence identify to a flagellin protein or immunogenic fragments thereof. Exemplary flagellin proteins include flagellin from *Salmonella typhi* (UniPro Entry number: Q56086), *Salmonella typhimurium* (A0A0C9DG09), *Salmonella enteritidis* (A0A0C9BAB7), and *Salmonella choleraesuis* (Q6V2X8).

In some embodiments, the flagellin polypeptide has at least 60%, 70%, 75%, 80%, 90%, 95%, 97%, 98%, or 99% sequence identify to a flagellin protein or immunogenic fragments thereof.

In some embodiments, the flagellin polypeptide is an immunogenic fragment. An immunogenic fragment is a portion of a flagellin protein that provokes an immune response. In some embodiments, the immune response is a TLR5 immune response. An example of an immunogenic fragment is a flagellin protein in which all or a portion of a hinge region has been deleted or replaced with other amino acids. For example, an antigenic polypeptide may be inserted in the hinge region. Hinge regions are the hypervariable regions of a flagellin. Hinge regions of a flagellin are also referred to as "D3 domain or region, "propeller domain or region," "hypervariable domain or region" and "variable domain or region." "At least a portion of a hinge region," as used herein, refers to any part of the hinge region of the flagellin, or the entirety of the hinge region. In other embodiments an immunogenic fragment of flagellin is a 20, 25, 30, 35, or 40 amino acid C-terminal fragment of flagellin.

The flagellin monomer is formed by domains D0 through D3. D0 and D1, which form the stem, are composed of tandem long alpha helices and are highly conserved among different bacteria. The D1 domain includes several stretches of amino acids that are useful for TLR5 activation. The entire D1 domain or one or more of the active regions within the domain are immunogenic fragments of flagellin. Examples of immunogenic regions within the D1 domain include residues 88-114 and residues 411-431 (in *Salmonella typhimurium* FliC flagellin). Within the 13 amino acids in the 88-100 region, at least 6 substitutions are permitted between *Salmonella* flagellin and other flagellins that still preserve TLR5 activation. Thus, immunogenic fragments of flagellin include flagellin like sequences that activate TLR5 and contain a 13 amino acid motif that is 53% or more identical to the *Salmonella* sequence in 88-100 of FliC (LQRVRELAVQSAN; SEQ ID NO: 31).

Pharmaceutical Formulations

Provided herein are compositions (e.g., pharmaceutical compositions), methods, kits and reagents for prevention or treatment of zoonotic disease in humans and other mammals, for example, zoonotic disease RNA (e.g., mRNA) vaccines can be used as therapeutic or prophylactic agents. They may be used in medicine to prevent and/or treat infectious disease.

In some embodiments, a zoonotic disease vaccine containing RNA polynucleotides as described herein can be administered to a subject (e.g., a mammalian subject, such as a human subject), and the RNA polynucleotides are translated in vivo to produce an antigenic polypeptide (antigen).

An "effective amount" of a zoonotic disease vaccine is based, at least in part, on the target tissue, target cell type, means of administration, physical characteristics of the RNA (e.g., length, nucleotide composition, and/or extent of modified nucleosides), other components of the vaccine, and other determinants, such as age, body weight, height, sex and general health of the subject. Typically, an effective amount of a zoonotic disease vaccine provides an induced or boosted immune response as a function of antigen production in the cells of the subject. In some embodiments, an effective amount of the zoonotic disease RNA vaccine containing RNA polynucleotides having at least one chemical modifications are more efficient than a composition containing a corresponding unmodified polynucleotide encoding the same antigen or a peptide antigen. Increased antigen production may be demonstrated by increased cell transfection (the percentage of cells transfected with the RNA vaccine), increased protein translation and/or expression from the polynucleotide, decreased nucleic acid degradation (as demonstrated, for example, by increased duration of protein translation from a modified polynucleotide), or altered antigen specific immune response of the host cell.

The term "pharmaceutical composition" refers to the combination of an active agent with a carrier, inert or active, making the composition especially suitable for diagnostic or therapeutic use in vivo or ex vivo. A "pharmaceutically acceptable carrier," after administered to or upon a subject, does not cause undesirable physiological effects. The carrier in the pharmaceutical composition must be "acceptable" also in the sense that it is compatible with the active ingredient and can be capable of stabilizing it. One or more solubilizing agents can be utilized as pharmaceutical carriers for delivery of an active agent. Examples of a pharmaceutically acceptable carrier include, but are not limited to, biocompatible vehicles, adjuvants, additives, and diluents to achieve a composition usable as a dosage form. Examples of other carriers include colloidal silicon oxide, magnesium stearate, cellulose, and sodium lauryl sulfate. Additional suitable pharmaceutical carriers and diluents, as well as pharmaceutical necessities for their use, are described in Remington's Pharmaceutical Sciences.

In some embodiments, RNA vaccines (including polynucleotides and their encoded polypeptides) in accordance with the present disclosure may be used for treatment or prevention of zoonotic disease. Zoonotic disease RNA vaccines may be administered prophylactically or therapeutically as part of an active immunization scheme to healthy individuals or early in infection during the incubation phase or during active infection after onset of symptoms. In some embodiments, the amount of RNA vaccines of the present disclosure provided to a cell, a tissue or a subject may be an amount effective for immune prophylaxis.

Zoonotic disease RNA (e.g., mRNA) vaccines may be administered with other prophylactic or therapeutic compounds. As a non-limiting example, a prophylactic or therapeutic compound may be an adjuvant or a booster. As used herein, when referring to a prophylactic composition, such as a vaccine, the term "booster" refers to an extra administration of the prophylactic (vaccine) composition. A booster (or booster vaccine) may be given after an earlier administration of the prophylactic composition. The time of administration between the initial administration of the prophylactic composition and the booster may be, but is not limited to, 1 minute, 2 minutes, 3 minutes, 4 minutes, 5 minutes, 6 minutes, 7 minutes, 8 minutes, 9 minutes, 10 minutes, 15 minutes, 20 minutes 35 minutes, 40 minutes, 45 minutes, 50 minutes, 55 minutes, 1 hour, 2 hours, 3 hours, 4 hours, 5 hours, 6 hours, 7 hours, 8 hours, 9 hours, 10 hours, hours, 12 hours, 13 hours, 14 hours, 15 hours, 16 hours, 17 hours, 18 hours, 19 hours, 20 hours, 21 hours, 22 hours, 23 hours, 1 day, 36 hours, 2 days, 3 days, 4 days, 5 days, 6 days, 1 week, 10 days, 2 weeks, 3 weeks, 1 month, 2 months, 3 months, 4 months, 5 months, 6 months, 7 months, 8 months, 9 months, 10 months, 11 months, 1 year, 18 months, 2 years, 3 years, 4 years, years, 6 years, 7 years, 8 years, 9 years, 10 years, 11 years, 12 years, 13 years, 14 years, 15 years, 16 years, 17 years, 18 years, 19 years, 20 years, 25 years, 30 years, 35 years, 40 years, 45 years, 50 years, 55 years, 60 years, 65 years, 70 years, 75 years, 80 years, 85 years, 90 years, 95 years or more than 99 years. In exemplary embodiments, the time of administration between the initial administration of the prophylactic composition and the booster may be, but is not limited to, 1 week, 2 weeks, 3 weeks, 1 month, 2 months, 3 months, 6 months or 1 year.

In some embodiments, zoonotic disease RNA vaccines may be administered intramuscularly, intranasally or intradermally, similarly to the administration of inactivated vaccines known in the art.

The zoonotic disease RNA vaccines may be utilized in various settings depending on the prevalence of the infection or the degree or level of unmet medical need. As a non-limiting example, the RNA vaccines may be utilized to treat and/or prevent a variety of infectious disease. RNA vaccines have superior properties in that they produce much larger antibody titers, better neutralizing immunity, produce more durable immune responses, and/or produce responses earlier than commercially available vaccines.

Provided herein are pharmaceutical compositions including zoonotic disease RNA vaccines and RNA vaccine compositions and/or complexes optionally in combination with one or more pharmaceutically acceptable excipients.

Zoonotic disease RNA (e.g., mRNA) vaccines may be formulated or administered alone or in conjunction with one or more other components. For instance, zoonotic disease RNA vaccines (vaccine compositions) may comprise other components including, but not limited to, adjuvants.

In some embodiments, zoonotic disease RNA vaccines do not include an adjuvant (they are adjuvant free).

Zoonotic disease RNA (e.g., mRNA) vaccines may be formulated or administered in combination with one or more pharmaceutically-acceptable excipients. In some embodiments, vaccine compositions comprise at least one additional active substances, such as, for example, a therapeutically-active substance, a prophylactically-active substance, or a combination of both. Vaccine compositions may be sterile, pyrogen-free or both sterile and pyrogen-free. General considerations in the formulation and/or manufacture of pharmaceutical agents, such as vaccine compositions, may be found, for example, in Remington: The Science and Practice of Pharmacy 21st ed., Lippincott Williams & Wilkins, 2005 (incorporated herein by reference in its entirety).

In some embodiments, zoonotic disease RNA vaccines are administered to humans, human patients or subjects. For the purposes of the present disclosure, the phrase "active ingredient" generally refers to the RNA vaccines or the polynucleotides contained therein, for example, RNA polynucleotides (e.g., mRNA polynucleotides) encoding antigens.

Formulations of the vaccine compositions described herein may be prepared by any method known or hereafter developed in the art of pharmacology. In general, such preparatory methods include the step of bringing the active ingredient (e.g., mRNA polynucleotide) into association with an excipient and/or one or more other accessory ingredients, and then, if necessary and/or desirable, dividing, shaping and/or packaging the product into a desired single- or multi-dose unit.

Relative amounts of the active ingredient, the pharmaceutically acceptable excipient, and/or any additional ingredients in a pharmaceutical composition in accordance with the disclosure will vary, depending upon the identity, size, and/or condition of the subject treated and further depending upon the route by which the composition is to be administered. By way of example, the composition may comprise between 0.1% and 100%, e.g., between 0.5 and 50%, between 1-30%, between 5-80%, at least 80% (w/w) active ingredient.

In some embodiments, zoonotic disease RNA vaccines are formulated using one or more excipients to: (1) increase stability; (2) increase cell transfection; (3) permit the sustained or delayed release (e.g., from a depot formulation); (4) alter the biodistribution (e.g., target to specific tissues or cell types); (5) increase the translation of encoded protein in vivo; and/or (6) alter the release profile of encoded protein (antigen) in vivo. In addition to traditional excipients such as any and all solvents, dispersion media, diluents, or other liquid vehicles, dispersion or suspension aids, surface active agents, isotonic agents, thickening or emulsifying agents, preservatives, excipients can include, without limitation, lipidoids, liposomes, lipid nanoparticles, polymers, lipoplexes, core-shell nanoparticles, peptides, proteins, cells transfected with zoonotic disease RNA vaccines (e.g., for transplantation into a subject), hyaluronidase, nanoparticle mimics and combinations thereof.

Dosing/Administration

Provided herein are compositions (e.g., pharmaceutical compositions), methods, kits and reagents for prevention and/or treatment of zoonotic disease in humans and other mammals, zoonotic disease RNA vaccines can be used as therapeutic or prophylactic agents. In some aspects, the RNA vaccines of the disclosure are used to provide prophylactic protection from zoonotic disease. In some aspects, the RNA vaccines of the disclosure are used to treat a zoonotic disease infection. In some embodiments, the zoonotic disease vaccines of the present disclosure are used in the priming of immune effector cells, for example, to activate peripheral blood mononuclear cells (PBMCs) ex vivo, which are then infused (re-infused) into a subject.

A subject may be any mammal, including non-human primate and human subjects. Typically, a subject is a human subject.

In some embodiments, the zoonotic disease vaccines are administered to a subject (e.g., a mammalian subject, such as a human subject) in an effective amount to induce an antigen-specific immune response. The RNA encoding the zoonotic disease antigen is expressed and translated in vivo to produce the antigen, which then stimulates an immune response in the subject.

Prophylactic protection from zoonotic disease can be achieved following administration of a zoonotic disease RNA vaccine of the present disclosure. Vaccines can be administered once, twice, three times, four times or more but it is likely sufficient to administer the vaccine once (optionally followed by a single booster). It is possible, although less desirable, to administer the vaccine to an infected individual to achieve a therapeutic response. Dosing may need to be adjusted accordingly.

A method of eliciting an immune response in a subject against zoonotic disease is provided in aspects of the present disclosure. The method involves administering to the subject a zoonotic disease RNA vaccine comprising at least one RNA (e.g., mRNA) having an open reading frame encoding at least one zoonotic disease antigen, thereby inducing in the subject an immune response specific to zoonotic disease antigen, wherein anti-antigen antibody titer in the subject is increased following vaccination relative to anti-antigen antibody titer in a subject vaccinated with a prophylactically effective dose of a traditional vaccine against the zoonotic disease. An "anti-antigen antibody" is a serum antibody the binds specifically to the antigen.

A prophylactically effective dose is an effective dose that prevents infection with the virus at a clinically acceptable level. In some embodiments, the effective dose is a dose listed in a package insert for the vaccine. A traditional vaccine, as used herein, refers to a vaccine other than the mRNA vaccines of the present disclosure. For instance, a traditional vaccine includes, but is not limited, to live microorganism vaccines, killed microorganism vaccines, subunit vaccines, protein antigen vaccines, DNA vaccines, virus like particle (VLP) vaccines, etc. In exemplary embodiments, a traditional vaccine is a vaccine that has achieved regulatory approval and/or is registered by a national drug regulatory body, for example the Food and Drug Administration (FDA) in the United States or the European Medicines Agency (EMA).

In some embodiments, the anti-antigen antibody titer in the subject is increased 1 log to log following vaccination relative to anti-antigen antibody titer in a subject vaccinated with a prophylactically effective dose of a traditional vaccine against the zoonotic disease or an unvaccinated subject. In some embodiments, the anti-antigen antibody titer in the subject is increased 1 log, 2 log, 3 log, 4 log, 5 log, or 10 log following vaccination relative to anti-antigen antibody titer in a subject vaccinated with a prophylactically effective dose of a traditional vaccine against the zoonotic disease or an unvaccinated subject.

A method of eliciting an immune response in a subject against a zoonotic disease is provided in other aspects of the disclosure. The method involves administering to the subject a zoonotic disease RNA vaccine comprising at least one RNA polynucleotide having an open reading frame encoding at least one zoonotic disease antigen, thereby inducing in the subject an immune response specific to zoonotic disease antigen, wherein the immune response in the subject is equivalent to an immune response in a subject vaccinated with a traditional vaccine against the zoonotic disease at 2 times to 100 times the dosage level relative to the RNA vaccine.

In some embodiments, the immune response in the subject is equivalent to an immune response in a subject vaccinated with a traditional vaccine at twice the dosage level relative to the zoonotic disease RNA vaccine. In some embodiments, the immune response in the subject is equivalent to an immune response in a subject vaccinated with a traditional vaccine at three times the dosage level relative to the zoonotic disease RNA vaccine. In some embodiments, the immune response in the subject is equivalent to an immune response in a subject vaccinated with a traditional vaccine at 4 times, 5 times, 10 times, 50 times, or 100 times the dosage level relative to the zoonotic disease RNA vaccine. In some embodiments, the immune response in the subject is equivalent to an immune response in a subject vaccinated with a traditional vaccine at 10 times to 1000 times the dosage level relative to the zoonotic disease RNA vaccine. In some embodiments, the immune response in the subject is equivalent to an immune response in a subject vaccinated with a traditional vaccine at 100 times to 1000 times the dosage level relative to the zoonotic disease RNA vaccine.

In other embodiments, the immune response is assessed by determining [protein] antibody titer in the subject. In other embodiments, the ability of serum or antibody from an immunized subject is tested for its ability to neutralize viral uptake or reduce zoonotic disease transformation of human B lymphocytes. In other embodiments, the ability to promote a robust T cell response(s) is measured using art recognized techniques.

Other aspects the disclosure provide methods of eliciting an immune response in a subject against a zoonotic disease by administering to the subject a zoonotic disease RNA vaccine comprising at least one RNA polynucleotide having an open reading frame encoding at least one zoonotic disease antigen, thereby inducing in the subject an immune response specific to zoonotic disease antigen, wherein the immune response in the subject is induced 2 days to 10 weeks earlier relative to an immune response induced in a subject vaccinated with a prophylactically effective dose of a traditional vaccine against the zoonotic disease. In some embodiments, the immune response in the subject is induced in a subject vaccinated with a prophylactically effective dose of a traditional vaccine at 2 times to 100 times the dosage level relative to the RNA vaccine.

In some embodiments, the immune response in the subject is induced 2 days, 3 days, 1 week, 2 weeks, 3 weeks, 5 weeks, or 10 weeks earlier relative to an immune response induced in a subject vaccinated with a prophylactically effective dose of a traditional vaccine.

Also provided herein are methods of eliciting an immune response in a subject against a zoonotic disease by administering to the subject a zoonotic disease RNA vaccine having an open reading frame encoding a first antigen, wherein the RNA polynucleotide does not include a stabilization element, and wherein an adjuvant is not co-formulated or co-administered with the vaccine.

Zoonotic disease RNA (e.g., mRNA) vaccines may be administered by any route which results in a therapeutically effective outcome. These include, but are not limited, to intradermal, intramuscular, intranasal, and/or subcutaneous administration. The present disclosure provides methods comprising administering RNA vaccines to a subject in need thereof. The exact amount required will vary from subject to subject, depending on the species, age, and general condition of the subject, the severity of the disease, the particular composition, its mode of administration, its mode of activity, and the like, zoonotic disease RNA (e.g., mRNA) vaccines compositions are typically formulated in dosage unit form for ease of administration and uniformity of dosage. It will be understood, however, that the total daily usage of zoonotic disease RNA (e.g., mRNA) vaccines compositions may be decided by the attending physician within the scope of sound medical judgment. The specific therapeutically effective, prophylactically effective, or appropriate imaging dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The effective amount of a zoonotic disease vaccine, as provided herein, may be as low as 20 µg, administered for example as a single dose or as two 10 µg doses. In some embodiments, the effective amount is a total dose of 20 µg-200 µg. For example, the effective amount may be a total dose of 20 µg, 25 µg, 30 µg, 35 µg, 40 µg, 45 µg, 50 µg, 55 µg, 60 µg, 65 µg, 70 µg, 75 µg, 80 µg, 85 µg, 90 µg, 95 µg, 100 µg, 110 µg, 120 µg, 130 µg, 140 µg, 150 µg, 160 µg, 170 µg, 180 µg, 190 µg or 200 µg. In some embodiments, the effective amount is a total dose of 25 µg-200 µg. In some embodiments, the effective amount is a total dose of 50 µg-200 µg.

In some embodiments, zoonotic disease RNA (e.g., mRNA) vaccines compositions may be administered at dosage levels sufficient to deliver 0.0001 mg/kg to 100 mg/kg, 0.001 mg/kg to 0.05 mg/kg, 0.005 mg/kg to 0.05 mg/kg, 0.001 mg/kg to 0.005 mg/kg, 0.05 mg/kg to 0.5 mg/kg, 0.01 mg/kg to 50 mg/kg, 0.1 mg/kg to 40 mg/kg, 0.5 mg/kg to 30 mg/kg, 0.01 mg/kg to 10 mg/kg, 0.1 mg/kg to 10 mg/kg, or 1 mg/kg to 25 mg/kg, of subject body weight per day, one or more times a day, per week, per month, etc. to obtain the desired therapeutic, diagnostic, prophylactic, or imaging effect (see e.g., the range of unit doses described in International Publication No. WO2013/078199, herein incorporated by reference in its entirety). The desired dosage may be delivered three times a day, two times a day, once a day, every other day, every third day, every week, every two weeks, every three weeks, every four weeks, every 2 months, every three months, every 6 months, etc. In certain embodiments, the desired dosage may be delivered using multiple administrations (e.g., two, three, four, five, six, seven, eight, nine, ten, eleven, twelve, thirteen, fourteen, or more administrations). When multiple administrations are employed, split dosing regimens such as those described herein may be used. In exemplary embodiments, zoonotic disease RNA (e.g., mRNA) vaccines compositions may be administered at dosage levels sufficient to deliver 0.0005 mg/kg to 0.01 mg/kg, e.g., about 0.0005 mg/kg to about 0.0075 mg/kg, e.g., about 0.0005 mg/kg, about 0.001 mg/kg, about 0.002 mg/kg, about 0.003 mg/kg, about 0.004 mg/kg or about 0.005 mg/kg.

In some embodiments, zoonotic disease RNA (e.g., mRNA) vaccine compositions may be administered once or twice (or more) at dosage levels sufficient to deliver 0.025 mg/kg to 0.250 mg/kg, 0.025 mg/kg to 0.500 mg/kg, 0.025 mg/kg to 0.750 mg/kg, or 0.025 mg/kg to 1.0 mg/kg.

In some embodiments, zoonotic disease RNA (e.g., mRNA) vaccine compositions may be administered twice (e.g., Day 0 and Day 7, Day 0 and Day 14, Day 0 and Day 21, Day 0 and Day 28, Day 0 and Day 60, Day 0 and Day 90, Day 0 and Day 120, Day 0 and Day 150, Day 0 and Day 180, Day 0 and 3 months later, Day 0 and 6 months later, Day 0 and 9 months later, Day 0 and 12 months later, Day 0 and 18 months later, Day 0 and 2 years later, Day 0 and 5 years later, or Day 0 and 10 years later) at a total dose of or at dosage levels sufficient to deliver a total dose of 0.0100 mg, 0.025 mg, 0.050 mg, 0.075 mg, 0.100 mg, 0.125 mg, 0.150 mg, 0.175 mg, 0.200 mg, 0.225 mg, 0.250 mg, 0.275 mg, 0.300 mg, 0.325 mg, 0.350 mg, 0.375 mg, 0.400 mg, 0.425 mg, 0.450 mg, 0.475 mg, 0.500 mg, 0.525 mg, 0.550 mg, 0.575 mg, 0.600 mg, 0.625 mg, 0.650 mg, 0.675 mg, 0.700 mg, 0.725 mg, 0.750 mg, 0.775 mg, 0.800 mg, 0.825 mg, 0.850 mg, 0.875 mg, 0.900 mg, 0.925 mg, 0.950 mg, 0.975 mg, or 1.0 mg. Higher and lower dosages and frequency of administration are encompassed by the present disclosure. For example, a zoonotic disease RNA (e.g., mRNA) vaccine composition may be administered three or four times.

In some embodiments, zoonotic disease RNA (e.g., mRNA) vaccine compositions may be administered twice (e.g., Day 0 and Day 7, Day 0 and Day 14, Day 0 and Day 21, Day 0 and Day 28, Day 0 and Day 60, Day 0 and Day 90, Day 0 and Day 120, Day 0 and Day 150, Day 0 and Day 180, Day 0 and 3 months later, Day 0 and 6 months later, Day 0 and 9 months later, Day 0 and 12 months later, Day 0 and 18 months later, Day 0 and 2 years later, Day 0 and 5 years later, or Day 0 and 10 years later) at a total dose of or at dosage levels sufficient to deliver a total dose of 0.010 mg, 0.025 mg, 0.100 mg or 0.400 mg.

In some embodiments, the zoonotic disease RNA (e.g., mRNA) vaccine for use in a method of vaccinating a subject is administered the subject a single dosage of between 10 µg/kg and 400 µg/kg of the nucleic acid vaccine in an effective amount to vaccinate the subject. In some embodiments, the RNA vaccine for use in a method of vaccinating a subject is administered the subject a single dosage of between 10 μg and 400 μg of the nucleic acid vaccine in an effective amount to vaccinate the subject. In some embodiments, a zoonotic disease RNA (e.g., mRNA) vaccine for use in a method of vaccinating a subject is administered to the subject as a single dosage of 25-1000 μg (e.g., a single dosage of mRNA encoding a zoonotic disease antigen). In some embodiments, a zoonotic disease RNA vaccine is administered to the subject as a single dosage of 25, 50, 100, 150, 200, 250, 300, 350, 400, 450, 500, 550, 600, 650, 700, 750, 800, 850, 900, 950 or 1000 μg. For example, a zoonotic disease RNA vaccine may be administered to a subject as a single dose of 25-100, 25-500, 50-100, 50-500, 50-1000, 100-500, 100-1000, 250-500, 250-1000, or 500-1000 μg. In some embodiments, a zoonotic disease RNA (e.g., mRNA) vaccine for use in a method of vaccinating a subject is administered to the subject as two dosages, the combination of which equals 25-1000 μg of the zoonotic disease RNA (e.g., mRNA) vaccine.

AN zoonotic disease RNA (e.g., mRNA) vaccine pharmaceutical composition described herein can be formulated into a dosage form described herein, such as an intranasal, intratracheal, or injectable (e.g., intravenous, intraocular, intravitreal, intramuscular, intradermal, intracardiac, intraperitoneal, and subcutaneous).

Vaccine Efficacy

Some aspects of the present disclosure provide formulations of the zoonotic disease RNA (e.g., mRNA) vaccine, wherein the zoonotic disease RNA vaccine is formulated in an effective amount to produce an antigen specific immune response in a subject (e.g., production of antibodies specific to an anti-zoonotic disease antigen). "An effective amount" is a dose of an zoonotic disease RNA (e.g., mRNA) vaccine effective to produce an antigen-specific immune response. Also provided herein are methods of inducing an antigen-specific immune response in a subject.

As used herein, an immune response to a vaccine or LNP of the present disclosure is the development in a subject of a humoral and/or a cellular immune response to a (one or more) zoonotic disease protein(s) present in the vaccine. For purposes of the present disclosure, a "humoral" immune response refers to an immune response mediated by antibody molecules, including, e.g., secretory (IgA) or IgG molecules, while a "cellular" immune response is one mediated by T-lymphocytes (e.g., CD4+ helper and/or CD8+ T cells (e.g., CTLs) and/or other white blood cells. One important aspect of cellular immunity involves an antigen-specific response by cytolytic T-cells (CTLs). CTLs have specificity for peptide antigens that are presented in association with proteins encoded by the major histocompatibility complex (MHC) and expressed on the surfaces of cells. CTLs help induce and promote the destruction of intracellular microbes or the lysis of cells infected with such microbes. Another aspect of cellular immunity involves and antigen-specific response by helper T-cells. Helper T-cells act to help stimulate the function, and focus the activity nonspecific effector cells against cells displaying peptide antigens in association with MHC molecules on their surface. A cellular immune response also leads to the production of cytokines, chemokines, and other such molecules produced by activated T-cells and/or other white blood cells including those derived from CD4+ and CD8+ T-cells.

In some embodiments, the antigen-specific immune response is characterized by measuring an anti-zoonotic disease antigen antibody titer produced in a subject administered an zoonotic disease RNA (e.g., mRNA) vaccine as provided herein. An antibody titer is a measurement of the amount of antibodies within a subject, for example, antibodies that are specific to a particular antigen (e.g., an anti-zoonotic disease antigen) or epitope of an antigen. Antibody titer is typically expressed as the inverse of the greatest dilution that provides a positive result. Enzyme-linked immunosorbent assay (ELISA) is a common assay for determining antibody titers, for example.

In some embodiments, an antibody titer is used to assess whether a subject has had an infection or to determine whether immunizations are required. In some embodiments, an antibody titer is used to determine the strength of an autoimmune response, to determine whether a booster immunization is needed, to determine whether a previous vaccine was effective, and to identify any recent or prior infections. In accordance with the present disclosure, an antibody titer may be used to determine the strength of an immune response induced in a subject by the zoonotic disease RNA (e.g., mRNA) vaccine.

In some embodiments, an anti-zoonotic disease antigen antibody titer produced in a subject is increased by at least 1 log relative to a control. For example, anti-zoonotic disease antigen antibody titer produced in a subject may be increased by at least 1.5, at least 2, at least 2.5, or at least 3 log relative to a control. In some embodiments, the anti-zoonotic disease antigen antibody titer produced in the subject is increased by 1, 1.5, 2, 2.5 or 3 log relative to a control. In some embodiments, the anti-zoonotic disease antigen antibody titer produced in the subject is increased by 1-3 log relative to a control. For example, the anti-zoonotic disease antigen antibody titer produced in a subject may be increased by 1-1.5, 1-2, 1-2.5, 1-3, 1.5-2, 1.5-2.5, 1.5-3, 2-2.5, 2-3, or 2.5-3 log relative to a control.

In some embodiments, the anti-zoonotic disease antigen antibody titer produced in a subject is increased at least 2 times relative to a control. For example, the anti-zoonotic disease antigen antibody titer produced in a subject may be increased at least 3 times, at least 4 times, at least 5 times, at least 6 times, at least 7 times, at least 8 times, at least 9 times, or at least 10 times relative to a control. In some embodiments, the anti-zoonotic disease antigen antibody titer produced in the subject is increased 2, 3, 4, 5, 6, 7, 8, 9, or 10 times relative to a control. In some embodiments, the anti-zoonotic disease antigen antibody titer produced in a subject is increased 2-10 times relative to a control. For example, the anti-zoonotic disease antigen antibody titer produced in a subject may be increased 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9, or 9-10 times relative to a control.

A control, in some embodiments, is the anti-zoonotic disease antigen antibody titer produced in a subject who has not been administered an zoonotic disease RNA (e.g., mRNA) vaccine. In some embodiments, a control is an anti-zoonotic disease antigen antibody titer produced in a subject administered a recombinant or purified zoonotic disease protein vaccine. Recombinant protein vaccines typically include protein antigens that either have been produced in a heterologous expression system (e.g., bacteria or yeast) or purified from large amounts of the pathogenic organism.

In some embodiments, the ability of an zoonotic disease vaccine to be effective is measured in a murine model. For example, the zoonotic disease vaccines may be administered to a murine model and the murine model assayed for induction of neutralizing antibody titers. Viral challenge studies may also be used to assess the efficacy of a vaccine of the present disclosure. For example, the zoonotic disease vaccines may be administered to a murine model, the murine model challenged with zoonotic disease antigen, and the murine model assayed for survival and/or immune response (e.g., neutralizing antibody response, T cell response (e.g., cytokine response)).

In some embodiments, an effective amount of an zoonotic disease RNA (e.g., mRNA) vaccine is a dose that is reduced compared to the standard of care dose of a recombinant zoonotic disease protein vaccine. A "standard of care," as provided herein, refers to a medical or psychological treatment guideline and can be general or specific. "Standard of care" specifies appropriate treatment based on scientific evidence and collaboration between medical professionals involved in the treatment of a given condition. It is the diagnostic and treatment process that a physician/clinician should follow for a certain type of patient, illness or clinical circumstance. A "standard of care dose," as provided herein, refers to the dose of a recombinant or purified zoonotic disease protein vaccine, or a live attenuated or inactivated zoonotic disease vaccine, or an zoonotic disease VLP vaccine, that a physician/clinician or other medical professional would administer to a subject to treat or prevent a zoonotic disease, or a zoonotic disease-related condition, while following the standard of care guideline for treating or preventing a zoonotic disease, or a zoonotic disease related condition.

In some embodiments, the anti-zoonotic disease antigen antibody titer produced in a subject administered an effective amount of a zoonotic disease RNA vaccine is equivalent to an anti-zoonotic disease antigen antibody titer produced in a control subject administered a standard of care dose of a recombinant or purified zoonotic disease protein vaccine, or a live attenuated or inactivated zoonotic disease vaccine, or a zoonotic disease VLP vaccine.

In some embodiments, an effective amount of a zoonotic disease RNA (e.g., mRNA) vaccine is a dose equivalent to an at least 2-fold reduction in a standard of care dose of a recombinant or purified zoonotic disease protein vaccine. For example, an effective amount of a zoonotic disease RNA vaccine may be a dose equivalent to an at least 3-fold, at least 4-fold, at least 5-fold, at least 6-fold, at least 7-fold, at least 8-fold, at least 9-fold, or at least 10-fold reduction in a standard of care dose of a recombinant or purified zoonotic disease protein vaccine. In some embodiments, an effective amount of a zoonotic disease RNA vaccine is a dose equivalent to an at least at least 100-fold, at least 500-fold, or at least 1000-fold reduction in a standard of care dose of a recombinant or purified zoonotic disease protein vaccine. In some embodiments, an effective amount of a zoonotic disease RNA vaccine is a dose equivalent to a 2-, 3-, 4-, 5-, 6-, 7-, 8-, 9-, 10-, 20-, 50-, 100-, 250-, 500-, or 1000-fold reduction in a standard of care dose of a recombinant or purified zoonotic disease protein vaccine. In some embodiments, the anti-zoonotic disease antigen antibody titer produced in a subject administered an effective amount of a zoonotic disease RNA vaccine is equivalent to an anti-zoonotic disease antigen antibody titer produced in a control subject administered the standard of care dose of a recombinant or protein zoonotic disease protein vaccine, or a live attenuated or inactivated zoonotic disease vaccine, or a zoonotic disease VLP vaccine. In some embodiments, an effective amount of a zoonotic disease RNA (e.g., mRNA) vaccine is a dose equivalent to a 2-fold to 1000-fold (e.g., 2-fold to 100-fold, 10-fold to 1000-fold) reduction in the standard of care dose of a recombinant or purified zoonotic disease protein vaccine, wherein the anti-zoonotic disease antigen antibody titer produced in the subject is equivalent to an anti-zoonotic disease antigen antibody titer produced in a control subject administered the standard of care dose of a recombinant or purified zoonotic disease protein vaccine, or a live attenuated or inactivated zoonotic disease vaccine, or a zoonotic disease VLP vaccine.

In some embodiments, the effective amount of a zoonotic disease RNA (e.g., mRNA) vaccine is a dose equivalent to a 2 to 1000-, 2 to 900-, 2 to 800-, 2 to 700-, 2 to 600-, 2 to 500-, 2 to 400-, 2 to 300-, 2 to 200-, 2 to 100-, 2 to 90-, 2 to 80-, 2 to 70-, 2 to 60-, 2 to 50-, 2 to 40-, 2 to 30-, 2 to 20-, 2 to 10-, 2 to 9-, 2 to 8-, 2 to 7-, 2 to 6-, 2 to 5-, 2 to 4-, 2 to 3-, 3 to 1000-, 3 to 900-, 3 to 800-, 3 to 700-, 3 to 600-, 3 to 500-, 3 to 400-, 3 to 3 to 00-, 3 to 200-, 3 to 100-, 3 to 90-, 3 to 80-, 3 to 70-, 3 to 60-, 3 to 50-, 3 to 40-, 3 to 30-, 3 to 20-, 3 to 10-, 3 to 9-, 3 to 8-, 3 to 7-, 3 to 6-, 3 to 5-, 3 to 4-, 4 to 1000-, 4 to 900-, 4 to 800-, 4 to 700-, 4 to 600-, 4 to 500-, 4 to 400-, 4 to 300-, 4 to 200-, 4 to 100-, 4 to 90-, 4 to 80-, 4 to 70-, 4 to 60-, 4 to 50, 4 to 40-, 4 to 30-, 4 to 20-, 4 to 10-, 4 to 9-, 4 to 8-, 4 to 7-, 4 to 6-, 4 to 5-, 4 to 4-, 5 to 1000-, 5 to 900-, 5 to 800-, 5 to 700-, 5 to 600-, 5 to 500-, 5 to 400-, 5 to 300-, 5 to 200-, 5 to 100-, 5 to 90-, 5 to 80-, 5 to 70-, 5 to 60-, 5 to 50-, 5 to 40-, 5 to 30-, 5 to 20-, 5 to 10-, 5 to 9-, 5 to 8, 5 to 7-, 5 to 6-, 6 to 1000-, 6 to 900-, 6 to 800-, 6 to 700-, 6 to 600-, 6 to 500-, 6 to 400-, 6 to 300-, 6 to 200-, 6 to 100-, 6 to 90-, 6 to 80-, 6 to 70-, 6 to 60-, 6 to 50-, 6 to 40-, 6 to 30-, 6 to 20-, 6 to 10-, 6 to 9-, 6 to 8-, 6 to 7-, 7 to 1000-, 7 to 900-, 7 to 800-, 7 to 700-, 7 to 600-, 7 to 500-, 7 to 400-, 7 to 300-, 7 to 200-, 7 to 100-, 7 to 90-, 7 to 80-, 7 to 70-, 7 to 60-, 7 to 50-, 7 to 40-, 7 to 30-, 7 to 20-, 7 to 10-, 7 to 9-, 7 to 8-, 8 to 1000-, 8 to 900-, 8 to 800-, 8 to 700-, 8 to 600-, 8 to 500-, 8 to 400-, 8 to 300-, 8 to 200-, 8 to 100-, 8 to 90-, 8 to 80-, 8 to 70-, 8 to 60-, 8 to 50-, 8 to 40-, 8 to 30-, 8 to 20-, 8 to 10-, 8 to 9-, 9 to 1000-, 9 to 900-, 9 to 800-, 9 to 700-, 9 to 600-, 9 to 500-, 9 to 400-, 9 to 300-, 9 to 200-, 9 to 100-, 9 to 90-, 9 to 80-, 9 to 70-, 9 to 60-, 9 to 50-, 9 to 40-, 9 to 30-, 9 to 20-, 9 to 10-, 10 to 1000-, 10 to 900-, 10 to 800-, 10 to 700-, 10 to 600-, 10 to 500-, 10 to 400-, 10 to 300-, 10 to 200-, 10 to 100-, 10 to 90-, 10 to 80-, 10 to 70-, 10 to 60-, 10 to 50-, 10 to 40-, 10 to 30-, 10 to 20-, 20 to 1000-, 20 to 900-, 20 to 800-, 20 to 700-, 20 to 600-, 20 to 500-, 20 to 400-, 20 to 300-, 20 to 200-, 20 to 100-, 20 to 90-, 20 to 80-, 20 to 70-, 20 to 60-, 20 to 50-, 20 to 40-, 20 to 30-, 30 to 1000-, 30 to 900-, 30 to 800-, 30 to 700-, 30 to 600-, 30 to 500-, 30 to 400-, 30 to 300-, 30 to 200-, 30 to 100-, 30 to 90-, 30 to 80-, 30 to 70-, 30 to 60-, 30 to 50-, 30 to 40-, 40 to 1000-, 40 to 900-, 40 to 800-, 40 to 700-, 40 to 600-, 40 to 500-, 40 to 400-, 40 to 300-, 40 to 200-, 40 to 100-, 40 to 90-, 40 to 80-, 40 to 70-, 40 to 60-, 40 to 50-, 50 to 1000-, 50 to 900-, 50 to 800-, 50 to 700-, 50 to 600-, 50 to 500-, 50 to 400-, 50 to 300-, 50 to 200-, 50 to 100-, 50 to 90-, 50 to 80-, 50 to 70-, 50 to 60-, 60 to 1000-, 60 to 900-, 60 to 800-, 60 to 700-, 60 to 600-, 60 to 500-, 60 to 400-, 60 to 300-, 60 to 200-, 60 to 100-, 60 to 90-, 60 to 80-, 60 to 70-, 70 to 1000-, 70 to 900-, 70 to 800-, 70 to 700-, 70 to 600-, 70 to 500-, 70 to 400-, 70 to 300-, 70 to 200-, 70 to 100-, 70 to 90-, 70 to 80-, 80 to 1000-, 80 to 900-, 80 to 800-, 80 to 700-, 80 to 600-, 80 to 500-, 80 to 400-, 80 to 300-, 80 to 200-, 80 to 100-, 80 to 90-, 90 to 1000-, 90 to 900-, 90 to 800-, 90 to 700-, 90 to 600-, 90 to 500-, 90 to 400-, 90 to 300-, 90 to 200-, 90 to 100-, 100 to 1000-, 100 to 900-, 100 to 800-, 100 to 700-, 100 to 600-, 100 to 500-, 100 to 400-, 100 to 300-, 100 to 200-, 200 to 1000-, 200 to 900-, 200 to 800-, 200 to 700-, 200 to 600-, 200 to 500-, 200 to 400-, 200 to 300-, 300 to 1000-, 300 to 900-, 300 to 800-, 300 to 700-, 300 to 600-, 300 to 500-, 300 to 400-, 400 to 1000-, 400 to 900-, 400 to 800-, 400 to 700-, 400 to 600-, 400 to 500-, 500 to 1000-, 500 to 900-, 500 to 800-, 500 to 700-, 500 to 600-, 600 to 1000-, 600 to 900-, 600 to 800-, 600 to 700-, 700 to 1000-, 700 to 900-, 700 to 800-, 800 to 1000-, 800 to 900-, or 900 to 1000-fold reduction in the standard of care dose of a recombinant zoonotic disease protein vaccine. In some embodiments, such as the foregoing, the anti-zoonotic disease antigen antibody titer produced in the subject is equivalent to an anti-zoonotic disease antigen antibody titer produced in a control subject administered the standard of care dose of a recombinant or purified zoonotic disease protein vaccine, or a live attenuated or inactivated zoonotic disease vaccine, or a zoonotic disease VLP vaccine. In some embodiments, the effective amount is a dose equivalent to (or equivalent to an at least) 2-, 3-, 4-, 5-, 6-, 7-, 8-, 9-, 10-, 20-, 30-, 40-, 50-, 60-, 70-, 80-, 90-, 100-, 110-, 120-, 130-, 140-, 150-, 160-, 170-, 1280-, 190-, 200-, 210-, 220-, 230-, 240-, 250-, 260-, 270-, 280-, 290-, 300-, 310-, 320-, 330-, 340-, 350-, 360-, 370-, 380-, 390-, 400-, 410-, 420-, 430-, 440-, 450-, 4360-, 470-, 480-, 490-, 500-, 510-, 520-, 530-, 540-, 550-, 560-, 5760-, 580-, 590-, 600-, 610-, 620-, 630-, 640-, 650-, 660-, 670-, 680-, 690-, 700-, 710-, 720-, 730-, 740-, 750-, 760-, 770-, 780-, 790-, 800-, 810-, 820-, 830-, 840-, 850-, 860-, 870-, 880-, 890-, 900-, 910-, 920-, 930-, 940-, 950-, 960-, 970-, 980-, 990-, or 1000-fold reduction in the standard of care dose of a recombinant zoonotic disease protein vaccine. In some embodiments, such as the foregoing, an anti-zoonotic disease antigen antibody titer produced in the subject is equivalent to an anti-zoonotic disease antigen antibody titer produced in a control subject administered the standard of care dose of a recombinant or purified zoonotic disease protein vaccine, or a live attenuated or inactivated zoonotic disease vaccine, or a zoonotic disease VLP vaccine.

In some embodiments, the effective amount of a zoonotic disease RNA (e.g., mRNA) vaccine is a total dose of 50-1000 pig. In some embodiments, the effective amount of a zoonotic disease RNA (e.g., mRNA) vaccine is a total dose of 50-1000, 50-900, 50-800, 50-700, 50-600, 50-500, 50-400, 50-300, 50-200, 50-100, 50-90, 50-80, 50-70, 50-60, 60-1000, 60-900, 60-800, 60-700, 60-600, 60-500, 60-400, 60-300, 60-200, 60-100, 60-90, 60-80, 60-70, 70-1000, 70-900, 70-800, 70-700, 70-600, 70-500, 70-400, 70-300, 70-200, 70-100, 70-90, 70-80, 80-1000, 80-900, 80-800, 80-700, 80-600, 80-500, 80-400, 80-300, 80-200, 80-100, 80-90, 90-1000, 90-900, 90-800, 90-700, 90-600, 90-500, 90-400, 90-300, 90-200, 90-100, 100-1000, 100-900, 100-800, 100-700, 100-600, 100-500, 100-400, 100-300, 100-200, 200-1000, 200-900, 200-800, 200-700, 200-600, 200-500, 200-400, 200-300, 300-1000, 300-900, 300-800, 300-700, 300-600, 300-500, 300-400, 400-1000, 400-900, 400-800, 400-700, 400-600, 400-500, 500-1000, 500-900, 500-800, 500-700, 500-600, 600-1000, 600-900, 600-800, 600-700, 700-1000, 700-900, 700-800, 800-1000, 800-900, or 900-1000 pig. In some embodiments, the effective amount of a zoonotic disease RNA (e.g., mRNA) vaccine is a total dose of 50, 100, 150, 200, 250, 300, 350, 400, 450, 500, 550, 600, 650, 700, 750, 800, 850, 900, 950 or 1000 pig. In some embodiments, the effective amount is a dose of 25-500 pig administered to the subject a total of two times. In some embodiments, the effective amount of a zoonotic disease RNA (e.g., mRNA) vaccine is a dose of 25-500, 25-400, 25-300, 25-200, 25-100, 25-50, 50-500, 50-400, 50-300, 50-200, 50-100, 100-500, 100-400, 100-300, 100-200, 150-500, 150-400, 150-300, 150-200, 200-500, 200-400, 200-300, 250-500, 250-400, 250-300, 300-500, 300-400, 350-500, 350-400, 400-500 or 450-500 µg administered to the subject a total of two times. In some embodiments, the effective amount of a zoonotic disease RNA (e.g., mRNA) vaccine is a total dose of 25, 50, 100, 150, 200, 250, 300, 350, 400, 450, or 500 µg administered to the subject a total of two times.

Vaccine efficacy may be assessed using standard analyses (see, e.g., Weinberg et al., J Infect Dis. 2010 Jun. 1; 201 (11): 1607-10). For example, vaccine efficacy may be measured by double-blind, randomized, clinical controlled trials. Vaccine efficacy may be expressed as a proportionate reduction in disease attack rate (AR) between the unvaccinated (ARU) and vaccinated (ARV) study cohorts and can be calculated from the relative risk (RR) of disease among the vaccinated group with use of the following formulas:

$$\text{Efficacy}=(\text{ARU}-\text{ARV})/\text{ARU}\times 100; \text{ and}$$

$$\text{Efficacy}=(1-\text{RR})\times 100.$$

Likewise, vaccine effectiveness may be assessed using standard analyses (see, e.g., Weinberg et al., J Infect Dis. 2010 Jun. 1; 201 (11): 1607-10). Vaccine effectiveness is an assessment of how a vaccine (which may have already proven to have high vaccine efficacy) reduces disease in a population. This measure can assess the net balance of benefits and adverse effects of a vaccination program, not just the vaccine itself, under natural field conditions rather than in a controlled clinical trial. Vaccine effectiveness is proportional to vaccine efficacy (potency) but is also affected by how well target groups in the population are immunized, as well as by other non-vaccine-related factors that influence the 'real-world' outcomes of hospitalizations, ambulatory visits, or costs. For example, a retrospective case control analysis may be used, in which the rates of vaccination among a set of infected cases and appropriate controls are compared. Vaccine effectiveness may be expressed as a rate difference, with use of the odds ratio (OR) for developing infection despite vaccination:

$$\text{Effectiveness}=(1-\text{OR})\times 100.$$

In some embodiments, efficacy of the zoonotic disease vaccine is at least 60% relative to unvaccinated control subjects. For example, efficacy of the zoonotic disease vaccine may be at least 65%, at least 70%, at least 75%, at least 80%, at least 85%, at least 95%, at least 98%, or 100% relative to unvaccinated control subjects.

Sterilizing Immunity. Sterilizing immunity refers to a unique immune status that prevents effective pathogen infection into the host. In some embodiments, the effective amount of a zoonotic disease vaccine of the present disclosure is sufficient to provide sterilizing immunity in the subject for at least 1 year. For example, the effective amount of a zoonotic disease vaccine of the present disclosure is sufficient to provide sterilizing immunity in the subject for at least 2 years, at least 3 years, at least 4 years, or at least 5 years. In some embodiments, the effective amount of a zoonotic disease vaccine of the present disclosure is sufficient to provide sterilizing immunity in the subject at an at least 5-fold lower dose relative to control. For example, the effective amount may be sufficient to provide sterilizing immunity in the subject at an at least 10-fold lower, 15-fold, or 20-fold lower dose relative to a control.

Detectable Antigen. In some embodiments, the effective amount of a zoonotic disease vaccine of the present disclosure is sufficient to produce detectable levels of zoonotic disease antigen as measured in serum of the subject at 1-72 hours post administration.

Titer. An antibody titer is a measurement of the amount of antibodies within a subject, for example, antibodies that are specific to a particular antigen (e.g., an anti-zoonotic disease antigen). Antibody titer is typically expressed as the inverse of the greatest dilution that provides a positive result. Enzyme-linked immunosorbent assay (ELISA) is a common assay for determining antibody titers, for example.

In some embodiments, the effective amount of a zoonotic disease vaccine of the present disclosure is sufficient to produce a 1,000-10,000 neutralizing antibody titer produced by neutralizing antibody against the zoonotic disease antigen as measured in serum of the subject at 1-72 hours post administration. In some embodiments, the effective amount is sufficient to produce a 1,000-5,000 neutralizing antibody titer produced by neutralizing antibody against the zoonotic disease antigen as measured in serum of the subject at 1-72 hours post administration. In some embodiments, the effective amount is sufficient to produce a 5,000-10,000 neutralizing antibody titer produced by neutralizing antibody against the zoonotic disease antigen as measured in serum of the subject at 1-72 hours post administration.

In some embodiments, the neutralizing antibody titer is at least 100 $NT_{50}$. For example, the neutralizing antibody titer may be at least 200, 300, 400, 500, 600, 700, 800, 900 or 1000 $NT_{50}$. In some embodiments, the neutralizing antibody titer is at least 10,000 $NT_{50}$.

In some embodiments, the neutralizing antibody titer is at least 100 neutralizing units per milliliter (NU/mL). For example, the neutralizing antibody titer may be at least 200, 300, 400, 500, 600, 700, 800, 900 or 1000 NU/mL. In some embodiments, the neutralizing antibody titer is at least 10,000 NU/mL.

In some embodiments, an anti-zoonotic disease antigen antibody titer produced in the subject is increased by at least 1 log relative to a control. For example, an anti-zoonotic disease antigen antibody titer produced in the subject may be increased by at least 2, 3, 4, 5, 6, 7, 8, 9 or log relative to a control.

In some embodiments, an anti-zoonotic disease antigen antibody titer produced in the subject is increased at least 2 times relative to a control. For example, an anti-zoonotic disease antigen antibody titer produced in the subject is increased by at least 3, 4, 5, 6, 7, 8, 9 or 10 times relative to a control.

In some embodiments, a geometric mean, which is the nth root of the product of n numbers, is generally used to describe proportional growth. Geometric mean, in some embodiments, is used to characterize antibody titer produced in a subject.

A control may be, for example, an unvaccinated subject, or a subject administered a live attenuated zoonotic disease vaccine, an inactivated zoonotic disease vaccine, or a protein subunit zoonotic disease vaccine.

ADDITIONAL EMBODIMENTS

One aspect of the disclosure is a Lassa virus (LASV) vaccine, comprising at least one RNA polynucleotide having an open reading frame encoding at least one LASV antigenic polypeptide. In some embodiments, the LASV antigenic polypeptide is a Lassa glycoprotein precursor GPC. In some embodiments, the LASV antigenic polypeptide is a structurally stabilized GPC. In some embodiments, the LASV antigenic polypeptide is a ectodomain of LASV glycoprotein 1 (GP1). In some embodiments, the LASV antigenic polypeptide is a glycoprotein. In some embodiments, the glycoprotein comprises amino acid residues 59-259 of the LASV glycoprotein precursor (GPC). In some embodiments, the LASV antigenic polypeptide is glycoprotein 2 (GP2). In some embodiments, the LASV antigenic polypeptide is a nucleocapsid protein (NP). In some embodiments, the LASV antigenic polypeptide is fused to a signal peptide.

In some embodiments, the LASV antigenic has an amino acid sequence that has at least 90% identity to an amino acid sequence identified by any one of SEQ ID NO: 1-3, but does not include wild-type protein sequence. In some embodiments, the LASV antigenic has an amino acid sequence that has at least 95% identity to an amino acid sequence identified by any one of SEQ ID NO: 1-3, but does not include wild-type protein sequence. In some embodiments, the LASV antigenic has an amino acid sequence that has at least 99% identity to an amino acid sequence identified by any one of SEQ ID NO: 1-3, but does not include wild-type protein sequence. In some embodiments, the LASV antigenic polypeptide has an amino acid sequence of any one of SEQ ID NO: 1-3.

In some embodiments, the at least one RNA polynucleotide has a nucleic acid sequence that has at least 80% identity to any one of SEQ ID NO: 6, 7, or 9, but does not include wild-type mRNA sequence. In some embodiments, the at least one RNA polynucleotide has a nucleic acid sequence that has at least 85% identity to any one of SEQ ID NO: 6, 7, or 9, but does not include wild-type mRNA sequence. In some embodiments, the at least one RNA polynucleotide has a nucleic acid sequence that has at least 90% identity to any one of SEQ ID NO: 6, 7, or 9, but does not include wild-type mRNA sequence. In some embodiments, the at least one RNA polynucleotide has a nucleic acid sequence that has at least 95% identity to any one of SEQ ID NO: 6, 7, or 9, but does not include wild-type mRNA sequence.

In some embodiments, the at least one RNA polynucleotide has a nucleic acid sequence that has at least 98% identity to any one of SEQ ID NO: 4-9, but does not include wild-type mRNA sequence. In some embodiments, the at least one RNA polynucleotide has a nucleic acid sequence of any one of SEQ ID NO: 6, 7, or 9. In some embodiments, the LASV antigenic polypeptide has membrane fusion activity, attaches to cell receptors, causes fusion of viral and cellular membranes, and/or is responsible for binding of the virus to a cell being infected. In some embodiments, the at least one RNA polynucleotide having an open reading frame encoding at least one LASV antigenic polypeptide comprises at least one chemical modification. In some embodiments, the chemical modification is selected from pseudouridine, N1-methylpseudouridine, N1-ethylpseudouridine, 2-thiouridine, 4'-thiouridine, 5-methylcytosine, 5-methyluridine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methoxyuridine and 2'-O-methyl uridine. In some embodiments, the chemical modification is in the carbon 5-position of the uracil. In some embodiments, the chemical modification is a N1-methylpseudouridine or N1-ethylpseudouridine. In some embodiments, at least 80% of the uracil in the open reading frame have a chemical modification. In some embodiments, at least 90% of the uracil in the open reading frame have a chemical modification. In some embodiments, 100% of the uracil in the open reading frame have a chemical modification. In some embodiments, 100% of the uracil in the open reading frame is modified to include N1-methyl pseudouridine at the 5-position of the uracil. In some embodiments, at least one RNA polynucleotide having an open reading frame encoding at least one LASV antigenic polypeptide further encodes at least one 5' terminal cap. In some embodiments, the 5' terminal cap is 7mG(5')ppp(5') NlmpNp.

In some embodiments, the RNA polynucleotide having an open reading frame encoding at least one LASV antigenic polypeptide is formulated in a cationic lipid nanoparticle. In some embodiments, the cationic lipid nanoparticle has a mean diameter of 50-200 nm. In some embodiments, the cationic lipid nanoparticle comprises a cationic lipid, a PEG-modified lipid, a sterol and a non-cationic lipid. In some embodiments, the cationic lipid nanoparticle comprises a molar ratio of about 20-60% cationic lipid, 0.5-15% PEG-modified lipid, 25-55% sterol, and 5-25% non-cationic lipid. In some embodiments, the cationic lipid is an ionizable cationic lipid and the non-cationic lipid is a neutral lipid, and the sterol is a cholesterol. In some embodiments, the cationic lipid is selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319). In some embodiments, the cationic lipid nanoparticle comprises a compound of Formula (I), optionally Compound 3, 18, 20, 25, 26, 29, 30, 60, 108-112, or 122. In some embodiments, the cationic lipid nanoparticle comprises a compound of Formula (II). In some embodiments, the cationic lipid nanoparticle has a polydispersity value of less than 0.4. In some embodiments, the cationic lipid nanoparticle has a net neutral charge at a neutral pH value. In some embodiments, further comprising an adjuvant.

In some embodiments, the open reading frame encoding at least one LASV antigenic polypeptide is codon-optimized. In some embodiments, the LASV vaccine is multivalent. In some embodiments, the LASV vaccine is formulated in an effective amount to produce an antigen-specific immune response. In some embodiments, the LASV vaccine is for use in a method of inducing an antigen specific immune response in a subject, the method comprising administering to the subject the LASV vaccine in an amount effective to produce an antigen specific immune response in the subject.

One aspect of the disclosure is a pharmaceutical composition for use in vaccination of a subject comprising an effective dose of the LASV vaccine as described herein, wherein the effective dose is sufficient to produce detectable levels of antigen as measured in serum of the subject at 1-72 hours post administration. In some embodiments, the cut off index of the antigen is 1-2.

One aspect of the disclosure is a pharmaceutical composition for use in vaccination of a subject comprising an effective dose of the LASV vaccine as described herein, wherein the effective dose is sufficient to produce a 1,000-10,000 neutralization titer produced by neutralizing antibody against said antigen as measured in serum of the subject at 1-72 hours post administration.

One aspect of the disclosure is a composition comprising the LASV vaccine as described herein formulated in a lipid nanoparticle comprising compounds of Formula (I), (IA) and/or Formula (II), discussed below.

One aspect of the disclosure is a method of inducing an immune response in a subject, the method comprising administering to the subject the LASV vaccine as described herein in an amount effective to produce an antigen-specific immune response in the subject. In some embodiments, the antigen specific immune response comprises a T cell response or a B cell response. In some embodiments, the subject is administered a single dose of the vaccine. In some embodiments, the subject is administered a booster dose of the vaccine. In some embodiments, the vaccine is administered to the subject by intradermal injection or intramuscular injection. In some embodiments, an anti-antigenic polypeptide antibody titer produced in the subject is increased by at least 1 log relative to a control. In some embodiments, an anti-antigenic polypeptide antibody titer produced in the subject is increased by 1-3 log relative to a control. In some embodiments, the anti-antigenic polypeptide antibody titer produced in the subject is increased at least 2 times relative to a control. In some embodiments, the anti-antigenic polypeptide antibody titer produced in the subject is increased 2-10 times relative to a control. In some embodiments, the control is an anti-antigenic polypeptide antibody titer produced in a subject who has not been administered a vaccine against the virus.

One aspect of the disclosure is a paramyxovirus vaccine, comprising: at least one RNA polynucleotide having an open reading frame encoding at least one Nipah virus (NiV) and/or Hendra virus (HeV) antigenic polypeptide. In some embodiments, the NiV and/or HeV antigenic polypeptide is a hemagglutinin-neuraminidase protein (HN) or hemagglutinin protein (H). In some embodiments, the NiV and/or HeV antigenic polypeptide is a glycoprotein (G). In some embodiments, the NiV and/or HeV antigenic polypeptide is an attachment glycoproteins which is a type II membrane protein. In some embodiments, the NiV and/or HeV antigenic polypeptide is a fusion (F) glycoprotein. In some embodiments, the F glycoprotein comprises a trimeric class I fusogenic envelope glycoprotein containing two heptad repeat (HR) regions and a hydrophobic fusion peptide.

In some embodiments, the NiV and/or HeV antigenic polypeptide is NiV antigenic polypeptide. In some embodiments, the NiV and/or HeV antigenic polypeptide is HeV antigenic polypeptide. In some embodiments, the NiV and/or HeV antigenic polypeptide is fused to a signal peptide. In some embodiments, the NiV and/or HeV antigenic has an amino acid sequence that has at least 90% identity to an amino acid sequence identified by any one of SEQ ID NO: 10-13, but does not include wild-type protein sequence. In some embodiments, the NiV and/or HeV antigenic has an amino acid sequence that has at least 95% identity to an amino acid sequence identified by any one of SEQ ID NO: 10-13, but does not include wild-type protein sequence. In some embodiments, the NiV and/or HeV antigenic has an amino acid sequence that has at least 99% identity to an amino acid sequence identified by any one of SEQ ID NO: 10-13, but does not include wild-type protein sequence. In some embodiments, the NiV and/or HeV antigenic polypeptide has an amino acid sequence of any one of SEQ ID NO: 10-13.

In some embodiments, the at least one RNA polynucleotide has a nucleic acid sequence that has at least 80% identity to any one of SEQ ID NO: 16 or 17, but does not include wild-type mRNA sequence.

In some embodiments, at least one RNA polynucleotide has a nucleic acid sequence that has at least 85% identity to SEQ ID NO: 16 or 17, but does not include wild-type mRNA sequence. In some embodiments, at least one RNA polynucleotide has a nucleic acid sequence that has at least 90% identity to SEQ ID NO: 16 or 17, but does not include wild-type mRNA sequence. In some embodiments, at least one RNA polynucleotide has a nucleic acid sequence that has at least 95% identity to SEQ ID NO: 16 or 17, but does not include wild-type mRNA sequence. In some embodiments, at least one RNA polynucleotide has a nucleic acid sequence that has at least 98% identity to SEQ ID NO: 16 or 17, but does not include wild-type mRNA sequence. In some embodiments, at least one RNA polynucleotide has a nucleic acid sequence of SEQ ID NO: 16 or 17.

In some embodiments, the antigenic polypeptide has membrane fusion activity, attaches to cell receptors, causes fusion of viral and cellular membranes, and/or is responsible for binding of the virus to a cell being infected. In some embodiments, at least one RNA polynucleotide comprises at least one chemical modification. In some embodiments, the chemical modification is selected from pseudouridine, N1-methylpseudouridine, N1-ethylpseudouridine, 2-thiouridine, 4'-thiouridine, 5-methylcytosine, 5-methyluridine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methoxyuridine and 2'-O-methyl uridine. In some embodiments, the chemical modification is in the 5-position of the uracil.

In some embodiments, the chemical modification is a N1-methylpseudouridine or N1-ethylpseudouridine. In some embodiments, at least 80% of the uracil in the open reading frame have a chemical modification. In some embodiments, at least 90% of the uracil in the open reading frame have a chemical modification. In some embodiments, 100% of the uracil in the open reading frame have a chemical modification. In some embodiments, 100% of the uracil in the open reading frame is modified to include N1-methyl pseudouridine at the 5-position of the uracil. In some embodiments, at least one RNA polynucleotide further encodes at least one 5' terminal cap. In some embodiments, the 5' terminal cap is 7mG(5')ppp(5')NlmpNp. In some embodiments, the RNA polynucleotide is formulated in a cationic lipid nanoparticle. In some embodiments, the cationic lipid nanoparticle has a mean diameter of 50-200 nm. In some embodiments, the cationic lipid nanoparticle comprises a cationic lipid, a PEG-modified lipid, a sterol and a non-cationic lipid. In some embodiments, the cationic lipid nanoparticle comprises a molar ratio of about 20-60% cationic lipid, 0.5-15% PEG-modified lipid, 25-55% sterol, and 5-25% non-cationic lipid. In some embodiments, the cationic lipid is an ionizable cationic lipid and the non-cationic lipid is a neutral lipid, and the sterol is a cholesterol.

In some embodiments, the cationic lipid is selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319). In some embodiments, the cationic lipid nanoparticle comprises a compound of Formula (I), optionally Compound 3, 18, 20, 25, 26, 29, 30, 60, 108-112, or 122. In some embodiments, the cationic lipid nanoparticle comprises a compound of Formula (II). In some embodiments, the cationic lipid nanoparticle has a polydispersity value of less than 0.4. In some embodiments, the cationic lipid nanoparticle has a net neutral charge at a neutral pH value. Some embodiments further comprise an adjuvant. In some embodiments, the open reading frame is codon-optimized. In some embodiments, the vaccine is multivalent. Some embodiments are formulated in an effective amount to produce an antigen-specific immune response. Some embodiments are for use in a method of inducing an antigen specific immune response in a subject, the method comprising administering to the subject the vaccine in an amount effective to produce an antigen specific immune response in the subject.

One aspect of the disclosure is a pharmaceutical composition for use in vaccination of a subject comprising an effective dose of the paramyxovirus vaccine as described herein, wherein the effective dose is sufficient to produce detectable levels of antigen as measured in serum of the subject at 1-72 hours post administration. In some embodiments, the cut off index of the antigen is 1-2.

One aspect of the disclosure is a pharmaceutical composition for use in vaccination of a subject comprising an effective dose of the paramyxovirus vaccine as described herein, wherein the effective dose is sufficient to produce a 1,000-10,000 neutralization titer produced by neutralizing antibody against said antigen as measured in serum of the subject at 1-72 hours post administration.

One aspect of the disclosure is a composition comprising the paramyxovirus vaccine as described herein formulated in a lipid nanoparticle comprising compounds of Formula (I), (IA), and/or Formula (II), discussed below.

One aspect of the disclosure is a method of inducing an immune response in a subject, the method comprising administering to the subject the paramyxovirus vaccine as described herein in an amount effective to produce an antigen-specific immune response in the subject. In some embodiments, the antigen specific immune response comprises a T cell response or a B cell response. In some embodiments, the subject is administered a single dose of the vaccine. In some embodiments, the subject is administered a booster dose of the vaccine. In some embodiments, the vaccine is administered to the subject by intradermal injection or intramuscular injection. In some embodiments, an anti-antigenic polypeptide antibody titer produced in the subject is increased by at least 1 log relative to a control. In some embodiments, an anti-antigenic polypeptide antibody titer produced in the subject is increased by 1-3 log relative to a control. In some embodiments, the anti-antigenic polypeptide antibody titer produced in the subject is increased at least 2 times relative to a control. In some embodiments, the anti-antigenic polypeptide antibody titer produced in the subject is increased 2-10 times relative to a control. In some embodiments, the control is an anti-antigenic polypeptide antibody titer produced in a subject who has not been administered a vaccine against the virus.

One aspect of the invention is a betacoronavirus vaccine, comprising: at least one ribonucleic acid (RNA) polynucleotide having an open reading frame encoding at least one MERS-CoV or SARS-like coronavirus WIV1 (SL-CoV-WIV1) antigenic polypeptide. In some embodiments, the antigenic polypeptide is a betacoronavirus structural protein. In some embodiments, the betacoronavirus structural protein is spike protein (S), envelope protein (E), nucleocapsid protein (N) or membrane protein (M). In some embodiments, the betacoronavirus structural protein is spike protein (S). In some embodiments, the antigenic polypeptide is a S1 subunit of the spike protein (S). In some embodiments, the antigenic polypeptide is a S2 subunit of the spike protein (S). In some embodiments, the antigenic polypeptide is an SL-CoV-WIV1 antigenic polypeptide. In some embodiments, the antigenic polypeptide is a MERS-CoV antigenic polypeptide. In some embodiments, the open reading from is codon-optimized. In some embodiments, the vaccine is multivalent. In some embodiments, at least one RNA polynucleotide encodes at least 2 antigenic polypeptides. In some embodiments, at least one RNA polynucleotide encodes at least 10 antigenic polypeptides. In some embodiments, at least one RNA polynucleotide encodes at least 100 antigenic polypeptides. In some embodiments, at least one RNA polynucleotide encodes 2-100 antigenic polypeptides.

In some embodiments, the MERS-CoV or SL-CoV-WIV1 antigenic polypeptide has an amino acid sequence that has at least 90% identity to an amino acid sequence identified by SEQ ID NO: 18, but does not include wild-type protein sequence. In some embodiments, the MERS-CoV or SL-CoV-WIV1 antigenic polypeptide has an amino acid sequence that has at least 95% identity to an amino acid sequence identified by SEQ ID NO: 18, but does not include wild-type protein sequence. In some embodiments, the MERS-CoV or SL-CoV-WIV1 antigenic polypeptide has an amino acid sequence of SEQ ID NO: 18.

In some embodiments, at least one RNA polynucleotide has a nucleic acid sequence that has at least 80% identity to SEQ ID NO: 19 or 20, but does not include wild-type mRNA sequence. In some embodiments, at least one RNA polynucleotide has a nucleic acid sequence that has at least 90% identity to SEQ ID NO: 19 or 20, but does not include wild-type mRNA sequence. In some embodiments, at least one RNA polynucleotide has a nucleic acid sequence of SEQ ID NO: 19 or 20.

In some embodiments, at least one RNA polynucleotide comprises at least one chemical modification. In some embodiments, the chemical modification is selected from pseudouridine, N1-methylpseudouridine, N1-ethylpseudouridine, 2-thiouridine, 4'-thiouridine, 5-methylcytosine, 5-methyluridine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methoxyuridine and 2'-O-methyl uridine. In some embodiments, the chemical modification is in the 5-position of the uracil. In some embodiments, the chemical modification is a N1-methylpseudouridine or N1-ethylpseudouridine. In some embodiments, at least 80% of the uracil in the open reading frame have a chemical modification. In some embodiments, at least 90% of the uracil in the open reading frame have a chemical modification. In some embodiments, 100% of the uracil in the open reading frame have a chemical modification. In some embodiments, 100% of the uracil in the open reading frame is modified to include N1-methyl pseudouridine at the 5-position of the uracil. In some embodiments, at least one RNA polynucleotide further encodes at least one 5' terminal cap. In some embodiments, the 5' terminal cap is 7mG(5')ppp(5')NlmpNp.

In some embodiments, the RNA polynucleotide is formulated in a cationic lipid nanoparticle. In some embodiments, the cationic lipid nanoparticle has a mean diameter of 50-nm. In some embodiments, the cationic lipid nanoparticle comprises a cationic lipid, a PEG-modified lipid, a sterol and a non-cationic lipid. In some embodiments, the cationic lipid nanoparticle comprises a molar ratio of about 20-60% cationic lipid, 0.5-15% PEG-modified lipid, 25-55% sterol, and 5-25% non-cationic lipid. In some embodiments, the cationic lipid is an ionizable cationic lipid and the non-cationic lipid is a neutral lipid, and the sterol is a cholesterol. In some embodiments, the cationic lipid is selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319). In some embodiments, the cationic lipid nanoparticle comprises a compound of Formula (I), optionally Compound 3, 18, 20, 25, 26, 29, 30, 60, 108-112, or 122. In some embodiments, the cationic lipid nanoparticle comprises a compound of Formula (II). In some embodiments, the cationic lipid nanoparticle has a polydispersity value of less than 0.4. In some embodiments, the cationic lipid nanoparticle has a net neutral charge at a neutral pH value. Some embodiments further comprise an adjuvant. In some embodiments, the open reading frame is codon-optimized. In some embodiments, the vaccine is multivalent. Some embodiments are formulated in an effective amount to produce an antigen-specific immune response. Some embodiments are for use in a method of inducing an antigen specific immune response in a subject, the method comprising administering to the subject the vaccine in an amount effective to produce an antigen specific immune response in the subject.

One aspect of the invention is a pharmaceutical composition for use in vaccination of a subject comprising an effective dose of the betacoronavirus vaccine as described herein, wherein the effective dose is sufficient to produce detectable levels of antigen as measured in serum of the subject at 1-72 hours post administration. In some embodiments, the cut off index of the antigen is 1-2.

One aspect of the invention is a pharmaceutical composition for use in vaccination of a subject comprising an effective dose of the betacoronavirus vaccine as described herein, wherein the effective dose is sufficient to produce a 1,000-10,000 neutralization titer produced by neutralizing antibody against said antigen as measured in serum of the subject at 1-72 hours post administration.

One aspect of the invention is a composition comprising the betacoronavirus vaccine as described herein formulated in a lipid nanoparticle comprising compounds of Formula (I):

(I)

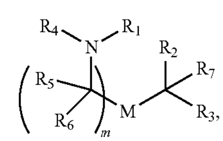

or a salt or isomer thereof, wherein: $R_1$ is selected from the group consisting of $C_{5-30}$ alkyl, $C_{5-20}$ alkenyl, —R*YR", —YR", and —R"M'R'; $R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle; $R_4$ is selected from the group consisting of a $C_{3-6}$ carbocycle, $—(CH_2)_nQ$, $—(CH_2)_nCHQR$, —CHQR, $—CQ(R)_2$, and unsubstituted $C_{1-6}$ alkyl, where Q is selected from a carbocycle, heterocycle, —OR, $—O(CH_2)_nN(R)_2$, —C(O)OR, —OC(O)R, $—CX_3$, $—CX_2H$, $—CXH_2$, —CN, $—N(R)_2$, $—C(O)N(R)_2$, —N(R)C(O)R, $—N(R)S(O)_2R$, $—N(R)C(O)N(R)_2$, $—N(R)C(S)N(R)_2$, $—N(R)R_8$, $—O(CH_2)_nOR$, $—N(R)C(=NR_9)N(R)_2$, $—N(R)C(=CHR_9)N(R)_2$, $—OC(O)N(R)_2$, —N(R)C(O)OR, —N(OR)C(O)R, $—N(OR)S(O)_2R$, —N(OR)C(O)OR, $—N(OR)C(O)N(R)_2$, $—N(OR)C(S)N(R)_2$, $—N(OR)C(=NR_9)N(R)_2$, $—N(OR)C(=CHR_9)N(R)_2$, $—C(=NR_9)N(R)_2$, $—C(=NR_9)R$, —C(O)N(R)OR, and $—C(R)N(R)_2C(O)OR$, and each n is independently selected from 1, 2, 3, 4, and 5; each $R_5$ is independently selected from the group consisting of $C_{1-3}$ alkyl, $C_{2-3}$ alkenyl, and H; each $R_6$ is independently selected from the group consisting of $C_{1-3}$ alkyl, $C_{2-3}$ alkenyl, and H; M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group; $R_7$ is selected from the group consisting of $C_{1-3}$ alkyl, $C_{2-3}$ alkenyl, and H; $R_8$ is selected from the group consisting of $C_{3-6}$ carbocycle and heterocycle; $R_9$ is selected from the group consisting of H, CN, NO$_2$, $C_{1-6}$ alkyl, —OR, —S(O)$_2$R, —S(O)$_2$N(R)$_2$, $C_{2-6}$ alkenyl, $C_{3-6}$ carbocycle and heterocycle; each R is independently selected from the group consisting of $C_{1-3}$ alkyl, $C_{2-3}$ alkenyl, and H; each R' is independently selected from the group consisting of $C_{1-18}$ alkyl, $C_{2-18}$ alkenyl, —R*YR", —YR", and H; each R" is independently selected from the group consisting of $C_{3-14}$ alkyl and $C_{3-14}$ alkenyl; each R* is independently selected from the group consisting of $C_{1-12}$ alkyl and $C_{2-12}$ alkenyl; each Y is independently a $C_{3-6}$ carbocycle; each X is independently selected from the group consisting of F, Cl, Br, and I; and m is selected from 5, 6, 7, 8, 9, 10, 11, 12, and 13.

In some embodiments, a subset of compounds of Formula (I) includes those in which when $R_4$ is —(CH$_2$)$_n$Q, —(CH$_2$)$_n$CHQR, —CHQR, or —CQ(R)$_2$, then (i) Q is not —N(R)$_2$ when n is 1, 2, 3, 4 or 5, or (ii) Q is not 5, 6, or 7-membered heterocycloalkyl when n is 1 or 2. In some embodiments, a subset of compounds of Formula (I) includes those in which $R_1$ is selected from the group consisting of $C_{5-30}$ alkyl, $C_{5-20}$ alkenyl, —R*YR", —YR", and —R"M'R'; $R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle; $R_4$ is selected from the group consisting of a $C_{3-6}$ carbocycle, —(CH$_2$)$_n$Q, —(CH$_2$)$_n$CHQR, —CHQR, —CQ(R)$_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —O(CH$_2$)$_n$N(R)$_2$, —C(O)OR, OC(O)R, —CX$_3$, —CX$_2$H, —CXH$_2$, —CN, —C(O)N(R)$_2$, —N(R)C(O)R, —N(R)S(O)$_2$R, —N(R)C(O)N(R)$_2$, —N(R)C(S)N(R)$_2$, —CRN(R)$_2$C(O)OR, —N(R)R$_8$, —O(CH$_2$)$_n$OR, —N(R)C(=NR$_9$)N(R)$_2$, —N(R)C(=CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=NR$_9$)N(R)$_2$, —N(OR)C(=CHR$_9$)N(R)$_2$, —C(=NR$_9$)N(R)$_2$, —C(=NR$_9$)R, —C(O)N(R)OR, and a 5- to 14-membered heterocycloalkyl having one or more heteroatoms selected from N, O, and S which is substituted with one or more substituents selected from oxo (=O), OH, amino, mono- or di-alkylamino, and $C_{1-3}$ alkyl, and each n is independently selected from 1, 2, 3, 4, and 5; each $R_5$ is independently selected from the group consisting of $C_{1-3}$ alkyl, $C_{2-3}$ alkenyl, and H; each $R_6$ is independently selected from the group consisting of $C_{1-3}$ alkyl, $C_{2-3}$ alkenyl, and H; M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group; $R_7$ is selected from the group consisting of $C_{1-3}$ alkyl, $C_{2-3}$ alkenyl, and H; $R_8$ is selected from the group consisting of $C_{3-6}$ carbocycle and heterocycle; $R_9$ is selected from the group consisting of H, CN, NO$_2$, $C_{1-6}$ alkyl, —OR, —S(O)$_2$R, —S(O)$_2$N(R)$_2$, $C_{2-6}$ alkenyl, $C_{3-6}$ carbocycle and heterocycle; each R is independently selected from the group consisting of $C_{1-3}$ alkyl, $C_{2-3}$ alkenyl, and H; each R' is independently selected from the group consisting of $C_{1-18}$ alkyl, $C_{2-18}$ alkenyl, —R*YR", —YR", and H; each R" is independently selected from the group consisting of $C_{3-14}$ alkyl and $C_{3-14}$ alkenyl; each R* is independently selected from the group consisting of $C_{1-12}$ alkyl and $C_{2-12}$ alkenyl; each Y is independently a $C_{3-6}$ carbocycle; each X is independently selected from the group consisting of F, Cl, Br, and I; and m is selected from 5, 6, 7, 8, 9, 10, 11, 12, and 13, or salts or isomers thereof.

In some embodiments, a subset of compounds of Formula (I) includes those in which $R_1$ is selected from the group consisting of $C_{5-30}$ alkyl, $C_{5-20}$ alkenyl, —R*YR", —YR", and —R"M'R'; $R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle; $R_4$ is selected from the group consisting of a $C_{3-6}$ carbocycle, —(CH$_2$)$_n$Q, —(CH$_2$)$_n$CHQR, —CHQR, —CQ(R)$_2$, and unsubstituted $C_{1-6}$ alkyl, where Q is selected from a $C_{3-6}$ carbocycle, a 5- to 14-membered heterocycle having one or more heteroatoms selected from N, O, and S, —OR, —O(CH$_2$)$_n$N(R)$_2$, —C(O)OR, —OC(O)R, —CX$_3$, —CX$_2$H, —CXH$_2$, —CN, —C(O)N(R)$_2$, —N(R)C(O)R, —N(R)S(O)$_2$R, —N(R)C(O)N(R)$_2$, —N(R)C(S)N(R)$_2$, —CRN(R)$_2$C(O)OR, —N(R)R$_8$, —O(CH$_2$)$_n$OR, —N(R)C(=NR$_9$)N(R)$_2$, —N(R)C(=CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=NR$_9$)N(R)$_2$, —N(OR)C(=CHR$_9$)N(R)$_2$, —C(=NR$_9$)R, —C(O)N(R)OR, and —C(=NR$_9$)N(R)$_2$, and each n is independently selected from 1, 2, 3, 4, and 5; and when Q is a 5- to 14-membered heterocycle and (i) $R_4$ is —(CH$_2$)$_n$Q in which n is 1 or 2, or (ii) $R_4$ is —(CH$_2$)$_n$CHQR in which n is 1, or (iii) $R_4$ is —CHQR, and —CQ(R)$_2$, then Q is either a 5- to 14-membered heteroaryl or 8- to 14-membered heterocycloalkyl; each $R_5$ is independently selected from the group consisting of $C_{1-3}$ alkyl, $C_{2-3}$ alkenyl, and H; each $R_6$ is independently selected from the group consisting of $C_{1-3}$ alkyl, $C_{2-3}$ alkenyl, and H; M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group; $R_7$ is selected from the group consisting of $C_{1-3}$ alkyl, $C_{2-3}$ alkenyl, and H; $R_8$ is selected from the group consisting of $C_{3-6}$ carbocycle and heterocycle; $R_9$ is selected from the group consisting of H, CN, NO$_2$, $C_{1-6}$ alkyl, —OR, —S(O)$_2$R, —S(O)$_2$N(R)$_2$, $C_{2-6}$ alkenyl, $C_{3-6}$ carbocycle and heterocycle; each R is independently selected from the group consisting of $C_{1-3}$ alkyl, $C_{2-3}$ alkenyl, and H; each R' is independently selected from the group consisting of $C_{1-18}$ alkyl, $C_{2-18}$ alkenyl, —R*YR", —YR", and H; each R" is independently selected from the group consisting of $C_{3-14}$ alkyl and $C_{3-14}$ alkenyl; each R* is independently selected from the group consisting of $C_{1-12}$ alkyl and $C_{2-12}$ alkenyl; each Y is independently a $C_{3-6}$ carbocycle; each X is independently selected from the group consisting of F, Cl, Br, and I; and m is selected from 5, 6, 7, 8, 9, 10, 11, 12, and 13, or salts or isomers thereof.

In some embodiments, the subset of compounds of Formula (I) includes those in which $R_1$ is selected from the group consisting of $C_{5-30}$ alkyl, $C_{5-20}$ alkenyl, —R*YR", —YR", and —R"M'R'; $R_2$ and $R_3$ are independently selected from the group consisting of H, $C_{2-14}$ alkyl, $C_{2-14}$ alkenyl, —R*YR", —YR", and —R*OR", or $R_2$ and $R_3$, together with the atom to which they are attached, form a heterocycle or carbocycle; $R_4$ is —(CH$_2$)$_n$Q or —(CH$_2$)$_n$CHQR, where Q is —N(R)$_2$, and n is selected from 3, 4, and 5; each $R_5$ is independently selected from the group consisting of $C_{1-3}$ alkyl, $C_{2-3}$ alkenyl, and H; each $R_6$ is independently selected from the group consisting of $C_{1-3}$ alkyl, $C_{2-3}$ alkenyl, and H; M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group; $R_7$ is selected from the group consisting of $C_{1-3}$ alkyl, $C_{2-3}$ alkenyl, and H; each R is independently selected from the group consisting of $C_{1-3}$ alkyl, $C_{2-3}$ alkenyl, and H; each R' is independently selected from the group consisting of CMS alkyl, $C_{2-18}$ alkenyl, —R*YR", —YR", and H; each R" is independently selected from the group consisting of $C_{3-14}$ alkyl and $C_{3-14}$ alkenyl; each R* is independently selected from the group consisting of $C_{1-12}$ alkyl and $C_{1-12}$ alkenyl; each Y is independently a $C_{3-6}$ carbocycle; each X is independently selected from the group consisting of F, Cl, Br, and I; and m is selected from 5, 6, 7, 8, 9, 10, 11, 12, and 13, or salts or isomers thereof.

In some embodiments, a subset of compounds of Formula (I) includes those in which $R_1$ is selected from the group consisting of $C_{5-30}$ alkyl, $C_{5-20}$ alkenyl, —R*YR", —YR", and —R"M'R'; $R_2$ and $R_3$ are independently selected from the group consisting of $C_{1-14}$ alkyl, $C_{2-14}$ alkenyl, —R*YR", —YR", and —R*OR", or $R_2$ and $R_3$, together with the atom to which they are attached, form a heterocycle or carbocycle; $R_4$ is selected from the group consisting of —(CH$_2$)$_n$Q, —(CH$_2$)$_n$CHQR, —CHQR, and —CQ(R)$_2$, where Q is —N(R)$_2$, and n is selected from 1, 2, 3, 4, and 5; each $R_5$ is independently selected from the group consisting of $C_{1-3}$ alkyl, $C_{2-3}$ alkenyl, and H; each $R_6$ is independently selected from the group consisting of $C_{1-3}$ alkyl, $C_{2-3}$ alkenyl, and H; M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group; $R_7$ is selected from the group consisting of $C_{1-3}$ alkyl, $C_{2-3}$ alkenyl, and H; each R is independently selected from the group consisting of $C_{1-3}$ alkyl, $C_{2-3}$ alkenyl, and H; each R' is independently selected from the group consisting of CMS alkyl, $C_{2-18}$ alkenyl, —R*YR", —YR", and H; each R" is independently selected from the group consisting of $C_{3-14}$ alkyl and $C_{3-14}$ alkenyl; each R* is independently selected from the group consisting of $C_{1-12}$ alkyl and $C_{1-12}$ alkenyl; each Y is independently a $C_{3-6}$ carbocycle; each X is independently selected from the group consisting of F, Cl, Br, and I; and m is selected from 5, 6, 7, 8, 9, 10, 11, 12, and 13, or salts or isomers thereof.

In some embodiments, a subset of compounds of Formula (I) includes those of Formula (IA): (IA), or a salt or isomer thereof, wherein 1 is selected from 1, 2, 3, 4, and 5; m is selected from 5, 6, 7, 8, and 9; $M_1$ is a bond or M'; $R_4$ is unsubstituted $C_{1-3}$ alkyl, or —(CH$_2$)$_n$Q, in which Q is OH, —NHC(S)N(R)$_2$, —NHC(O)N(R)$_2$, —N(R)C(O)R, —N(R)S(O)$_2$R, —N(R)R$_8$, —NHC(=NR$_9$)N(R)$_2$, —NHC(=CHR$_9$)N(R)$_2$, —OC(O)N(R)$_2$, —N(R)C(O)OR, heteroaryl or heterocycloalkyl; M and M' are independently selected from —C(O)O—, —OC(O)—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl.

One aspect of the invention is a method of inducing an immune response in a subject, the method comprising administering to the subject the betacoronavirus vaccine as described herein in an amount effective to produce an antigen-specific immune response in the subject. In some embodiments, the antigen specific immune response comprises a T cell response or a B cell response. In some embodiments, the subject is administered a single dose of the vaccine. In some embodiments, the subject is administered a booster dose of the vaccine. In some embodiments, the vaccine is administered to the subject by intradermal injection or intramuscular injection.

In some embodiments, an anti-antigenic polypeptide antibody titer produced in the subject is increased by at least 1 log relative to a control. In some embodiments, an anti-antigenic polypeptide antibody titer produced in the subject is increased by 1-3 log relative to a control. In some embodiments, the anti-antigenic polypeptide antibody titer produced in the subject is increased at least 2 times relative to a control. In some embodiments, the anti-antigenic polypeptide antibody titer produced in the subject is increased 2-10 times relative to a control. In some embodiments, the control is an anti-antigenic polypeptide antibody titer produced in a subject who has not been administered a vaccine against the virus.

EXAMPLES

Example 1: Ebola Vaccine Immunogenicity Study 8-10 week old female Balb/c mice were immunized intramuscularly with 10 μg of Ebola mRNA vaccines or recombinant Zaire ebolavirus Glycoprotein on day 0 and 14. Serum samples were collected on day 21, 33, 52 and 77 to measure antibody response.

Animals receiving 2 doses of the Ebola mRNA vaccine antigens had high levels of GP specific IgG titers 1 week after 2nd dose (FIG. 2). The results from this study were used to select a lead vaccine candidate to be tested in a Guinea pig challenge model.

Example 2: Guinea Pig Challenge Model

Guinea pigs (n=5) were immunized intramuscularly with 20 μg of select mRNA vaccine constructs (AG1 and AG2) on Day 0 and 21. Three weeks after the second dose, animals were challenged with 1000 pfu (XLD50) through Intraperitoneal injection of Guinea pig adapted Zaire Ebola virus strain Mayinga-76. Serial bleeds were collected 3, 6, 9 and 12 days after challenge to measure viremia. Animals were monitored for morbidity and mortality for 4 weeks after challenge (FIG. 3).

All animals receiving the mRNA vaccine (AG1 and AG2) were completely protected in the lethal challenge model while all placebo treated animals succumbed to infection by day 10. Furthermore, animals receiving Ebola GP mRNA vaccines did not demonstrate any significant morbidity or weight loss after challenge.

Example 3: Product Development Strategy

Two Phase 1/2 clinical trials are planned and will be a safety, immunogenicity and dose-selection studies in non-endemic and endemic settings. The first clinical study (FIH) will be initiated in the US and will include approximately 90 subjects. Three dose levels of investigational vaccine will be tested compared to placebo in a staggered manner. To mitigate risk of different immunogenicity in subjects from endemic and non-endemic setting, the second clinical study in endemic setting will be initiated in collaboration with a local clinical study site. Following evaluation of immunogenicity and safety data from both clinical studies (at 1 month post-vaccination), a dose of vaccine for further development will be selected.

Example 4: PIV3 mRNA Vaccine as a Demonstration

An mRNA vaccine was designed based on the PIV3 fusion protein and tested in two animal models, cotton rat and African green monkey, for immunogenicity and protection from viral challenge.

First, cotton rats were dosed 10 μg, or 25 μg of the mRNA PIV3 vaccine, placebo, or formalin inactivated (FI) PIV3 vaccine at days 0 and 28. Blood was collected pre-dose and on days 27 and 56 (28 days post dose 2) for immunogenicity testing by viral neutralization assay. On day 57 the animals were challenged with PIV3 and viral titer measured 5 days post challenge on lung and nose samples.

Figure 9:
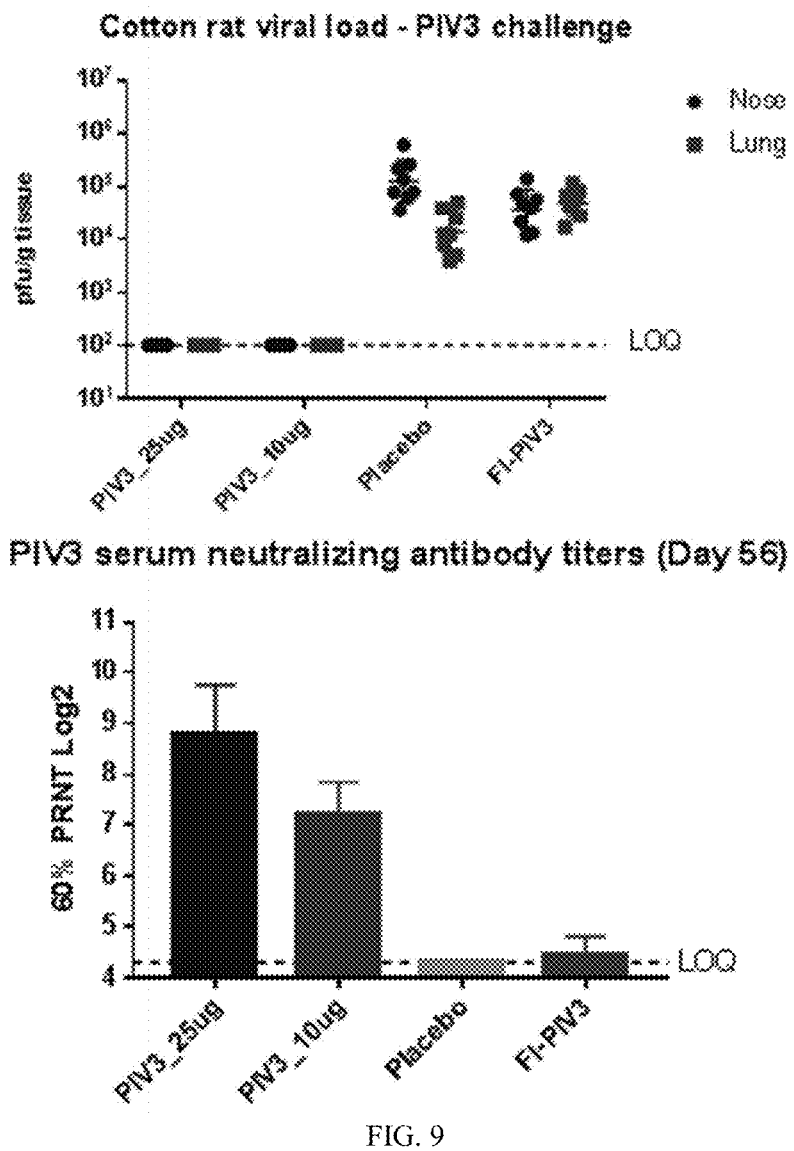
FIG. 9 shows viral titers (top panel) and serum PIV3 neutralizing antibody titers (bottom panel) in cotton rats.

As shown in FIG. 9, both the 10 μg and 25 μg doses of mRNA vaccine completely protected cotton rats from a challenge that results in viral loads of 4 to 5 logs in lung and nose respectively, while FI vaccine showed no significant protection. The right panel shows that this protection was the result of neutralizing titers in the range of 7 to 9 logs.

Figure 10:
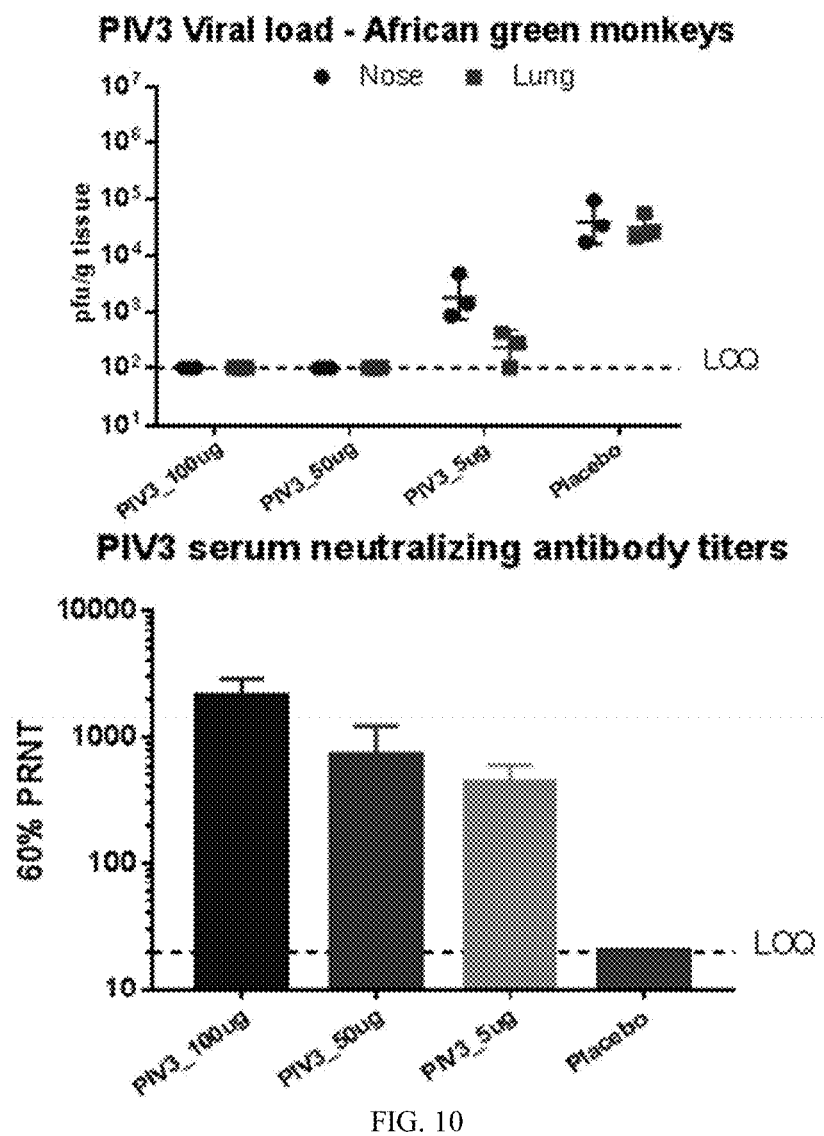
FIG. 10 shows viral titers (top panel) and serum PIV3 neutralizing antibody titers (bottom panel) in African green monkeys.

The second model used to assess our mRNA PIV3 vaccine was African green monkey, which were screened as PIV3 seronegative before the experiment. The design was similar to the cotton rat study, but with animals dosed at 5, 25, or 50 ug of the vaccine. As shown in FIG. 10, absolute neutralizing titers in serum were lower than in the cotton rat model, however the 25 and 50 μg doses still conferred complete protection from detectable viral load. The 5 ug dose resulted in a reduction in viral load at 5 days post challenge of approximately 1.5 to 2 logs in nose and lung, respectively, relative to placebo.

While the results above suggest a high probability of success in generating an mRNA vaccine based on Nipah F protein, soluble Nipah glycoprotein (G) vaccines have also been shown to be protective in vivo. Leveraging the flexibility of this mRNA platform we will design and test constructs of the Nipah and Hendra glycoprotein G protein as well, ultimately testing the efficacy of F and G alone and in combination at different ratios. This flexible mRNA technology allows multiple constructs to be combined and administered as one vaccine. It also enables selection of the ideal ratio of antigens to elicit the optimal immune response.

Example 5: MERS-CoV Spike Protein mRNA Vaccine

Mouse Immunogenicity

To determine the immunogenicity of MERS-CoV spike protein mRNA vaccine, female balb/c mice were immunized intramuscularly with 10 μg of the vaccine on Day 0 and 28. Virus neutralizing (VN) antibody titers in the mouse sera in response to MERS spike protein mRNA vaccine measured on Day 0, 21, 42 and 56 using an in vitro neutralization assay. All animals were confirmed to be seronegative at the beginning of the study.

Figure 11:
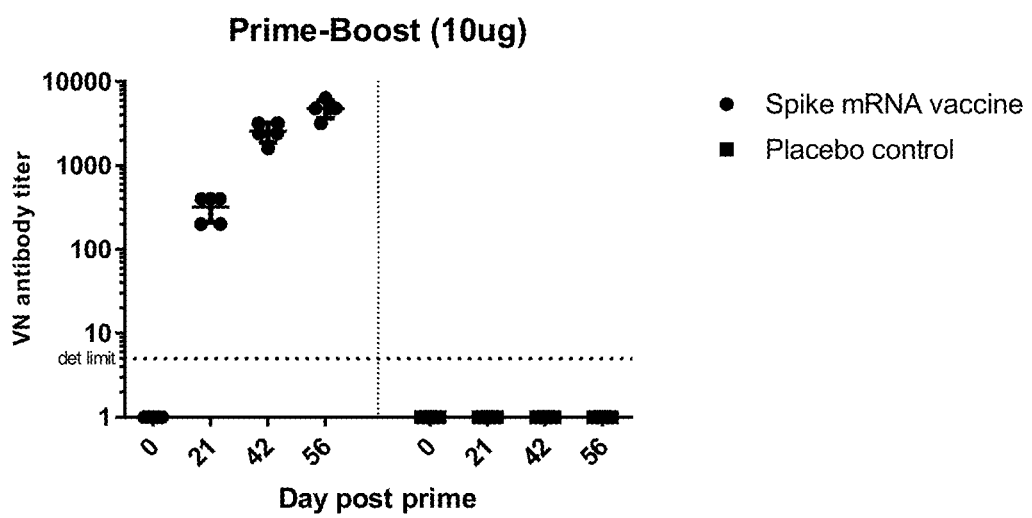
FIG. 11 shows VN titers in Balb/C mice after 2-dose immunization with MERS-CoV spike protein mRNA vaccine.

As shown in FIG. 11, a single dose of the mRNA vaccine induced neutralizing antibodies with an average serum titer of 1:320 on day 21. After the second dose on day 21, the VN antibody titers were boosted to 1:3000 by day 42 and further boosted up to 1:4800 by day 56. In contrast, placebo treated mice had no detectable VN antibody titer throughout the study.

Rabbit Challenge

*Oryctolagus cuniculus* (Rabbit) has been recently identified as a suitable animal model for MERS-CoV infection. The sequence homology for the receptor gene for MERS-CoV, DPP4(dipeptidyl peptidase 4), between humans and rabbits is such that it allows proficient infection of rabbits with MERS-CoV (Ra et al., *J Virol* 2014; Haagmans et al., *J Virol*, 2015). Nevertheless, replication of MERS-CoV in rabbits require a very high viral inoculum administered through the intra-nasal and intra-tracheal route.

In order to assess the efficacy of MERS-CoV spike protein mRNA vaccine, 6 month old New Zealand white rabbits were challenged 6 weeks after prime with EMC/2012 MERS-CoV. The vaccine was tested in a one or two dose regimen, with the boost spaced 3 weeks apart on day for group 2, and each dose was 20 μg. Nasal and Throat swabs were collected from one day prior to challenge; to the end of study, 4 days post challenge. Serum from animals was collected on Day 0, 21, 35, 42 and 47 for measuring virus neutralizing antibody titers.

Figure 12:
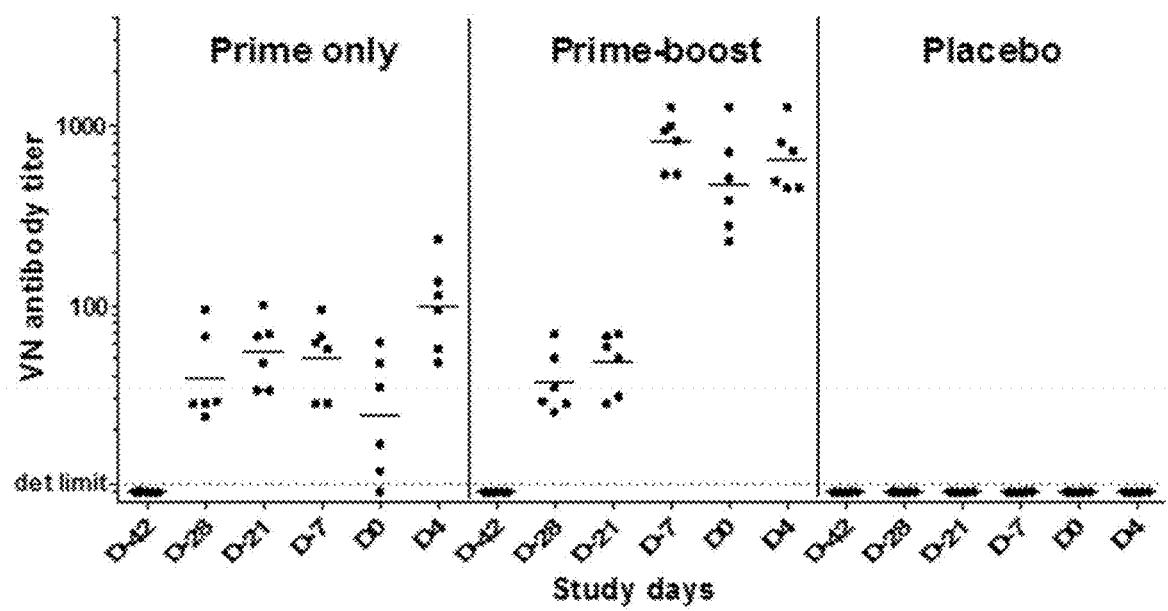
FIG. 12 shows VN titers against MERS-CoV after prime only (left), prime-boost (middle) or placebo (right) treatment. Individual values are shown as well as the geometric mean titer.

In the Single dose group (prime only), all animals became VN positive two weeks after the vaccination and remained equally high until one week before challenge. At the time of challenge (day 0) a minor decrease in VN antibodies was observed, which was boosted upon challenge virus MERS-CoV (see FIG. 12). Similarly, all animals receiving 2 doses (prime-boost) of the vaccine became VN positive two weeks after the first vaccination and responses were boosted after the second vaccination on day −21. VN antibody responses remained high until the time of challenge and were not further boosted upon challenge on day 0. No VN antibody responses could be detected in any of the placebo treated animals during the vaccination and challenge phase of the study (FIG. 12).

Analysis of PCR and Virus Titration in Rabbit Nose Swabs

In the prime only group (1a), virus could be detected by PCR on day 1 after challenge in all animals. Three animals remained PCR positive until the end of follow up, while 3 animals became PCR negative in within 2 to 4 days post challenge (FIG. 13, Panel A). None of the PCR positive signals detected after challenge could be confirmed by virus titration (FIG. 13, Panel D).

In the prime-boost group (1b), virus could be detected by PCR on day 1 after challenge in three out of six animals, which remained positive on day 2 after challenge and were PCR negative by day 3 post challenge (FIG. 13, Panel B). None of the PCR positive signals detected after challenge could be confirmed by virus titration (FIG. 13, Panel E).

Analysis of PCR and Virus Titration in Rabbit Throat Swabs

In the prime only group (1a), virus could be detected by PCR on day 1 after challenge in all animals. One animal remained PCR positive until day 3 after challenge, however all animals were PCR negative day 4 post challenge (FIG. 14, Panel A). None of the PCR positive signals detected after challenge could be confirmed by virus titration (FIG. 14, Panel D).

In the prime-boost group (1b), virus could be detected by PCR day 1 after challenge in three out of six animals and all were PCR negative the following day. Additionally, two of these animals were PCR positive on the last day of follow up (FIG. 14, Panel B). PCR signals could not be detected in any of the other three animals. None of the PCR positive signals detected after challenge could be confirmed by virus titration (FIG. 14, Panel E).

In all placebo animals (group 2) virus could be detected by PCR on day 1 after challenge and remained PCR positive until the last sample that was analyzed. Only three PCR positive signals could be confirmed by virus titration (FIG. 14, Panels C and F).

Viral loads were also measured in the right nasal turbinates post mortem at the day of scheduled euthanasia (4 dpi). Levels of viral RNA were measured using a MERS- CoV-specific TaqMan PCR and levels of infectious (replication competent) virus using Vero cell culture.

Of the prime only group, samples from 2 out of 6 animals were positive by PCR, but all were undetectable by virus titration. The remaining four animals of group 1a were negative in PCR and virus titration. In the prime-boost group, 1 of 6 animals was positive by PCR, which again could not be detected by virus titration. The remaining five animals of group 1b were negative in PCR and virus titration. Finally all placebo animals were positive by PCR and in four animals the PCR positive signal could be confirmed by virus titration.

Analysis of Viral Load in Rabbit Lungs

Figure 15:
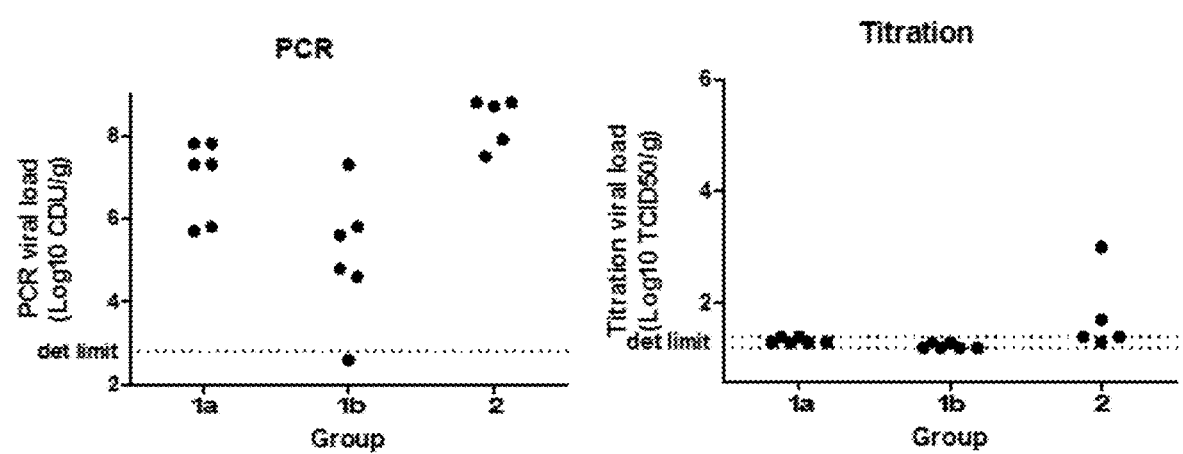
FIG. 15 shows MERS-CoV PCR (left panel) and titration (right panel) results in pooled lung samples after challenge in prime only (1a), prime-boost (1b) or placebo (2) treated groups. Individual values are shown as well as the (range of the) lower limit of detection of PCR (2.8 log 10 CDU/g) and virus titration (1.2-1.4 log 10 TCID50/g).

Rabbit lungs were dissected into 9 separated regions post mortem for individual for assessment of viral load by region of the lung. For determining the viral load in the total lung the different sections of the lungs were pooled (equal amount of material for each section) and these samples were tested by both PCR and titration (FIG. 15). Results by PCR showed that only one animal in the prime-boost group was PCR negative in the lungs. In contrast, while PCR positive signals could be detected in almost all animals, virus titration on the total lung samples resulted in only two positive animals, both in the placebo group.

Summary

The patterns of viral load observed by PCR and by titration observed in each of the sample types in the rabbit challenge model are suggestive of a high level of protection from viral replication. The lack of any replicating virus in most of the vaccinated animal samples indicates that any PCR signal found in those same samples is likely due to the detection of residual nucleic acid sequences from input virus during the challenge itself.

The body of the immunogenicity and viral challenge data indicate that the vaccines of the invention generate robust immunologic responses with high neutralizing titers that are protective from viral replication upon challenge.

EQUIVALENTS

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one." It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The terms "about" and "substantially" preceding a numerical value mean±10% of the recited numerical value.

Where a range of values is provided, each value between the upper and lower ends of the range are specifically contemplated and described herein.

The entire contents of International Application Nos. PCT/US2015/027400, PCT/US2016/043348, PCT/US2016/043332, PCT/US2016/058327, PCT/US2016/058324, PCT/US2016/058314, PCT/US2016/058310, PCT/US2016/058321, PCT/US2016/058297, PCT/US2016/058319, and PCT/US2016/058314 are incorporated herein by reference.

SEQUENCES

It should be understood that any of the mRNA sequences described herein may include a 5' UTR and/or a 3' UTR. The UTR sequences may be selected from the following sequences, or other known UTR sequences may be used. It should also be understood that any of the mRNA constructs described herein may further comprise a poly A tail and/or cap (e.g., 7mG(5')ppp(5')NlmpNp). Further, while many of the mRNAs and encoded antigen sequences described herein include a signal peptide and/or a peptide tag (e.g., C-terminal His tag), it should be understood that the indicated signal peptide and/or peptide tag may be substituted for a different signal peptide and/or peptide tag, or the signal peptide and/or peptide tag may be omitted.

Exemplary Sequences: Human IgG kappa signal sequence included in protein and nucleic acid sequences are underlined

```
Lassa_GPC protein
                                                             (SEQ ID NO: 1)
MGQIVTFFQEVPHVIEEVMNIVLIALSLLAILKGIYNVATCGLFGLVSFLLLCGRSCSTTYKGVYELQTLELD

MASLNMTMPLSCTKNNSHHYIMVGNETGLELTLTNTSIINHKFCNLSDAHKKDLYDHALMSIISTFHLSIPN

FNQYEAMSCDFNGGKISVQYNLSHTYAVDAANHCGTIANGVLQTFMRMAWGGSYIALDSGKGSWDCIM

TSYQYLIIQNTTWEDHCQFSRPSPIGYLGLLSQRTRDIYISRRLLGTFTWTLSDSEGNETPGGYCLTRWMLIE

AELKCFGNTAVAKCNEKHDEEFCDMLRLFDFNKQAIMRLKTEAQMSIQLINKAVNALINDQLIMKNHLRD

IMGIPYCNYSKYWYLNHTVTGKTSLPRCWLVSNGSYLNETRFSDDIEQQADNMITEMLQKEYLDRQGKTP

LGLVDLFVFSTSFYLISIFLHLVKIPTHRHIIGKPCPKPHRLNHMGICSCGLYKHPGVPVKWKR

Lassa_GPC nucleic acid
                                                             (SEQ ID NO: 4)
ATGGGCCAGATCGTGACATTCTTCCAAGAGGTGCCCCACGTGATCGAGGAAGTGATGAACATCGTCCT

GATCGCCCTGAGCCTGCTGGCCATCCTGAAGGGCATCTACAACGTGGCCACCTGTGGCCTGTTTGGCC

TGGTGTCATTCCTGCTGCTGTGCGGCAGAAGCTGCAGCACCACATACAAGGGCGTGTACGAGCTGCAG
```

```
ACCCTGGAACTGGATATGGCCAGCCTGAACATGACCATGCCTCTGAGCTGCACCAAGAACAACAGCC
ACCACTACATCATGGTCGGAAACGAGACAGGACTGGAACTGACCCTGACCAACACCAGCATCATCAA
CCACAAGTTCTGCAACCTGAGCGACGCCCACAAGAAGGACCTGTACGATCACGCCCTGATGAGCATCA
TCTCCACCTTCCACCTGAGCATCCCCAACTTCAACCAGTACGAGGCCATGAGCTGCGACTTCAACGGC
GGCAAGATCAGCGTGCAGTACAATCTGAGCCACACCTACGCCGTGGACGCCGCCAATCACTGTGGCAC
AATTGCCAATGGCGTGCTGCAGACATTCATGCGGATGGCCTGGGGCGGCTCTTATATCGCCCTGGATT
CTGGCAAAGGCAGCTGGGACTGCATCATGACCAGCTACCAGTACCTGATCATCCAGAACACCACCTGG
GAAGATCACTGCCAGTTCAGCAGACCCTCTCCTATCGGCTATCTGGGCCTGCTGAGCCAGAGAACCCG
GGACATCTACATCAGCAGAAGGCTGCTGGGCACCTTCACCTGGACACTGTCTGACAGCGAGGGCAAC
GAAACACCTGGCGGCTACTGCCTGACCAGATGGATGCTGATTGAGGCCGAGCTGAAGTGCTTCGGCAA
TACCGCCGTGGCCAAGTGCAACGAGAAGCACGACGAGGAATTCTGCGACATGCTGCGGCTGTTCGATT
TCAACAAGCAGGCCATCATGCGGCTCAAGACCGAGGCTCAGATGTCCATCCAGCTGATCAACAAGGC
CGTGAATGCCCTGATCAACGATCAGCTCATCATGAAGAACCACCTCCGGGATATCATGGGCATCCCTT
ACTGCAACTACAGCAAGTACTGGTATCTCAACCACACCGTGACCGGCAAGACCAGCCTGCCTAGATGT
TGGCTGGTGTCCAACGGCAGCTACCTGAACGAGACACGGTTCAGCGACGACATCGAGCAGCAGGCCG
ACAACATGATCACCGAGATGCTGCAGAAAGAGTACCTGGACCGGCAGGGCAAGACACCTCTGGGACT
CGTGGATCTGTTCGTGTTCAGCACCAGCTTCTACCTGATCTCTATCTTCCTGCACCTGGTCAAGATCCC
CACACACCGGCACATCATCGGCAAGCCCTGTCCTAAGCCTCACCGGCTGAACCACATGGGAATCTGTA
GCTGCGGCCTGTACAAGCACCCTGGCGTGCCAGTGAAGTGGAAGAGA
```

Lassa_GPC mRNA (SEQ ID NO: 6)

```
AUGGGCCAGAUCGUGACAUUCUUCCAAGAGGUGCCCCACGUGAUCGAGGAAGUGAUGAACAUCGU
CCUGAUCGCCCUGAGCCUGCUGGCCAUCCUGAAGGGCAUCUACAACGUGGCCACCGUGGCCUGUU
UGGCCUGGUGUCAUUCCUGCUGCUGUGCGGCAGAAGCUGCAGCACCACAUACAAGGGCGUGUACGA
GCUGCAGACCCUGGAACUGGAUAUGGCCAGCCUGAACAUGACCAUGCCUCUGAGCUGCACCAAGAA
CAACAGCCACCACUACAUCAUGGUCGGAAACGAGACAGGACUGGAACUGACCCUGACCAACACCAG
CAUCAUCAACCACAAGUUCUGCAACCUGAGCGACGCCCACAAGAAGGACCUGUACGAUCACGCCCU
GAUGAGCAUCAUCUCCACCUUCCACCUGAGCAUCCCCAACUUCAACCAGUACGAGGCCAUGAGCUG
CGACUUCAACGGCGGCAAGAUCAGCGUGCAGUACAAUCUGAGCCACACCUACGCCGUGGACGCCGC
CAAUCACUGUGGCACAAUUGCCAAUGGCGUGCUGCAGACAUUCAUGCGGAUGGCCUGGGGCGGCUC
UUAUAUCGCCCUGGAUUCUGGCAAAGGCAGCUGGGACUGCAUCAUGACCAGCUACCAGUACCUGAU
CAUCCAGAACACCACCUGGGAAGAUCACUGCCAGUUCAGCAGACCCUCUCCUAUCGGCUAUCUGGG
CCUGCUGAGCCAGAGAACCCGGGACAUCUACAUCAGCAGAAGGCUGCUGGGCACCUUCACCUGGAC
ACUGUCUGACAGCGAGGGCAACGAAACACCUGGCGGCUACUGCCUGACCAGAUGGAUGCUGAUUGA
GGCCGAGCUGAAGUGCUUCGGCAAUACCGCCGUGGCCAAGUGCAACGAGAAGCACGACGAGGAAUU
CUGCGACAUGCUGCGGCUGUUCGAUUUCAACAAGCAGGCCAUCAUGCGGCUCAAGACCGAGGCUCA
GAUGUCCAUCCAGCUGAUCAACAAGGCCGUGAAUGCCCUGAUCAACGAUCAGCUCAUCAUGAAGAA
CCACCUCCGGGAUAUCAUGGGCAUCCCUUACUGCAACUACAGCAAGUACUGGUAUCUCAACCACAC
CGUGACCGGCAAGACCAGCCUGCCUAGAUGUUGGCUGGUGUCCAACGGCAGCUACCUGAACGAGAC
ACGGUUCAGCGACGACAUCGAGCAGCAGGCCGACAACAUGAUCACCGAGAUGCUGCAGAAAGAGUA
CCUGGACCGGCAGGGCAAGACACCUCUGGGACUCGUGGAUCUGUUCGUGUUCAGCACCAGCUUCUA
```

```
CCUGAUCUCUAUCUUCCUGCACCUGGUCAAGAUCCCCACACACCGGCACAUCAUCGGCAAGCCCUG

UCCUAAGCCUCACCGGCUGAACCACAUGGGAAUCUGUAGCUGCGGCCUGUACAAGCACCCUGGCGU

GCCAGUGAAGUGGAAGAGA
```

Lassa_Nucleoprotein with or without signal sequence - protein (SEQ ID NO: 2)
```
MSASKEVKSFLWTQSLRRELSGYCSNIKLQVVKDAQALLHGLDFSEVSNVQRLMRKQKRDDGDLKRLRD

LNQAVNNLVELKSTQQKSVLRVGTLSSDDLLVLAADLEKLKSKVVRTERPLSSGIYMGNLSSQQLDQRKA

LLNMIGMTGGNGGRNTTSDGIVRVWDVKNAELLNNQFGTMPSLTLACLTKQGQVDLNDAVQALTDLGLI

YTAKYPNSSDLDRLAQSHPILNMIDTKKSSLNISGYNFSLGAAVKAGACMLDGGNMLETIKVSPQTMDGIL

KSILKVKRSLGMFISDTPGERNPYENILYKICLSGDGWPYIASRTSIVGRAWENTVVDLESDNKPQKTGNGG

SNKSLQSAGFAAGLTYSQLMTLKDSMLQLDPNAKTWMDIEGRPEDPVEIALYQPSSGCYIHFFREPTDLKQ

FKQDAKYSHGIDVTDLFAAQPGLTSAVIEALPRNMVITCQGSEDIRKLLESQGRRDIKLIDISLSKVDSRKFE

NAVWDQFKDLCHMHTGIVVEKKKRGGKEEITPHCALMDCIMFDAAVSGGVDAKVLRAVLPRDMVFRTS

TPKVVL
```

(SEQ ID NO: 3)
```
METPAQLLFLLLLWLPDTTGMSASKEVKSFLWTQSLRRELSGYCSNIKLQVVKDAQALLHGLDFSEVSNV

QRLMRKQKRDDGDLKRLRDLNQAVNNLVELKSTQQKSVLRVGTLSSDDLLVLAADLEKLKSKVVRTERP

LSSGIYMGNLSSQQLDQRKALLNMIGMTGGNGGRNTTSDGIVRVWDVKNAELLNNQFGTMPSLTLACLT

KQGQVDLNDAVQALTDLGLIYTAKYPNSSDLDRLAQSHPILNMIDTKKSSLNISGYNFSLGAAVKAGACM

LDGGNMLETIKVSPQTMDGILKSILKVKRSLGMFISDTPGERNPYENILYKICLSGDGWPYIASRTSIVGRAW

ENTVVDLESDNKPQKTGNGGSNKSLQSAGFAAGLTYSQLMTLKDSMLQLDPNAKTWMDIEGRPEDPVEIA

LYQPSSGCYIHFFREPTDLKQFKQDAKYSHGIDVTDLFAAQPGLTSAVIEALPRNMVITCQGSEDIRKLLESQ

GRRDIKLIDISLSKVDSRKFENAVWDQFKDLCHMHTGIVVEKKKRGGKEEITPHCALMDCIMFDAAVSGG

VDAKVLRAVLPRDMVFRTSTPKVVL
```

Lassa_Nucleoprotein with or without signal sequence - nucleic acid (SEQ ID NO: 5)
```
ATGGAGACTCCTGCCCAGCTCTTGTTCCTTTTGCTATTGTGGCTTCCCGACACCACCGGCATGAGCGCC

AGCAAGGAGGTCAAGAGCTTCCTCTGGACCCAGAGCCTAAGAAGAGAGCTTAGCGGCTACTGCAGCA

ACATCAAGCTTCAGGTGGTGAAGGACGCCCAGGCCCTGCTGCACGGCCTGGACTTCAGCGAGGTGAG

CAACGTGCAGAGACTGATGAGAAAGCAGAAGCGAGACGACGGCGACCTGAAGCGTCTGCGGGACCTG

AACCAGGCCGTGAACAACCTGGTGGAGCTTAAGAGCACCCAGCAGAAGTCTGTGCTGAGAGTGGGCA

CCCTGAGCAGCGACGACCTGCTGGTGCTGGCCGCCGACCTGGAGAAGCTGAAGTCTAAGGTCGTCAG

AACCGAGCGGCCATTGAGCTCAGGCATCTACATGGGCAACCTTAGCAGTCAGCAGCTGGACCAGAGA

AAGGCCTTGCTGAACATGATCGGCATGACCGGCGGCAACGGCGGCAGAAACACCACCAGCGACGGCA

TCGTGAGAGTGTGGGACGTGAAGAACGCCGAGCTACTCAACAACCAGTTCGGCACCATGCCCAGCCT

GACCCTGGCCTGCCTGACCAAGCAGGGCCAGGTGGACCTCAATGACGCCGTGCAGGCACTAACCGAC

CTTGGCCTGATCTACACCGCCAAGTACCCCAACTCTTCAGACCTGGACAGACTGGCGCAGTCCCACCC

CATCTTAAATATGATTGACACCAAGAAGTCATCCCTTAACATCAGTGGCTACAACTTCAGCCTGGGCG

CCGCCGTGAAGGCCGGCGCCTGCATGCTGGACGGCGGAAATATGCTGGAAACTATCAAGGTGAGCCC

TCAGACCATGGACGGTATCCTGAAGTCCATTTTGAAGGTTAAGAGATCCCTGGGTATGTTCATCAGCG

ACACCCCAGGCGAGAGAAACCCCTACGAGAACATCCTGTACAAGATCTGCCTGAGTGGCGACGGCTG

GCCCTACATCGCGAGCAGAACCAGCATCGTGGGAAGGGCCTGGGAGAACACCGTGGTGGATCTTGAG

AGCGACAACAAGCCCCAGAAGACCGGAAATGGCGGTTCAAACAAGAGCCTGCAGAGCGCCGGCTTCG
```

-continued

CCGCCGGCCTGACCTACAGCCAGCTGATGACCCTGAAGGACAGCATGCTACAATTGGATCCCAACGCC

AAGACTTGGATGGACATCGAGGGCAGACCCGAGGACCCCGTGGAGATCGCCCTGTACCAGCCCTCAT

CCGGCTGCTACATCCACTTCTTCAGAGAGCCCACAGATCTGAAGCAGTTCAAGCAGGACGCGAAGTAT

AGCCATGGCATAGACGTCACCGATTTATTCGCGGCCCAGCCGGGCCTTACGAGCGCCGTGATCGAGGC

GCTGCCCAGAAACATGGTGATCACCTGCCAGGGCAGCGAGGACATCAGAAAGCTCCTTGAATCTCAA

GGCCGGAGAGATATTAAGCTGATAGATATCAGCTTATCTAAGGTTGACAGCAGAAAGTTCGAGAACG

CTGTATGGGACCAATTCAAGGACCTGTGCCACATGCATACGGGCATAGTGGTAGAGAAGAAGAAGCG

TGGCGGAAAGGAGGAGATCACACCTCACTGCGCCCTGATGGACTGCATCATGTTCGACGCGGCAGTCT

CCGGCGGCGTCGACGCAAAGGTCCTCCGGGCCGTGCTGCCAAGGGACATGGTGTTCCGGACAAGCAC

CCCTAAGGTAGTGCTG

Lassa_Nucleoprotein with or without signal sequence - mRNA (SEQ ID NO: 7)

<u>AUGGAGACUCCUGCCCAGCUCUUGUUCCUUUUGCUAUUGUGGCUUCCC</u>GACACCACCGGCAUGAGC

GCCAGCAAGGAGGUCAAGAGCUUCCUCUGGACCCAGAGCCUAAGAAGAGAGCUUAGCGGCUACUGC

AGCAACAUCAAGCUUCAGGUGGUGAAGGACGCCCAGGCCCUGCUGCACGGCCUGGACUUCAGCGAG

GUGAGCAACGUGCAGAGACUGAUGAGAAAGCAGAAGCGAGACGACGGCGACCUGAAGCGUCUGCG

GGACCUGAACCAGGCCGUGAACAACCUGGUGGAGCUUAAGAGCACCCAGCAGAAGUCUGUGCUGAG

AGUGGGCACCCUGAGCAGCGACGACCUGCUGGUGCUGGCCGCCGACCUGGAGAAGCUGAAGUCUAA

GGUCGUCAGAACCGAGCGGCCAUUGAGCUCAGGCAUCUACAUGGGCAACCUUAGCAGUCAGCAGCU

GGACCAGAGAAAGGCCUUGCUGAACAUGAUCGGCAUGACCGGCGGCAACGGCGGCAGAAACACCAC

CAGCGACGGCAUCGUGAGAGUGUGGGACGUGAAGAACGCCGAGCUACUCAACAACCAGUUCGGCAC

CAUGCCCAGCCUGACCCUGGCCUGCCUGACCAAGCAGGGCCAGGUGGACCUCAAUGACGCCGUGCA

GGCACUAACCGACCUUGGCCUGAUCUACACCGCCAAGUACCCCAACUCUUCAGACCUGGACAGACU

GGCGCAGUCCCACCCCAUCUUAAAUAUGAUUGACACCAAGAAGUCAUCCCUUAACAUCAGUGGCUA

CAACUUCAGCCUGGGCGCCGCCGUGAAGGCCGGCGCCUGCAUGCUGGACGGCGGAAAUAUGCUGGA

AACUAUCAAGGUGAGCCCUCAGACCAUGGACGGUAUCCUGAAGUCCAUUUUGAAGGUUAAGAGAU

CCCUGGGUAUGUUCAUCAGCGACACCCCAGGCGAGAGAAACCCCUACGAGAACAUCCUGUACAAGA

UCUGCCUGAGUGGCGACGGCUGGCCCUACAUCGCGAGCAGAACCAGCAUCGUGGGAAGGGCCUGGG

AGAACACCGUGGUGGAUCUUGAGAGCGACAACAAGCCCCAGAAGACCGGAAAUGGCGGUUCAAAC

AAGAGCCUGCAGAGCGCCGGCUUCGCCGCCGGCCUGACCUACAGCCAGCUGAUGACCCUGAAGGAC

AGCAUGCUACAAUUGGAUCCCAACGCCAAGACUUGGAUGGACAUCGAGGGCAGACCCGAGGACCCC

GUGGAGAUCGCCCUGUACCAGCCCUCAUCCGGCUGCUACAUCCACUUCUUCAGAGAGCCCACAGAU

CUGAAGCAGUUCAAGCAGGACGCGAAGUAUAGCCAUGGCAUAGACGUCACCGAUUUAUUCGCGGCC

CAGCCGGGCCUUACGAGCGCCGUGAUCGAGGCGCUGCCCAGAAACAUGGUGAUCACCUGCCAGGGC

AGCGAGGACAUCAGAAAGCUCCUUGAAUCUCAAGGCCGGAGAGAUAUUAAGCUGAUAGAUAUCAG

CUUAUCUAAGGUUGACAGCAGAAAGUUCGAGAACGCUGUAUGGGACCAAUUCAAGGACCUGUGCC

ACAUGCAUACGGGCAUAGUGGUAGAGAAGAAGAAGCGUGGCGGAAAGGAGGAGAUCACACCUCAC

UGCGCCCUGAUGGACUGCAUCAUGUUCGACGCGGCAGUCUCCGGCGGCGUCGACGCAAAGGUCCUC

CGGGCCGUGCUGCCAAGGGACAUGGUGUUCCGGACAAGCACCCCUAAGGUAGUGCUG (SEQ ID NO: 8)

ATGAGCGCCAGCAAGGAGGTCAAGAGCTTCCTCTGGACCCAGAGCCTAAGAAGAGAGCTTAGCGGCT

ACTGCAGCAACATCAAGCTTCAGGTGGTGAAGGACGCCCAGGCCCTGCTGCACGGCCTGGACTTCAGC

-continued

```
GAGGTGAGCAACGTGCAGAGACTGATGAGAAAGCAGAAGCGAGACGACGGCGACCTGAAGCGTCTG
CGGGACCTGAACCAGGCCGTGAACAACCTGGTGGAGCTTAAGAGCACCCAGCAGAAGTCTGTGCTGA
GAGTGGGCACCCTGAGCAGCGACGACCTGCTGGTGCTGGCCGCCGACCTGGAGAAGCTGAAGTCTAA
GGTCGTCAGAACCGAGCGGCCATTGAGCTCAGGCATCTACATGGGCAACCTTAGCAGTCAGCAGCTGG
ACCAGAGAAAGGCCTTGCTGAACATGATCGGCATGACCGGCGGCAACGGCGGCAGAAACACCACCAG
CGACGGCATCGTGAGAGTGTGGGACGTGAAGAACGCCGAGCTACTCAACAACCAGTTCGGCACCATG
CCCAGCCTGACCCTGGCCTGCCTGACCAAGCAGGGCCAGGTGGACCTCAATGACGCCGTGCAGGCACT
AACCGACCTTGGCCTGATCTACACCGCCAAGTACCCCAACTCTTCAGACCTGGACAGACTGGCGCAGT
CCCACCCCATCTTAAATATGATTGACACCAAGAAGTCATCCCTTAACATCAGTGGCTACAACTTCAGC
CTGGGCGCCGCCGTGAAGGCCGGCGCCTGCATGCTGGACGGCGGAAATATGCTGGAAACTATCAAGG
TGAGCCCTCAGACCATGGACGGTATCCTGAAGTCCATTTTGAAGGTTAAGAGATCCCTGGGTATGTTC
ATCAGCGACACCCCAGGCGAGAGAAACCCCTACGAGAACATCCTGTACAAGATCTGCCTGAGTGGCG
ACGGCTGGCCCTACATCGCGAGCAGAACCAGCATCGTGGGAAGGGCCTGGGAGAACACCGTGGTGGA
TCTTGAGAGCGACAACAAGCCCCAGAAGACCGGAAATGGCGGTTCAAACAAGAGCCTGCAGAGCGCC
GGCTTCGCCGCCGGCCTGACCTACAGCCAGCTGATGACCCTGAAGGACAGCATGCTACAATTGGATCC
CAACGCCAAGACTTGGATGGACATCGAGGGCAGACCCGAGGACCCCGTGGAGATCGCCCTGTACCAG
CCCTCATCCGGCTGCTACATCCACTTCTTCAGAGAGCCCACAGATCTGAAGCAGTTCAAGCAGGACGC
GAAGTATAGCCATGGCATAGACGTCACCGATTTATTCGCGGCCCAGCCGGGCCTTACGAGCGCCGTGA
TCGAGGCGCTGCCCAGAAACATGGTGATCACCTGCCAGGGCAGCGAGGACATCAGAAAGCTCCTTGA
ATCTCAAGGCCGGAGAGATATTAAGCTGATAGATATCAGCTTATCTAAGGTTGACAGCAGAAAGTTCG
AGAACGCTGTATGGGACCAATTCAAGGACCTGTGCCACATGCATACGGGCATAGTGGTAGAGAAGAA
GAAGCGTGGCGGAAAGGAGGAGATCACACCTCACTGCGCCCTGATGGACTGCATCATGTTCGACGCG
GCAGTCTCCGGCGGCGTCGACGCAAAGGTCCTCCGGGCCGTGCTGCCAAGGGACATGGTGTTCCGGAC
AAGCACCCCTAAGGTAGTGCTG
``` mRNA
                                                                (SEQ ID NO: 9)
```
AUGAGCGCCAGCAAGGAGGUCAAGAGCUUCCUCUGGACCCAGAGCCUAAGAAGAGAGCUUAGCGGC
UACUGCAGCAACAUCAAGCUUCAGGUGGUGAAGGACGCCCAGGCCCUGCUGCACGGCCUGGACUUC
AGCGAGGUGAGCAACGUGCAGAGACUGAUGAGAAAGCAGAAGCGAGACGACGGCGACCUGAAGCG
UCUGCGGGACCUGAACCAGGCCGUGAACAACCUGGUGGAGCUUAAGAGCACCCAGCAGAAGUCUGU
GCUGAGAGUGGGCACCCUGAGCAGCGACGACCUGCUGGUGCUGGCCGCCGACCUGGAGAAGCUGAA
GUCUAAGGUCGUCAGAACCGAGCGGCCAUUGAGCUCAGGCAUCUACAUGGGCAACCUUAGCAGUCA
GCAGCUGGACCAGAGAAAGGCCUUGCUGAACAUGAUCGGCAUGACCGGCGGCAACGGCGGCAGAAA
CACCACCAGCGACGGCAUCGUGAGAGUGUGGGACGUGAAGAACGCCGAGCUACUCAACAACCAGUU
CGGCACCAUGCCCAGCCUGACCCUGGCCUGCCUGACCAAGCAGGGCCAGGUGGACCUCAAUGACGC
CGUGCAGGCACUAACCGACCUUGGCCUGAUCUACACCGCCAAGUACCCCAACUCUUCAGACCUGGA
CAGACUGGCGCAGUCCCACCCCAUCUUAAAUAUGAUUGACACCAAGAAGUCAUCCCUUAACAUCAG
UGGCUACAACUUCAGCCUGGGCGCCGCCGUGAAGGCCGGCGCCUGCAUGCUGGACGGCGGAAAUAU
GCUGGAAACUAUCAAGGUGAGCCCUCAGACCAUGGACGGUAUCCUGAAGUCCAUUUUGAAGGUUA
AGAGAUCCCUGGGUAUGUUCAUCAGCGACACCCCAGGCGAGAGAAACCCCUACGAGAACAUCCUGU
ACAAGAUCUGCCUGAGUGGCGACGGCUGGCCCUACAUCGCGAGCAGAACCAGCAUCGUGGGAAGGG
CCUGGGAGAACACCGUGGUGGAUCUUGAGAGCGACAACAAGCCCCAGAAGACCGGAAAUGGCGGU
```

-continued

```
UCAAACAAGAGCCUGCAGAGCGCCGGCUUCGCCGCCGGCCUGACCUACAGCCAGCUGAUGACCCUG
AAGGACAGCAUGCUACAAUUGGAUCCCAACGCCAAGACUUGGAUGGACAUCGAGGGCAGACCCGAG
GACCCCGUGGAGAUCGCCCUGUACCAGCCCUCAUCCGGCUGCUACAUCCACUUCUUCAGAGAGCCC
ACAGAUCUGAAGCAGUUCAAGCAGGACGCGAAGUAUAGCCAUGGCAUAGACGUCACCGAUUUAUU
CGCGGCCCAGCCGGGCCUUACGAGCGCCGUGAUCGAGGCGCUGCCCAGAAACAUGGUGAUCACCUG
CCAGGGCAGCGAGGACAUCAGAAAGCUCCUUGAAUCUCAAGGCCGGAGAGAUAUUAAGCUGAUAG
AUAUCAGCUUAUCUAAGGUUGACAGCAGAAAGUUCGAGAACGCUGUAUGGGACCAAUUCAAGGAC
CUGUGCCACAUGCAUACGGGCAUAGUGGUAGAGAAGAAGAAGCGUGGCGGAAAGGAGGAGAUCAC
ACCUCACUGCGCCCUGAUGGACUGCAUCAUGUUCGACGCGGCAGUCUCCGGCGGCGUCGACGCAAA
GGUCCUCCGGGCCGUGCUGCCAAGGGACAUGGUGUUCCGGACAAGCACCCCUAAGGUAGUGCUG
```

Nipah_G (SEQ ID NO: 10)

METPAQLLFLLLLWLPDTTGMPAENKKVRFENTTSDKGKNPSKVIKSYYGTMDIKKINEGLLDSKILSAFN
TVIALLGSIVIIVMNIMIIQNYTRSTDNQAVIKDALQGIQQQIKGLADKIGTEIGPKVSLIDTSSTITIPANIGLL
GSKISQSTASINENVNEKCKFTLPPLKIHECNISCPNPLPFREYRPQTEGVSNLVGLPDNICLQKTSNQILKPK
LISYTLPVVGQSGTCITDPLLAMDEGYFAYSHLERIGSCSRGVSKQRIIGVGEVLDRGDEVPSLFMTNVWTP
PNPNTVYHCSAVYNNEFYYVLCAVSTVGDPILNSTYWSGSLMMTRLAVKPKSNGGGYNQHQLALRSIEK
GRYDKVMPYGPSGIKQGDTLYFPAVGFLVRTEFKYNDSNCPITKCQYSKPENCRLSMGIRPNSHYILRSGLL
KYNLSDGENPKIVFIEISDQRLSIGSPSKVYDSLGQPVFYQASFSWDTMIKFGDVQTVNPLVVNWRDNTVIS
RPGQSQCPRFNTCPEICWEGVYNDAFLIDRINWISAGVFLDSNQTAENPVFTVFKDNEILYRAQLASEDTNA
QKTITNCFLLKNKIWCISLVEIYDTGDNVIRPKLFAVKIPEQCT (SEQ ID NO: 11)

MPAENKKVRFENTTSDKGKNPSKVIKSYYGTMDIKKINEGLLDSKILSAFNTVIALLGSIVIIVMNIMIIQNYT
RSTDNQAVIKDALQGIQQQIKGLADKIGTEIGPKVSLIDTSSTITIPANIGLLGSKISQSTASINENVNEKCKFT
LPPLKIHECNISCPNPLPFREYRPQTEGVSNLVGLPDNICLQKTSNQILKPKLISYTLPVVGQSGTCITDPLLA
MDEGYFAYSHLERIGSCSRGVSKQRIIGVGEVLDRGDEVPSLFMTNVWTPPNPNTVYHCSAVYNNEFYYV
LCAVSTVGDPILNSTYWSGSLMMTRLAVKPKSNGGGYNQHQLALRSIEKGRYDKVMPYGPSGIKQGDTLY
FPAVGFLVRTEFKYNDSNCPITKCQYSKPENCRLSMGIRPNSHYILRSGLLKYNLSDGENPKIVFIEISDQRLS
IGSPSKVYDSLGQPVFYQASFSWDTMIKFGDVQTVNPLVVNWRDNTVISRPGQSQCPRFNTCPEICWEGVY
NDAFLIDRINWISAGVFLDSNQTAENPVFTVFKDNEILYRAQLASEDTNAQKTITNCFLLKNKIWCISLVEIY
DTGDNVIRPKLFAVKIPEQCT (SEQ ID NO: 14)

```
ATGGAAACCCCTGCTCAGCTGCTGTTCCTGCTGCTGCTGTGGCTGCCTGATACAACAGGCATGCCCGCC
GAGAACAAGAAAGTTCGCTTCGAGAACACCACCAGCGACAAGGGCAAGAACCCCAGCAAAGTGATCA
AGAGCTACTACGGCACCATGGACATCAAGAAGATCAACGAGGGCCTGCTGGACAGCAAGATCCTGAG
CGCCTTCAACACCGTGATTGCCCTGCTGGGCTCTATCGTGATCATCGTGATGAACATCATGATCATCCA
GAACTACACCCGGTCCACCGACAACCAGGCCGTGATTAAGGATGCTCTGCAGGGAATCCAGCAGCAG
ATCAAAGGCCTGGCCGACAAGATCGGCACAGAGATCGGCCCTAAGGTGTCCCTGATCGACACCAGCA
GCACCATCACAATCCCCGCCAATATCGGACTGCTGGGATCCAAGATCAGCCAGAGCACCGCCAGCATC
AACGAGAACGTGAACGAGAAGTGCAAGTTCACCCTGCCTCCACTGAAGATCCACGAGTGCAACATCA
GCTGCCCCAATCCTCTGCCATTCAGAGAGTACAGACCCCAGACAGAGGGCGTGTCCAATCTCGTGGGC
CTGCCTGACAATATCTGCCTGCAGAAGACCAGCAACCAGATCCTGAAGCCTAAGCTGATCTCCTACAC
```

-continued

ACTGCCCGTCGTGGGCCAGAGCGGCACCTGTATTACAGATCCTCTGCTGGCCATGGACGAGGGCTACT

TTGCCTACAGCCACCTGGAAAGAATCGGCAGCTGTAGCCGGGGAGTGTCCAAGCAGAGAATCATCGG

CGTGGGCGAAGTGCTGGATAGAGGCGACGAAGTGCCCAGCCTGTTCATGACCAATGTGTGGACCCCTC

CTAATCCTAACACCGTGTACCACTGCAGCGCCGTGTACAACAACGAGTTCTACTACGTGCTGTGCGCC

GTGTCCACAGTGGGCGACCCTATCCTGAACAGCACCTATTGGAGCGGCAGCCTGATGATGACCAGACT

GGCCGTGAAGCCCAAGAGCAATGGCGGCGGATACAACCAGCATCAGCTGGCCCTGCGGTCCATCGAG

AAGGGCAGATACGACAAAGTGATGCCTTACGGCCCCAGCGGCATCAAGCAAGGCGATACCCTGTACT

TTCCCGCCGTGGGATTTCTCGTGCGGACCGAGTTCAAGTACAACGACAGCAACTGCCCCATCACCAAG

TGCCAGTACAGCAAGCCCGAGAACTGCAGACTGAGCATGGGCATCAGACCCAACAGCCACTACATCC

TGAGAAGCGGCCTGCTGAAGTACAACCTGAGCGACGGCGAGAACCCCAAGATCGTGTTCATCGAGAT

CAGCGACCAGCGGCTGTCTATCGGCAGCCCTAGCAAGGTGTACGACTCTCTGGGACAGCCAGTGTTCT

ACCAGGCCTCCTTCAGCTGGGACACCATGATCAAGTTCGGCGACGTGCAGACCGTGAATCCCCTGGTG

GTCAACTGGCGGGACAATACCGTGATCAGCAGACCTGGCCAGTCTCAGTGCCCCAGATTCAACACATG

CCCCGAGATCTGTTGGGAAGGCGTGTACAATGACGCCTTCCTGATCGATCGGATCAACTGGATCTCTG

CCGGCGTGTTCCTGGACTCCAATCAGACAGCCGAGAATCCTGTGTTCACCGTGTTCAAGGACAATGAG

ATCCTGTATCGGGCCCAGCTGGCCTCCGAGGATACAAATGCCCAGAAGACAATCACCAACTGCTTTCT

GCTCAAGAACAAGATCTGGTGCATCAGCCTGGTGGAAATCTACGACACCGGCGACAACGTGATCAGG

CCCAAGCTGTTCGCCGTGAAGATCCCTGAGCAGTGCACA mRNA (SEQ ID NO: 16)

AUGGAAACCCCUGCUCAGCUGCUGUUCCUGCUGCUGCUGUGGCUGCCUGAUACAACAGGCAUGCCC

GCCGAGAACAAGAAAGUUCGCUUCGAGAACACCACCAGCGACAAGGGCAAGAACCCCAGCAAAGUG

AUCAAGAGCUACUACGGCACCAUGGACAUCAAGAAGAUCAACGAGGGCCUGCUGGACAGCAAGAUC

CUGAGCGCCUUCAACACCGUGAUUGCCCUGCUGGGCUCUAUCGUGAUCAUCGUGAUGAACAUCAUG

AUCAUCCAGAACUACACCCGGUCCACCGACAACCAGGCCGUGAUUAAGGAUGCUCUGCAGGGAAUC

CAGCAGCAGAUCAAAGGCCUGGCCGACAAGAUCGGCACAGAGAUCGGCCCUAAGGUGUCCCUGAUC

GACACCAGCAGCACCAUCACAAUCCCCGCCAAUAUCGGACUGCUGGGAUCCAAGAUCAGCCAGAGC

ACCGCCAGCAUCAACGAGAACGUGAACGAGAAGUGCAAGUUCACCCUGCCUCCACUGAAGAUCCAC

GAGUGCAACAUCAGCUGCCCCAAUCCUCUGCCAUUCAGAGAGUACAGACCCCAGACAGAGGGCGUG

UCCAAUCUCGUGGGCCUGCCUGACAAUAUCUGCCUGCAGAAGACCAGCAACCAGAUCCUGAAGCCU

AAGCUGAUCUCCUACACACUGCCCGUCGUGGGCCAGAGCGGCACCUGUAUUACAGAUCCUCUGCUG

GCCAUGGACGAGGGCUACUUUGCCUACAGCCACCUGGAAAGAAUCGGCAGCUGUAGCCGGGGAGUG

UCCAAGCAGAGAAUCAUCGGCGUGGGCGAAGUGCUGGAUAGAGGCGACGAAGUGCCCAGCCUGUU

CAUGACCAAUGUGUGGACCCCUCCUAAUCCUAACACCGUGUACCACUGCAGCGCCGUGUACAACAA

CGAGUUCUACUACGUGCUGUGCGCCGUGUCCACAGUGGGCGACCCUAUCCUGAACAGCACCUAUUG

GAGCGGCAGCCUGAUGAUGACCAGACUGGCCGUGAAGCCCAAGAGCAAUGGCGGCGGAUACAACCA

GCAUCAGCUGGCCCUGCGGUCCAUCGAGAAGGGCAGAUACGACAAAGUGAUGCCUUACGGCCCCAG

CGGCAUCAAGCAAGGCGAUACCCUGUACUUUCCCGCCGUGGGAUUUCUCGUGCGGACCGAGUUCAA

GUACAACGACAGCAACUGCCCCAUCACCAAGUGCCAGUACAGCAAGCCCGAGAACUGCAGACUGAG

CAUGGGCAUCAGACCCAACAGCCACUACAUCCUGAGAAGCGGCCUGCUGAAGUACAACCUGAGCGA

CGGCGAGAACCCCAAGAUCGUGUUCAUCGAGAUCAGCGACCAGCGGCUGUCUAUCGGCAGCCCUAG

CAAGGUGUACGACUCUCUGGGACAGCCAGUGUUCUACCAGGCCUCCUUCAGCUGGGACACCAUGAU

-continued

```
CAAGUUCGGCGACGUGCAGACCGUGAAUCCCCUGGUGGUCAACUGGCGGGACAAUACCGUGAUCAG

CAGACCUGGCCAGUCUCAGUGCCCCAGAUUCAACACAUGCCCCGAGAUCUGUUGGGAAGGCGUGUA

CAAUGACGCCUUCCUGAUCGAUCGGAUCAACUGGAUCUCUGCCGGCGUGUUCCUGGACUCCAAUCA

GACAGCCGAGAAUCUGUGUUCACCGUGUUCAAGGACAAUGAGAUCCUGUAUCGGGCCCAGCUGGC

CUCCGAGGAUACAAAUGCCCAGAAGACAAUCACCAACUGCUUUCUGCUCAAGAACAAGAUCUGGUG

CAUCAGCCUGGUGGAAAUCUACGACACCGGCGACAACGUGAUCAGGCCCAAGCUGUUCGCCGUGAA

GAUCCCUGAGCAGUGCACA
```

Nipah_F (SEQ ID NO: 12)
```
METPAQLLFLLLLWLPDTTGILHYEKLSKIGLVKGITRKYKIKSNPLTKDIVIKMIPNVSNMSQCTGSVMEN
YKTRLNGILTPIKGALEIYKNNTHDLVGDVRLAGVIMAGVAIGIATAAQITAGVALYEAMKNADNINKLKS
SIESTNEAVVKLQETAEKTVYVLTALQDYINTNLVPTIDKISCKQTELSLDLALSKYLSDLLFVFGPNLQDPV
SNSMTIQAISQAFGGNYETLLRTLGYATEDFDDLLESDSITGQIIYVDLSGYYIIVRVYFPILTEIQQAYIQELL
PVSFNNDNSEWISIVPNFILVRNTLISNIEIGFCLITKRSVICNQDYATPMTNNMRECLTGSTEKCPRELVVSS
HVPRFALSNGVLFANCISVTCQCQTTGRAISQSGEQTLLMIDNTTCPTAVLGNVIISLGKYLGSVNYNSEGIA
IGPPVFTDKVDISSQISSMNQSLQQSKDYIKEAQRLLDTVNPSLISMLSMIILYVLSIASLCIGLITFISFIIVEKK
RNTYSRLEDRRVRPTSSGDLYYIGT
```

(SEQ ID NO: 13)
```
ILHYEKLSKIGLVKGITRKYKIKSNPLTKDIVIKMIPNVSNMSQCTGSVMENYKTRLNGILTPIKGALEIYKN
NTHDLVGDVRLAGVIMAGVAIGIATAAQITAGVALYEAMKNADNINKLKSSIESTNEAVVKLQETAEKTV
YVLTALQDYINTNLVPTIDKISCKQTELSLDLALSKYLSDLLFVFGPNLQDPVSNSMTIQAISQAFGGNYETL
LRTLGYATEDFDDLLESDSITGQIIYVDLSGYYIIVRVYFPILTEIQQAYIQELLPVSFNNDNSEWISIVPNFILV
RNTLISNIEIGFCLITKRSVICNQDYATPMTNNMRECLTGSTEKCPRELVVSSHVPRFALSNGVLFANCISVT
CQCQTTGRAISQSGEQTLLMIDNTTCPTAVLGNVIISLGKYLGSVNYNSEGIAIGPPVFTDKVDISSQISSMNQ
SLQQSKDYIKEAQRLLDTVNPSLISMLSMIILYVLSIASLCIGLITFISFIIVEKKRNTYSRLEDRRVRPTSSGDL
YYIGT
```

(SEQ ID NO: 15)
```
ATGGAAACCCCTGCTCAGCTGCTGTTCCTGCTGCTGCTGTGGCTGCCTGATACAACAGGCATGCCCGCC

GAGAACAAGAAAGTTCGCTTCGAGAACACCACCAGCGACAAGGGCAAGAACCCCAGCAAAGTGATCA

AGAGCTACTACGGCACCATGGACATCAAGAAGATCAACGAGGGCCTGCTGGACAGCAAGATCCTGAG

CGCCTTCAACACCGTGATTGCCCTGCTGGGCTCTATCGTGATCATCGTGATGAACATCATGATCATCCA

GAACTACACCCGGTCCACCGACAACCAGGCCGTGATTAAGGATGCTCTGCAGGGAATCCAGCAGCAG

ATCAAAGGCCTGGCCGACAAGATCGGCACAGAGATCGGCCCTAAGGTGTCCCTGATCGACACCAGCA

GCACCATCACAATCCCCGCCAATATCGGACTGCTGGGATCCAAGATCAGCCAGAGCACCGCCAGCATC

AACGAGAACGTGAACGAGAAGTGCAAGTTCACCCTGCCTCCACTGAAGATCCACGAGTGCAACATCA

GCTGCCCCAATCCTCTGCCATTCAGAGAGTACAGACCCCAGACAGAGGGCGTGTCCAATCTCGTGGGC

CTGCCTGACAATATCTGCCTGCAGAAGACCAGCAACCAGATCCTGAAGCCTAAGCTGATCTCCTACAC

ACTGCCCGTCGTGGGCCAGAGCGGCACCTGTATTACAGATCCTCTGCTGGCCATGGACGAGGGCTACT

TTGCCTACAGCCACCTGGAAAGAATCGGCAGCTGTAGCCGGGGAGTGTCCAAGCAGAGAATCATCGG

CGTGGGCGAAGTGCTGGATAGAGGCGACGAAGTGCCCAGCCTGTTCATGACCAATGTGTGGACCCCTC

CTAATCCTAACACCGTGTACCACTGCAGCGCCGTGTACAACAACGAGTTCTACTACGTGCTGTGCGCC

GTGTCCACAGTGGGCGACCCTATCCTGAACAGCACCTATTGGAGCGGCAGCCTGATGATGACCAGACT
```

-continued

```
GGCCGTGAAGCCCAAGAGCAATGGCGGCGGATACAACCAGCATCAGCTGGCCCTGCGGTCCATCGAG

AAGGGCAGATACGACAAAGTGATGCCTTACGGCCCCAGCGGCATCAAGCAAGGCGATACCCTGTACT

TTCCCGCCGTGGGATTTCTCGTGCGGACCGAGTTCAAGTACAACGACAGCAACTGCCCCATCACCAAG

TGCCAGTACAGCAAGCCCGAGAACTGCAGACTGAGCATGGGCATCAGACCCAACAGCCACTACATCC

TGAGAAGCGGCCTGCTGAAGTACAACCTGAGCGACGGCGAGAACCCCAAGATCGTGTTCATCGAGAT

CAGCGACCAGCGGCTGTCTATCGGCAGCCCTAGCAAGGTGTACGACTCTCTGGGACAGCCAGTGTTCT

ACCAGGCCTCCTTCAGCTGGGACACCATGATCAAGTTCGGCGACGTGCAGACCGTGAATCCCCTGGTG

GTCAACTGGCGGGACAATACCGTGATCAGCAGACCTGGCCAGTCTCAGTGCCCCAGATTCAACACATG

CCCCGAGATCTGTTGGGAAGGCGTGTACAATGACGCCTTCCTGATCGATCGGATCAACTGGATCTCTG

CCGGCGTGTTCCTGGACTCCAATCAGACAGCCGAGAATCCTGTGTTCACCGTGTTCAAGGACAATGAG

ATCCTGTATCGGGCCCAGCTGGCCTCCGAGGATACAAATGCCCAGAAGACAATCACCAACTGCTTTCT

GCTCAAGAACAAGATCTGGTGCATCAGCCTGGTGGAAATCTACGACACCGGCGACAACGTGATCAGG

CCCAAGCTGTTCGCCGTGAAGATCCCTGAGCAGTGCACA
``` mRNA (SEQ ID NO: 17)

```
AUGGAAACCCCUGCUCAGCUGCUGUUCCUGCUGCUGCUGUGGCUGCCUGAUACAACAGGCAUGCCC

GCCGAGAACAAGAAAGUUCGCUUCGAGAACACCACCAGCGACAAGGGCAAGAACCCCAGCAAAGUG

AUCAAGAGCUACUACGGCACCAUGGACAUCAAGAAGAUCAACAGGGCCUGCUGGACAGCAAGAUC

CUGAGCGCCUUCAACACCGUGAUUGCCCUGCUGGGCUCUAUCGUGAUCAUCGUGAUGAACAUCAUG

AUCAUCCAGAACUACACCCGGUCCACCGACAACCAGGCCGUGAUUAAGGAUGCUCUGCAGGGAAUC

CAGCAGCAGAUCAAAGGCCUGGCCGACAAGAUCGGCACAGAGAUCGGCCCUAAGGUGUCCCUGAUC

GACACCAGCAGCACCAUCACAAUCCCCGCCAAUAUCGGACUGCUGGGAUCCAAGAUCAGCCAGAGC

ACCGCCAGCAUCAACGAGAACGUGAACGAGAAGUGCAAGUUCACCCUGCCUCCACUGAAGAUCCAC

GAGUGCAACAUCAGCUGCCCCAAUCCUCUGCCAUUCAGAGAGUACAGACCCCAGACAGAGGGCGUG

UCCAAUCUCGUGGGCCUGCCUGACAAUAUCUGCCUGCAGAAGACCAGCAACCAGAUCCUGAAGCCU

AAGCUGAUCUCCUACACACUGCCCGUCGUGGGCCAGAGCGGCACCUGUAUUACAGAUCCUCUGCUG

GCCAUGGACGAGGGCUACUUUGCCUACAGCCACCUGGAAAGAAUCGGCAGCUGUAGCCGGGGAGUG

UCCAAGCAGAGAAUCAUCGGCGUGGGCGAAGUGCUGGAUAGAGGCGACGAAGUGCCCAGCCUGUU

CAUGACCAAUGUGUGGACCCCUCCUAAUCCUAACACCGUGUACCACUGCAGCGCCGUGUACAACAA

CGAGUUCUACUACGUGCUGUGCGCCGUGUCCACAGUGGGCGACCCUAUCCUGAACAGCACCUAUUG

GAGCGGCAGCCUGAUGAUGACCAGACUGGCCGUGAAGCCCAAGAGCAAUGGCGGCGGAUACAACCA

GCAUCAGCUGGCCCUGCGGUCCAUCGAGAAGGGCAGAUACGACAAAGUGAUGCCUUACGGCCCCAG

CGGCAUCAAGCAAGGCGAUACCCUGUACUUUCCCGCCGUGGGAUUUCUCGUGCGGACCGAGUUCAA

GUACAACGACAGCAACUGCCCCAUCACCAAGUGCCAGUACAGCAAGCCCGAGAACUGCAGACUGAG

CAUGGGCAUCAGACCCAACAGCCACUACAUCCUGAGAAGCGGCCUGCUGAAGUACAACCUGAGCGA

CGGCGAGAACCCCAAGAUCGUGUUCAUCGAGAUCAGCGACCAGCGGCUGUCUAUCGGCAGCCCUAG

CAAGGUGUACGACUCUCUGGGACAGCCAGUGUUCUACCAGGCCUCCUUCAGCUGGGACACCAUGAU

CAAGUUCGGCGACGUGCAGACCGUGAAUCCCCUGGUGGUCAACUGGCGGGACAAUACCGUGAUCAG

CAGACCUGGCCAGUCUCAGUGCCCCAGAUUCAACACAUGCCCCGAGAUCUGUUUGGGAAGGCGUGUA

CAAUGACGCCUUCCUGAUCGAUCGGAUCAACUGGAUCUCUGCCGGCGUGUUCCUGGACUCCAAUCA

GACAGCCGAGAAUCCUGUGUUCACCGUGUUCAAGGACAAUGAGAUCCUGUAUCGGGCCCAGCUGGC
```

-continued

CUCCGAGGAUACAAAUGCCCAGAAGACAAUCACCAACUGCUUUCUGCUCAAGAACAAGAUCUGGUG

CAUCAGCCUGGUGGAAAUCUACGACACCGGCGACAACGUGAUCAGGCCCAAGCUGUUCGCCGUGAA

GAUCCCUGAGCAGUGCACA

>gi|940378825|gb|ALK02457.1|spikeprotein[SARS-likecoronavirusWIV16]

(SEQ ID NO: 18)

MFIFLFFLTLTSGSDLESCTTFDDVQAPNYPQHSSSRRGVYYPDEIFRSDTLYLTQDLFLPFYSNVTGFHTINH

RFDNPVIPFKDGVYFAATEKSNVVRGWVFGSTMNNKSQSVIIINNSTNVVIRACNFELCDNPFFAVSKPTGT

QTHTMIFDNAFNCTFEYISDSFSLDVAEKSGNFKHLREFVFKNKDGFLYVYKGYQPIDVVRDLPSGFNILKPI

FKLPLGINITNFRAILTAFLPAQDTWGTSAAAYFVGYLKPATFMLKYDENGTITDAVDCSQNPLAELKCSV

KSFEIDKGIYQTSNFRVAPSKEVVRFPNITNLCPFGEVFNATTFPSVYAWERKRISNCVADYSVLYNSTSFST

FKCYGVSATKLNDLCFSNVYADSFVVKGDDVRQIAPGQTGVIADYNYKLPDDFTGCVLAWNTRNIDATQT

GNYNYKYRSLRHGKLRPFERDISNVPFSPDGKPCTPPAFNCYWPLNDYGFYITNGIGYQPYRVVVLSFELLN

APATVCGPKLSTDLIKNQCVNFNFNGLTGTGVLTPSSKRFQPFQQFGRDVLDFTDSVRDPKTSEILDISPCSF

GGVSVITPGTNTSSEVAVLYQDVNCTDVPVAIHADQLTPSWRVYSTGNNVFQTQAGCLIGAEHVDTSYEC

DIPIGAGICASYHTVSSLRSTSQKSIVAYTMSLGADSSIAYSNNTIAIPTNFSISITTEVMPVSMAKTSVDCNM

YICGDSTECANLLLQYGSFCTQLNRALSGIAVEQDRNTREVFAQVKQMYKTPTLKDFGGFNFSQILPDPLKP

TKRSFIEDLLFNKVTLADAGFMKQYGECLGDINARDLICAQKFNGLTVLPPLLTDDMIAAYTAALVSGTAT

AGWTFGAGAALQIPFAMQMAYRFNGIGVTQNVLYENQKQIANQFNKAISQIQESLTTTSTALGKLQDVVN

QNAQALNTLVKQLSSNFGAISSVLNDILSRLDKVEAEVQIDRLITGRLQSLQTYVTQQLIRAAEIRASANLA

ATKMSECVLGQSKRVDFCGKGYHLMSFPQAAPHGVVFLHVTYVPSQERNFTTAPAICHEGKAYFPREGVF

VFNGTSWFITQRNFFSPQIITTDNTFVSGSCDVVIGIINNTVYDPLQPELDSFKEELDKYFKNHTSPDVDLGDI

SGINASVVNIQKEIDRLNEVAKNLNESLIDLQELGKYEQYIKWPWYVWLGFIAGLIAIVMVTILLCCMTSCC

SCLKGACSCGSCCKFDEDDSEPVLKGVKLHYT

>WIV16_FL_CO_Spike (SEQ ID NO: 19)

ATGTTTATCTTCCTGTTCTTCCTGACCCTGACCAGCGGCAGCGACCTGGAAAGCTGCACCACCTTCGAC

GACGTGCAGGCCCCCAACTACCCTCAGCACAGCTCTAGCAGACGGGGCGTGTACTACCCCGACGAGAT

CTTCAGAAGCGACACCCTGTACCTGACCCAGGACCTGTTCCTGCCCTTCTACAGCAACGTGACCGGCTT

CCACACCATCAACCACAGATTCGACAACCCCGTGATCCCCTTCAAGGACGGGGTGTACTTTGCCGCCA

CCGAGAAGTCCAATGTCGTGCGGGGATGGGTGTTCGGCAGCACCATGAACAACAAGAGCCAGAGCGT

GATCATCATCAACAACAGCACCAACGTCGTGATCCGGGCCTGCAACTTCGAGCTGTGCGACAACCCAT

TCTTCGCCGTGTCCAAGCCCACCGGCACCCAGACCCACACCATGATCTTCGACAACGCCTTCAACTGC

ACCTTCGAGTACATCAGCGACAGCTTCAGCCTGGACGTGGCCGAGAAAGCGGCAACTTCAAGCACCT

GAGAGAATTCGTGTTCAAGAACAAGGACGGCTTCCTGTACGTGTACAAGGGCTACCAGCCCATCGACG

TCGTGCGCGATCTGCCCAGCGGCTTCAACATCCTGAAGCCCATCTTCAAGCTGCCCCTGGGCATCAAC

ATCACCAACTTCCGGGCTATCCTGACCGCCTTCCTGCCCGCCCAGGATACCTGGGGAACAAGCGCCGC

TGCCTACTTCGTGGGCTACCTGAAGCCTGCCACCTTCATGCTGAAGTACGACGAGAACGGCACCATCA

CCGACGCCGTGGACTGCAGCCAGAATCCTCTGGCCGAGCTGAAGTGCAGCGTGAAGTCCTTCGAGATC

GACAAGGGCATCTACCAGACCAGCAACTTCAGAGTGGCCCCCAGCAAGGAAGTCGTGCGGTTCCCCA

ATATCACCAACCTGTGCCCCTTCGGCGAGGTGTTCAACGCCACCACCTTTCCCAGCGTGTACGCCTGGG

AGCGGAAGCGGATCAGCAACTGCGTGGCCGACTACAGCGTGCTGTACAACTCCACCAGCTTCTCCACC

TTCAAGTGCTACGGCGTGTCCGCCACCAAGCTGAACGACCTGTGCTTCAGCAATGTGTACGCCGACTC

-continued

```
CTTCGTCGTGAAGGGCGACGATGTGCGCCAGATCGCCCCTGGACAGACAGGCGTGATCGCCGATTACA

ACTACAAGCTGCCTGACGACTTCACCGGCTGCGTGCTGGCCTGGAACACCAGAAACATCGACGCCACC

CAGACAGGCAACTACAATTACAAGTACAGAAGCCTGCGGCACGGCAAGCTGCGGCCCTTCGAGAGGG

ACATCTCCAACGTGCCCTTCAGCCCCGACGGCAAGCCTTGTACCCCCCTGCCTTTAACTGCTACTGGC

CCCTGAACGACTACGGCTTCTACATCACAAACGGCATCGGCTATCAGCCCTACCGGGTGGTGGTGCTG

TCCTTTGAGCTGCTGAATGCCCCTGCCACCGTGTGCGGCCCTAAGCTGAGCACCGACCTGATCAAGAA

CCAGTGCGTGAACTTCAACTTCAACGGCCTGACCGGCACCGGCGTGCTGACACCTAGCAGCAAGAGAT

TCCAGCCCTTCCAGCAGTTCGGCCGGGACGTGCTGGATTTCACCGACAGCGTGCGGGACCCCAAGACC

AGCGAGATCCTGGACATCAGCCCCTGCAGCTTCGGCGGAGTGTCCGTGATCACCCCCGGCACCAATAC

CAGCTCTGAGGTGGCCGTGCTGTATCAGGACGTGAACTGCACCGATGTGCCCGTGGCCATCCACGCCG

ATCAGCTGACCCCATCTTGGCGGGTGTACTCCACCGGCAACAACGTGTTCCAGACACAAGCCGGCTGC

CTGATCGGAGCCGAGCACGTGGACACCAGCTACGAGTGCGACATCCCTATCGGCGCTGGCATCTGCGC

CAGCTACCACACCGTGTCCAGCCTGAGAAGCACCAGCCAGAAATCTATCGTGGCCTACACCATGAGCC

TGGGCGCCGACAGCTCTATCGCCTACTCCAACAACACAATCGCCATCCCCACCAATTTCAGCATCTCC

ATCACCACCGAAGTGATGCCCGTGTCCATGGCCAAGACCTCCGTGGATTGCAACATGTACATCTGCGG

CGACAGCACCGAGTGCGCCAACCTGCTGCTGCAGTACGGCAGCTTCTGCACCCAGCTGAACAGAGCCC

TGAGCGGAATCGCCGTGGAACAGGACAGAAACACCCGGGAAGTGTTCGCCCAAGTGAAGCAGATGTA

TAAGACCCCCACCCTGAAGGATTTCGGCGGCTTTAACTTCAGCCAGATCCTGCCCGACCCTCTGAAGC

CTACCAAGCGGAGCTTCATCGAGGACCTGCTGTTCAACAAAGTGACCCTGGCCGACGCCGGCTTTATG

AAGCAGTATGGCGAGTGCCTGGGCGACATCAACGCCCGGGATCTGATCTGCGCCCAGAAGTTTAACG

GACTGACCGTGCTGCCCCCTCTGCTGACCGACGATATGATCGCCGCCTACACAGCCGCCCTGGTGTCT

GGCACAGCTACCGCCGGATGGACATTTGGAGCTGGCGCCGCTCTGCAGATCCCCTTTGCCATGCAGAT

GGCCTACCGGTTCAATGGCATCGGCGTGACCCAGAATGTGCTGTACGAGAACCAGAAGCAGATCGCC

AACCAGTTCAACAAGGCCATTAGCCAGATTCAGGAAAGCCTGACCACCACCAGCACCGCCCTGGGCA

AACTGCAGGACGTCGTGAACCAGAACGCCCAGGCCCTGAACACCCTCGTGAAGCAGCTGAGCAGCAA

TTTCGGCGCCATCAGCTCCGTGCTGAACGATATCCTGAGCAGACTGGACAAGGTGGAAGCAGAGGTGC

AGATCGACCGGCTGATCACCGGCAGACTGCAGAGCCTGCAGACCTACGTGACACAGCAGCTGATTAG

AGCCGCCGAGATCAGGGCCAGCGCCAATCTGGCCGCCACAAAGATGAGCGAGTGTGTGCTGGGCCAG

AGCAAGCGGGTGGACTTCTGCGGCAAGGGCTATCACCTGATGAGCTTCCCCCAGGCCGCTCCTCACGG

CGTGGTGTTTCTGCACGTGACATACGTGCCCAGCCAGGAACGGAACTTCACCACCGCCCCAGCCATCT

GCCACGAGGGCAAGGCCTACTTCCCCCGGGAAGGCGTGTTCGTGTTTAACGGCACCTCCTGGTTTATC

ACCCAGCGGAATTTCTTCAGTCCGCAGATCATCACCACAGACAACACCTTCGTGTCCGGCAGCTGCGA

CGTCGTGATTGGCATCATTAACAACACCGTGTACGACCCCCTGCAGCCCGAGCTGGACAGCTTCAAAG

AGGAACTGGACAAGTACTTCAAGAACCACACCTCCCCCGACGTGGACCTGGGCGATATCTCCGGCATC

AATGCCAGCGTCGTGAATATCCAGAAAGAGATCGATCGCCTGAACGAGGTGGCCAAGAACCTGAATG

AGAGCCTGATCGACCTGCAGGAACTGGGGAAGTACGAGCAGTACATCAAGTGGCCTTGGTACGTGTG

GCTGGGCTTTATCGCCGGCCTGATCGCCATCGTGATGGTCACCATCCTGCTGTGCTGCATGACCAGCTG

TTGCAGCTGTCTGAAGGGCGCCTGCAGCTGTGGCTCCTGCTGCAAGTTCGATGAGGACGACAGCGAGC

CTGTGCTGAAAGGCGTGAAGCTGCACTACACC
```

(SEQ ID NO: 20)

```
AUGUUUAUCUUCCUGUUCUUCCUGACCCUGACCAGCGGCAGCGACCUGGAAAGCUGCACCACCUUC
GACGACGUGCAGGCCCCCAACUACCCUCAGCACAGCUCUAGCAGACGGGGCGUGUACUACCCCGAC
GAGAUCUUCAGAAGCGACACCCUGUACCUGACCCAGGACCUGUUCCUGCCCUUCUACAGCAACGUG
ACCGGCUUCCACACCAUCAACCACAGAUUCGACAACCCCGUGAUCCCCUUCAAGGACGGGGUGUAC
UUUGCCGCCACCGAGAAGUCCAAUGUCGUGCGGGGAUGGGUGUUCGGCAGCACCAUGAACAACAAG
AGCCAGAGCGUGAUCAUCAUCAACAACAGCACCAACGUCGUGAUCCGGGCCUGCAACUUCGAGCUG
UGCGACAACCCAUUCUUCGCCGUGUCCAAGCCCACCGGCACCCAGACCCACACCAUGAUCUUCGAC
AACGCCUUCAACUGCACCUUCGAGUACAUCAGCGACAGCUUCAGCCUGGACGUGGCCGAGAAAGC
GGCAACUUCAAGCACCUGAGAGAAUUCGUGUUCAAGAACAAGGACGGCUUCCUGUACGUGUACAA
GGGCUACCAGCCCAUCGACGUCGUGCGCGAUCUGCCCAGCGGCUUCAACAUCCUGAAGCCCAUCUU
CAAGCUGCCCCUGGGCAUCAACAUCACCAACUUCCGGGCUAUCCUGACCGCCUUCCUGCCCGCCCAG
GAUACCUGGGGAACAAGCGCCGCUGCCUACUUCGUGGGCUACCUGAAGCUGCCACCUUCAUGCUG
AAGUACGACGAGAACGGCACCAUCACCGACGCCGUGGACUGCAGCCAGAAUCCUCUGGCCGAGCUG
AAGUGCAGCGUGAAGUCCUUCGAGAUCGACAAGGGCAUCUACCAGACCAGCAACUUCAGAGUGGCC
CCCAGCAAAGAAGUCGUGCGGUUCCCCAAUAUCACCAACCUGUGCCCCUUCGGCGAGGUGUUCAAC
GCCACCACCUUUCCCAGCGUGUACGCCUGGGAGCGGAAGCGGAUCAGCAACUGCGUGGCCGACUAC
AGCGUGCUGUACAACUCCACCAGCUUCUCCACCUUCAAGUGCUACGGCGUGUCCGCCACCAAGCUG
AACGACCUGUGCUUCAGCAAUGUGUACGCCGACUCCUUCGUCGUGAAGGGCGACGAUGUGCGCCAG
AUCGCCCCUGGACAGACAGGCGUGAUCGCCGAUUACAACUACAAGCUGCCUGACGACUUCACCGGC
UGCGUGCUGGCCUGGAACACCAGAAACAUCGACGCCACCCAGACAGGCAACUACAAUUACAAGUAC
AGAAGCCUGCGGCACGGCAAGCUGCGGCCCUUCGAGAGGGACAUCUCCAACGUGCCCUUCAGCCCC
GACGGCAAGCCUUGUACCCCCCCUGCCUUUAACUGCUACUGGCCCCUGAACGACUACGGCUUCUAC
AUCACAAACGGCAUCGGCUAUCAGCCCUACCGGGUGGUGGUGCUGUCCUUUGAGCUGCUGAAUGCC
CCUGCCACCGUGUGCGGCCCUAAGCUGAGCACCGACCUGAUCAAGAACCAGUGCGUGAACUUCAAC
UUCAACGGCCUGACCGGCACCGGCGUGCUGACACCUAGCAGCAAGAGAUUCCAGCCCUUCCAGCAG
UUCGGCCGGGACGUGCUGGAUUUCACCGACAGCGUGCGGGACCCCAAGACCAGCGAGAUCCUGGAC
AUCAGCCCCUGCAGCUUCGGCGGAGUGUCCGUGAUCACCCCGGCACCAAUACCAGCUCUGAGGUG
GCCGUGCUGUAUCAGGACGUGAACUGCACCGAUGUGCCCGUGGCCAUCCACGCCGAUCAGCUGACC
CCAUCUUGGCGGGUGUACUCCACCGGCAACAACGUGUUCCAGACACAAGCCGGCUGCCUGAUCGGA
GCCGAGCACGUGGACACCAGCUACGAGUGCGACAUCCCUAUCGGCGCUGGCAUCUGCGCCAGCUAC
CACACCGUGUCCAGCCUGAGAAGCACCAGCCAGAAAUCUAUCGUGGCCUACACCAUGAGCCUGGGC
GCCGACAGCUCUAUCGCCUACUCCAACAACACAAUCGCCAUCCCCACCAAUUUCAGCAUCUCCAUC
ACCACCGAAGUGAUGCCCGUGUCCAUGGCCAAGACCUCCGUGGAUUGCAACAUGUACAUCUGCGGC
GACAGCACCGAGUGCGCCAACCUGCUGCUGCAGUACGGCAGCUUCUGCACCCAGCUGAACAGAGCC
CUGAGCGGAAUCGCCGUGGAACAGGACAGAAACACCCGGGAAGUGUUCGCCCAAGUGAAGCAGAU
GUAUAAGACCCCCACCCUGAAGGAUUUCGGCGGCUUUAACUUCAGCCAGAUCCUGCCCGACCCUCU
GAAGCCUACCAAGCGGAGCUUCAUCGAGGACCUGCUGUUCAACAAAGUGACCCUGGCCGACGCCGG
CUUUAUGAAGCAGUAUGGCGAGUGCCUGGGCGACAUCAACGCCCGGGAUCUGAUCUGCGCCCAGAA
GUUUAACGGACUGACCGUGCUGCCCCCUCUGCUGACCGACGAUAUGAUCGCCGCCUACACAGCCGC
CCUGGUGUCUGGCACAGCUACCGCCGGAUGGACAUUUGGAGCUGGCGCCGCUCUGCAGAUCCCCUU
```

-continued

```
UGCCAUGCAGAUGGCCUACCGGUUCAAUGGCAUCGGCGUGACCCAGAAUGUGCUGUACGAGAACCA

GAAGCAGAUCGCCAACCAGUUCAACAAGGCCAUUAGCCAGAUUCAGGAAAGCCUGACCACCACCAG

CACCGCCCUGGGCAAACUGCAGGACGUCGUGAACCAGAACGCCCAGGCCCUGAACACCCUCGUGAA

GCAGCUGAGCAGCAAUUUCGGCGCCAUCAGCUCCGUGCUGAACGAUAUCCUGAGCAGACUGGACAA

GGUGGAAGCAGAGGUGCAGAUCGACCGGCUGAUCACCGGCAGACUGCAGAGCCUGCAGACCUACGU

GACACAGCAGCUGAUUAGAGCCGCCGAGAUCAGGGCCAGCGCCAAUCUGGCCGCCACAAAGAUGAG

CGAGUGUGUGCUGGGCCAGAGCAAGCGGGUGGACUUCUGCGGCAAGGGCUAUCACCUGAUGAGCU

UCCCCCAGGCCGCUCCUCACGGCGUGGUGUUUCUGCACGUGACAUACGUGCCCAGCCAGGAACGGA

ACUUCACCACCGCCCCAGCCAUCUGCCACGAGGGCAAGGCCUACUUCCCCCGGGAAGGCGUGUUCG

UGUUUAACGGCACCUCCUGGUUUAUCACCCAGCGGAAUUUCUUCAGUCCGCAGAUCAUCACCACAG

ACAACACCUUCGUGUCCGGCAGCUGCGACGUCGUGAUUGGCAUCAUUAACAACACCGUGUACGACC

CCCUGCAGCCCGAGCUGGACAGCUUCAAAGAGGAACUGGACAAGUACUUCAAGAACCACACCUCCC

CCGACGUGGACCUGGGCGAUAUCUCCGGCAUCAAUGCCAGCGUCGUGAAUAUCCAGAAAGAGAUCG

AUCGCCUGAACGAGGUGGCCAAGAACCUGAAUGAGAGCCUGAUCGACCUGCAGGAACUGGGGAAG

UACGAGCAGUACAUCAAGUGGCCUUGGUACGUGUGGCUGGGCUUUAUCGCCGGCCUGAUCGCCAUC

GUGAUGGUCACCAUCCUGCUGUGCUGCAUGACCAGCUGUUGCAGCUGUCUGAAGGGCGCCUGCAGC

UGUGGCUCCUGCUGCAAGUUCGAUGAGGACGACAGCGAGCCUGUGCUGAAAGGCGUGAAGCUGCA

CUACACC
```

---

What is claimed is:

1. A composition comprising:
   (a) a messenger ribonucleic acid (mRNA) comprising an open reading frame (ORF) encoding a fusion protein, wherein the fusion protein comprises a Nipah virus F protein and a Nipah virus G protein; and
   (b) a lipid nanoparticle, wherein the lipid nanoparticle comprises 45-55 mol % ionizable lipid, 5-25 mol % neutral lipid, 35-45 mol % sterol, and 0.5-5 mol % polyethylene glycol (PEG)-modified lipid, wherein the ionizable lipid is a compound of Formula (I):

$$\begin{array}{c}\text{(I)}\\ R_4\diagdown N \diagup R_1 \\ \Big(R_5 \diagdown\!\!\!\diagup\!\!\!\diagdown R_2\!\!\diagup R_7 \\ R_6 \quad M \quad R_3\Big)_m \end{array}$$

and wherein
   $R_1$ is R"M'R' or $C_{5-20}$ alkenyl;
   $R_2$ and $R_3$ are each independently selected from $C_{1-14}$ alkyl and $C_{2-14}$ alkenyl;
   $R_4$ is —$(CH_2)_nQ$, wherein Q is OH and n is selected from 3, 4, and 5;
   M and M' are each independently —OC(O)— or —C(O)O—;
   $R_5$, $R_6$, and $R_7$ are each H;
   R' is a linear $C_{1-12}$ alkyl, or $C_{1-12}$ alkyl substituted with $C_{6-9}$ alkyl;
   R" is $C_{3-14}$ alkyl;
   m is selected from 5, 6, 7, 8, 9, 10, 11, 12, and 13.

2. The composition of claim 1, wherein:
   $R_1$ is R"M'R';
   $R_2$ and $R_3$ are each independently $C_{1-14}$ alkyl;
   $R_4$ is —$(CH_2)_nQ$, wherein Q is OH and n is 4;
   M and M' are each independently —OC(O)—;
   $R_5$, $R_6$, and $R_7$ are each H;
   R' is $C_{1-12}$ alkyl substituted with $C_{6-9}$ alkyl;
   R" is $C_{3-14}$ alkyl; and
   m is 6.

3. The composition of claim 1, wherein:
   $R_1$ is $C_{5-20}$ alkenyl;
   $R_2$ and $R_3$ are each independently $C_{1-14}$ alkyl;
   $R_4$ is —$(CH_2)_nQ$, wherein Q is OH and n is 3;
   M is —C(O)O—;
   $R_5$, $R_6$, and $R_7$ are each H; and
   m is 6.

4. The composition of claim 1, wherein the compound is:

(Compound 1)

5. The composition of claim 1, wherein the sterol is cholesterol.

6. The composition of claim 1, wherein the neutral lipid is 1,2-distearoyl-sn-glycero-3-phosphocholine (DSPC).

7. The composition of claim 1, wherein the PEG-modified lipid is PEG-DMG.

8. The composition of claim 1, wherein the sterol is cholesterol, the neutral lipid is DSPC, and the PEG-modified lipid is PEG-DMG.

9. The composition of claim 2, wherein the sterol is cholesterol, the neutral lipid is DSPC, and the PEG-modified lipid is PEG-DMG.

10. The composition of claim 3, wherein the sterol is cholesterol, the neutral lipid is DSPC, and the PEG-modified lipid is PEG-DMG.

11. The composition of claim 4, wherein the sterol is cholesterol, the neutral lipid is DSPC, and the PEG-modified lipid is PEG-DMG.

12. The composition of claim 1, wherein the ORF comprises chemically-modified uracil residues.

13. The composition of claim 12, wherein 100% of the uracil residues of the ORF comprises N1-methylpseudouridine.

14. The composition of claim 2, wherein the ORF comprises chemically-modified uracil residues.

15. The composition of claim 14, wherein 100% of the uracil residues of the ORF comprises N1-methylpseudouridine.

16. The composition of claim 3, wherein the ORF comprises chemically-modified uracil residues.

17. The composition of claim 16, wherein 100% of the uracil residues of the ORF comprises N1-methylpseudouridine.

18. The composition of claim 4, wherein the ORF comprises chemically-modified uracil residues.

19. The composition of claim 18, wherein 100% of the uracil residues of the ORF comprises N1-methylpseudouridine.

20. The composition of claim 1, wherein the Nipah virus F protein of the fusion protein comprises an amino acid sequence that has at least 90% identity with the amino acid sequence of SEQ ID NO: 13, and the Nipah virus G protein of the fusion protein comprises an amino acid sequence that has at least 90% identity with the amino acid sequence of SEQ ID NO: 11.

* * * * *

SEQUENCE LISTING

<160> NUMBER OF SEQ ID NOS: 31

<210> SEQ ID NO 1
<211> LENGTH: 490
<212> TYPE: PRT
<213> ORGANISM: Artificial sequence
<220> FEATURE:
<223> OTHER INFORMATION: Synthetic Polypeptide

<400> SEQUENCE: 1

```
Met Gly Gln Ile Val Thr Phe Phe Gln Glu Val Pro His Val Ile Glu
1               5                   10                  15

Glu Val Met Asn Ile Val Leu Ile Ala Leu Ser Leu Leu Ala Ile Leu
            20                  25                  30

Lys Gly Ile Tyr Asn Val Ala Thr Cys Gly Leu Phe Gly Leu Val Ser
        35                  40                  45

Phe Leu Leu Leu Cys Gly Arg Ser Cys Ser Thr Thr Tyr Lys Gly Val
    50                  55                  60

Tyr Glu Leu Gln Thr Leu Glu Leu Asp Met Ala Ser Leu Asn Met Thr
65                  70                  75                  80

Met Pro Leu Ser Cys Thr Lys Asn Asn Ser His His Tyr Ile Met Val
                85                  90                  95

Gly Asn Glu Thr Gly Leu Glu Leu Thr Leu Thr Asn Thr Ser Ile Ile
            100                 105                 110

Asn His Lys Phe Cys Asn Leu Ser Asp Ala His Lys Lys Asp Leu Tyr
        115                 120                 125

Asp His Ala Leu Met Ser Ile Ile Ser Thr Phe His Leu Ser Ile Pro
    130                 135                 140
```

```
Asn Phe Asn Gln Tyr Glu Ala Met Ser Cys Asp Phe Asn Gly Gly Lys
145                 150                 155                 160

Ile Ser Val Gln Tyr Asn Leu Ser His Thr Tyr Ala Val Asp Ala Ala
            165                 170                 175

Asn His Cys Gly Thr Ile Ala Asn Gly Val Leu Gln Thr Phe Met Arg
            180                 185                 190

Met Ala Trp Gly Gly Ser Tyr Ile Ala Leu Asp Ser Gly Lys Gly Ser
        195                 200                 205

Trp Asp Cys Ile Met Thr Ser Tyr Gln Tyr Leu Ile Ile Gln Asn Thr
        210                 215                 220

Thr Trp Glu Asp His Cys Gln Phe Ser Arg Pro Ser Pro Ile Gly Tyr
225                 230                 235                 240

Leu Gly Leu Leu Ser Gln Arg Thr Arg Asp Ile Tyr Ile Ser Arg Arg
            245                 250                 255

Leu Leu Gly Thr Phe Thr Trp Thr Leu Ser Asp Ser Glu Gly Asn Glu
            260                 265                 270

Thr Pro Gly Gly Tyr Cys Leu Thr Arg Trp Met Leu Ile Glu Ala Glu
        275                 280                 285

Leu Lys Cys Phe Gly Asn Thr Ala Val Ala Lys Cys Asn Glu Lys His
290                 295                 300

Asp Glu Glu Phe Cys Asp Met Leu Arg Leu Phe Asp Phe Asn Lys Gln
305                 310                 315                 320

Ala Ile Met Arg Leu Lys Thr Glu Ala Gln Met Ser Ile Gln Leu Ile
            325                 330                 335

Asn Lys Ala Val Asn Ala Leu Ile Asn Asp Gln Leu Ile Met Lys Asn
            340                 345                 350

His Leu Arg Asp Ile Met Gly Ile Pro Tyr Cys Asn Tyr Ser Lys Tyr
        355                 360                 365

Trp Tyr Leu Asn His Thr Val Thr Gly Lys Thr Ser Leu Pro Arg Cys
        370                 375                 380

Trp Leu Val Ser Asn Gly Ser Tyr Leu Asn Glu Thr Arg Phe Ser Asp
385                 390                 395                 400

Asp Ile Glu Gln Gln Ala Asp Asn Met Ile Thr Glu Met Leu Gln Lys
            405                 410                 415

Glu Tyr Leu Asp Arg Gln Gly Lys Thr Pro Leu Gly Leu Val Asp Leu
            420                 425                 430

Phe Val Phe Ser Thr Ser Phe Tyr Leu Ile Ser Ile Phe Leu His Leu
        435                 440                 445

Val Lys Ile Pro Thr His Arg His Ile Ile Gly Lys Pro Cys Pro Lys
        450                 455                 460

Pro His Arg Leu Asn His Met Gly Ile Cys Ser Cys Gly Leu Tyr Lys
465                 470                 475                 480

His Pro Gly Val Pro Val Lys Trp Lys Arg
            485                 490

<210> SEQ ID NO 2
<211> LENGTH: 569
<212> TYPE: PRT
<213> ORGANISM: Artificial sequence
<220> FEATURE:
<223> OTHER INFORMATION: Synthetic Polypeptide

<400> SEQUENCE: 2

Met Ser Ala Ser Lys Glu Val Lys Ser Phe Leu Trp Thr Gln Ser Leu
1               5                   10                  15
```

```
Arg Arg Glu Leu Ser Gly Tyr Cys Ser Asn Ile Lys Leu Gln Val Val
                 20                  25                  30

Lys Asp Ala Gln Ala Leu Leu His Gly Leu Asp Phe Ser Glu Val Ser
         35                  40                  45

Asn Val Gln Arg Leu Met Arg Lys Gln Lys Arg Asp Asp Gly Asp Leu
     50                  55                  60

Lys Arg Leu Arg Asp Leu Asn Gln Ala Val Asn Asn Leu Val Glu Leu
 65                  70                  75                  80

Lys Ser Thr Gln Gln Lys Ser Val Leu Arg Val Gly Thr Leu Ser Ser
                 85                  90                  95

Asp Asp Leu Leu Val Leu Ala Ala Asp Leu Glu Lys Leu Lys Ser Lys
             100                 105                 110

Val Val Arg Thr Glu Arg Pro Leu Ser Ser Gly Ile Tyr Met Gly Asn
         115                 120                 125

Leu Ser Ser Gln Gln Leu Asp Gln Arg Lys Ala Leu Leu Asn Met Ile
     130                 135                 140

Gly Met Thr Gly Gly Asn Gly Gly Arg Asn Thr Thr Ser Asp Gly Ile
145                 150                 155                 160

Val Arg Val Trp Asp Val Lys Asn Ala Glu Leu Leu Asn Asn Gln Phe
                165                 170                 175

Gly Thr Met Pro Ser Leu Thr Leu Ala Cys Leu Thr Lys Gln Gly Gln
            180                 185                 190

Val Asp Leu Asn Asp Ala Val Gln Ala Leu Thr Asp Leu Gly Leu Ile
        195                 200                 205

Tyr Thr Ala Lys Tyr Pro Asn Ser Ser Asp Leu Asp Arg Leu Ala Gln
210                 215                 220

Ser His Pro Ile Leu Asn Met Ile Asp Thr Lys Lys Ser Ser Leu Asn
225                 230                 235                 240

Ile Ser Gly Tyr Asn Phe Ser Leu Gly Ala Ala Val Lys Ala Gly Ala
                245                 250                 255

Cys Met Leu Asp Gly Gly Asn Met Leu Glu Thr Ile Lys Val Ser Pro
            260                 265                 270

Gln Thr Met Asp Gly Ile Leu Lys Ser Ile Leu Lys Val Lys Arg Ser
        275                 280                 285

Leu Gly Met Phe Ile Ser Asp Thr Pro Gly Glu Arg Asn Pro Tyr Glu
    290                 295                 300

Asn Ile Leu Tyr Lys Ile Cys Leu Ser Gly Asp Gly Trp Pro Tyr Ile
305                 310                 315                 320

Ala Ser Arg Thr Ser Ile Val Gly Arg Ala Trp Glu Asn Thr Val Val
                325                 330                 335

Asp Leu Glu Ser Asp Asn Lys Pro Gln Lys Thr Gly Asn Gly Gly Ser
            340                 345                 350

Asn Lys Ser Leu Gln Ser Ala Gly Phe Ala Ala Gly Leu Thr Tyr Ser
        355                 360                 365

Gln Leu Met Thr Leu Lys Asp Ser Met Leu Gln Leu Asp Pro Asn Ala
    370                 375                 380

Lys Thr Trp Met Asp Ile Glu Gly Arg Pro Glu Asp Pro Val Glu Ile
385                 390                 395                 400

Ala Leu Tyr Gln Pro Ser Ser Gly Cys Tyr Ile His Phe Phe Arg Glu
                405                 410                 415

Pro Thr Asp Leu Lys Gln Phe Lys Gln Asp Ala Lys Tyr Ser His Gly
            420                 425                 430

Ile Asp Val Thr Asp Leu Phe Ala Ala Gln Pro Gly Leu Thr Ser Ala
```

```
            435                 440                 445
Val Ile Glu Ala Leu Pro Arg Asn Met Val Ile Thr Cys Gln Gly Ser
    450                 455                 460

Glu Asp Ile Arg Lys Leu Leu Glu Ser Gln Gly Arg Arg Asp Ile Lys
465                 470                 475                 480

Leu Ile Asp Ile Ser Leu Ser Lys Val Asp Ser Arg Lys Phe Glu Asn
                485                 490                 495

Ala Val Trp Asp Gln Phe Lys Asp Leu Cys His Met His Thr Gly Ile
            500                 505                 510

Val Val Glu Lys Lys Lys Arg Gly Gly Lys Glu Glu Ile Thr Pro His
            515                 520                 525

Cys Ala Leu Met Asp Cys Ile Met Phe Asp Ala Ala Val Ser Gly Gly
            530                 535                 540

Val Asp Ala Lys Val Leu Arg Ala Val Leu Pro Arg Asp Met Val Phe
545                 550                 555                 560

Arg Thr Ser Thr Pro Lys Val Val Leu
                565
```

<210> SEQ ID NO 3
<211> LENGTH: 589
<212> TYPE: PRT
<213> ORGANISM: Artificial sequence
<220> FEATURE:
<223> OTHER INFORMATION: Synthetic Polypeptide

<400> SEQUENCE: 3

```
Met Glu Thr Pro Ala Gln Leu Leu Phe Leu Leu Leu Leu Trp Leu Pro
1               5                   10                  15

Asp Thr Thr Gly Met Ser Ala Ser Lys Glu Val Lys Ser Phe Leu Trp
            20                  25                  30

Thr Gln Ser Leu Arg Arg Glu Leu Ser Gly Tyr Cys Ser Asn Ile Lys
        35                  40                  45

Leu Gln Val Val Lys Asp Ala Gln Ala Leu Leu His Gly Leu Asp Phe
    50                  55                  60

Ser Glu Val Ser Asn Val Gln Arg Leu Met Arg Lys Gln Lys Arg Asp
65                  70                  75                  80

Asp Gly Asp Leu Lys Arg Leu Arg Asp Leu Asn Gln Ala Val Asn Asn
                85                  90                  95

Leu Val Glu Leu Lys Ser Thr Gln Gln Lys Ser Val Leu Arg Val Gly
            100                 105                 110

Thr Leu Ser Ser Asp Asp Leu Leu Val Leu Ala Ala Asp Leu Glu Lys
        115                 120                 125

Leu Lys Ser Lys Val Val Arg Thr Glu Arg Pro Leu Ser Ser Gly Ile
    130                 135                 140

Tyr Met Gly Asn Leu Ser Ser Gln Gln Leu Asp Gln Arg Lys Ala Leu
145                 150                 155                 160

Leu Asn Met Ile Gly Met Thr Gly Gly Asn Gly Arg Asn Thr Thr
                165                 170                 175

Ser Asp Gly Ile Val Arg Val Trp Asp Val Lys Asn Ala Glu Leu Leu
            180                 185                 190

Asn Asn Gln Phe Gly Thr Met Pro Ser Leu Thr Leu Ala Cys Leu Thr
        195                 200                 205

Lys Gln Gly Gln Val Asp Leu Asn Asp Ala Val Gln Ala Leu Thr Asp
    210                 215                 220

Leu Gly Leu Ile Tyr Thr Ala Lys Tyr Pro Asn Ser Ser Asp Leu Asp
```

```
                225                 230                 235                 240
Arg Leu Ala Gln Ser His Pro Ile Leu Asn Met Ile Asp Thr Lys Lys
                    245                 250                 255
Ser Ser Leu Asn Ile Ser Gly Tyr Asn Phe Ser Leu Gly Ala Ala Val
                260                 265                 270
Lys Ala Gly Ala Cys Met Leu Asp Gly Gly Asn Met Leu Glu Thr Ile
            275                 280                 285
Lys Val Ser Pro Gln Thr Met Asp Gly Ile Leu Lys Ser Ile Leu Lys
        290                 295                 300
Val Lys Arg Ser Leu Gly Met Phe Ile Ser Asp Thr Pro Gly Glu Arg
305                 310                 315                 320
Asn Pro Tyr Glu Asn Ile Leu Tyr Lys Ile Cys Leu Ser Gly Asp Gly
                325                 330                 335
Trp Pro Tyr Ile Ala Ser Arg Thr Ser Ile Val Gly Arg Ala Trp Glu
                340                 345                 350
Asn Thr Val Val Asp Leu Glu Ser Asp Asn Lys Pro Gln Lys Thr Gly
                355                 360                 365
Asn Gly Gly Ser Asn Lys Ser Leu Gln Ser Ala Gly Phe Ala Ala Gly
        370                 375                 380
Leu Thr Tyr Ser Gln Leu Met Thr Leu Lys Asp Ser Met Leu Gln Leu
385                 390                 395                 400
Asp Pro Asn Ala Lys Thr Trp Met Asp Ile Glu Gly Arg Pro Glu Asp
                405                 410                 415
Pro Val Glu Ile Ala Leu Tyr Gln Pro Ser Ser Gly Cys Tyr Ile His
                420                 425                 430
Phe Phe Arg Glu Pro Thr Asp Leu Lys Gln Phe Lys Gln Asp Ala Lys
            435                 440                 445
Tyr Ser His Gly Ile Asp Val Thr Asp Leu Phe Ala Ala Gln Pro Gly
        450                 455                 460
Leu Thr Ser Ala Val Ile Glu Ala Leu Pro Arg Asn Met Val Ile Thr
465                 470                 475                 480
Cys Gln Gly Ser Glu Asp Ile Arg Lys Leu Leu Glu Ser Gln Gly Arg
                485                 490                 495
Arg Asp Ile Lys Leu Ile Asp Ile Ser Leu Ser Lys Val Asp Ser Arg
                500                 505                 510
Lys Phe Glu Asn Ala Val Trp Asp Gln Phe Lys Asp Leu Cys His Met
            515                 520                 525
His Thr Gly Ile Val Val Glu Lys Lys Arg Gly Gly Lys Glu Glu
        530                 535                 540
Ile Thr Pro His Cys Ala Leu Met Asp Cys Ile Met Phe Asp Ala Ala
545                 550                 555                 560
Val Ser Gly Gly Val Asp Ala Lys Val Leu Arg Ala Val Leu Pro Arg
                565                 570                 575
Asp Met Val Phe Arg Thr Ser Thr Pro Lys Val Val Leu
                580                 585

<210> SEQ ID NO 4
<211> LENGTH: 1470
<212> TYPE: DNA
<213> ORGANISM: Artificial sequence
<220> FEATURE:
<223> OTHER INFORMATION: Synthetic Polynucleotide

<400> SEQUENCE: 4
atgggccaga tcgtgacatt cttccaagag gtgccccacg tgatcgagga agtgatgaac      60
```

```
atcgtcctga tcgccctgag cctgctggcc atcctgaagg gcatctacaa cgtggccacc    120
tgtggcctgt ttggcctggt gtcattcctg ctgctgtgcg gcagaagctg cagcaccaca    180
tacaagggcg tgtacgagct gcagaccctg gaactggata tggccagcct gaacatgacc    240
atgcctctga gctgcaccaa gaacaacagc caccactaca tcatggtcgg aaacgagaca    300
ggactggaac tgaccctgac caacaccagc atcatcaacc acaagttctg caacctgagc    360
gacgcccaca gaaggacct gtacgatcac gccctgatga gcatcatctc caccttccac    420
ctgagcatcc ccaacttcaa ccagtacgag gccatgagct gcgacttcaa cggcggcaag    480
atcagcgtgc agtacaatct gagccacacc tacgccgtgg acgccgccaa tcactgtggc    540
acaattgcca atggcgtgct gcagacattc atgcggatgg cctggggcgg ctcttatatc    600
gccctggatt ctggcaaagg cagctgggac tgcatcatga ccagctacca gtacctgatc    660
atccagaaca ccacctggga agatcactgc cagttcagca gaccctctcc tatcggctat    720
ctgggcctgc tgagccagag aacccgggac atctacatca gcagaaggct gctgggcacc    780
ttcacctgga cactgtctga cagcgagggc aacgaaacac ctggcggcta ctgcctgacc    840
agatggatgt gattgaggc cgagctgaag tgcttcggca ataccgccgt ggccaagtgc    900
aacgagaagc acgacgagga attctgcgac atgctgcggc tgttcgattt caacaagcag    960
gccatcatgc ggctcaagac cgaggctcag atgtccatcc agctgatcaa caaggccgtg   1020
aatgccctga tcaacgatca gctcatcatg aagaaccacc tccgggatat catgggcatc   1080
ccttactgca actacagcaa gtactggtat ctcaaccaca ccgtgaccgg caagaccagc   1140
ctgcctagat gttggctggt gtccaacggc agctacctga cgagacacg gttcagcgac   1200
gacatcgagc agcaggccga caacatgatc accgagatgc tgcagaaaga gtacctggac   1260
cggcagggca agacacctct gggactcgtg gatctgttcg tgttcagcac cagcttctac   1320
ctgatctcta tcttcctgca cctggtcaag atccccacac accggcacat catcggcaag   1380
ccctgtccta gcctcaccg gctgaaccac atgggaatct gtagctgcgg cctgtacaag   1440
caccctggcg tgccagtgaa gtggaagaga                                     1470
```

<210> SEQ ID NO 5
<211> LENGTH: 1767
<212> TYPE: DNA
<213> ORGANISM: Artificial sequence
<220> FEATURE:
<223> OTHER INFORMATION: Synthetic Polynucleotide

<400> SEQUENCE: 5

```
atggagactc ctgcccagct cttgttcctt ttgctattgt ggcttcccga caccaccggc     60
atgagcgcca gcaaggaggt caagagcttc tctggaccc agagcctaag aagagagctt    120
agcggctact gcagcaacat caagcttcag gtggtgaagg acgcccaggc cctgctgcac    180
ggcctggact tcagcgaggt gagcaacgtg cagagactga tgagaaagca gaagcgagac    240
gacggcgacc tgaagcgtct gcgggacctg aaccaggccg tgaacaacct ggtggagctt    300
aagagcaccc agcagaagtc tgtgctgaga gtgggccaccc tgagcagcga cgacctgctg    360
gtgctggccg ccgacctgga aagctgaag tctaaggtcg tcagaaccga gcggccattg    420
agctcaggca tctacatggg caaccttagc agtcagcagc tggaccagag aaaggccttg    480
ctgaacatga tcggcatgac cggcggcaac ggcggcagaa acaccaccag cgacggcatc    540
gtgagagtgt gggacgtgaa gaacgccgag ctactcaaca ccagttcgg caccatgccc    600
```

```
agcctgaccc tggcctgcct gaccaagcag ggccaggtgg acctcaatga cgccgtgcag    660
gcactaaccg accttggcct gatctacacc gccaagtacc ccaactcttc agacctggac    720
agactggcgc agtcccaccc catcttaaat atgattgaca ccaagaagtc atcccttaac    780
atcagtggct acaacttcag cctgggcgcc gccgtgaagg ccggcgcctg catgctggac    840
ggcggaaata tgctggaaac tatcaaggtg agccctcaga ccatggacgg tatcctgaag    900
tccattttga aggttaagag atccctgggt atgttcatca gcgacacccc aggcgagaga    960
aaccccctacg agaacatcct gtacaagatc tgcctgagtg gcgacggctg ccctacatc   1020
gcgagcagaa ccagcatcgt gggaagggcc tgggagaaca ccgtggtgga tcttgagagc   1080
gacaacaagc cccagaagac cggaaatggc ggttcaaaca gagcctgca gagcgccggc    1140
ttcgccgccg gcctgaccta cagccagctg atgaccctga aggacagcat gctacaattg   1200
gatcccaacg ccaagacttg gatggacatc gagggcagac cgaggacccc cgtggagatc   1260
gccctgtacc agccctcatc cggctgctac atccacttct tcagagagcc cacagatctg   1320
aagcagttca gcaggacgc gaagtatagc catggcatag acgtcaccga tttattcgcg    1380
gcccagccgg ccttacgag cgccgtgatc gaggcgctgc cagaaacat ggtgatcacc     1440
tgccagggca gcgaggacat cagaaagctc cttgaatctc aaggccggag agatattaag   1500
ctgatagata tcagcttatc taaggttgac agcagaaagt tcgagaacgc tgtatgggac   1560
caattcaagg acctgtgcca catgcatacg ggcatagtgg tagagaagaa gaagcgtggc   1620
ggaaaggagg agatcacacc tcactgcgcc ctgatggact gcatcatgtt cgacgcggca   1680
gtctccggcg gcgtcgacgc aaaggtcctc cgggccgtgc tgccaaggga catggtgttc   1740
cggacaagca ccctaaggt agtgctg                                         1767

<210> SEQ ID NO 6
<211> LENGTH: 1470
<212> TYPE: RNA
<213> ORGANISM: Artificial sequence
<220> FEATURE:
<223> OTHER INFORMATION: Synthetic Polynucleotide

<400> SEQUENCE: 6
augggccaga ucgugacauu cuccaagag gugccccacg ugaucgagga agugaugaac      60
aucguccuga ucgcccugag ccugcuggcc auccugaagg gcaucuacaa cguggccacc    120
uguggccugu uggccuggu gcauuccug cugcugugcg gcagaagcug cagcaccaca     180
uacaagggcg uguacgagcu gcagacccug aacuggauA uggccagccu gaacaugacc    240
augccucuga gcugcaccaa gaacaacagc caccacuaca ucauggucgg aaacgagaca   300
ggacuggaac ugacccugac caacaccagc aucaucaacc acaaguucug caaccugagc   360
gacgcccaca agaaggaccu guacgaucac gcccugauga gcaucaucuc caccuccac   420
cugagcaucc ccaacuucaa ccaguacgag gccaugagcu cgacuucaa cggcggcaag   480
aucagcgugc aguacaaucu gagccacacc uacgccgugg acgccgccaa ucacuguggc   540
acaauugcca auggcgugcu gcagacauuc augcggaugg ccuggggcgg cucuuauauc   600
gcccuggauu cuggcaaagg cagcugggac ugcaucauga ccagcuacca guaccugauc   660
auccagaaca ccaccuggga agaucacgc caguucagca gacccucucc uaucggcuau   720
cuggccugc ugagccagag aacccggac aucuacauca gcagaaggcu gcugggcacc    780
uucaccugga cacugucuga cagcgagggc aacgaaacac cuggcggcua cugccugacc   840
agauggaugc ugauugaggc cgagcugaag ugcuucggca auaccgccgu ggccaagugc   900
```

-continued

```
aacgagaagc acgacgagga auucugcgac augcugcggc uguucgauuu caacaagcag    960
gccaucaugc ggcucaagac cgaggcucag auguccaucc agcugaucaa caaggccgug   1020
aaugcccuga ucaacgauca gcucaucaug aagaaccacc uccgggauau caugggcauc   1080
ccuuacugca acuacagcaa guacuggdau cucaaccaca ccgugaccgg caagaccagc   1140
```
(Note: line 4 above — reading: ccuuacugca acuacagcaa guacugguau cucaaccaca ccgugaccgg caagaccagc   1140)

```
cugccuagau guuggcuggu guccaacggc agcuaccuga acgagacacg guucagcgac   1200
gacaucgagc agcaggccga caacaugauc accgagaugc ugcagaaaga guaccuggac   1260
cggcagggca agacaccucu gggacucgug gaucuguucg guucagcac cagcuucuac    1320
```
(line: cggcagggca agacaccucu gggacucgug gaucuguucg guucagcac cagcuucuac   1320)

```
cugaucucua ucuuccugca ccuggucaag auccccacac accggcacau caucggcaag   1380
cccuguccua agccucaccg gcugaaccac augggaaucu guagcugcgg ccuguacaag   1440
cacccuggcg ugccagugaa guggaagaga                                    1470
```

<210> SEQ ID NO 7
<211> LENGTH: 1767
<212> TYPE: RNA
<213> ORGANISM: Artificial sequence
<220> FEATURE:
<223> OTHER INFORMATION: Synthetic Polynucleotide

<400> SEQUENCE: 7

```
auggagacuc cugcccagcu cuuguuccuu uugcuauugu ggcuucccga caccaccggc     60
augagcgcca gcaaggaggu caagagcuuc cucuggaccc agagccuaag aagagagcuu   120
agcggcuacu gcagcaacau caagcuucag guggugaagg acgcccaggc ccugcugcac   180
ggccuggacu ucagcgaggu gagcaacgug cagagacuga ugagaaagca gaagcgagac   240
gacggcgacc ugaagcgucu gcgggaccug aaccaggccg ugaacaaccu gguggagcuu   300
aagagcaccc agcagaaguc ugugcugaga gugggcaccc ugcagcagcga cgaccugcug   360
```
(line: aagagcaccc agcagaaguc ugugcugaga gugggcaccc ugcagcgcga cgaccugcug   360)

```
gugcuggccg ccgaccugga gaagcugaag ucuaaggucg ucagaaccga gcggccauug   420
agcucaggca ucuacauggg caaccuuagc agucagcagc uggaccagag aaaggccuug   480
cugaacauga ucggcaugac cggcggcaac ggcggcagaa acaccaccag cgacggcauc   540
gugagagugu gggacgugaa gaacgccgag cuacucaaca accaguucgg caccaugccc   600
agccugaccc uggccugccu gaccaagcag ggccagguug accucaauga cgccgugcag   660
```
(line: ...ggccaggugg accucaauga cgccgugcag   660)

```
gcacuaaccg accuuggccu gaucuacacc gccaaguacc caacucuuc agaccuggac    720
```
(line: gcacuaaccg accuuggccu gaucuacacc gccaaguacc caacucuuuc agaccuggac   720)

```
agacuggcgc aguccacccc caucuuaaau augauugaca ccaagaaguc aucccuuaac   780
aucaguggcu acaacuucag ccuggcgcc gccgugaagg ccggcgccug caugcuggac    840
```
(line: aucaguggcu acaacuucag ccuggcgccc gccgugaagg ccggcgccug caugcuggac   840)

```
ggcggaaaua ugcuggaaac uaucaaggug agcccucaga ccauggacgg uauccugaag   900
uccauuuuga agguuaagag aucccugggu auguucauca gcgacaccc aggcgagaga   960
```
(line: ...gcgacacccc aggcgagaga   960)

```
aaccccuacg agaacauccu guacaagauc ugccugagug gcgacggcug gcccuacauc   1020
gcgagcagaa ccagcaucgu gggaagggcc ugggagaaca ccguggugga ucuugagagc   1080
gacaacaagc cccagaagac cggaaauggc gguucaaaca agagccugca gagcgccggc   1140
uucgccgccg gccugaccua cagccagcug augacccuga aggacagcau gcuacaauug   1200
gaucccaacg ccaagacuug gauggacauc gagggcagac cgaggacccc cguggagauc   1260
gcccuguacc agcccucauc cggcugcuac auccacuucu ucagagagcc cacagaucug   1320
```
(line: gcccuguacc agcccucauc cggcugcuac auccacuucu ucagagagcc cacagaucug   1320)

```
aagcaguuca gcaggacgc gaaguauagc cauggcauag acgucaccga uuuauucgcg   1380
```
(line: aagcaguuca gcaggacgc gaaguauagc cauggcauag acgucaccga uuuauucgcg   1380)

```
gcccagccgg gccuuacgag cgccgugauc gaggcgcugc ccagaaacau ggugaucacc   1440
```

| | |
|---|---|
| ugccagggca gcgaggacau cagaaagcuc cuugaaucuc aaggccggag agauauuaag | 1500 |
| cugauagaua ucagcuuauc uaagguugac agcagaaagu ucgagaacgc uguaugggac | 1560 |
| caauucaagg accugugcca caugcauacg ggcauagugg uagagaagaa gaagcguggc | 1620 |
| ggaaaggagg agaucacacc ucacugcgcc cugauggacu gcaucauguu cgacgcggca | 1680 |
| gucuccggcg gcgucgacgc aaagguccuc cgggccgugc ugccaaggga cauggugutc | 1740 |
| cggacaagca ccccuaaggu agugcug | 1767 |

```
<210> SEQ ID NO 8
<211> LENGTH: 1707
<212> TYPE: DNA
<213> ORGANISM: Artificial sequence
<220> FEATURE:
<223> OTHER INFORMATION: Synthetic Polynucleotide

<400> SEQUENCE: 8
```

| | |
|---|---|
| atgagcgcca gcaaggaggt caagagcttc ctctggaccc agagcctaag aagagagctt | 60 |
| agcggctact gcagcaacat caagcttcag gtggtgaagg acgccaggc cctgctgcac | 120 |
| ggcctggact tcagcgaggt gagcaacgtg cagagactga tgagaaagca gaagcgagac | 180 |
| gacggcgacc tgaagcgtct gcgggacctg aaccaggccg tgaacaacct ggtggagctt | 240 |
| aagagcaccc agcagaagtc tgtgctgaga gtgggcaccc tgagcagcga cgacctgctg | 300 |
| gtgctggccc cgacctgga gaagctgaag tctaaggtcg tcagaaccga gcggccattg | 360 |
| agctcaggca tctacatggg caaccttagc agtcagcagc tggaccagag aaaggccttg | 420 |
| ctgaacatga tcggcatgac cggcggcaac ggcggcagaa acaccaccag cgacggcatc | 480 |
| gtgagagtgt gggacgtgaa gaacgccgag ctactcaaca accagttcgg caccatgccc | 540 |
| agcctgaccc tggcctgcct gaccaagcag ggccaggtgg acctcaatga cgccgtgcag | 600 |
| gcactaaccg accttggcct gatctacacc gccaagtacc ccaactcttc agacctggac | 660 |
| agactggcgc agtcccaccc catcttaaat atgattgaca ccaagaagtc atcccttaac | 720 |
| atcagtggct acaacttcag cctgggcgcc gccgtgaagg ccggcgcctg catgctggac | 780 |
| ggcggaaata tgctggaaac tatcaaggtg agccctcaga ccatgacgg tatcctgaag | 840 |
| tccatttga aggttaagag atccctgggt atgttcatca gcgacacccc aggcgagaga | 900 |
| aaccctacg agaacatcct gtacaagatc tgcctgagtg gcgacggctg gcctacatc | 960 |
| gcgagcagaa ccagcatcgt gggaagggcc tgggagaaca ccgtggtgga tcttgagagc | 1020 |
| gacaacaagc cccagaagac cggaaatggc ggttcaaaca agagcctgca gagccggc | 1080 |
| ttcgccgccg gcctgaccta cagccagctg atgaccctga aggacagcat gctacaattg | 1140 |
| gatcccaacg ccaagacttg gatggacatc gagggcagac ccgaggaccc cgtggagatc | 1200 |
| gccctgtacc agccctcatc cggctgctac atccacttct tcagagagcc cacagatctg | 1260 |
| aagcagttca gcaggacgc gaagtatagc catggcatag acgtcaccga tttattcgcg | 1320 |
| gcccagccgg gccttacgag cgccgtgatc gaggcgctgc cagaaacat ggtgatcacc | 1380 |
| tgccagggca gcgaggacat cagaaagctc cttgaatctc aaggccggag agatattaag | 1440 |
| ctgatagata tcagcttatc taaggttgac agcagaaagt tcgagaacgc tgtatgggac | 1500 |
| caattcaagg acctgtgcca catgcatacg ggcatagtgg tagagaagaa gaagcgtggc | 1560 |
| ggaaaggagg agatcacacc tcactgcgcc ctgatggact gcatcatgtt cgacgcggca | 1620 |
| gtctccggcg gcgtcgacgc aaaggtcctc cgggccgtgc tgccaaggga catggtgttc | 1680 |
| cggacaagca cccctaaggt agtgctg | 1707 |

<210> SEQ ID NO 9
<211> LENGTH: 1707
<212> TYPE: RNA
<213> ORGANISM: Artificial sequence
<220> FEATURE:
<223> OTHER INFORMATION: Synthetic Polynucleotide

<400> SEQUENCE: 9

| | | | | | | |
|---|---|---|---|---|---|---|
| augagcgcca | gcaaggaggu | caagagcuuc | cucuggaccc | agagccuaag | aagagagcuu | 60 |
| agcggcuacu | gcagcaacau | caagcuucag | guggugaagg | acgcccaggc | ccugcugcac | 120 |
| ggccuggacu | ucagcgaggu | gagcaacgug | cagagacuga | ugagaaagca | gaagcgagac | 180 |
| gacggcgacc | ugaagcgucu | gcgggaccug | aaccaggccg | ugaacaaccu | gguggagcuu | 240 |
| aagagcaccc | agcagaaguc | ugugcugaga | gugggcaccc | ugagcagcga | cgaccugcug | 300 |
| gugcuggccg | ccgaccugga | gaagcugaag | ucuaaggucg | ucagaaccga | gcggccauug | 360 |
| agcucaggca | ucuacauggg | caaccuuagc | agucagcagc | uggaccagag | aaaggccuug | 420 |
| cugaacauga | ucggcaugac | cggcggcaac | ggcggcagaa | acaccaccag | cgacggcauc | 480 |
| gugagagugu | gggacgugaa | gaacgccgag | cuacucaaca | accaguucgg | caccaugccc | 540 |
| agccugaccc | uggccugccu | gaccaagcag | ggccaggugg | accucaauga | cgccgugcag | 600 |
| gcacuaaccg | accuuggccu | gaucuacacc | gccaaguacc | ccaacucuuc | agaccuggac | 660 |
| agacuggcgc | agucccaccc | caucuuaaau | augauugaca | ccaagaaguc | auccuuaac | 720 |
| aucaguggcu | acaacuucag | ccugggcgcc | gccgugaagg | ccggcgccug | caugcuggac | 780 |
| ggcggaaaua | ugcuggaaac | uaucaaggug | agcccucaga | ccauggacgg | uauccugaag | 840 |
| uccauuuuga | gguuaagag | aucccugggu | auguucauca | gcgacacccc | aggcgagaga | 900 |
| aaccccuacg | agaacauccu | guacaagauc | ugccugagug | gcgacggcug | gcccuacauc | 960 |
| gcgagcagaa | ccagcaucgu | gggaaggggc | ugggagaaca | ccguggugga | ucuugagagc | 1020 |
| gacaacaagc | cccagaagac | cggaaauggc | gguucaaaca | gagccugca | gagcgccggc | 1080 |
| uucgccgccg | gccugaccua | cagccagcug | augacccuga | aggacagcau | gcuacaauug | 1140 |
| gaucccaacg | ccaagacuug | gauggacauc | gagggcagac | ccgaggaccc | cguggagauc | 1200 |
| gcccuguacc | agcccucauc | cggcugcuac | auccacuucu | ucagagagcc | cacagaucug | 1260 |
| aagcaguuca | gcaggacgc | gaaguauagc | cauggcauag | cgucaccga | uuuauucgcg | 1320 |
| gcccagccgg | gccuuacgag | cgccgugauc | gaggcgcugc | cagaaacau | ggugaucacc | 1380 |
| ugccagggca | gcgaggacau | cagaaagcuc | cuugaaucuc | aaggccggag | agauauuaag | 1440 |
| cugauagaua | ucagcuuauc | uaagguugac | agcagaaagu | ucgagaacgc | uguaugggac | 1500 |
| caauucaagg | accugugcca | caugcauacg | ggcauagugg | uagagaagaa | gaagcguggc | 1560 |
| ggaaaggagg | agaucacacc | ucacugcgcc | cugauggacu | gcaucauguu | cgacgcggca | 1620 |
| gucuccggcg | gcgucgacgc | aaaggccuc | cgggccgugc | ugccaaggga | cauggguuc | 1680 |
| cggacaagca | ccccuaaggu | agugcug | | | | 1707 |

<210> SEQ ID NO 10
<211> LENGTH: 622
<212> TYPE: PRT
<213> ORGANISM: Artificial sequence
<220> FEATURE:
<223> OTHER INFORMATION: Synthetic Polypeptide

<400> SEQUENCE: 10

-continued

```
Met Glu Thr Pro Ala Gln Leu Leu Phe Leu Leu Leu Trp Leu Pro
1               5                   10                  15

Asp Thr Thr Gly Met Pro Ala Glu Asn Lys Lys Val Arg Phe Glu Asn
            20                  25                  30

Thr Thr Ser Asp Lys Gly Lys Asn Pro Ser Lys Val Ile Lys Ser Tyr
            35                  40                  45

Tyr Gly Thr Met Asp Ile Lys Lys Ile Asn Glu Gly Leu Leu Asp Ser
50                  55                  60

Lys Ile Leu Ser Ala Phe Asn Thr Val Ile Ala Leu Leu Gly Ser Ile
65                  70                  75                  80

Val Ile Ile Val Met Asn Ile Met Ile Gln Asn Tyr Thr Arg Ser
                85                  90                  95

Thr Asp Asn Gln Ala Val Ile Lys Asp Ala Leu Gln Gly Ile Gln Gln
            100                 105                 110

Gln Ile Lys Gly Leu Ala Asp Lys Ile Gly Thr Glu Ile Gly Pro Lys
            115                 120                 125

Val Ser Leu Ile Asp Thr Ser Ser Thr Ile Thr Ile Pro Ala Asn Ile
            130                 135                 140

Gly Leu Leu Gly Ser Lys Ile Ser Gln Ser Thr Ala Ser Ile Asn Glu
145                 150                 155                 160

Asn Val Asn Glu Lys Cys Lys Phe Thr Leu Pro Pro Leu Lys Ile His
                165                 170                 175

Glu Cys Asn Ile Ser Cys Pro Asn Pro Leu Pro Phe Arg Glu Tyr Arg
                180                 185                 190

Pro Gln Thr Glu Gly Val Ser Asn Leu Val Gly Leu Pro Asp Asn Ile
            195                 200                 205

Cys Leu Gln Lys Thr Ser Asn Gln Ile Leu Lys Pro Lys Leu Ile Ser
210                 215                 220

Tyr Thr Leu Pro Val Val Gly Gln Ser Gly Thr Cys Ile Thr Asp Pro
225                 230                 235                 240

Leu Leu Ala Met Asp Glu Gly Tyr Phe Ala Tyr Ser His Leu Glu Arg
                245                 250                 255

Ile Gly Ser Cys Ser Arg Gly Val Ser Lys Gln Arg Ile Ile Gly Val
                260                 265                 270

Gly Glu Val Leu Asp Arg Gly Asp Glu Val Pro Ser Leu Phe Met Thr
            275                 280                 285

Asn Val Trp Thr Pro Pro Asn Pro Asn Thr Val Tyr His Cys Ser Ala
            290                 295                 300

Val Tyr Asn Asn Glu Phe Tyr Tyr Val Leu Cys Ala Val Ser Thr Val
305                 310                 315                 320

Gly Asp Pro Ile Leu Asn Ser Thr Tyr Trp Ser Gly Ser Leu Met Met
            325                 330                 335

Thr Arg Leu Ala Val Lys Pro Lys Ser Asn Gly Gly Tyr Asn Gln
            340                 345                 350

His Gln Leu Ala Leu Arg Ser Ile Glu Lys Gly Arg Tyr Asp Lys Val
            355                 360                 365

Met Pro Tyr Gly Pro Ser Gly Ile Lys Gln Gly Asp Thr Leu Tyr Phe
            370                 375                 380

Pro Ala Val Gly Phe Leu Val Arg Thr Glu Phe Lys Tyr Asn Asp Ser
385                 390                 395                 400

Asn Cys Pro Ile Thr Lys Cys Gln Tyr Ser Lys Pro Glu Asn Cys Arg
            405                 410                 415

Leu Ser Met Gly Ile Arg Pro Asn Ser His Tyr Ile Leu Arg Ser Gly
```

-continued

```
                420             425             430
Leu Leu Lys Tyr Asn Leu Ser Asp Gly Glu Asn Pro Lys Ile Val Phe
            435                 440                 445

Ile Glu Ile Ser Asp Gln Arg Leu Ser Ile Gly Ser Pro Ser Lys Val
        450                 455                 460

Tyr Asp Ser Leu Gly Gln Pro Val Phe Tyr Gln Ala Ser Phe Ser Trp
465                 470                 475                 480

Asp Thr Met Ile Lys Phe Gly Asp Val Gln Thr Val Asn Pro Leu Val
                485                 490                 495

Val Asn Trp Arg Asp Asn Thr Val Ile Ser Arg Pro Gly Gln Ser Gln
            500                 505                 510

Cys Pro Arg Phe Asn Thr Cys Pro Glu Ile Cys Trp Glu Gly Val Tyr
        515                 520                 525

Asn Asp Ala Phe Leu Ile Asp Arg Ile Asn Trp Ile Ser Ala Gly Val
            530                 535                 540

Phe Leu Asp Ser Asn Gln Thr Ala Glu Asn Pro Val Phe Thr Val Phe
545                 550                 555                 560

Lys Asp Asn Glu Ile Leu Tyr Arg Ala Gln Leu Ala Ser Glu Asp Thr
                565                 570                 575

Asn Ala Gln Lys Thr Ile Thr Asn Cys Phe Leu Leu Lys Asn Lys Ile
            580                 585                 590

Trp Cys Ile Ser Leu Val Glu Ile Tyr Asp Thr Gly Asp Asn Val Ile
        595                 600                 605

Arg Pro Lys Leu Phe Ala Val Lys Ile Pro Glu Gln Cys Thr
            610                 615                 620

<210> SEQ ID NO 11
<211> LENGTH: 602
<212> TYPE: PRT
<213> ORGANISM: Artificial sequence
<220> FEATURE:
<223> OTHER INFORMATION: Synthetic Polypeptide

<400> SEQUENCE: 11

Met Pro Ala Glu Asn Lys Lys Val Arg Phe Glu Asn Thr Thr Ser Asp
1               5                   10                  15

Lys Gly Lys Asn Pro Ser Lys Val Ile Lys Ser Tyr Tyr Gly Thr Met
            20                  25                  30

Asp Ile Lys Lys Ile Asn Glu Gly Leu Leu Asp Ser Lys Ile Leu Ser
        35                  40                  45

Ala Phe Asn Thr Val Ile Ala Leu Leu Gly Ser Ile Val Ile Ile Val
    50                  55                  60

Met Asn Ile Met Ile Ile Gln Asn Tyr Thr Arg Ser Thr Asp Asn Gln
65                  70                  75                  80

Ala Val Ile Lys Asp Ala Leu Gln Gly Ile Gln Gln Gln Ile Lys Gly
                85                  90                  95

Leu Ala Asp Lys Ile Gly Thr Glu Ile Gly Pro Lys Val Ser Leu Ile
            100                 105                 110

Asp Thr Ser Ser Thr Ile Thr Ile Pro Ala Asn Ile Gly Leu Leu Gly
        115                 120                 125

Ser Lys Ile Ser Gln Ser Thr Ala Ser Ile Asn Glu Asn Val Asn Glu
    130                 135                 140

Lys Cys Lys Phe Thr Leu Pro Pro Leu Lys Ile His Glu Cys Asn Ile
145                 150                 155                 160

Ser Cys Pro Asn Pro Leu Pro Phe Arg Glu Tyr Arg Pro Gln Thr Glu
```

-continued

```
              165                 170                 175
Gly Val Ser Asn Leu Val Gly Leu Pro Asp Asn Ile Cys Leu Gln Lys
            180                 185                 190

Thr Ser Asn Gln Ile Leu Lys Pro Lys Leu Ile Ser Tyr Thr Leu Pro
            195                 200                 205

Val Val Gly Gln Ser Gly Thr Cys Ile Thr Asp Pro Leu Leu Ala Met
            210                 215                 220

Asp Glu Gly Tyr Phe Ala Tyr Ser His Leu Glu Arg Ile Gly Ser Cys
225                 230                 235                 240

Ser Arg Gly Val Ser Lys Gln Arg Ile Ile Gly Val Gly Val Leu
            245                 250                 255

Asp Arg Gly Asp Glu Val Pro Ser Leu Phe Met Thr Asn Val Trp Thr
            260                 265                 270

Pro Pro Asn Pro Asn Thr Val Tyr His Cys Ser Ala Val Tyr Asn Asn
            275                 280                 285

Glu Phe Tyr Tyr Val Leu Cys Ala Val Ser Thr Val Gly Asp Pro Ile
            290                 295                 300

Leu Asn Ser Thr Tyr Trp Ser Gly Ser Leu Met Met Thr Arg Leu Ala
305                 310                 315                 320

Val Lys Pro Lys Ser Asn Gly Gly Tyr Asn Gln His Gln Leu Ala
            325                 330                 335

Leu Arg Ser Ile Glu Lys Gly Arg Tyr Asp Lys Val Met Pro Tyr Gly
            340                 345                 350

Pro Ser Gly Ile Lys Gln Gly Asp Thr Leu Tyr Phe Pro Ala Val Gly
            355                 360                 365

Phe Leu Val Arg Thr Glu Phe Lys Tyr Asn Asp Ser Asn Cys Pro Ile
370                 375                 380

Thr Lys Cys Gln Tyr Ser Lys Pro Glu Asn Cys Arg Leu Ser Met Gly
385                 390                 395                 400

Ile Arg Pro Asn Ser His Tyr Ile Leu Arg Ser Gly Leu Leu Lys Tyr
            405                 410                 415

Asn Leu Ser Asp Gly Glu Asn Pro Lys Ile Val Phe Ile Glu Ile Ser
            420                 425                 430

Asp Gln Arg Leu Ser Ile Gly Ser Pro Ser Lys Val Tyr Asp Ser Leu
            435                 440                 445

Gly Gln Pro Val Phe Tyr Gln Ala Ser Phe Ser Trp Asp Thr Met Ile
            450                 455                 460

Lys Phe Gly Asp Val Gln Thr Val Asn Pro Leu Val Val Asn Trp Arg
465                 470                 475                 480

Asp Asn Thr Val Ile Ser Arg Pro Gly Gln Ser Gln Cys Pro Arg Phe
            485                 490                 495

Asn Thr Cys Pro Glu Ile Cys Trp Glu Gly Val Tyr Asn Asp Ala Phe
            500                 505                 510

Leu Ile Asp Arg Ile Asn Trp Ile Ser Ala Gly Val Phe Leu Asp Ser
            515                 520                 525

Asn Gln Thr Ala Glu Asn Pro Val Phe Thr Val Phe Lys Asp Asn Glu
            530                 535                 540

Ile Leu Tyr Arg Ala Gln Leu Ala Ser Glu Asp Thr Asn Ala Gln Lys
545                 550                 555                 560

Thr Ile Thr Asn Cys Phe Leu Leu Lys Asn Lys Ile Trp Cys Ile Ser
            565                 570                 575

Leu Val Glu Ile Tyr Asp Thr Gly Asp Asn Val Ile Arg Pro Lys Leu
            580                 585                 590
```

```
Phe Ala Val Lys Ile Pro Glu Gln Cys Thr
        595                 600

<210> SEQ ID NO 12
<211> LENGTH: 540
<212> TYPE: PRT
<213> ORGANISM: Artificial sequence
<220> FEATURE:
<223> OTHER INFORMATION: Synthetic Polypeptide

<400> SEQUENCE: 12

Met Glu Thr Pro Ala Gln Leu Leu Phe Leu Leu Leu Leu Trp Leu Pro
1               5                   10                  15

Asp Thr Thr Gly Ile Leu His Tyr Glu Lys Leu Ser Lys Ile Gly Leu
            20                  25                  30

Val Lys Gly Ile Thr Arg Lys Tyr Lys Ile Lys Ser Asn Pro Leu Thr
        35                  40                  45

Lys Asp Ile Val Ile Lys Met Ile Pro Asn Val Ser Asn Met Ser Gln
50                  55                  60

Cys Thr Gly Ser Val Met Glu Asn Tyr Lys Thr Arg Leu Asn Gly Ile
65                  70                  75                  80

Leu Thr Pro Ile Lys Gly Ala Leu Glu Ile Tyr Lys Asn Asn Thr His
                85                  90                  95

Asp Leu Val Gly Asp Val Arg Leu Ala Gly Val Ile Met Ala Gly Val
            100                 105                 110

Ala Ile Gly Ile Ala Thr Ala Ala Gln Ile Thr Ala Gly Val Ala Leu
        115                 120                 125

Tyr Glu Ala Met Lys Asn Ala Asp Asn Ile Asn Lys Leu Lys Ser Ser
130                 135                 140

Ile Glu Ser Thr Asn Glu Ala Val Val Lys Leu Gln Glu Thr Ala Glu
145                 150                 155                 160

Lys Thr Val Tyr Val Leu Thr Ala Leu Gln Asp Tyr Ile Asn Thr Asn
                165                 170                 175

Leu Val Pro Thr Ile Asp Lys Ile Ser Cys Lys Gln Thr Glu Leu Ser
            180                 185                 190

Leu Asp Leu Ala Leu Ser Lys Tyr Leu Ser Asp Leu Leu Phe Val Phe
        195                 200                 205

Gly Pro Asn Leu Gln Asp Pro Val Ser Asn Ser Met Thr Ile Gln Ala
210                 215                 220

Ile Ser Gln Ala Phe Gly Gly Asn Tyr Glu Thr Leu Leu Arg Thr Leu
225                 230                 235                 240

Gly Tyr Ala Thr Glu Asp Phe Asp Asp Leu Leu Glu Ser Asp Ser Ile
                245                 250                 255

Thr Gly Gln Ile Ile Tyr Val Asp Leu Ser Gly Tyr Tyr Ile Ile Val
            260                 265                 270

Arg Val Tyr Phe Pro Ile Leu Thr Glu Ile Gln Gln Ala Tyr Ile Gln
        275                 280                 285

Glu Leu Leu Pro Val Ser Phe Asn Asn Asp Asn Ser Glu Trp Ile Ser
290                 295                 300

Ile Val Pro Asn Phe Ile Leu Val Arg Asn Thr Leu Ile Ser Asn Ile
305                 310                 315                 320

Glu Ile Gly Phe Cys Leu Ile Thr Lys Arg Ser Val Ile Cys Asn Gln
                325                 330                 335

Asp Tyr Ala Thr Pro Met Thr Asn Asn Met Arg Glu Cys Leu Thr Gly
            340                 345                 350
```

Ser Thr Glu Lys Cys Pro Arg Glu Leu Val Ser Ser His Val Pro
                355                 360                 365

Arg Phe Ala Leu Ser Asn Gly Val Leu Phe Ala Asn Cys Ile Ser Val
            370                 375                 380

Thr Cys Gln Cys Gln Thr Thr Gly Arg Ala Ile Ser Gln Ser Gly Glu
385                 390                 395                 400

Gln Thr Leu Leu Met Ile Asp Asn Thr Thr Cys Pro Thr Ala Val Leu
                405                 410                 415

Gly Asn Val Ile Ile Ser Leu Gly Lys Tyr Leu Gly Ser Val Asn Tyr
            420                 425                 430

Asn Ser Glu Gly Ile Ala Ile Gly Pro Pro Val Phe Thr Asp Lys Val
            435                 440                 445

Asp Ile Ser Ser Gln Ile Ser Ser Met Asn Gln Ser Leu Gln Gln Ser
            450                 455                 460

Lys Asp Tyr Ile Lys Glu Ala Gln Arg Leu Leu Asp Thr Val Asn Pro
465                 470                 475                 480

Ser Leu Ile Ser Met Leu Ser Met Ile Ile Leu Tyr Val Leu Ser Ile
                485                 490                 495

Ala Ser Leu Cys Ile Gly Leu Ile Thr Phe Ile Ser Phe Ile Ile Val
            500                 505                 510

Glu Lys Lys Arg Asn Thr Tyr Ser Arg Leu Glu Asp Arg Arg Val Arg
            515                 520                 525

Pro Thr Ser Ser Gly Asp Leu Tyr Tyr Ile Gly Thr
            530                 535                 540

<210> SEQ ID NO 13
<211> LENGTH: 520
<212> TYPE: PRT
<213> ORGANISM: Artificial sequence
<220> FEATURE:
<223> OTHER INFORMATION: Synthetic Polypeptide

<400> SEQUENCE: 13

Ile Leu His Tyr Glu Lys Leu Ser Lys Ile Gly Leu Val Lys Gly Ile
1               5                   10                  15

Thr Arg Lys Tyr Lys Ile Lys Ser Asn Pro Leu Thr Lys Asp Ile Val
                20                  25                  30

Ile Lys Met Ile Pro Asn Val Ser Asn Met Ser Gln Cys Thr Gly Ser
            35                  40                  45

Val Met Glu Asn Tyr Lys Thr Arg Leu Asn Gly Ile Leu Thr Pro Ile
50                  55                  60

Lys Gly Ala Leu Glu Ile Tyr Lys Asn Asn Thr His Asp Leu Val Gly
65                  70                  75                  80

Asp Val Arg Leu Ala Gly Val Ile Met Ala Gly Val Ala Ile Gly Ile
                85                  90                  95

Ala Thr Ala Ala Gln Ile Thr Ala Gly Val Ala Leu Tyr Glu Ala Met
            100                 105                 110

Lys Asn Ala Asp Asn Ile Asn Lys Leu Lys Ser Ser Ile Glu Ser Thr
        115                 120                 125

Asn Glu Ala Val Val Lys Leu Gln Glu Thr Ala Glu Lys Thr Val Tyr
        130                 135                 140

Val Leu Thr Ala Leu Gln Asp Tyr Ile Asn Thr Asn Leu Val Pro Thr
145                 150                 155                 160

Ile Asp Lys Ile Ser Cys Lys Gln Thr Glu Leu Ser Leu Asp Leu Ala
                165                 170                 175

Leu Ser Lys Tyr Leu Ser Asp Leu Leu Phe Val Phe Gly Pro Asn Leu
            180                 185                 190

Gln Asp Pro Val Ser Asn Ser Met Thr Ile Gln Ala Ile Ser Gln Ala
            195                 200                 205

Phe Gly Gly Asn Tyr Glu Thr Leu Leu Arg Thr Leu Gly Tyr Ala Thr
210                 215                 220

Glu Asp Phe Asp Asp Leu Leu Glu Ser Asp Ser Ile Thr Gly Gln Ile
225                 230                 235                 240

Ile Tyr Val Asp Leu Ser Gly Tyr Tyr Ile Ile Val Arg Val Tyr Phe
            245                 250                 255

Pro Ile Leu Thr Glu Ile Gln Gln Ala Tyr Ile Gln Glu Leu Leu Pro
            260                 265                 270

Val Ser Phe Asn Asn Asp Asn Ser Glu Trp Ile Ser Ile Val Pro Asn
            275                 280                 285

Phe Ile Leu Val Arg Asn Thr Leu Ile Ser Asn Ile Glu Ile Gly Phe
            290                 295                 300

Cys Leu Ile Thr Lys Arg Ser Val Ile Cys Asn Gln Asp Tyr Ala Thr
305                 310                 315                 320

Pro Met Thr Asn Asn Met Arg Glu Cys Leu Thr Gly Ser Thr Glu Lys
            325                 330                 335

Cys Pro Arg Glu Leu Val Val Ser Ser His Val Pro Arg Phe Ala Leu
            340                 345                 350

Ser Asn Gly Val Leu Phe Ala Asn Cys Ile Ser Val Thr Cys Gln Cys
            355                 360                 365

Gln Thr Thr Gly Arg Ala Ile Ser Gln Ser Gly Glu Gln Thr Leu Leu
            370                 375                 380

Met Ile Asp Asn Thr Thr Cys Pro Thr Ala Val Leu Gly Asn Val Ile
385                 390                 395                 400

Ile Ser Leu Gly Lys Tyr Leu Gly Ser Val Asn Tyr Asn Ser Glu Gly
            405                 410                 415

Ile Ala Ile Gly Pro Pro Val Phe Thr Asp Lys Val Asp Ile Ser Ser
            420                 425                 430

Gln Ile Ser Ser Met Asn Gln Ser Leu Gln Gln Ser Lys Asp Tyr Ile
            435                 440                 445

Lys Glu Ala Gln Arg Leu Leu Asp Thr Val Asn Pro Ser Leu Ile Ser
450                 455                 460

Met Leu Ser Met Ile Ile Leu Tyr Val Leu Ser Ile Ala Ser Leu Cys
465                 470                 475                 480

Ile Gly Leu Ile Thr Phe Ile Ser Phe Ile Ile Val Glu Lys Lys Arg
            485                 490                 495

Asn Thr Tyr Ser Arg Leu Glu Asp Arg Arg Val Arg Pro Thr Ser Ser
            500                 505                 510

Gly Asp Leu Tyr Tyr Ile Gly Thr
            515                 520

<210> SEQ ID NO 14
<211> LENGTH: 1866
<212> TYPE: DNA
<213> ORGANISM: Artificial sequence
<220> FEATURE:
<223> OTHER INFORMATION: Synthetic Polynucleotide

<400> SEQUENCE: 14
atggaaaccc ctgctcagct gctgttcctg ctgctgctgt ggctgcctga tacaacaggc    60

```
atgcccgccg agaacaagaa agttcgcttc gagaacacca ccagcgacaa gggcaagaac      120
cccagcaaag tgatcaagag ctactacggc accatggaca tcaagaagat caacgagggc      180
ctgctggaca gcaagatcct gagcgccttc aacaccgtga ttgccctgct gggctctatc      240
gtgatcatcg tgatgaacat catgatcatc cagaactaca cccggtccac cgacaaccag      300
gccgtgatta aggatgctct gcagggaatc cagcagcaga tcaaaggcct ggccgacaag      360
atcggcacag atcggccc taaggtgtcc ctgatcgaca ccagcagcac catcacaatc        420
cccgccaata tcggactgct gggatccaag atcagccaga gcaccgccag catcaacgag      480
aacgtgaacg agaagtgcaa gttcaccctg cctccactga agatccacga gtgcaacatc      540
agctgcccca atcctctgcc attcagagag tacagacccc agacagaggg cgtgtccaat      600
ctcgtgggcc tgcctgacaa tatctgcctg cagaagacca gcaaccagat cctgaagcct      660
aagctgatct cctacacact gcccgtcgtg ggccagagcg cacctgtat tacagatcct       720
ctgctggcca tggacgaggg ctactttgcc tacagccacc tggaaagaat cggcagctgt      780
agccggggag tgtccaagca gagaatcatc ggcgtgggcg aagtgctgga tagaggcgac      840
gaagtgccca gcctgttcat gaccaatgtg tggaccctc ctaatcctaa caccgtgtac       900
cactgcagcc ccgtgtacaa caacgagttc tactacgtgc tgtgcgccgt gtccacagtg      960
ggcgacccta tcctgaacag cacctattgg agcggcagcc tgatgatgac cagactggcc     1020
gtgaagccca gagcaatgg cggcggatac aaccagcatc agctggccct gcggtccatc      1080
gagaagggca gatacgacaa agtgatgcct acggcccca gcggcatcaa gcaaggcgat      1140
accctgtact ttcccgccgt gggatttctc gtgcggaccg agttcaagta caacgacagc     1200
aactgcccca tcaccaagtg ccagtacagc aagcccgaga actgcagact gagcatgggc     1260
atcagaccca cagccacta catcctgaga agcggcctgc tgaagtacaa cctgagcgac      1320
ggcgagaacc ccaagatcgt gttcatcgag atcagcgacc agcggctgtc tatcggcagc     1380
cctagcaagg tgtacgactc tctgggacag ccagtgttct accaggcctc cttcagctgg     1440
gacaccatga tcaagttcgg cgacgtgcag accgtgaatc ccctggtggt caactggcgg     1500
gacaataccg tgatcagcag acctggccag tctcagtgcc ccagattcaa cacatgcccc     1560
gagatctgtt gggaaggcgt gtacaatgac gccttcctga tcgatcggat caactggatc     1620
tctgccggcg tgttcctgga ctccaatcag acagccgaga tcctgtgtt caccgtgttc     1680
aaggacaatg agatcctgta cgggcccag ctggcctccg aggatacaaa tgcccagaag      1740
acaatcacca actgctttct gctcaagaac aagatctggt gcatcagcct ggtggaaatc     1800
tacgacaccg gcgacaacgt gatcaggccc aagctgttcg ccgtgaagat ccctgagcag     1860
tgcaca                                                                 1866
```

<210> SEQ ID NO 15
<211> LENGTH: 1866
<212> TYPE: DNA
<213> ORGANISM: Artificial sequence
<220> FEATURE:
<223> OTHER INFORMATION: Synthetic Polynucleotide
<400> SEQUENCE: 15

```
atggaaaccc ctgctcagct gctgttcctg ctgctgctgt ggctgcctga tacaacaggc       60
atgcccgccg agaacaagaa agttcgcttc gagaacacca ccagcgacaa gggcaagaac      120
cccagcaaag tgatcaagag ctactacggc accatggaca tcaagaagat caacgagggc      180
ctgctggaca gcaagatcct gagcgccttc aacaccgtga ttgccctgct gggctctatc      240
```

```
gtgatcatcg tgatgaacat catgatcatc cagaactaca cccggtccac cgacaaccag    300
gccgtgatta aggatgctct gcagggaatc cagcagcaga tcaaaggcct ggccgacaag    360
atcggcacag atcggcccc taaggtgtcc ctgatcgaca ccagcagcac catcacaatc    420
cccgccaata tcggactgct gggatccaag atcagccaga gcaccgccag catcaacgag    480
aacgtgaacg agaagtgcaa gttcaccctg cctccactga agatccacga gtgcaacatc    540
agctgcccca atcctctgcc attcagagag tacagacccc agacagaggg cgtgtccaat    600
ctcgtgggcc tgcctgacaa tatctgcctg cagaagacca gcaaccagat cctgaagcct    660
aagctgatct cctacacact gcccgtcgtg gccagagcg gcacctgtat tacagatcct    720
ctgctggcca tggacgaggg ctactttgcc tacagccacc tggaaagaat cggcagctgt    780
agccggggag tgtccaagca gagaatcatc ggcgtgggcg aagtgctgga tagaggcgac    840
gaagtgccca gcctgttcat gaccaatgtg tggaccccctc ctaatcctaa caccgtgtac    900
cactgcagcg ccgtgtacaa caacgagttc tactacgtgc tgtgcgccgt gtccacagtg    960
ggcgacccta tcctgaacag cacctattgg agcggcagcc tgatgatgac cagactggcc   1020
gtgaagccca gagcaatgg cggcggatac aaccagcatc agctggccct gcggtccatc   1080
gagaagggca gatacgacaa agtgatgcct tacgccccca gcggcatcaa gcaaggcgat   1140
accctgtact ttcccgccgt gggatttctc gtgcggaccg agttcaagta caacgacagc   1200
aactgcccca tcaccaagtg ccagtacagc aagcccgaga actgcagact gagcatgggc   1260
atcagaccca cagccacta catcctgaga agcggcctgc tgaagtacaa cctgagcgac   1320
ggcgagaacc ccaagatcgt gttcatcgag atcagcgacc agcggctgtc tatcggcagc   1380
cctagcaagg tgtacgactc tctgggacag ccagtgttct accaggcctc cttcagctgg   1440
gacaccatga tcaagttcgg cgacgtgcag accgtgaatc cctggtggt caactggcgg   1500 gacaataccg tgatcagcag acctggccag tctcagtgcc ccagattcaa cacatgcccc   1560
gagatctgtt gggaaggcgt gtacaatgac gccttcctga tcgatcggat caactggatc   1620
tctgccggcg tgttcctgga ctccaatcag acagccgaga tcctgtgttt caccgtgttc   1680
aaggacaatg agatcctgta tcgggcccag ctggcctccg aggatacaaa tgcccagaag   1740
acaatcacca actgctttct gctcaagaac aagatctggt gcatcagcct ggtggaaatc   1800
tacgacaccg cgacaacgt gatcaggccc aagctgttcg ccgtgaagat ccctgagcag   1860
tgcaca                                                              1866
```

<210> SEQ ID NO 16
<211> LENGTH: 1866
<212> TYPE: RNA
<213> ORGANISM: Artificial sequence
<220> FEATURE:
<223> OTHER INFORMATION: Synthetic Polynucleotide

<400> SEQUENCE: 16

```
auggaaaccc ugcucagcu gcuguuccug cugcugcugu ggcugccuga uacaacaggc    60
augcccgccg agaacaagaa aguucgcuuc gagaacacca ccagcgacaa gggcaagaac   120
cccagcaaag ugaucaagag cuacuacggc accauggaca ucaagaagau caacgagggc   180
cugcuggaca gcaagaguccu gagcgccuuc aacaccguga uugcccugcu gggcucuauc   240
gugaucaucg ugaugaacau caugaucauc cagaacuaca cccgguccac cgacaaccag   300
gccgugauua aggaugcucu gcagggaauc cagcagcaga ucaaaggccu ggccgacaag   360
```

| | |
|---|---|
| aucggcacag agaucggccc uaaggugucc cugaucgaca ccagcagcac caucacaauc | 420 |
| cccgccaaua ucggacugcu gggauccaag aucagccaga gcaccgccag caucaacgag | 480 |
| aacgugaacg agaagugcaa guucacccug ccuccacuga agauccacga gugcaacauc | 540 |
| agcugcccca auccucugcc auucagagag uacagacccc agacagaggg cguguccaau | 600 |
| cucgugggcc ugccugacaa uaucugccug cagaagacca gcaaccagau ccugaagccu | 660 |
| aagcugaucu ccuacacacu gcccgucgug ggccagagcg gcaccuguau uacagauccu | 720 |
| cugcuggcca uggacgaggg cuacuuugcc uacagccacc uggaaagaau cggcagcugu | 780 |
| agccggggag uguccaagca gagaaucauc ggcgugggcg aagugcugga uagaggcgac | 840 |
| gaagugccca gccuguucau gaccaaugug uggacccccu cuaauccuaa caccguguac | 900 |
| cacugcagcg ccguguacaa caacgaguuc uacuacgugc ugugcgccgu guccacagug | 960 |
| ggcgacccua uccugaacag caccuauugg agcggcagcc ugaugaugac cagacuggcc | 1020 |
| gugaagccca gagcaauggc ggcggauac aaccagcauc agcuggcccu gcgguccauc | 1080 |
| gagaagggca gauacgacaa agugaugccu uacggcccca gcggcaucaa gcaaggcgau | 1140 |
| acccuguacu uccccgccgu gggauuucuc gugcggaccg aguucaagua caacgacagc | 1200 |
| aacugcccca ucaccaagug ccaguacagc aagcccgaga cugcagacu gagcaugggc | 1260 |
| aucagaccca acagccacua cauccugaga agcggccugc ugaaguacaa ccugagcgac | 1320 |
| ggcgagaacc ccaagaucgu guucaucgag aucagcgacc agcggcuguc uauccggcagc | 1380 |
| ccuagcaagg uguacgacuc ucugggacag ccagaguucu accaggccuc cuucagcugg | 1440 |
| gacaccauga ucaaguucgg cgacgugcag accgugaauc cccggugggu caacuggcgg | 1500 |
| gacaauaccg ugaucagcag accuggccag ucucagugcc ccagauucaa cacaugcccc | 1560 |
| gagaucuguu gggaaggcgu guacaaugac gccuuccuga ucgaucggau caacuggauc | 1620 |
| ucugccggcg uguuccugga cuccaaucag acagccgaga auccugguu caccguguuc | 1680 |
| aaggacaaug agauccugua ucgggcccag cuggccuccg aggauacaaa ugcccagaag | 1740 |
| acaaucacca acugcuuucu gcucaagaac aagaucuggu gcaucagccu gguggaaauc | 1800 |
| uacgacaccg cgacaacgu gaucaggccc aagcuguucg ccgugaagau cccugagcag | 1860 |
| ugcaca | 1866 |

<210> SEQ ID NO 17
<211> LENGTH: 1866
<212> TYPE: RNA
<213> ORGANISM: Artificial sequence
<220> FEATURE:
<223> OTHER INFORMATION: Synthetic Polynucleotide

<400> SEQUENCE: 17

| | |
|---|---|
| auggaaaccc cugcucagcu gcuguuccug cugcugcugu ggcugccuga uacaacaggc | 60 |
| augcccgccg agaacaagaa aguucgcuuc gagaacacca ccagcgacaa gggcaagaac | 120 |
| cccagcaaag ugaucaagag cuacuacggc accauggaca ucaagaagau caacgagggc | 180 |
| cugcuggaca gcaagauccu gagcgccuuc aacaccguga uugcccugcu gggcucuauc | 240 |
| gugaucaucg ugaugaacau caugaucauc cagaacuaca cccgguccac cgacaaccag | 300 |
| gccgugauua aggaugcucu gcagggaauc cagcagcaga ucaaggccu ggccgacaag | 360 |
| aucggcacag agaucggccc uaaggugucc cugaucgaca ccagcagcac caucacaauc | 420 |
| cccgccaaua ucggacugcu gggauccaag aucagccaga gcaccgccag caucaacgag | 480 |
| aacgugaacg agaagugcaa guucacccug ccuccacuga agauccacga gugcaacauc | 540 |

```
agcugcccca auccucugcc auucagagag uacagacccc agacagaggg cguguccaau    600
cucgugggcc ugccugacaa uaucugccug cagaagacca gcaaccagau ccugaagccu    660
aagcugaucu ccuacacacu gcccgucgug ggccagagcg gcaccuguau uacagauccu    720
cugcuggcca uggacgaggg cuacuuugcc uacagccacc uggaaagaau cggcagcugu    780
agccggggag uguccaagca gagaaucauc ggcguggcg aagugcugga uagaggcgac    840
gaagugccca gccuguucau gaccaaugug uggacccccuc cuaauccuaa caccguguac    900
cacugcagcg ccguguacaa caacgaguuc uacuacgugc ugugcgccgu guccacagug    960
ggcgacccua uccugaacag caccuauugg agcggcagcc ugaugaugac cagacuggcc   1020
gugaagccca gagcaauggc cggcggauac aaccagcauc agcuggcccu gcgguccauc   1080
gagaagggca gauacgacaa agugaugccu uacggcccca gcggcaucaa gcaaggcgau   1140
acccuguacu uccccgccgu gggauuucuc gugcggaccg aguucaagua caacgacagc   1200
aacugcccca ucaccaagug ccaguacagc aagcccgaga acugcagacu gagcaugggc   1260
aucagaccca acagccacua cauccugaga agcggccugc ugaaguacaa ccugagcgac   1320
ggcgagaacc ccaagaucgu guucaucgag aucagcgacc agcggcguc uaucggcagc   1380 ccuagcaagg uguacgacuc ucugggacag ccaguguucu accaggccuc cuucagcugg   1440
gacaccauga ucaaguucgg cgacgugcag accgugaauc cccugguggu caacuggcgg   1500
gacaauaccg ugaucagcag accuggccag ucucagugcc ccagauucaa cacaugcccc   1560
gagaucuguu gggaaggcgu guacaaugac gccuuccuga ucgaucggau caacuggauc   1620
ucugccggcg uguccuugga cuccaaucag acagccgaga auccuguguu caccguguuc   1680
aaggacaaug agauccugua ucgggcccag cuggccuccg aggauacaaa ugcccagaag   1740
acaaucacca acugcuuucu gcucaagaac aagaucuggu gcaucagccu gguggaaauc   1800
uacgacaccg gcgacaacgu gaucaggccc aagcuguucg ccgugaagau cccugagcag   1860
ugcaca                                                              1866
```

<210> SEQ ID NO 18
<211> LENGTH: 1255
<212> TYPE: PRT
<213> ORGANISM: Artificial sequence
<220> FEATURE:
<223> OTHER INFORMATION: Synthetic Polypeptide

<400> SEQUENCE: 18

```
Met Phe Ile Phe Leu Phe Phe Leu Thr Leu Thr Ser Gly Ser Asp Leu
1               5                   10                  15

Glu Ser Cys Thr Thr Phe Asp Asp Val Gln Ala Pro Asn Tyr Pro Gln
            20                  25                  30

His Ser Ser Arg Arg Gly Val Tyr Tyr Pro Asp Glu Ile Phe Arg
        35                  40                  45

Ser Asp Thr Leu Tyr Leu Thr Gln Asp Leu Phe Leu Pro Phe Tyr Ser
    50                  55                  60

Asn Val Thr Gly Phe His Thr Ile Asn His Arg Phe Asp Asn Pro Val
65                  70                  75                  80

Ile Pro Phe Lys Asp Gly Val Tyr Phe Ala Ala Thr Glu Lys Ser Asn
                85                  90                  95

Val Val Arg Gly Trp Val Phe Gly Ser Thr Met Asn Asn Lys Ser Gln
            100                 105                 110

Ser Val Ile Ile Ile Asn Asn Ser Thr Asn Val Val Ile Arg Ala Cys
```

```
            115                 120                 125
Asn Phe Glu Leu Cys Asp Asn Pro Phe Phe Ala Val Ser Lys Pro Thr
130                 135                 140

Gly Thr Gln Thr His Thr Met Ile Phe Asp Asn Ala Phe Asn Cys Thr
145                 150                 155                 160

Phe Glu Tyr Ile Ser Asp Ser Phe Ser Leu Asp Val Ala Glu Lys Ser
                165                 170                 175

Gly Asn Phe Lys His Leu Arg Glu Phe Val Phe Lys Asn Lys Asp Gly
                180                 185                 190

Phe Leu Tyr Val Tyr Lys Gly Tyr Gln Pro Ile Asp Val Val Arg Asp
                195                 200                 205

Leu Pro Ser Gly Phe Asn Ile Leu Lys Pro Ile Phe Lys Leu Pro Leu
210                 215                 220

Gly Ile Asn Ile Thr Asn Phe Arg Ala Ile Leu Thr Ala Phe Leu Pro
225                 230                 235                 240

Ala Gln Asp Thr Trp Gly Thr Ser Ala Ala Tyr Phe Val Gly Tyr
                245                 250                 255

Leu Lys Pro Ala Thr Phe Met Leu Lys Tyr Asp Glu Asn Gly Thr Ile
                260                 265                 270

Thr Asp Ala Val Asp Cys Ser Gln Asn Pro Leu Ala Glu Leu Lys Cys
                275                 280                 285

Ser Val Lys Ser Phe Glu Ile Asp Lys Gly Ile Tyr Gln Thr Ser Asn
290                 295                 300

Phe Arg Val Ala Pro Ser Lys Glu Val Val Arg Phe Pro Asn Ile Thr
305                 310                 315                 320

Asn Leu Cys Pro Phe Gly Glu Val Phe Asn Ala Thr Thr Phe Pro Ser
                325                 330                 335

Val Tyr Ala Trp Glu Arg Lys Arg Ile Ser Asn Cys Val Ala Asp Tyr
                340                 345                 350

Ser Val Leu Tyr Asn Ser Thr Ser Phe Ser Thr Phe Lys Cys Tyr Gly
                355                 360                 365

Val Ser Ala Thr Lys Leu Asn Asp Leu Cys Phe Ser Asn Val Tyr Ala
                370                 375                 380

Asp Ser Phe Val Val Lys Gly Asp Asp Val Arg Gln Ile Ala Pro Gly
385                 390                 395                 400

Gln Thr Gly Val Ile Ala Asp Tyr Asn Tyr Lys Leu Pro Asp Asp Phe
                405                 410                 415

Thr Gly Cys Val Leu Ala Trp Asn Thr Arg Asn Ile Asp Ala Thr Gln
                420                 425                 430

Thr Gly Asn Tyr Asn Tyr Lys Tyr Arg Ser Leu Arg His Gly Lys Leu
                435                 440                 445

Arg Pro Phe Glu Arg Asp Ile Ser Asn Val Pro Phe Ser Pro Asp Gly
450                 455                 460

Lys Pro Cys Thr Pro Pro Ala Phe Asn Cys Tyr Trp Pro Leu Asn Asp
465                 470                 475                 480

Tyr Gly Phe Tyr Ile Thr Asn Gly Ile Gly Tyr Gln Pro Tyr Arg Val
                485                 490                 495

Val Val Leu Ser Phe Glu Leu Leu Asn Ala Pro Ala Thr Val Cys Gly
                500                 505                 510

Pro Lys Leu Ser Thr Asp Leu Ile Lys Asn Gln Cys Val Asn Phe Asn
                515                 520                 525

Phe Asn Gly Leu Thr Gly Thr Gly Val Leu Thr Pro Ser Ser Lys Arg
530                 535                 540
```

```
Phe Gln Pro Phe Gln Gln Phe Gly Arg Asp Val Leu Asp Phe Thr Asp
545                 550                 555                 560

Ser Val Arg Asp Pro Lys Thr Ser Glu Ile Leu Asp Ile Ser Pro Cys
                565                 570                 575

Ser Phe Gly Gly Val Ser Val Ile Thr Pro Gly Thr Asn Thr Ser Ser
            580                 585                 590

Glu Val Ala Val Leu Tyr Gln Asp Val Asn Cys Thr Asp Val Pro Val
        595                 600                 605

Ala Ile His Ala Asp Gln Leu Thr Pro Ser Trp Arg Val Tyr Ser Thr
    610                 615                 620

Gly Asn Asn Val Phe Gln Thr Gln Ala Gly Cys Leu Ile Gly Ala Glu
625                 630                 635                 640

His Val Asp Thr Ser Tyr Glu Cys Asp Ile Pro Ile Gly Ala Gly Ile
                645                 650                 655

Cys Ala Ser Tyr His Thr Val Ser Ser Leu Arg Ser Thr Ser Gln Lys
                660                 665                 670

Ser Ile Val Ala Tyr Thr Met Ser Leu Gly Ala Asp Ser Ser Ile Ala
            675                 680                 685

Tyr Ser Asn Asn Thr Ile Ala Ile Pro Thr Asn Phe Ser Ile Ser Ile
690                 695                 700

Thr Thr Glu Val Met Pro Val Ser Met Ala Lys Thr Ser Val Asp Cys
705                 710                 715                 720

Asn Met Tyr Ile Cys Gly Asp Ser Thr Glu Cys Ala Asn Leu Leu Leu
                725                 730                 735

Gln Tyr Gly Ser Phe Cys Thr Gln Leu Asn Arg Ala Leu Ser Gly Ile
                740                 745                 750

Ala Val Glu Gln Asp Arg Asn Thr Arg Glu Val Phe Ala Gln Val Lys
            755                 760                 765

Gln Met Tyr Lys Thr Pro Thr Leu Lys Asp Phe Gly Gly Phe Asn Phe
    770                 775                 780

Ser Gln Ile Leu Pro Asp Pro Leu Lys Pro Thr Lys Arg Ser Phe Ile
785                 790                 795                 800

Glu Asp Leu Leu Phe Asn Lys Val Thr Leu Ala Asp Ala Gly Phe Met
                805                 810                 815

Lys Gln Tyr Gly Glu Cys Leu Gly Asp Ile Asn Ala Arg Asp Leu Ile
                820                 825                 830

Cys Ala Gln Lys Phe Asn Gly Leu Thr Val Leu Pro Pro Leu Leu Thr
            835                 840                 845

Asp Asp Met Ile Ala Ala Tyr Thr Ala Ala Leu Val Ser Gly Thr Ala
    850                 855                 860

Thr Ala Gly Trp Thr Phe Gly Ala Gly Ala Ala Leu Gln Ile Pro Phe
865                 870                 875                 880

Ala Met Gln Met Ala Tyr Arg Phe Asn Gly Ile Gly Val Thr Gln Asn
                885                 890                 895

Val Leu Tyr Glu Asn Gln Lys Gln Ile Ala Asn Gln Phe Asn Lys Ala
                900                 905                 910

Ile Ser Gln Ile Gln Glu Ser Leu Thr Thr Thr Ser Thr Ala Leu Gly
            915                 920                 925

Lys Leu Gln Asp Val Val Asn Gln Asn Ala Gln Ala Leu Asn Thr Leu
    930                 935                 940

Val Lys Gln Leu Ser Ser Asn Phe Gly Ala Ile Ser Ser Val Leu Asn
945                 950                 955                 960
```

| | | | | | | | | | | |
|---|---|---|---|---|---|---|---|---|---|---|
|Asp|Ile|Leu|Ser|Arg|Leu|Asp|Lys|Val|Glu|Ala Glu Val Gln Ile Asp|

```
Asp Ile Leu Ser Arg Leu Asp Lys Val Glu Ala Glu Val Gln Ile Asp
            965                 970                 975

Arg Leu Ile Thr Gly Arg Leu Gln Ser Leu Gln Thr Tyr Val Thr Gln
            980                 985                 990

Gln Leu Ile Arg Ala Ala Glu Ile Arg Ala Ser Ala Asn Leu Ala Ala
            995                 1000                1005

Thr Lys Met Ser Glu Cys Val Leu Gly Gln Ser Lys Arg Val Asp
        1010                1015                1020

Phe Cys Gly Lys Gly Tyr His Leu Met Ser Phe Pro Gln Ala Ala
        1025                1030                1035

Pro His Gly Val Val Phe Leu His Val Thr Tyr Val Pro Ser Gln
        1040                1045                1050

Glu Arg Asn Phe Thr Thr Ala Pro Ala Ile Cys His Glu Gly Lys
        1055                1060                1065

Ala Tyr Phe Pro Arg Glu Gly Val Phe Val Phe Asn Gly Thr Ser
        1070                1075                1080

Trp Phe Ile Thr Gln Arg Asn Phe Phe Ser Pro Gln Ile Ile Thr
        1085                1090                1095

Thr Asp Asn Thr Phe Val Ser Gly Ser Cys Asp Val Val Ile Gly
        1100                1105                1110

Ile Ile Asn Asn Thr Val Tyr Asp Pro Leu Gln Pro Glu Leu Asp
        1115                1120                1125

Ser Phe Lys Glu Glu Leu Asp Lys Tyr Phe Lys Asn His Thr Ser
        1130                1135                1140

Pro Asp Val Asp Leu Gly Asp Ile Ser Gly Ile Asn Ala Ser Val
        1145                1150                1155

Val Asn Ile Gln Lys Glu Ile Asp Arg Leu Asn Glu Val Ala Lys
        1160                1165                1170

Asn Leu Asn Glu Ser Leu Ile Asp Leu Gln Glu Leu Gly Lys Tyr
        1175                1180                1185

Glu Gln Tyr Ile Lys Trp Pro Trp Tyr Val Trp Leu Gly Phe Ile
        1190                1195                1200

Ala Gly Leu Ile Ala Ile Val Met Val Thr Ile Leu Leu Cys Cys
        1205                1210                1215

Met Thr Ser Cys Cys Ser Cys Leu Lys Gly Ala Cys Ser Cys Gly
        1220                1225                1230

Ser Cys Cys Lys Phe Asp Glu Asp Asp Ser Glu Pro Val Leu Lys
        1235                1240                1245

Gly Val Lys Leu His Tyr Thr
        1250                1255

<210> SEQ ID NO 19
<211> LENGTH: 3765
<212> TYPE: DNA
<213> ORGANISM: Artificial sequence
<220> FEATURE:
<223> OTHER INFORMATION: Synthetic Polynucleotide

<400> SEQUENCE: 19
atgtttatct tcctgttctt cctgaccctg accagcggca cgacctgga aagctgcacc      60 accttcgacg acgtgcaggc ccccaactac cctcagcaca gctctagcag acggggcgtg    120 tactacccg acgagatctt cagaagcgac accctgtacc tgacccagga cctgttcctg    180
cccttctaca gcaacgtgac cggcttccac catcaacc acagattcga caaccccgtg      240
atccccttca aggacggggt gtactttgcc gccaccgaga gtccaatgt cgtgcgggga    300
```

```
tgggtgttcg gcagcaccat gaacaacaag agccagagcg tgatcatcat caacaacagc    360
accaacgtcg tgatccgggc ctgcaacttc gagctgtgcg acaacccatt cttcgccgtg    420
tccaagccca ccggcaccca gacccacacc atgatcttcg acaacgcctt caactgcacc    480
ttcgagtaca tcagcgacag cttcagcctg gacgtggccg agaaaagcgg caacttcaag    540
cacctgagag aattcgtgtt caagaacaag gacggcttcc tgtacgtgta cagggctac    600
cagcccatcg acgtcgtgcg cgatctgccc agcggcttca acatcctgaa gcccatcttc    660
aagctgcccc tgggcatcaa catcaccaac ttccgggcta tcctgaccgc cttcctgccc    720
gcccaggata cctggggaac aagcgccgct gcctacttcg tgggctacct gaagcctgcc    780
accttcatgc tgaagtacga cgagaacggc accatcaccg acgccgtgga ctgcagccag    840
aatcctctgg ccgagctgaa gtgcagcgtg aagtccttcg agatcgacaa gggcatctac    900
cagaccagca acttcagagt ggcccccagc aaagaagtcg tgcggttccc caatatcacc    960
aacctgtgcc ccttcggcga ggtgttcaac gccaccacct ttcccagcgt gtacgcctgg   1020
gagcggaagc ggatcagcaa ctgcgtggcc gactacagcg tgctgtacaa ctccaccagc   1080
ttctccacct tcaagtgcta cggcgtgtcc gccaccaagc tgaacgacct gtgcttcagc   1140
aatgtgtacg ccgactcctt cgtcgtgaag ggcgacgatg tgcgccagat cgcccctgga   1200
cagacaggcg tgatcgccga ttacaactac aagctgcctg acgacttcac cggctgcgtg   1260
ctggcctgga acaccagaaa catcgacgcc acccagacag caactacaa ttacaagtac   1320
agaagcctgc ggcacggcaa gctgcggccc ttcgagaggg acatctccaa cgtgcccttc   1380
agccccgacg gcaagccttg taccccccct gcctttaact gctactggcc cctgaacgac   1440
tacggcttct acatcacaaa cggcatcggc tatcagccct accgggtggt ggtgctgtcc   1500
tttgagctgc tgaatgcccc tgccaccgtg tgcggcccta agctgagcac cgacctgatc   1560
aagaaccagt gcgtgaactt caacttcaac ggcctgaccg gcaccggcgt gctgacacct   1620
agcagcaaga gattccagcc cttccagcag ttcggccggg acgtgctgga tttcaccgac   1680
agcgtgcggg accccaagac cagcgagatc ctggacatca gccccctgca gttcggcgga   1740
gtgtccgtga tcacccccgg caccaatacc agctctgagg tggccgtgct gtatcaggac   1800
gtgaactgca ccgatgtgcc cgtggccatc cacgccgatc agctgacccc atcttggcgg   1860
gtgtactcca ccggcaacaa cgtgttccag acacaagccg gctgcctgat cggagccgag   1920
cacgtggaca ccagctacga gtgcgacatc cctatcggcg ctggcatctg cgccagctac   1980
cacaccgtgt ccgcctgag aagcaccagc cagaaatcta tcgtggccta caccatgagc   2040
ctgggcgccg acagctctat cgcctactcc aacaacacaa tcgccatccc caccaatttc   2100
agcatctcca tcaccaccga agtgatgccc gtgtccatgg ccaagacctc cgtggattgc   2160
aacatgtaca tctgcggcga cagcaccgag tgcgccaacc tgctgctgca gtacggcagc   2220
ttctgcaccc agctgaacag agccctgagc ggaatcgccg tggaacagga cagaaacacc   2280
cgggaagtgt tcgcccaagt gaagcagatg tataagaccc ccaccctgaa ggatttcggc   2340
ggctttaact tcagccagat cctgcccgac cctctgaagc ctaccaagcg gagcttcatc   2400
gaggacctgc tgttcaacaa agtgaccctg gccgacgccg gtttatgaa gcagtatggc   2460
gagtgcctgg gcgacatcaa cgccgggat ctgatctgcg cccagaagtt taacggactg   2520
accgtgctgc cccctctgct gaccgacgat atgatcgccg cctacacagc cgccctggtg   2580
tctggcacag ctaccgccgg atggacattt ggagctggcg ccgctctgca gatccccttt   2640
```

```
gccatgcaga tggcctaccg gttcaatggc atcggcgtga cccagaatgt gctgtacgag   2700
aaccagaagc agatcgccaa ccagttcaac aaggccatta gccagattca ggaaagcctg   2760
accaccacca gcaccgccct gggcaaactg caggacgtcg tgaaccagaa cgcccaggcc   2820
ctgaacaccc tcgtgaagca gctgagcagc aatttcggcg ccatcagctc cgtgctgaac   2880
gatatcctga gcagactgga caaggtggaa gcagaggtgc agatcgaccg gctgatcacc   2940
ggcagactgc agagcctgca gacctacgtg acacagcagc tgattagagc cgccgagatc   3000
agggccagcg ccaatctggc cgccacaaag atgagcgagt gtgtgctggg ccagagcaag   3060
cgggtggact ctgcggcaa gggctatcac ctgatgagct cccccaggc cgctcctcac     3120 ggcgtggtgt ttctgcacgt gacatacgtg cccagccagg aacggaactt caccaccgcc   3180
ccagccatct gccacgaggg caaggcctac ttcccccggg aaggcgtgtt cgtgtttaac   3240
ggcacctcct ggtttatcac ccagcggaat ttcttcagtc cgcagatcat caccacagac   3300
aacaccttcg tgtccggcag ctgcgacgtc gtgattggca tcattaacaa caccgtgtac   3360 gacccctgc agcccgagct ggacagcttc aaagaggaac tggacaagta cttcaagaac    3420
cacacctccc ccgacgtgga cctgggcgat atctccggca tcaatgccag cgtcgtgaat   3480
atccagaaag agatcgatcg cctgaacgag gtggccaaga acctgaatga gagcctgatc   3540
gacctgcagg aactggggaa gtacgagcag tacatcaagt ggccttggta cgtgtggctg   3600
ggctttatcg ccggcctgat cgccatcgtg atggtcacca cctgctgtgt ctgcatgacc   3660
agctgttgca gctgtctgaa gggcgcctgc agctgtggct cctgctgcaa gttcgatgag   3720
gacgacagcg agcctgtgct gaaaggcgtg aagctgcact acacc                   3765
```

<210> SEQ ID NO 20
<211> LENGTH: 3765
<212> TYPE: RNA
<213> ORGANISM: Artificial sequence
<220> FEATURE:
<223> OTHER INFORMATION: Synthetic Polynucleotide

<400> SEQUENCE: 20

```
auguuuaucu uccuguucuu ccugacccug accagcggca gcgaccugga aagcugcacc    60
accuucgacg acgugcaggc ccccaacuac ccucagcaca gcucuagcag acggggcgug   120
uacuaccccg acgagaucuu cagaagcgac acccuguacc ugaccaggag ccuguuccug   180
cccuucuaca gcaacgugac cggcuuccac accaucaacc acagauucga caaccccgug   240
auccccuuca aggacggggu guacuuugcc gccaccgaga aguccaaugu cgugcgggga   300
uggguguucg gcagcaccau gaacaacaag agccagagcg ugaucaucau caacaacagc   360
accaacgucg uauccgggc cugcaacuuc gagcugugcg acaacccauu cuucgccgug   420
uccaagccca ccggcacccca gacccacacc augaucuucg acaacgccuu caacugcacc   480
uucgaguaca ucagcgacag cuucagccug gacguggccg agaaaagcgg caacuucaag   540
caccugagag aauucgugu caagaacaag gacggcuucc uguacgugua caagggcuac   600
cagcccaucg acgucgugcg cgaucugccc agcggcuuca acauccugaa gcccaucuuc   660
aagcugcccc uggcaucaa caucaccaac uucggcua ccugaccgc cuuccugccc     720 gcccaggaua ccuggggaac aagcgccgcu gccuacuucg ugggcuaccu gaagccugcc   780
accuucaugc ugaaguacga cgagaacggc accaucaccg acgccgugga cugcagccag   840
aauccucugg ccgagcugaa gugcagcgug aaguccuucg agaucgacaa gggcaucuac   900
cagaccagca acuucagagu ggcccccagc aaagaagucg ugcgguuccc caauaucacc   960
```

```
aaccugugcc ccuucggcga ggoguucaac gccaccaccu uucccagcgu guacgccugg    1020
gagcggaagc ggaucagcaa cugcguggcc gacuacagcg ugcuguacaa ucccaccagc    1080
uucuccaccu ucaagugcua cggcgugucc gccaccaagc ugaacgaccu gugcuucagc    1140
aaugaguacg ccgacuccuu cgucgugaag ggcgacgaug ugcgccagau cgccccugga    1200
cagacaggcg ugaucgccga uuacaacuac aagcugccug acgacuucac cggcugcgug    1260
cuggccugga acaccagaaa caucgacgcc acccagacag gcaacuacaa uuacaaguac    1320
agaagccugc ggcacggcaa gcugcggccc uucgagaggg acaucuccaa cgugcccuuc    1380
agccccgacg gcaagccuug uacccccccu gccuuuaacu gcuacuggcc ccugaacgac    1440
uacggcuucu acaucacaaa cggcaucggc uaucagcccu accgggaggu ggugcugucc    1500
uuugagcugc ugaaugcccc ugccaccgug ugcggcccua agcugagcac cgaccugauc    1560
aagaaccagu gcgugaacuu caacuucaac ggccugaccg caccggcgu gcugacaccu    1620 agcagcaaga gauuccagcc cuuccagcag uucggccggg acgugcugga uuucaccgac    1680
agcgugcggg accccaagac cagcgagauc cuggacauca gcccccugcag cuucggcgga    1740 guguccguga ucaccccccgg caccaauacc agcucugagg uggccgugcu guaucaggac    1800
gugaacugca ccgaugugcc cguggccauc cacgccgauc agcugacccc aucuuggcgg    1860
uguuacucca ccggcaacaa cguguuccag acacaagccg gcugccugau cggagccgag    1920
cacguggaca ccagcuacga gugcgacauc ccaucggcg cuggcaucug cgccagcuac    1980
cacaccgugu ccagccugag aagcaccagc cagaaaucua ucguggccua caccaugagc    2040
cugggcgccg acagcucuau cgccuacucc aacaacacaa ucgccaucc caccaauuuc    2100 agcaucucca ucaccaccga agugaugccc guguccaugg ccaagaccuc cguggauugc    2160
aacauguaca ucugcggcga cagcaccgag ugcgccaacc ugcugcugca guacggcagc    2220
uucugcaccc agcugaacag agcccugagc ggaaucgccg uggaacagga cagaaacacc    2280
cgggaagugu ucgccaagu gaagcagaug uauaagaccc ccacccugaa ggauuucggc    2340
ggcuuuaacu ucagccagau ccugcccgac ccucugaagc cuaccaagcg agcuucauc    2400 gaggaccugc uguucaacaa agugacccug gccgacgccg gcuuuaugaa gcaguauggc    2460
gagugccugg gcgacaucaa cgcccgggau cugaucugcg cccagaaguu uaacggacug    2520
accgugcugc ccccucugcu gaccgacgau augaucgccg gcuauagcag cgcccuggug    2580
ucuggcacag cuaccgccgg auggacauuu ggagcuggcg ccgcucugca gauccccuuu    2640
gccaugcaga uggccuaccg guucaauggc aucggcguga cccagaaugu gcuuacgag    2700 aaccagaagc agaucgccaa ccaguucaac aaggccauua gccagauuca ggaaagccug    2760
accaccacca gcaccgcccu gggcaaacug caggacgucu gaaccagaa cgcccaggcc    2820 cugaacaccc ucgugaagca gcugagcagc aauuucggcg ccaucagcuc cgugcugaac    2880
gauauccuga gcagacugga caaggugaa gcagaggugc agaucgaccg gcugaucacc    2940
ggcagacugc agagccugca gaccuacgug acacagcagc ugauuagagc cgccgagauc    3000
agggccagcg ccaaucuggc cgccacaaag augagcgagu gugucugg ccagagcaag    3060 cggguggacu ucugcggcaa gggcuaucac cugaugagcu uccccaggc cgcuccucac    3120 ggcguggugu ucugcacgu gacauacgug cccagccagg aacggaacuu caccaccgcc    3180
ccagccaucu gccacgaggg caaggccuac uuccccccggg aaggcgaguu cguguuaaac    3240
ggcaccuccu ggaagguac ccagcggaau uucuucaguc cgcagaucau caccacagac    3300
```

```
aacaccuucg uguccggcag cugcgacguc gugauuggca ucauuaacaa caccguguac    3360 gaccccugc agcccgagcu ggacagcuuc aaagaggaac uggacaagua cuucaagaac     3420
cacaccuccc ccgacgugga ccugggcgau aucuccggca ucaaugccag cgucgugaau    3480
auccagaaag agaucgaucg ccugaacgag guggccaaga accugaauga gagccugauc    3540
gaccugcagg aacuggggaa guacgagcag uacaucaagu ggccuuggua cguguggcug    3600
ggcuuuaucg ccggccugau cgccaucgug auggucacca uccugcugug cugcaugacc    3660
agcuguugca gcugucugaa gggcgccugc agcuguggcu ccugcugcaa guucgaugag    3720
gacgacagcg agccugugcu gaaaggcgug aagcugcacu acacc                    3765
```

<210> SEQ ID NO 21
<211> LENGTH: 30
<212> TYPE: PRT
<213> ORGANISM: Artificial sequence
<220> FEATURE:
<223> OTHER INFORMATION: Synthetic Polypeptide

<400> SEQUENCE: 21

```
Met Asp Ser Lys Gly Ser Ser Gln Lys Gly Ser Arg Leu Leu Leu Leu
1               5                   10                  15

Leu Val Val Ser Asn Leu Leu Leu Pro Gln Gly Val Val Gly
            20                  25                  30
```

<210> SEQ ID NO 22
<211> LENGTH: 18
<212> TYPE: PRT
<213> ORGANISM: Artificial sequence
<220> FEATURE:
<223> OTHER INFORMATION: Synthetic Polypeptide

<400> SEQUENCE: 22

```
Met Asp Trp Thr Trp Ile Leu Phe Leu Val Ala Ala Ala Thr Arg Val
1               5                   10                  15

His Ser
```

<210> SEQ ID NO 23
<211> LENGTH: 20
<212> TYPE: PRT
<213> ORGANISM: Artificial sequence
<220> FEATURE:
<223> OTHER INFORMATION: Synthetic Polypeptide

<400> SEQUENCE: 23

```
Met Glu Thr Pro Ala Gln Leu Leu Phe Leu Leu Leu Leu Trp Leu Pro
1               5                   10                  15

Asp Thr Thr Gly
            20
```

<210> SEQ ID NO 24
<211> LENGTH: 24
<212> TYPE: PRT
<213> ORGANISM: Artificial sequence
<220> FEATURE:
<223> OTHER INFORMATION: Synthetic Polypeptide

<400> SEQUENCE: 24

```
Met Leu Gly Ser Asn Ser Gly Gln Arg Val Val Phe Thr Ile Leu Leu
1               5                   10                  15

Leu Leu Val Ala Pro Ala Tyr Ser
            20
```

```
<210> SEQ ID NO 25
<211> LENGTH: 17
<212> TYPE: PRT
<213> ORGANISM: Artificial sequence
<220> FEATURE:
<223> OTHER INFORMATION: Synthetic Polypeptide

<400> SEQUENCE: 25

Met Lys Cys Leu Leu Tyr Leu Ala Phe Leu Phe Ile Gly Val Asn Cys
1               5                   10                  15

Ala

<210> SEQ ID NO 26
<211> LENGTH: 15
<212> TYPE: PRT
<213> ORGANISM: Artificial sequence
<220> FEATURE:
<223> OTHER INFORMATION: Synthetic Polypeptide

<400> SEQUENCE: 26

Met Trp Leu Val Ser Leu Ala Ile Val Thr Ala Cys Ala Gly Ala
1               5                   10                  15

<210> SEQ ID NO 27
<211> LENGTH: 9
<212> TYPE: RNA
<213> ORGANISM: Artificial sequence
<220> FEATURE:
<223> OTHER INFORMATION: Synthetic Polynucleotide

<400> SEQUENCE: 27 ccrccaugg                                                                 9

<210> SEQ ID NO 28
<211> LENGTH: 11
<212> TYPE: RNA
<213> ORGANISM: Artificial sequence
<220> FEATURE:
<223> OTHER INFORMATION: Synthetic Polynucleotide

<400> SEQUENCE: 28
gggauccuac c                                                             11

<210> SEQ ID NO 29
<211> LENGTH: 9
<212> TYPE: RNA
<213> ORGANISM: Artificial sequence
<220> FEATURE:
<223> OTHER INFORMATION: Synthetic Polynucleotide
<220> FEATURE:
<221> NAME/KEY: misc_feature
<222> LOCATION: (8)..(9)
<223> OTHER INFORMATION: n can be u or a

<400> SEQUENCE: 29 uuauuuann                                                                 9

<210> SEQ ID NO 30

<400> SEQUENCE: 30

000

<210> SEQ ID NO 31
<211> LENGTH: 13
<212> TYPE: PRT
```

```
<213> ORGANISM: Artificial sequence
<220> FEATURE:
<223> OTHER INFORMATION: Synthetic Polypeptide

<400> SEQUENCE: 31

Leu Gln Arg Val Arg Glu Leu Ala Val Gln Ser Ala Asn
1               5                   10
```